United States Patent
Enomoto et al.

(10) Patent No.: US 8,193,237 B2
(45) Date of Patent: Jun. 5, 2012

(54) INDOLE DERIVATIVE HAVING IκB KINASE β INHIBITORY ACTIVITY

(75) Inventors: Hiroshi Enomoto, Ikoma (JP); Kenji Kawashima, Ikoma (JP); Kazuhiro Kudou, Ikoma (JP); Minoru Yamamoto, Ikoma (JP); Masaaki Murai, Ikoma (JP); Takaaki Inaba, Ikoma (JP); Noriko Ishizaka, Ikoma (JP)

(73) Assignee: Santen Pharmaceutical Co., Ltd., Osaka (JP)

( * ) Notice: Subject to any disclaimer, the term of this patent is extended or adjusted under 35 U.S.C. 154(b) by 106 days.

(21) Appl. No.: 12/448,826

(22) PCT Filed: Jan. 15, 2008

(86) PCT No.: PCT/JP2008/050342
§ 371 (c)(1),
(2), (4) Date: Jul. 9, 2009

(87) PCT Pub. No.: WO2008/087933
PCT Pub. Date: Jul. 24, 2008

(65) Prior Publication Data
US 2010/0041628 A1    Feb. 18, 2010

(30) Foreign Application Priority Data
Jan. 15, 2007 (JP) ................. 2007-005554

(51) Int. Cl.
*A61K 31/404* (2006.01)
*C07D 209/12* (2006.01)
(52) U.S. Cl. ...................... 514/419; 548/483
(58) Field of Classification Search .......... 548/483; 514/419
See application file for complete search history.

(56) References Cited

U.S. PATENT DOCUMENTS

| | | |
|---|---|---|
| 2002/0107252 A1 | 8/2002 | Baxter et al. |
| 2003/0229047 A1 | 12/2003 | Joshi-Hangal et al. |
| 2004/0235821 A1 | 11/2004 | Griffiths et al. |
| 2004/0242573 A1 | 12/2004 | Faull et al. |
| 2005/0054631 A1 | 3/2005 | Jiang et al. |
| 2005/0159474 A1 | 7/2005 | Arnould |
| 2005/0203075 A1 | 9/2005 | Agoston et al. |
| 2006/0058522 A1 | 3/2006 | Faull et al. |
| 2006/0111431 A1 | 5/2006 | Morley et al. |
| 2006/0116419 A1 | 6/2006 | Callahan et al. |
| 2007/0208057 A1 | 9/2007 | Zeldis |
| 2007/0275962 A1 | 11/2007 | Koul et al. |
| 2008/0269200 A1 | 10/2008 | Baldwin et al. |
| 2008/0293802 A1 | 11/2008 | Kerns |
| 2010/0041628 A1 | 2/2010 | Enomoto et al. |
| 2011/0124668 A1 | 5/2011 | Kawashima et al. |

FOREIGN PATENT DOCUMENTS

| | | |
|---|---|---|
| WO | 96/20191 | 7/1996 |
| WO | WO 96/20196 A1 | 7/1996 |
| WO | WO 01/58890 A1 | 8/2001 |
| WO | 2004/009582 A1 | 1/2004 |
| WO | WO 2004/009582 A1 | 1/2004 |
| WO | 2004/053087 A2 | 6/2004 |
| WO | WO 2005/123745 A1 | 12/2005 |
| WO | WO 2006/036031 A1 | 4/2006 |
| WO | 2007/002481 A2 | 1/2007 |
| WO | 2008/087933 A1 | 7/2008 |

OTHER PUBLICATIONS

Rheumatoid arthritis [online] retrived on Aug. 26, 2010 for the internet. URL; http://www.mayoclinic.com/health/rheumatoid-arthritis/DS00020.*
Age-related macular degeneration [online] retrieved on Aug. 26, 2010 for the internet. URL; http://www.medicinenet.com/script/main/art.asp?articlekey=10008.*
A. Kumar et al, "Nuclear factor—κB: its role in health and disease" *J. Mol. Med.*, 82, pp. 434-448 (2004).
Communication dated Jul. 26, 2010 (7 pages) in EP 08 70 3206 including the International Search Report and European Search Opinion.
Gazzete Chimica Italiana 48, II, 1918, pp. 151-182, with English translation of p. 170, line 22 to p. 171, line 7.
A. Bingham et al, "A novel series of potent and selective IKK2 inhibitors", Bioorganic & Medicinal Chemistry Letters, 2004, 14, pp. 409-412.
M. Mor et al, "Synthesis, Pharmacological Characterization and QSAR Studies on 2-Substituted Indole Melatonin Keceptor Ligands", Bioorganic & Medicinal Chemistry, 2001, 9, pp. 1045-1057.

* cited by examiner

*Primary Examiner* — Shawquia E Young
(74) *Attorney, Agent, or Firm* — Holtz, Holtz, Goodman & Chick, P.C.

(57) ABSTRACT

Disclosed is a compound represented by the general formula (1) or a salt thereof. The compound or a salt thereof has an inhibitory activity on IKKβ and is therefore useful as preventive and/or therapeutic agent for a disease associated with IKKβ. In the formula, $R^1$ represents a hydrogen atom, a lower alkyl group, an aryl group, a hydroxy group, or the like; $R^2$ represents a halogen atom, a lower alkyl group, a lower alkenyl group, a lower alkynyl group, or the like; and m represents 0, 1, 2, or the like.

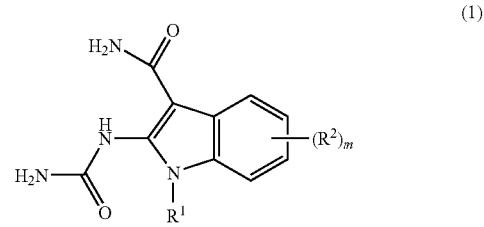

(1)

24 Claims, No Drawings

INDOLE DERIVATIVE HAVING IκB KINASE β INHIBITORY ACTIVITY

This application is the U.S. national phase application of International Application PCT/JP2008/050342 filed Jan. 15, 2008.

TECHNICAL FIELD

The present invention relates to a novel indole derivative or a salt thereof useful as a pharmaceutical having IκB kinase β (hereinafter referred to as "IKKβ") inhibitory activity. The derivative or a salt thereof has the IKKβ inhibitory activity and is therefore useful as a preventive and/or therapeutic agent for diseases associated with IKKβ.

BACKGROUND ART

Nuclear factor κB (hereinafter referred to as "NF-κB") associated with signaling from the outside of a cell to the inside of a nucleous is a transcription factor associated with expression of many genes induced in immunological/inflammatory reactions. NF-κB as the transcription factor forms a complex with a control protein generally called IκB and is localized as being inactive in cytoplasm. When the IκB of the complex is phosphorylated by a kinase called IKKβ, degradation of IκB is developed. NF-κB that is released due to the IκB degradation becomes active and translocates from the cytoplasm to the nucleous to activate transcription of a target gene, thereby enhancing production of cytokines such as a tumor necrosis factor (hereinafter referred to as "TNF"), interleukin-1 (hereinafter referred to as "IL-1"), and interleukin-6 (hereinafter referred to as "IL-6") and cell proliferation.

Therefore, it is possible to inhibit activation of NF-κB by way of control of IKKβ, which makes it possible to suppress the production of cytokines such as TNF, IL-1 and IL-6 and the cell proliferation, thereby realizing prevention and/or treatment of diseases associated with the factors.

Various diseases such as rheumatoid arthritis, asthma, diabetes, and cancer have been known as the diseases associated with IKKβ (see Journal of Molecular Medicine, 82, 434-448 (2004) and WO 06/036031).

As compounds having IKKβ inhibitory activity, condensed furan derivatives disclosed in WO 06/036031, aromatic heterocyclic 5-membered ring carboxamide derivatives disclosed in WO 01/58890, substituted thiophene carboxamide derivatives disclosed in WO 04/009582, and the like have been known.

Compounds having a urea structure at the 2-position of an indole ring are disclosed in Gazzete Chimica Italiana 48, II, 151-182 (1918), and compounds having an amide structure at the 3-position of an indole ring are disclosed in WO 96/020196. However, these publications do not contain any specific disclosure nor suggestion of compounds having a urea structure at the 2-position and an amide structure at the 3-position of an indole ring and do not refer to the IKKβ inhibitory effect of these compounds at all.

DISCLOSURE OF THE PRESENT INVENTION

Problems to be Solved

Synthesis and research of a novel indole derivative and discovery of a pharmacological action of the derivative are very interesting subjects.

Means for Solving the Problem

The inventors conducted synthesis of and research on novel indole derivatives having a novel chemical structure and succeeded in creating many novel compounds.

As a result of study on pharmacological action of the derivative or a salt thereof, the inventors found that the derivative or a salt thereof has the IKKβ inhibitory activity and is useful as a pharmaceutical, thereby accomplishing the present invention.

More specifically, the present invention relates to a compound represented by the following general formula (1) or a salt thereof (hereinafter referred to as "the present compound") and a pharmaceutical composition comprising the present compound or a salt thereof. Also, a preferred invention for medicinal use relates to an IKKβ inhibitor, and examples of a target disease of the IKKβ inhibitor include diseases associated with IKKβ, such as an inflammatory disease, an autoimmune disease, an allergic disease, an infectious disease, a degenerative disease, a vascular disease, a nerve/sensory organ disease, an endocrine/metabolic disease, a neoplastic disease, a congenital disease, a traumatic disease, and an adverse reaction after organ transplantation, and more specific examples of such diseases include keratitis, conjunctivitis, uveitis, osteoarthritis, chronic obstructive pulmonary disease, bronchitis, pneumonia, hepatitis, pancreatitis, nephritis, sepsis, systemic inflammatory response syndrome, rheumatoid arthritis, psoriasis, multiple sclerosis, Crohn's disease, ulcerative colitis, systemic erythematosus, Sjogren's syndrome, multiple myositis, dermatomyositis, asthma, allergic rhinitis, hives, atopic dermatitis, age-related macular degeneration, retinopathy of prematurity, polypoidal choroidal vasculopathy, retinal vein occlusion, diabetes and its complication (diabetic retinopathy, diabetic macular edema, diabetic neuropathy, diabetic nephropathy), leukemia, multiple myeloma, malignant lymphoma, solid cancer, cachexia, Alzheimer's disease, Parkinson's syndrome, cerebral infarction, cerebral apoplexy, glaucoma, acquired immune deficiency syndrome, osteoporosis, obesity, fibrosis, gout, fever, headache, acute/chronic pain, hypertension, hyperlipidemia, arteriosclerosis, cardiac infarct, angina, dystrophia, acute respiratory distress syndrome, and the like.

A particularly preferred invention for medicinal use relates to preventive or therapeutic agent for these diseases, comprising the present compound as an active ingredient.

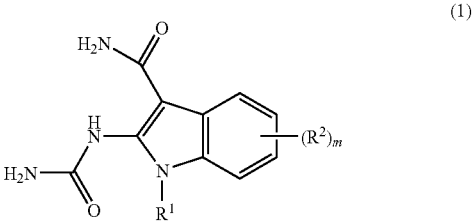

(1)

[wherein $R^1$ represents a hydrogen atom, a lower alkyl group which may have a substituent, an aryl group which may have a substituent, a hydroxy group, or a lower alkoxy group which may have a substituent;

$R^2$ represents a halogen atom, a lower alkyl group which may have a substituent, a lower alkenyl group which may have a substituent, a lower alkynyl group which may have a substituent, $-X_1-COR^3$, $-X_1-COOR^3$, $-X_1-CON$-

$R^aR^b$, —$X_1$—$SR^3$, —$X_1$—$NR^aR^b$, —$X_1$—NHCO—$R^3$, —$X_1$—CN, —$X_1$—$N_3$, or a group represented by the following general formula (2):

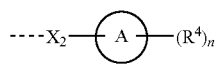

(2)

wherein $X_1$ represents a single bond, a lower alkylene group which may have a substituent, a lower alkenylene group which may have a substituent, or a lower alkynylene group which may have a substituent;

$R^3$ represents a hydrogen atom, a lower alkyl group which may have a substituent, or a lower alkenyl group which may have a substituent;

$R^a$ and $R^b$ may be the same or different and each represents a hydrogen atom, a lower alkyl group which may have a substituent, a lower alkenyl group which may have a substituent, a lower alkoxy group which may have a substituent, a lower alkylsulfonyl group which may have a substituent, or an arylsulfonyl group which may have a substituent;

$X_2$ represents a single bond, a lower alkylene group which may have a substituent, a lower alkenylene group which may have a substituent, a lower alkynylene group which may have a substituent, —$X_3$—CO—, —$X_3$—CONH—, —$X_3$—S—, —$X_3$—NH—, —$X_3$—NHCO—, or —$X_3$—NHCONH—;

$X_3$ represents a single bond, a lower alkylene group which may have a substituent, a lower alkenylene group which may have a substituent, or a lower alkynylene group which may have a substituent, the ring A represents a hydrocarbon ring or a heterocyclic ring;

$R^4$ represents a halogen atom, a lower alkyl group which may have a substituent, —$X_4$—$OR^5$, —$X_4$—$OCOR^5$, —$X_4$—$COR^5$, —$X_4$—$COOR^5$, —$X_4$—$CONR^cR^d$, —$X_4$—$SR^5$, —$X_4$—$SOR^5$, —$X_4$—$SONR^cR^d$, —$X_4$—$SO_2R^5$, —$X_4$—$SO_2NR^cR^d$, —$X_4$—$NR^cR^d$, —$X_4$—$NHCOR^5$, —$X_4$—$NHCOOR^5$, —$X_4$—$NHSOR^5$, —$X_4$—$NHSO_2R^5$, —$X_4$—CN, or —$X_4$—$NO_2$;

$X_4$ represents a single bond, a lower alkylene group which may have a substituent, or a lower cycloalkylene group which may have a substituent;

$R^5$ represents a hydrogen atom, a lower alkyl group which may have a substituent, a lower cycloalkyl group which may have a substituent, or an aryl group which may have a substituent;

$R^c$ and $R^d$ may be the same or different and each represents a hydrogen atom, a lower alkyl group which may have a substituent, a lower cycloalkyl group which may have a substituent, an aryl group which may have a substituent, or a heterocyclic group which may have a substituent;

$R^c$ and $R^d$ may be joined to each other to form a monocyclic saturated heterocyclic ring which may have a substituent;

m represents 0, 1, 2, 3, or 4, provided that $R^2$ may be the same or different when m is 2, 3, or 4; and n represents 0, 1, 2, 3, or 4, provided that $R^4$ may be the same or different when n is 2, 3, or 4.

Hereinafter the same shall apply.

ADVANTAGEOUS EFFECT OF THE PRESENT INVENTION

The present invention provides a novel indole derivative or a salt thereof. The present compound has excellent IKKβ inhibitory activity and is useful as an IKKβ inhibitor. Particularly, the present compound is useful as preventive or therapeutic agent for a disease associated with IKKβ, such as an inflammatory disease, an autoimmune disease, an allergic disease, an infectious disease, a degenerative disease, a vascular disease, a nerve/sensory organ disease, an endocrine/metabolic disease, a neoplastic disease, a congenital disease, a traumatic disease, or an adverse reaction after organ transplantation, and more specific examples of such diseases include keratitis, conjunctivitis, uveitis, osteoarthritis, chronic obstructive pulmonary disease, bronchitis, pneumonia, hepatitis, pancreatitis, nephritis, sepsis, systemic inflammatory response syndrome, rheumatoid arthritis, psoriasis, multiple sclerosis, Crohn's disease, ulcerative colitis, systemic erythematosus, Sjogren's syndrome, multiple myositis, dermatomyositis, asthma, allergic rhinitis, hives, atopic dermatitis, age-related macular degeneration, retinopathy of prematurity, polypoidal choroidal vasculopathy, retinal vein occlusion, diabetes and its complication (diabetic retinopathy, diabetic macular edema, diabetic neuropathy, diabetic nephropathy), leukemia, multiple myeloma, malignant lymphoma, solid cancer, cachexia, Alzheimer's disease, Parkinson's syndrome, cerebral infarction, cerebral apoplexy, glaucoma, acquired immune deficiency syndrome, osteoporosis, obesity, fibrosis, gout, fever, headache, acute/chronic pain, hypertension, hyperlipidemia, arteriosclerosis, cardiac infarct, angina, dystrophia, acute respiratory distress syndrome, and the like.

BEST MODE FOR CARRYING OUT THE PRESENT INVENTION

Hereinafter, definitions of terms and phrases (atoms, groups, rings, and the like) to be used in this specification will be described in detail. Further, when other definitions of terms and phrases are applied to the definitions of terms and phrases mentioned below, preferred ranges of the respective definitions can also be applied.

The term "halogen atom" means a fluorine, chlorine, bromine, or iodine atom.

The term "lower alkyl group" means a straight-chain or branched alkyl group having 1 to 8, preferably 1 to 6, carbon atoms.

Specific examples thereof include methyl, ethyl, n-propyl, n-butyl, n-pentyl, n-hexyl, n-heptyl, n-octyl, isopropyl, isobutyl, sec-butyl, tert-butyl, and isopentyl groups and the like.

The term "lower alkenyl group" means a straight-chain or branched alkenyl group having 2 to 8, preferably 2 to 6, carbon atoms. Specific examples thereof include vinyl, propenyl, butenyl, pentenyl, hexenyl, heptenyl, octenyl, isopropenyl, 2-methyl-1-propenyl, and 2-methyl-2-butenyl groups and the like.

The term "lower alkynyl group" means a straight-chain or branched alkynyl group having 2 to 8, preferably 2 to 6, carbon atoms. Specific examples thereof include ethynyl, propynyl, butynyl, pentynyl, hexynyl, heptynyl, octynyl, isobutynyl, and isopentynyl groups and the like.

The term "lower cycloalkyl group" means a cycloalkyl group having 3 to 8, preferably 3 to 6, carbon atoms. Specific examples thereof include a cyclopropyl, cyclobutyl, cyclopentyl, cyclohexyl, cycloheptyl, or cyclooctyl group.

The term "aryl group" means a residue formed by removing one hydrogen atom from a monocyclic aromatic hydrocarbon group having 6 to 14 carbon atoms or a bicyclic or tricyclic condensed polycyclic aromatic hydrocarbon. Specific examples thereof include phenyl, naphthyl, anthryl, and phenanthryl groups and the like.

The term "lower alkoxy group" means a group in which the hydrogen atom of a hydroxy group is substituted by a lower alkyl group. Specific examples thereof include methoxy, ethoxy, n-propoxy, n-butoxy, n-pentyloxy, n-hexyloxy, n-heptyloxy, n-octyloxy, isopropoxy, isobutoxy, sec-butoxy, tert-butoxy, and isopentyloxy groups and the like.

The term "lower cycloalkyloxy group" means a group in which the hydrogen atom of a hydroxy group is substituted by a lower cycloalkyl group. Specific examples thereof include cyclopropyloxy, cyclobutyloxy, cyclopentyloxy, cyclohexyloxy, cycloheptyloxy, and cyclooctyloxy groups and the like.

The term "aryloxy group" means a group in which the hydrogen atom of a hydroxy group is substituted by an aryl group. Specific examples thereof include phenoxy, naphthoxy, anthryloxy, and phenanthryloxy groups and the like.

The term "lower alkylcarbonyl group" means a group in which the hydrogen atom of a formyl group is substituted by a lower alkyl group. Specific examples thereof include methylcarbonyl, ethylcarbonyl, n-propylcarbonyl, n-butylcarbonyl, n-pentylcarbonyl, n-hexylcarbonyl, n-heptylcarbonyl, n-octylcarbonyl, isopropylcarbonyl, isobutylcarbonyl, sec-butylcarbonyl, tert-butylcarbonyl, and isopentylcarbonyl groups and the like.

The term "lower cycloalkylcarbonyl group" means a group in which the hydrogen atom of a formyl group is substituted by a lower cycloalkyl group. Specific examples thereof include a cyclopropylcarbonyl, cyclobutylcarbonyl, cyclopentylcarbonyl, cyclohexylcarbonyl, cycloheptylcarbonyl, or cyclooctylcarbonyl group.

The term "arylcarbonyl group" means a group in which the hydrogen atom of a formyl group is substituted by an aryl group. Specific examples thereof include phenylcarbonyl, naphthylcarbonyl, anthrylcarbonyl, and phenanthrylcarbonyl groups and the like.

The term "lower alkoxycarbonyl group" means a group in which the hydrogen atom of a formyl group is substituted by a lower alkoxy group. Specific examples thereof include methoxycarbonyl, ethoxycarbonyl, n-propoxycarbonyl, n-butoxycarbonyl, n-pentyloxycarbonyl, n-hexyloxycarbonyl, n-heptyloxycarbonyl, n-octyloxycarbonyl, isopropoxycarbonyl, isobutoxycarbonyl, sec-butoxycarbonyl, tert-butoxycarbonyl, and isopentyloxycarbonyl groups and the like.

The term "lower cycloalkyloxycarbonyl group" means a group in which the hydrogen atom of a formyl group is substituted by a lower cycloalkyloxy group. Specific examples thereof include cyclopropyloxycarbonyl, cyclobutyloxycarbonyl, cyclopentyloxycarbonyl, cyclohexyloxycarbonyl, cycloheptyloxycarbonyl, and cyclooctyloxycarbonyl groups and the like.

The term "aryloxycarbonyl group" means a group in which the hydrogen atom of a formyl group is substituted by an aryloxy group. Specific examples thereof include phenoxycarbonyl, naphthoxycarbonyl, anthryloxycarbonyl, and phenanthryloxycarbonyl groups and the like.

The term "lower alkylthio group" means a group in which the hydrogen atom of a mercapto group is substituted by a lower alkyl group. Specific examples thereof include methylthio, ethylthio, n-propylthio, n-butylthio, n-pentylthio, n-hexylthio, n-heptylthio, n-octylthio, isopropylthio, isobutylthio, sec-butylthio, tert-butylthio, and isopentylthio groups and the like.

The term "lower cycloalkylthio group" means a group in which the hydrogen atom of a mercapto group is substituted by a lower cycloalkyl group. Specific examples thereof include cyclopropylthio, cyclobutylthio, cyclopentylthio, cyclohexylthio, cycloheptylthio, and cyclooctylthio groups and the like.

The term "arylthio group" means a group in which the hydrogen atom of a mercapto group is substituted by an aryl group. Specific examples thereof include phenylthio, naphthylthio, anthrylthio, and phenanthrylthio groups and the like.

The term "lower alkylsulfinyl group" means a group in which the hydroxy of a sulfinic acid group is substituted by a lower alkyl group. Specific examples thereof include methylsulfinyl, ethylsulfinyl, n-propylsulfinyl, n-butylsulfinyl, n-pentylsulfinyl, n-hexylsulfinyl, n-heptylsulfinyl, n-octylsulfinyl, isopropylsulfinyl, isobutylsulfinyl, sec-butylsulfinyl, tert-butylsulfinyl, and isopentyl sulfinyl groups and the like.

The term "arylsulfinyl group" means a group in which the hydroxy of a sulfinic acid group is substituted by an aryl group. Specific examples thereof include phenylsulfinyl, naphthylsulfinyl, anthrylsulfinyl, and phenanthrylsulfinyl groups and the like.

The term "lower alkylsulfonyl group" means a group in which the hydroxy of a sulfonic acid group is substituted by a lower alkyl group. Specific examples thereof include methylsulfonyl, ethylsulfonyl, n-propylsulfonyl, n-butylsulfonyl, n-pentylsulfonyl, n-hexylsulfonyl, n-heptylsulfonyl, n-octylsulfonyl, isopropylsulfonyl, isobutylsulfonyl, sec-butylsulfonyl, tert-butylsulfonyl, and isopentylsulfonyl groups and the like.

The term "arylsulfonyl group" means a group in which the hydroxy of a sulfonic acid group is substituted by an aryl group. Specific examples thereof include phenylsulfonyl, naphthylsulfonyl, anthrylsulfonyl, and phenanthrylsulfonyl groups and the like.

The term "hydrocarbon ring" means a saturated or unsaturated monocyclic hydrocarbon, bicyclic hydrocarbon, or tricyclic hydrocarbon having 3 to 10 carbon atoms.

Specific examples of the saturated monocyclic hydrocarbon include cyclopropane, cyclobutane, cyclopentane, cyclohexane, cycloheptane, cyclooctane, and the like.

Specific examples of the saturated bicyclic hydrocarbon include octahydropentalene, octahydroindene, decahydronaphthalene, and the like.

Specific examples of the saturated tricyclic hydrocarbon include adamantane and the like.

Specific examples of the unsaturated monocyclic hydrocarbon include cyclopentene, cyclohexene, cyclopentadiene, cyclohexadiene, benzene, and the like.

Specific examples of the unsaturated bicyclic hydrocarbon include indane, 1,2,3,4-tetrahydronaphthalene, naphthalene, and the like.

Specific examples of the unsaturated tricyclic hydrocarbon include adamantene and the like.

The term "heterocyclic ring" means a saturated or unsaturated monocyclic heterocyclic ring or a bicyclic or tricyclic condensed polycyclic heterocyclic ring having in the ring one or a plurality of hetero atoms selected from nitrogen atoms, oxygen atoms, sulfur atoms, and boron atoms.

Specific examples of the saturated monocyclic heterocyclic ring include those having a nitrogen atom in a ring such as aziridine, azetidine, pyrrolidine, pyrazolidine, imidazolidine, triazolidine, piperidine, hexahydropyridazine, hexahydropyrimidine, piperazine, homopiperidine, and homopiperazine, those having an oxygen atom in a ring such as tetrahydrofuran, tetrahydropyran, [1,4]dioxane, and [1,2]dioxirane, those having a sulfur atom in a ring such as tetrahydrothiophene, tetrahydrothiopyran, and dithiolane, those having a nitrogen atom and an oxygen atom in a ring such as oxazolidine, isooxazolidine, and morpholine, those having a nitrogen atom and a sulfur atom in a ring such as thiazolidine, isothiazolidine, and thiomorpholine, those having an oxygen atom and a born atom in a ring such as dioxaborane, and the like.

Each of the saturated monocyclic heterocyclic rings may be condensed with a benzene ring or the like to form a bicyclic or tricyclic condensed polycyclic heterocyclic ring such as dihydroindole, dihydroindazole, dihydrobenzimidazole, tetrahydroquinoline, tetrahydroisoquinoline, tetrahydrocinnoline, tetrahydrophthalazine, tetrahydroquinazoline, tetrahydroquinoxaline, dihydrobenzofuran, dihydroisobenzofuran, chromane, isochromane, benzo[1,3]dioxole, 2,3-dihydrobenzo[1,4]dioxin, dihydrobenzothiophene, dihydroisobenzothiophene, thiochromane, isothiochromane, dihydrobenzoxazole, dihydrobenzisooxazole, dihydrobenzoxazine, dihydrobenzothiazole, dihydrobenzisothiazole, dihydrobenzothiazine, xanthene, 4a-carbazole, perimidine, or the like.

Specific examples of the unsaturated monocyclic heterocyclic ring include those having a nitrogen atom in a ring such as dihydropyrrole, pyrrole, dihydropyrazole, pyrazole, dihydroimidazole, imidazole, dihydrotriazole, triazole, tetrahydropyridine, dihydropyridine, pyridine, tetrahydropyridazine, dihydropyridazine, pyridazine, tetrahydropyrimidine, dihydropyrimidine, pyrimidine, tetrahydropyrazine, dihydropyrazine, and pyrazine, those having an oxygen atom in a ring such as dihydrofuran, furan, dihydropyran, and pyran, those having a sulfur atom in a ring such as dihydrothiophene, thiophene, dihydrothiopyran, and thiopyran, those having a nitrogen atom and an oxygen atom in a ring such as dihydrooxazole, oxazole, dihydroisooxazole, isooxazole, dihydrooxazine, and oxazine, those having a nitrogen atom and a sulfur atom in a ring such as dihydrothiazole, thiazole, dihydroisothiazole, isothiazole, dihydrothiazine, and thiazine, and the like.

Each of the unsaturated monocyclic heterocyclic rings may be condensed with a benzene ring or the like to form a bicyclic or tricyclic condensed polycyclic heterocyclic ring such as indole, indazole, benzimidazole, benzotriazole, dihydroquinoline, quinoline, dihydroisoquinoline, isoquinoline, phenanthridine, dihydrocinnoline, cinnoline, dihydrophthalazine, phthalazine, dihydroquinazoline, quinazoline, dihydroquinoxaline, quinoxaline, benzofuran, isobenzofuran, chromene, isochromene, benzothiophene, isobenzothiophene, thiochromene, isothiochromene, benzoxazole, benzisoxazole, benzoxazine, benzothiazole, 4,5,6,7-tetrahydrobenzothiazole, benzisothiazole, benzothiazine, phenoxanthine, carbazole, β-carboline, phenanthridine, acridine, phenanthroline, phenazine, phenothiazine, phenoxazine, and the like.

Further, in each of these heterocyclic rings, when the heterocyclic ring has two hydrogen atoms on an identical carbon atoms, the hydrogen atoms may be substituted by an oxo group to form heterocyclic ketone such as 2-pyrrolidone, 4-piperidone, 4-thiazolidone, pyran-4-(4H)-one, pyrazine-2-(3H)-one, and the like, and such heterocyclic ketones are encompassed in the scope of the heterocyclic ring of the present invention.

The term "heterocyclic group" means a residue formed by removing one hydrogen atom from a heterocyclic ring.

The term "lower alkylene group" means a straight-chain or branched alkylene group having 1 to 8, preferably 1 to 6, carbon atoms. Specific examples thereof include methylene, ethylene, trimethylene, tetramethylene, pentamethylene, hexamethylene, heptamethylene, octamethylene, methylmethylene, dimethylmethylene, 1-methyltrimethylene, 2-methyltrimethylene, 1-methyltetramethylene, 2-methyltetramethylene, ethylmethylene, ethylethylene, 1-ethyltrimethylene, 2-ethyltrimethylene, 2,2-dimethyltrimethylene, and the like.

The term "lower alkenylene group" means a straight-chain or branched alkenylene group having 2 to 8, preferably 2 to 6, carbon atoms. Specific examples thereof include those containing one or a plurality of double bonds in ethylene, trimethylene, tetramethylene, pentamethylene, hexamethylene, heptamethylene, octamethylene, methylmethylene, 1-methyltrimethylene, 2-methyltrimethylene, 1-methyltetramethylene, 2-methyltetramethylene, ethylmethylene, ethylethylene, 1-ethyltrimethylene, 2-ethyltrimethylene, and the like.

The term "lower alkynylene group" means a straight-chain or branched alkynylene group having 2 to 8, preferably 2 to 6, carbon atoms. Specific examples thereof include those containing one or a plurality of triple bonds in ethylene, trimethylene, tetramethylene, pentamethylene, hexamethylene, heptamethylene, octamethylene, 1-methyltrimethylene, 1-methyltetramethylene, 2-methyltetramethylene, ethylmethylene, ethylethylene, 1-ethyltrimethylene, 2-ethyltrimethylene, and the like.

The term "lower cycloalkylene group" includes a residue formed by removing one hydrogen atom from a lower cycloalkyl group. Specific examples thereof include a cyclopropylene, cyclobutylene, cyclopentylene, cyclohexylene, cycloheptylene, or cyclooctylene group.

Each of the above-described terms "lower alkylene group", "lower alkenylene group", "lower alkynylene group", and "lower cycloalkylene group" means a divalent group in which two hydrogen atoms on the same or different carbon atoms are removed.

The term "lower alkylsilyl group" means a group in which a hydrogen atom of a silyl group is substituted by one or a plurality of lower alkyl groups. Specific examples thereof include monomethylsilyl, dimethylsilyl, trimethylsilyl, triethylsilyl, triisopropylsilyl, and the like.

The term "halogeno-lower alkyl group", "halogeno-lower alkenyl group", "halogeno-lower alkynyl group", and/or "halogeno-lower alkoxy group" mean or means "lower alkyl group", "lower alkenyl group", "lower alkynyl group", and/or "lower alkoxy group" having one or a plurality of halogen atoms as a substituent.

The term "lower cycloalkyl lower alkyl group", "lower cycloalkyl lower alkenyl group", "lower cycloalkyl lower alkynyl group", and/or "lower cycloalkyl lower alkoxy group" mean or means "lower alkyl group", "lower alkenyl group", "lower alkynyl group", and/or "lower alkoxy group" having one or a plurality of lower cycloalkyl groups as a substituent.

The term "aryl-lower alkyl group", "aryl-lower alkenyl group", "aryl-lower alkynyl group", and/or "aryl-lower alkoxy group" mean or means "lower alkyl group", "lower alkenyl group", "lower alkynyl group", and/or "lower alkoxy group" having one or a plurality of aryl groups as a substituent.

The term "heterocyclic lower alkyl group", "heterocyclic lower alkenyl group", "heterocyclic lower alkynyl group", and/or "heterocyclic lower alkoxy group" mean or means "lower alkyl group", "lower alkenyl group", "lower alkynyl group", and/or "lower alkoxy group" having one or a plurality of heterocyclic groups as a substituent.

The term "hydroxy lower alkyl group", "hydroxy lower alkenyl group", "hydroxy lower alkynyl group", and/or "hydroxy lower alkoxy group" mean or means "lower alkyl group", "lower alkenyl group", "lower alkynyl group", and/or "lower alkoxy group" having one or a plurality of hydroxy groups as a substituent.

The term "lower alkoxy lower alkyl group", "lower alkoxy lower alkenyl group", "lower alkoxy lower alkynyl group", and/or "lower alkoxy lower alkoxy group" mean or means "lower alkyl group", "lower alkenyl group", "lower alkynyl group", and/or "lower alkoxy group" having one or a plurality of lower alkoxy groups as a substituent.

The term "cyano lower alkyl group", "cyano lower alkenyl group", "cyano lower alkynyl group", and/or "cyano lower alkoxy group" mean or means "lower alkyl group", "lower alkenyl group", "lower alkynyl group", and/or "lower alkoxy group" having one or a plurality of cyano groups as a substituent.

The term "nitro lower cycloalkyl group", "nitroaryl group" and/or "nitro-heterocyclic group" mean or means "lower cycloalkyl group", "aryl group", and/or "heterocyclic group" having one or a plurality of nitro groups as a substituent.

The term "lower alkl lower cycloalkyl group", lower alkyl aryl group" and/or "lower alkyl heterocyclic group" mean or means "lower cycloalkyl group", "aryl group" and/or "heterocyclic group" having one or a plurality of lower alkyl group as a substituent.

The term "lower alkyl group which may have a substituent", "lower alkenyl group which may have a substituent", "lower alkynyl group which may have a substituent", "lower alkoxy group which may have a substituent", "lower alkylsulfonyl group which may have a substituent", "lower alkylene group which may have a substituent", "lower alkenylene group which may have a substituent" and/or "lower alkynylene group which may have a substituent" mean or means "lower alkyl group", "lower alkenyl group", "lower alkynyl group", "lower alkoxy group", "lower alkyl sulfonyl group", "lower alkylene group", "lower alkenylene group" and/or "lower alkynylene group" which may have one or a plurality of substituents selected from the group consisting of a halogen atom, a lower cycloalkyl group, an aryl group which may have a substituent, a heterocyclic group, a nitro group, a cyano group, an oxo group, a lower alkylsilyl group, $—OR^p$, $—COR^q$, $—COOR^r$, $—CONR^sR^t$, and $—NR^uR^v$.

The term "lower cycloalkyl group which may have a substituent", "aryl group which may have a substituent", "heterocyclic group which may have a substituent", "monocyclic saturated heterocyclic ring which may have a substituent", "arylsulfonyl group which may have a substituent", and/or "lower cycloalkylene group which may have a substituent" mean or means "lower cycloalkyl group", "aryl group", "heterocyclic group", "monocyclic saturated heterocyclic ring", "arylsulfonyl group", and/or "lower cycloalkylene group" which may have one or a plurality of substituents selected from the group consisting of a halogen atom, a lower alkyl group, a lower alkenyl group, a lower alkynyl group, a lower cycloalkyl group, an aryl group, a heterocyclic group, a nitro group, a cyano group, an oxo group, a lower alkylsilyl group, $—OR^p$, $—COR^q$, $—COOR^r$, $—CONR^sR^t$, and $—NR^uR^v$.

Wherein, $R^p$, $R^q$, $R^r$, $R^s$, $R^t$, $R^u$, and $R^v$ may be the same or different and each represents a group selected from the group consisting of a hydrogen atom, a lower alkyl group, a lower alkenyl group, a lower alkynyl group, a lower cycloalkyl group, an aryl group, a heterocyclic group, and a lower alkoxycarbonyl group.

The term "Groups" in "a plurality of groups" used in the present invention may be the same or different, and the number of the groups may preferably be 2 or 3, particularly preferably 2. The hydrogen atom, the halogen atom, and the ring are also encompassed in the concept of "group".

In the present invention, in the case where "m" and "n" represents 2, 3, or 4, a plurality of $R^2$ and a plurality of $R^4$ may be the same or different.

The case wherein "m" and/or "n" represents 0 means absence of $R^2$ and/or $R^4$, i.e. these substituents are not present.

The term "IKKβ inhibitor" means one capable of exhibiting a pharmaceutical action by inhibiting IKKβ. Examples of a disease associated with IKKβ include inflammatory diseases, autoimmune diseases, allergic diseases, infectious diseases, degenerative diseases, vascular diseases, nerve/sensory organ diseases, endocrine/metabolic disease, neoplastic diseases, congenital diseases, traumatic diseases, and adverse reactions after organ transplantation, and more specific examples include keratitis, conjunctivitis, uveitis, osteoarthritis, chronic obstructive pulmonary disease, bronchitis, pneumonia, hepatitis, pancreatitis, nephritis, sepsis, systemic inflammatory response syndrome, rheumatoid arthritis, psoriasis, multiple sclerosis, Crohn's disease, ulcerative colitis, systemic erythematosus, Sjogren's syndrome, multiple myositis, dermatomyositis, asthma, allergic rhinitis, hives, atopic dermatitis, age-related macular degeneration, retinopathy of prematurity, polypoidal choroidal vasculopathy, retinal vein occlusion, diabetes and its complication (diabetic retinopathy, diabetic macular edema, diabetic neuropathy, diabetic nephropathy), leukemia, multiple myeloma, malignant lymphoma, solid cancer, cachexia, Alzheimer's disease, Parkinson's syndrome, cerebral infarction, cerebral apoplexy, glaucoma, acquired immune deficiency syndrome, osteoporosis, obesity, fibrosis, gout, fever, headache, acute/chronic pain, hypertension, hyperlipidemia, arteriosclerosis, cardiac infarct, angina, dystrophia, acute respiratory distress syndrome, and the like.

The above specific diseases are described for better understanding of the present invention and not for limiting the present invention, and there is no particularly limitation on diseases insofar as the diseases are associated with IKKβ. Also, IKKβ is deeply linked with the transcription factor NF-κB and cytokine production (TNF, IL-1, IL-6, etc.), and diseases associated with these factors are included in the diseases associated with IKKβ of the present invention.

In the present compound, The term "salt" is not particularly limited insofar as the salt is pharmaceutically acceptable, and examples of the salt include a salt with an inorganic acid such as hydrochloric acid, hydrobromic acid, hydroiodic acid, nitric acid, sulfuric acid, and phosphoric acid, a salt with an organic acid such as acetic acid, fumaric acid, maleic acid, succinic acid, citric acid, tartaric acid, adipic acid, gluconic acid, glucoheptic acid, glucuronic acid, terephthalic acid, methanesulfonic acid, lactic acid, hippuric acid, 1,2-ethanedisulfonic acid, isethionic acid, lactobionic acid, oleic acid, pamoic acid, polygalacturonic acid, stearic acid, tannin acid, trifluoromethanesulfonic acid, benzenesulfonic acid, p-toluenesulfonic acid, lauryl ester sulfate, methyl sulfate, naphthalenesulfonic acid, and sulfosalicylic acid, a quaternary ammonium salt with methyl bromide, methyl iodide, and the like, a salt with a halogen ion such as a bromine ion, a chlorine ion, and an iodine ion, a salt with an alkali metal such as lithium, sodium, and potassium, a salt with an alkali earth metal such as calcium and magnesium, a metal salt with iron, zinc, and the like, a salt with ammonia, a salt with organic amine such as triethylenediamine, 2-aminoethanol, 2,2-iminobis(ethanol), 1-deoxy-1-methylamino-2-D-sorbitol, 2-amino-2-hydroxymethyl-1,3-propanediol, procaine, and N,N-bis(phenylmethyl)-1,2-ethanediamine, and the like.

In the case where a geometric isomer and/or an optical isomer are/is present in the present compound, such isomers are encompassed in the scope of the present invention.

In the case where a hydrate and/or a solvate are/is present in the present compound, such hydrate and/or solvate are/is encompassed in the scope of the present invention.

In the case where there is proton tautomerism in the present compound, the tautomers thereof are also encompassed in the present invention.

In the case where there are crystalline polymorphisms and/or crystalline polymorphism groups (crystalline polymorphism systems) in the present compound, the polymorphisms and/or crystalline polymorphism groups (crystalline polymorphism systems) thereof are also encompassed in the present invention. Here, the crystalline polymorphism groups (crystalline polymorphism systems) mean individual crystal forms in respective stages when the crystal forms are changed by conditions for the production, crystallization, storage, or the like of the crystals thereof and/or states thereof (the states include also a formulated state) and/or all the processes thereof.

(a) Preferred examples in the present compound include a compound or a salt thereof in which the groups in the compound represented by the general formula (1) or a salt thereof are as described below.

(a1) $R^1$ represents a hydrogen atom, a lower alkyl group, an aryl-lower alkyl group, an aryl group, a nitroaryl group, a hydroxy group, a lower alkoxy group, or an aryl-lower alkoxy group; and/or (a2) $R^2$ represents a halogen atom, a lower alkyl group, a halogeno-lower alkyl group, a lower alkenyl group, a halogeno-lower alkenyl group, a lower alkynyl group, a halogeno-lower alkynyl group, $-X_1-COR^3$, $-X_1-COOR^3$, $-X_1-CONR^aR^b$, $-X_1-SR^3$, $-X_1-NR^aR^b$, $-X_1-NHCO-R^3$, $-X_1-CN$, $-X_1-N_3$, or a group represented by the following general formula (2):

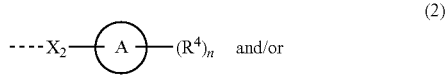

(2)

(a3) $X_1$ represents a single bond, a lower alkylene group, a lower alkenylene group, or a lower alkynylene group; and/or (a4) $R^3$ represents a hydrogen atom, a lower alkyl group, a halogeno-lower alkyl group, an aryl-lower alkyl group, a heterocyclic lower alkyl group, a hydroxy lower alkyl group, a lower alkoxy lower alkyl group, a cyano lower alkyl group, a lower alkenyl group, a halogeno-lower alkenyl group, an aryl-lower alkenyl group, a heterocyclic lower alkenyl group, a hydroxy lower alkenyl group, a lower alkoxy lower alkenyl group, or a cyano lower alkenyl group; and/or (a5) $R^a$ and $R^b$ may be the same or different and each represents a hydrogen atom, a lower alkyl group, an aryl-lower alkyl group, a heterocyclic lower alkyl group, a hydroxy lower alkyl group, a lower alkoxy lower alkyl group, a cyano lower alkyl group, a lower alkenyl group, an aryl-lower alkenyl group, a heterocyclic lower alkenyl group, a hydroxy lower alkenyl group, a lower alkoxy lower alkenyl group, a cyano lower alkenyl group, an aryl-lower alkoxy group, a heterocyclic lower alkoxy group, a hydroxy lower alkoxy group, a lower alkoxy lower alkoxy group, a cyano lower alkoxy group, a lower alkylsulfonyl group, or an aryl sulfonyl group; and/or (a6) $X_2$ represents a single bond, a lower alkylene group, a lower alkenylene group, a lower alkynylene group, $-X_3-CO-$, $-X_3-CONH-$, $-X_3-S-$, $-X_3-NH-$, $-X_3-NHCO-$, or $-X_3-NHCONH-$; and/or (a7) $X_3$ represents a single bond, a lower alkylene group, a lower alkenylene group, or a lower alkynylene group; and/or (a8) the ring A represents a hydrocarbon ring or a heterocyclic ring; and/or (a9) $R^4$ represents a halogen atom, a lower alkyl group, a halogeno-lower alkyl group, $-X_4-OR^5$, $-X_4-OCOR^5$, $-X_4-COR^5$, $-X_4-COOR^5$, $-X_4-CONR^cR^d$, $-X_4-SR^5$, $-X_4-SOR^5$, $-X_4-SONR^cR^d$, $-X_4-SO_2R^5$, $-X_4-SO_2NR^cR^d$, $-X_4-NR^cR^d$, $-X_4-NHCOR^5$, $-X_4-NHCOOR^5$, $-X_4-NHSOR^5$, $-X_4-NHSO_2R^5$, $-X_4-CN$, or $-X_4-NO_2$; and/or (a10) $X_4$ represents a single bond, a lower alkylene group, or a lower cycloalkylene group; and/or (a11) $R^5$ represents a hydrogen atom, a lower alkyl group, halogeno-lower alkyl group, a lower cycloalkyl lower alkyl group, an aryl-lower alkyl group, a lower cycloalkyl group, or an aryl group; and/or (a12) $R^c$ and $R^d$ may be the same or different and each represents a hydrogen atom, a lower alkyl group, a hydroxy lower alkyl group, a lower alkoxy lower alkyl group, a lower alkyl group having $-NR^eR^f$ as a substituent, a lower cycloalkyl group, a lower alkyl lower cycloalkyl group, an aryl group, a lower alkylaryl group, a heterocyclic group, or a lower alkyl heterocyclic group;

$R^c$ and $R^d$ may be joined to each other to form a monocyclic saturated heterocyclic ring; and/or (a13) $R^e$ and $R^f$ may be the same or different and each represents a hydrogen atom or a lower alkyl group; $R^e$ and $R^f$ may be joined to each other to form a monocyclic saturated heterocyclic ring; and/or (a14) m represents 0, 1, 2, 3, or 4, provided that $R^2$ may be the same or different when m is 2, 3, or 4; and/or (a15) n may be 0, 1, 2, 3, or 4, provided that $R^4$ may be the same or different when n is 2, 3, or 4.

That is, the examples include compounds and salts thereof obtained by combining one or more selected from the above-described (a1), (a2), (a3), (a4), (a5), (a6), (a7), (a8), (a9), (a10), (a11), (a12), (a13), (a14), and (a15) in the compound represented by the general formula (1).

(b) Preferred examples in the present compound include a compound or a salt thereof in which the groups in the compound represented by the general formula (1) or a salt thereof are as described below.

(b1) $R^1$ represents a hydrogen atom, a lower alkyl group, an aryl-lower alkyl group, a nitroaryl group, or a hydroxy group; and/or (b2) $R^2$ represents a halogen atom, a lower alkyl group, a halogeno-lower alkyl group, a lower alkenyl group, a lower alkynyl group, $-X_1-COR^3$, $-X_1-COOR^3$, $-X_1-CONR^aR^b$, $-X_1-SR^3$, $-X_1-NR^aR^b$, $-X_1-NHCO-R^3$, $-X_1-CN$, $-X_1-N_3$, or a group represented by the following general formula (2):

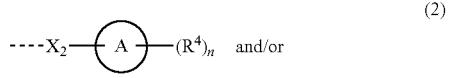

(2)

(b3) $X_1$ represents a single bond, a lower alkylene group, a lower alkenylene group, or a lower alkynylene group; and/or (b4) $R^3$ represents a hydrogen atom, a lower alkyl group, a halogeno-lower alkyl group, an aryl-lower alkyl group, a heterocyclic lower alkyl group, a hydroxy lower alkyl group, a cyano lower alkyl group, or a lower alkenyl group; and/or (b5) $R^a$ and $R^b$ may be the same or different and each represents a hydrogen atom, a lower alkyl group, an aryl-lower alkyl group, a heterocyclic lower alkyl group, a hydroxy lower alkyl group, a cyano lower alkyl group, a lower alkenyl group, a lower alkoxy group, or an arylsulfonyl group; and/or (b6) $X_2$ represents a single bond, a lower alkylene group, a lower alkenylene group, a lower alkynylene group, $-X_3-CO-$, $-X_3-CONH-$, $-X_3-S-$, $-X_3-NH-$, $-X_3-NHCO-$, or $-X_3-NHCONH-$; and/or (b7) $X_3$ represents a single bond, a lower alkylene group, a lower alkenylene group, or a lower alkynylene group; and/or (b8) the ring A represents a hydrocarbon ring or a heterocyclic ring; and/or (b9) $R^4$ represents a halogen atom, a lower alkyl group, a halogeno-lower alkyl group, $-X_4-OR^5$, $-X_4-OCOR^5$, $-X_4-COR^5$, $-X_4-COOR^5$, $-X_4-CONR^cR^d$, $-X_4-SO_2R^5$, $-X_4-SO_2NR^cR^d$, $-X_4-NR^cR^d$, $-X_4-NHCOR^5$, $-X_4-NHCOOR^5$, $-X_4-NHSO_2R^5$, $-X_4-CN$, or $-X_4-NO_2$; and/or (b10) $X_4$ represents a single bond, a lower alkylene group, or a lower cycloalkylene group; and/or (b11) $R^5$ represents a hydrogen atom, a lower alkyl group, halogeno-lower alkyl group, an aryl-lower alkyl group, or an aryl group; and/or (b12) $R^c$ and $R^d$ may be the same or different and each represents a hydrogen atom, a lower alkyl group, a hydroxy lower alkyl group, a lower alkoxy lower alkyl group, a lower alkyl group having —$NR^eR^f$ as a substituent, a lower cycloalkyl group, a heterocyclic group, or a lower alkyl heterocyclic group;

$R^c$ and $R^d$ may be joined to each other to form a monocyclic saturated heterocyclic ring; and/or (b13) $R^e$ and $R^f$ may be the same or different and each represents a hydrogen atom or a lower alkyl group;

$R^e$ and $R^f$ may be joined to each other to form a monocyclic saturated heterocyclic ring; and/or (b14) m represents 0, 1, or 2, provided that $R^2$ may be the same or different when m is 2; and/or (b15) n may be 0, 1, 2, 3, or 4, provided that $R^4$ may be the same or different when n is 2, 3, or 4.

That is, the examples include compounds and salts thereof obtained by combining one or more selected from the above-described (b1), (b2), (b3), (b4), (b5), (b6), (b7), (b8), (b9), (b10), (b11), (b12), (b13), (b14), and (b15) in the compound represented by the general formula (1).

(c) Preferred examples in the present compound include a compound or a salt thereof in which the groups in the compound represented by the general formula (1) or a salt thereof are as described below.

(c1) $R^1$ represents a hydrogen atom, a lower alkyl group, an aryl-lower alkyl group, a nitroaryl group, or a hydroxy group; and/or (c2) $R^2$ represents a halogen atom, a lower alkyl group, a halogeno-lower alkyl group, a lower alkenyl group, a lower alkynyl group, —$X_1$—$COOR^3$, —$X_1$—$SR^3$, —$X_1$—$NR^aR^b$, —$X_1$—NHCO—$R^3$, or a group represented by the following general formula (2):

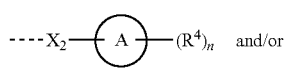

(2)

and/or (c3) $X_1$ represents a single bond, a lower alkylene group, or a lower alkynylene group; and/or (c4) $R^3$ represents a hydrogen atom, a lower alkyl group, or an aryl-lower alkyl group; and/or (c5) $R^a$ and $R^b$ may be the same or different and each represents a hydrogen atom or a lower alkyl group; and/or (c6) $X_2$ represents a single bond, a lower alkylene group, a lower alkynylene group, —$X_3$—NHCO—, or —$X_3$—NH-CONH—; and/or (c7) $X_3$ represents a single bond; and/or (c8) the ring A represents a hydrocarbon ring or a heterocyclic ring; and/or (c9) $R^4$ represents a halogen atom, a lower alkyl group, —$X_4$—$OR^5$, —$X_4$—$NR^cR^d$, —$X_4$—$NHSO_2R^5$, —$X_4$—CN, or —$X_4$—$NO_2$; and/or (c10) $X_4$ represents a single bond or a lower alkylene group; and/or (c11) $R^5$ represents a hydrogen atom or a lower alkyl group; and/or (c12) $R^c$ and $R^d$ may be the same or different and each represents a hydrogen atom, a lower alkyl group, a lower alkyl group having —$NR^eR^f$ as a substituent, or a lower cycloalkyl group; and/or (c13) $R^e$ and $R^f$ may be joined to each other to form a monocyclic saturated heterocyclic ring; and/or (c14) m represents 0, 1, or 2, provided that $R^2$ may be the same or different when m is 2; and/or (c15) n may be 0, 1, or 2, provided that $R^4$ may be the same or different when n is 2.

That is, the examples include compounds and salts thereof obtained by combining one or more selected from the above-described (c1), (c2), (c3), (c4), (c5), (c6), (c7), (c8), (c9), (c10), (c11), (c12), (c13), (c14), and (c15) in the compound represented by the general formula (1).

(d) Preferred examples of the ring A in the general formula (1) include the following rings.

The ring A may preferably be a hydrocarbon ring, more preferably a hydrocarbon ring selected from the group consisting of cyclopropane, cyclopentane, cyclohexane, cyclohexene, adamantane, benzene, and naphthalene, and particularly preferably a hydrocarbon ring selected from the group consisting of cyclohexane and benzene.

A compound and a salt thereof having the above-described ring A and satisfying the above-described conditions (a), (b), and/or (c) may particularly be preferred.

(e) Another preferred examples of the ring A in the general formula (1) include the following rings.

The ring A may preferably be a heterocyclic ring, more preferably a heterocyclic ring selected from the group consisting of pyrrolidine, pyrrolidone, pyrrole, imidazole, pyrazole, indole, pyridine, pyrimidine, quinoline, furan, benzofuran, thiophene, benzothiophene, isoxazole, thiazole, morpholine, thiomorpholine, dioxaborane, and dithiolane, and particularly preferably a heterocyclic ring selected from the group consisting of pyrrolidine, pyrrole, indole, pyridine, quinoline, furan, thiophene, and dithiolane.

A compound and a salt thereof having the above-described ring A and satisfying the above-described conditions (a), (b), and/or (c) may particularly be preferred.

(f) Particularly preferred specific examples in the present invention are the compounds or their salts as shown below.

2-Aminocarbonylamino-6-bromo-1-hydroxyindole-3-carboxamide,

2-Aminocarbonylamino-5-methylindole-3-carboxamide,

6-Acetylamino-2-aminocarbonylaminoindole-3-carboxamide,

2-Aminocarbonylamino-6-benzoylaminoindole-3-carboxamide,

2-Aminocarbonylamino-6-(3-phenylureido)indole-3-carboxamide,

2-Aminocarbonylamino-6-dimethylaminoindole-3-carboxamide,

2-Aminocarbonylamino-6-(pyrrolidin-1-yl)indole-3-carboxamide,

2-Aminocarbonylamino-6-(pyrrol-1-yl)indole-3-carboxamide,

2-Aminocarbonylaminoindole-3-carboxamide,

2-Aminocarbonylamino-6-bromo-7-methylindole-3-carboxamide,

2-Aminocarbonylamino-6-trifluoromethylindole-3-carboxamide,

2-Aminocarbonylamino-6-methoxycarbonylindole-3-carboxamide,

2-Aminocarbonylamino-6-bromoindole-3-carboxamide,

2-Aminocarbonylamino-6-(4-fluorophenyl)indole-3-carboxamide,

2-Aminocarbonylamino-6-phenylindole-3-carboxamide,

2-Aminocarbonylamino-6-(3-methoxyphenyl)indole-3-carboxamide,

2-Aminocarbonylamino-6-(thiophen-2-yl)indole-3-carboxamide,
2-Aminocarbonylamino-6-(pyridin-3-yl)indole-3-carboxamide,
2-Aminocarbonylamino-6-(2-fluorophenyl)indole-3-carboxamide,
2-Aminocarbonylamino-6-(3-fluorophenyl)indole-3-carboxamide,
2-Aminocarbonylamino-6-(3-cyanophenyl)indole-3-carboxamide,
2-Aminocarbonylamino-6-(3-nitrophenyl)indole-3-carboxamide,
2-Aminocarbonylamino-6-(3-methylsulfonylaminophenyl)indole-3-carboxamide,
2-Aminocarbonylamino-6-(thiophen-3-yl)indole-3-carboxamide,
2-Aminocarbonylamino-6-(furan-2-yl)indole-3-carboxamide,
2-Aminocarbonylamino-6-(furan-3-yl)indole-3-carboxamide,
2-Aminocarbonylamino-6-(2-chlorothiophen-3-yl)indole-3-carboxamide,
2-Aminocarbonylamino-6-(quinolin-3-yl)indole-3-carboxamide,
2-Aminocarbonylamino-6-vinylindole-3-carboxamide,
2-Aminocarbonylamino-6-[(E)-3-methoxy-1-propenyl]indole-3-carboxamide,
2-Aminocarbonylamino-6-(indol-5-yl)indole-3-carboxamide,
2-Aminocarbonylamino-6-[(E)-1-pentenyl]indole-3-carboxamide,
2-Aminocarbonylamino-6-(4-dimethylaminophenyl)indole-3-carboxamide,
2-Aminocarbonylamino-6-(furan-3-yl)-7-methylindole-3-carboxamide,
2-Aminocarbonylamino-6-(pyrrol-2-yl)indole-3-carboxamide,
2-Aminocarbonylamino-6-[3-(2-hydroxyethyl)phenyl]indole-3-carboxamide,
2-Aminocarbonylamino-6-(pyridin-4-yl)indole-3-carboxamide,
2-Aminocarbonylamino-6-(4-hydroxymethyl-3-methoxyphenyl)indole-3-carboxamide, 2-Aminocarbonylamino-6-(2-chloropyridin-4-yl)indole-3-carboxamide,
2-Aminocarbonylamino-6-[(1R)-3-(1-hydroxyethyl)phenyl]indole-3-carboxamide
2-Aminocarbonylamino-6-[(1S)-3-(1-hydroxyethyl)phenyl]indole-3-carboxamide
2-Aminocarbonylamino-6-(4-aminomethylphenyl)indole-3-carboxamide,
2-Aminocarbonylamino-6-[4-(1-aminoethyl)phenyl]indole-3-carboxamide,
2-Aminocarbonylamino-6-[4-(1-amino-1-methylethyl)phenyl]indole-3-carboxamide,
2-Aminocarbonylamino-6-phenylethynylindole-3-carboxamide,
2-Aminocarbonylamino-6-(3-hydroxy-1-propynyl)indole-3-carboxamide,
2-Aminocarbonylamino-6-(3-dimethylamino-1-propynyl)indole-3-carboxamide,
2-Aminocarbonylamino-6-ethynylindole-3-carboxamide,
2-Aminocarbonylamino-6-ethylindole-3-carboxamide,
2-Aminocarbonylamino-6-cyclohexylindole-3-carboxamide,
2-Aminocarbonylamino-6-(4-hydroxybutyl)indole-3-carboxamide,
2-Aminocarbonylamino-6-(3-dimethylaminopropyl)indole-3-carboxamide,
2-Aminocarbonylamino-6-(3-methoxypropyl)indole-3-carboxamide,
2-Aminocarbonylamino-6-(3-hydroxymethylphenyl)indole-3-carboxamide,
2-Aminocarbonylamino-6-(5-hydroxymethylfuran-2-yl)indole-3-carboxamide,
2-Aminocarbonylamino-6-(3-isopropylaminomethyl phenyl)indole-3-carboxamide,
2-Aminocarbonylamino-6-[3-(2-hydroxyethylaminomethyl)phenyl]indole-3-carboxamide,
2-Aminocarbonylamino-6-(5-cyclopropylaminomethylfuran-2-yl)indole-3-carboxamide,
2-Aminocarbonylamino-6-(5-methylaminomethylthiophen-2-yl)indole-3-carboxamide,
2-Aminocarbonylamino-6-hydroxymethylindole-3-carboxamide,
2-Aminocarbonylamino-6-(1,3-dithiolan-2-yl)indole-3-carboxamide,
2-Aminocarbonylamino-6-(pyrrolidin-1-ylcarbonyl)indole-3-carboxamide,
2-Aminocarbonylamino-6-benzylaminocarbonylindole-3-carboxamide,
2-Aminocarbonylamino-6-(pyrrolidin-1-ylmethyl)indole-3-carboxamide, and
2-Aminocarbonylamino-6-ethylthiomethylindole-3-carboxamide The present compounds can be prepared according to the following methods. Each specific process for preparing the present compounds is described in detail in later Examples (section of Production example). The terms "Hal" and "Boc" used in the following synthetic routes represent a halogen atom and tert-butoxycarbonyl group, respectively. The terms $(R)_i$ and $(R)_j$ mean arbitrary substituents which are indicated by $R^2$ and/or $R^4$, respectively, and the terms i and j indicate 0, 1, 2 or 3.

The processes for preparing the present compounds are divided roughly into the following methods, and the suitable method can be chosen according to the kind of substituents.

The present compounds (1) can be prepared according to synthetic route 1. Namely, the present compounds (1) can be obtained by the reaction of compound (II) with trichloroacetyl isocyanate in an organic solvent such as tetrahydrofuran (THF) or N,N-dimethylformamide (DMF) at −80° C. to room temperature for 1 hour to 3 hours, followed by the addition of ammonia methanol solution and stirring this mixture at 0° C. to room temperature for 1 hour to 24 hours.

Synthetic route 1

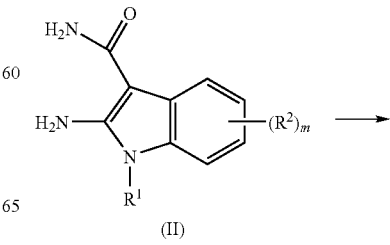

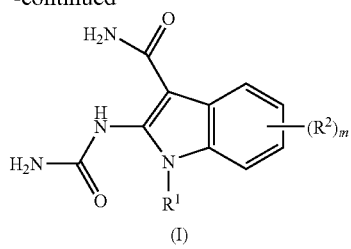

Compound (II)-(a) and compound (II)-(b) can be prepared according to synthetic route 2. Namely, compound (V) can be obtained by the reaction of compound (III) with cyanoacetamide (IV) in an organic solvent such as THF or DMF in the presence of a base such as sodium hydride at 0° C. to 80° C. for 1 hour to 24 hours. Compound (II)-(a) and compound (II)-(b) can be obtained by the reaction of the given compound (V) in an organic solvent such as toluene with metal powder such as iron or zinc and with acetic acid at room temperature to 100° C. for 30 minutes to 3 hours. Compound (VI) can be obtained by the reaction of compound (V) in an organic solvent such as methanol or DMF in the presence of palladium on activated carbon under hydrogen atmosphere at room temperature to 60° C. for 1 hour to 24 hours. Compound (VI) can be obtained by the reaction of compound (V) with sodium hydrosulfite in ammonia aqueous solution at 0° C. to room temperature for 30 minutes to 24 hours. Compound (II)-(a) can be also obtained by the reaction of the given compound (VI) in an organic solvent such as 1,4-dioxane or DMF at room temperature to 150° C. for 1 hour to 24 hours.

Compound (II)-(a) can be also prepared according to synthetic route 3 as described in Journal of Heterocyclic Chemistry, 44, 419-424 (2007). Namely, compound (IX) can be obtained by the reaction of hydroxylamine (VII) ($Y^a$ indicates acetyl group or benzoyl group) with malononitrile (VIII) in an organic solvent such as chloroform or THF in the presence of a base such as triethylamine at 0° C. to 80° C. for 1 hour to 6 hours. Compound (II)-(a) can be obtained by the reaction of the given compound (IX) in an organic solvent such as methanol in the presence of a base such as sodium methoxide or triethylamine at room temperature to 80° C. for 30 minutes to 3 hours.

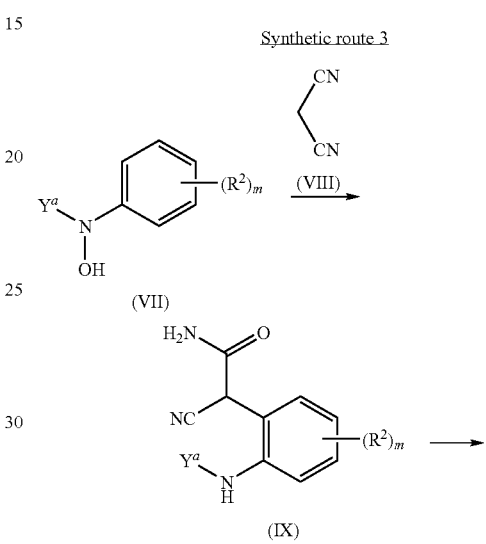

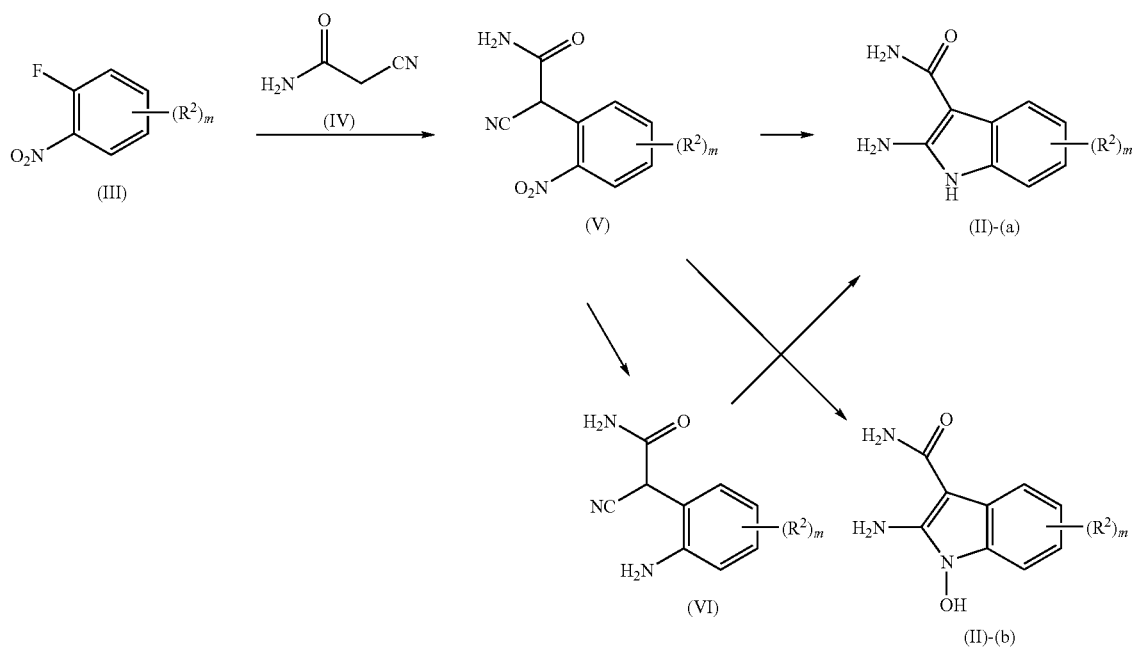

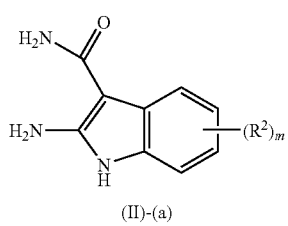

(II)-(a)

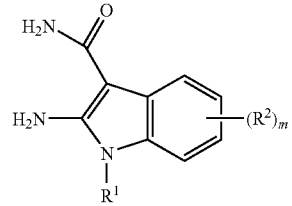

(II)-(c)

Compound (II)-(c) (R$^1$ indicates lower alkyl groups which may have substituents or aryl groups which may have substituents) can be prepared according to synthetic route 4. Namely, compound (II)-(c) can be obtained by the reaction of compound (II)-(a) with halide (X) (alkyl halide or aryl halide) in an organic solvent such as THF or DMF in the presence of a base such as sodium hydride at 0° C. to 100° C. for 1 hour to 24 hours.

The present compounds (I)-(a) (X$^2$ indicates single bond) can be prepared according to synthetic route 5. Namely, the present compounds (I)-(a) can be obtained by the reaction of the present compounds (I)-(b) with a boronic acid (XI) in a solution mixture of water and an organic solvent such as 1,4-dioxane or DMF in the presence of an organometallic complex catalyst such as tetrakis(triphenylphosphine)palladium (0) or tris(dibenzylideneacetone)dipalladium and a base such as sodium hydrogen carbonate or triethylamine at room temperature to 150° C. for 1 hour to 24 hours. The present compounds (I)-(c) can be obtained by the reaction of the present compounds (I)-(b) with bis(pinacolato)diboron (XII) in a solution mixture of water and an organic solvent such as 1,4-dioxane or dimethylsulfoxide (DMSO) in the presence of an organometallic complex catalyst such as tetrakis(triphenylphosphine)palladium (0) or tris(dibenzylideneacetone) dipalladium and a base such as potassium acetate or triethylamine at room temperature to 150° C. for 1 hour to 24 hours. The present compounds (I)-(a) can be also obtained by the reaction of the given present compounds (I)-(c) with halide (XIII) in a solution mixture of water and an organic solvent such as 1,4-dioxane or DMF in the presence of an organometallic complex catalyst, such as tetrakis(triphenylphosphine) palladium (0) or tris(dibenzylideneacetone)dipalladium and a base such as sodium hydrogen carbonate or triethylamine at room temperature to 150° C. for 1 hour to 24 hours.

Synthetic route 4

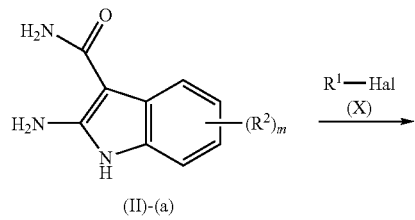

Synthetic route 5

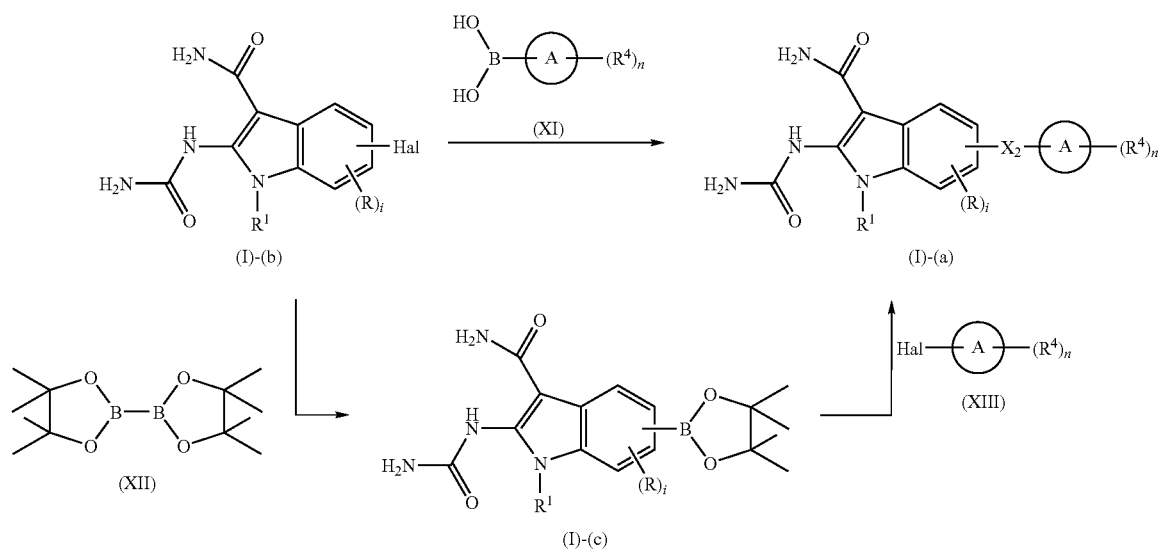

The present compounds (I)-(d) ($X^4$ indicates methylene group) can be prepared according to synthetic route 6. Namely, the present compounds (I)-(d) can be obtained the reaction of the present compounds (I)-(e) with an amine (XIV) in an organic solvent such as methanol or THF at room temperature to 100° C. for 1 hour to 24 hours, followed by the addition of a reducing reagent such as sodium borohydride or sodium cyanoborohydride and stirring this mixture at 0° C. to 100° C. for 1 hour to 24 hours.

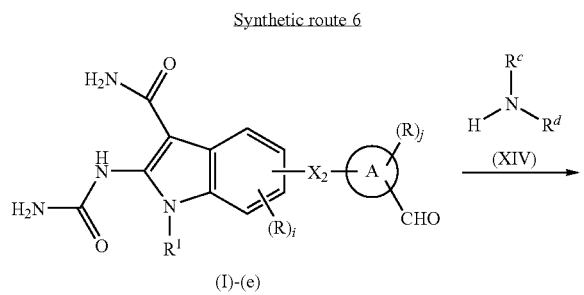

which may have a substituent). Namely, the present compounds (I)-(f) can be obtained by the reaction of the present compounds (I)-(b) and 1-alkyne (XV) in a solution mixture of water and organic solvent such as 1,4-dioxane or DMF in the presence of an organometallic complex catalyst such as tetrakis(triphenylphosphine)palladium (0) or tris(dibenzylideneacetone)dipalladium, a copper salt such as copper iodide (I) or copper bromide (I) and a base such as sodium hydrogen carbonate or triethylamine at room temperature to 150° C. for 1 hour to 24 hours. And the present compounds (I)-(g) can be obtained by the reaction of the present compounds (I)-(b) with a boronic acid ester (XVI) in a solution mixture of water and an organic solvent such as 1,4-dioxane or DMF in the presence of an organometallic complex catalyst such as tetrakis(triphenylphosphine)palladium (0) or tris(dibenzylideneacetone)dipalladium and a base such as sodium hydrogen carbonate or triethylamine at room temperature to 150° C. for 1 hour to 24 hours. Also, the present compounds (I)-(h) can be obtained by the reaction of the present compounds (I)-(f) or the present compounds (I)-(g) in an organic solvent such as methanol or DMF in the presence of palladium on activated carbon under hydrogen atmosphere at room temperature to 100° C. for 1 hour to 24 hours.

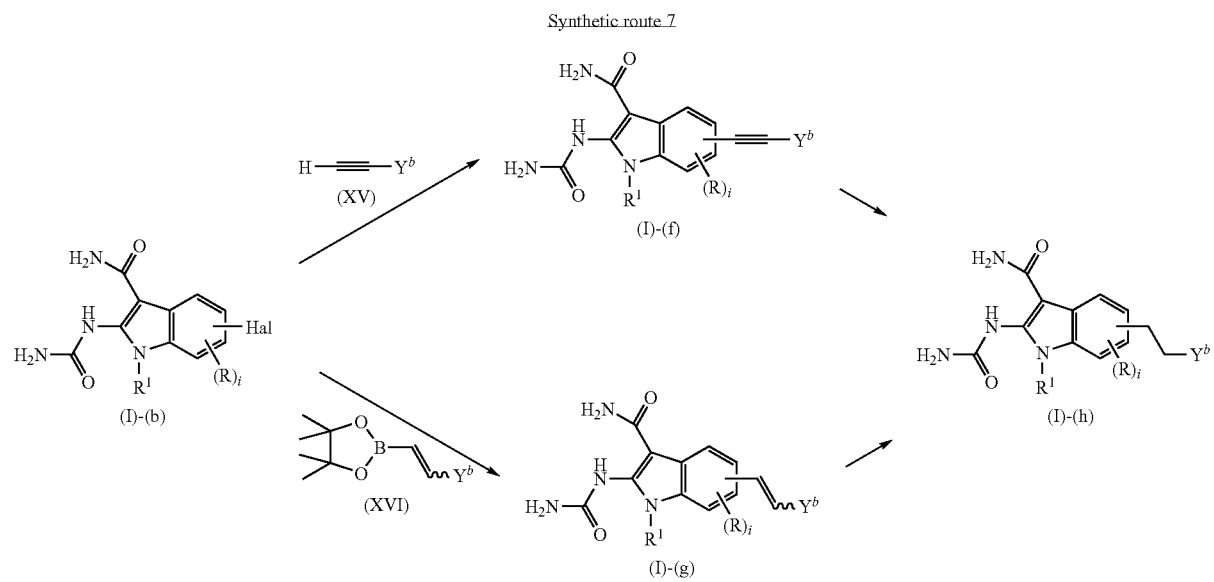

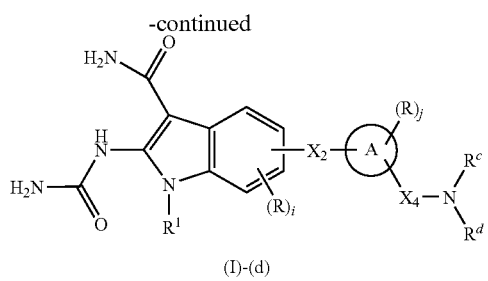

The present compounds (I)-(f), the present compounds (I)-(g) and the present compounds (I)-(h) can be prepared according to synthetic route 7 ($Y^b$ indicates lower alkyl group The present compounds (I)-(i) can be prepared according to synthetic route 8. Namely, the present compounds (I)-(k) can be obtained by the reaction of the present compounds (I)-(j) in water or in an organic solvent such as methanol or ethanol in the presence of a base such as sodium hydroxide or lithium hydroxide at room temperature to 100° C. for 1 hour to 24 hours. The present compounds (I)-(i) can be obtained by the reaction of the given compound (I)-(k) with an amine (XVII) in an organic solvent such as dichloromethane or DMF in the presence of a coupling reagent such as N,N-dicyclohexylcarbodiimide or O-(7-azabenzotriazol-1-yl)-N, N,N',N-tetramethyluroniumhexafluorophosphate and a base such as N,N-diisopropylethylamine at 0° C. to 100° C. for 1 hour to 24 hours.

Synthetic route 8

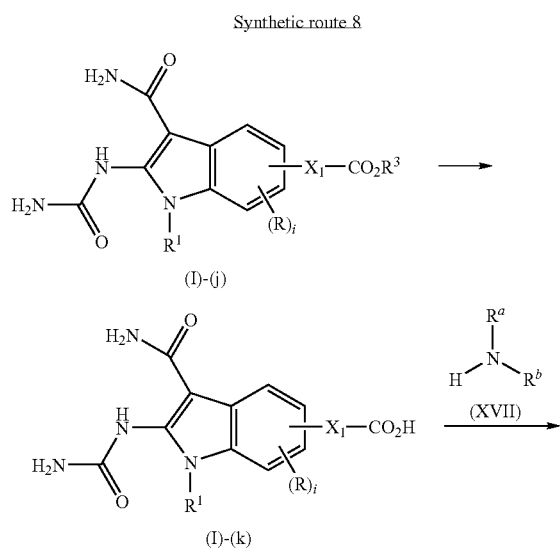

Namely, the present compounds (I)-(n) can be obtained by the reaction of the present compounds (I)-(j) in an organic solvent such as diethyl ether or THF in the presence of a reducing reagent such as diisobutylaluminium hydride at −80° C. to room temperature for 30 minutes to 6 hours. The present compounds (I)-(o) can be obtained by the reaction of the given present compounds (I)-(n) in an organic solvent such as dichloromethane or DMSO in the presence of oxidizing reagent such as 2-iodoxybenzoic acid at −80° C. to room temperature for 30 minutes to 6 hours. The present compounds (I)-(l) can be obtained by the reaction of the given present compounds (I)-(o) with an amine (XVII) in an organic solvent such as methanol or THF at room temperature to 100° C. for 1 hour to 24 hours, followed by the addition of a reducing reagent such as sodium borohydride or sodium cyanoborohydride and stirring this mixture at 0° C. to 100° C. for 1 hour to 24 hours. And the present compounds (I)-(m) can be obtained by the reaction of the present compounds (I)-(o) and a thiol (XVIII) in an organic solvent such as dichloromethane in the presence of trifluoroacetic acid at 0° C. to room temperature for 5 minutes to 1 hour, followed by the addition of pyridine-borane complex and stirring this mixture at 0° C. to room temperature for 5 minutes to 1 hour.

Synthetic route 9

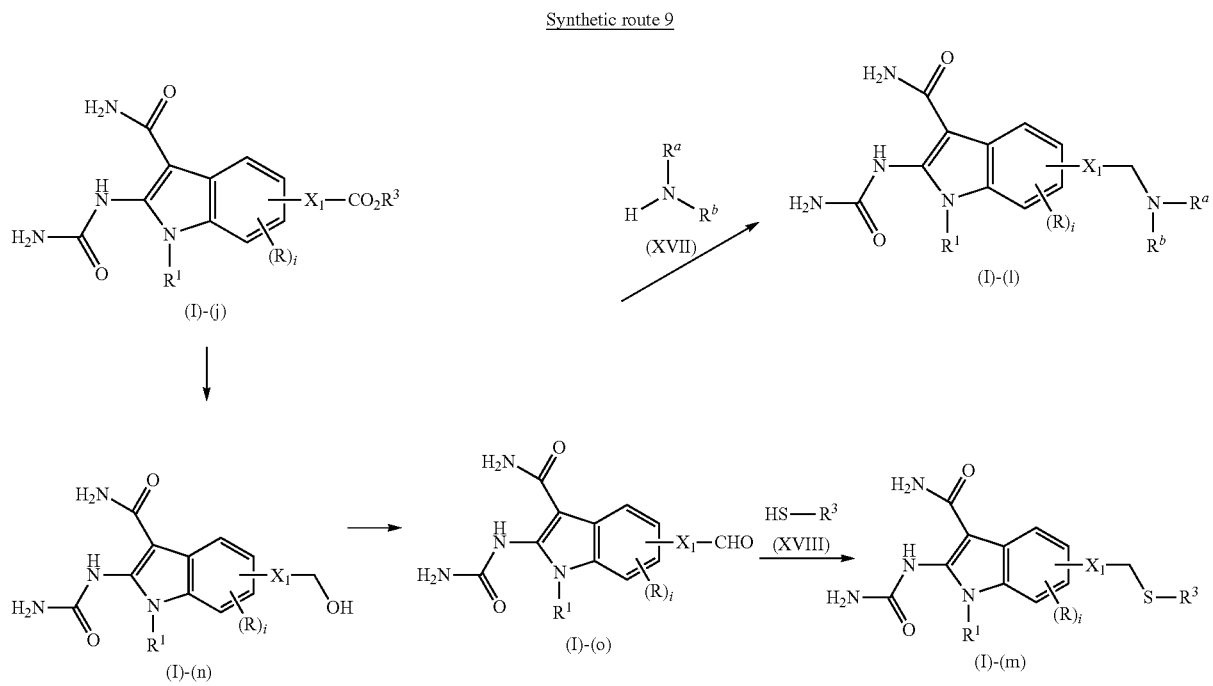

-continued

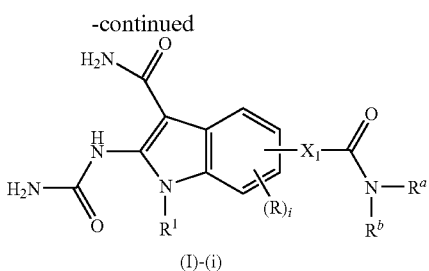

The present compounds (I)-(l) and the present compounds (I)-(m) can be prepared according to synthetic route 9.

Compound (II)-(d) can be prepared according to synthetic route 10. Namely, compound (XXI) can be obtained by the reaction of compound (XIX) with alkyl halide (XX) in an organic solvent such as THF or acetonitrile in the presence of a base such as triethylamine or pyridine at 0° C. to 50° C. for 1 hour to 24 hours. Compound (XXIII) can be obtained by the reaction of the given compound (XXI) with alkyl halide (XXII) as mentioned above. Compound (II)-(d) can be obtained by the reaction of the given compound (XXIII) in an organic solvent such as dichloromethane and 1,4-dioxane in the presence of an acid such as hydrochloric acid or trifluoroacetic acid at 0° C. to 50° C. for 1 hour to 24 hours.

Synthetic route 10

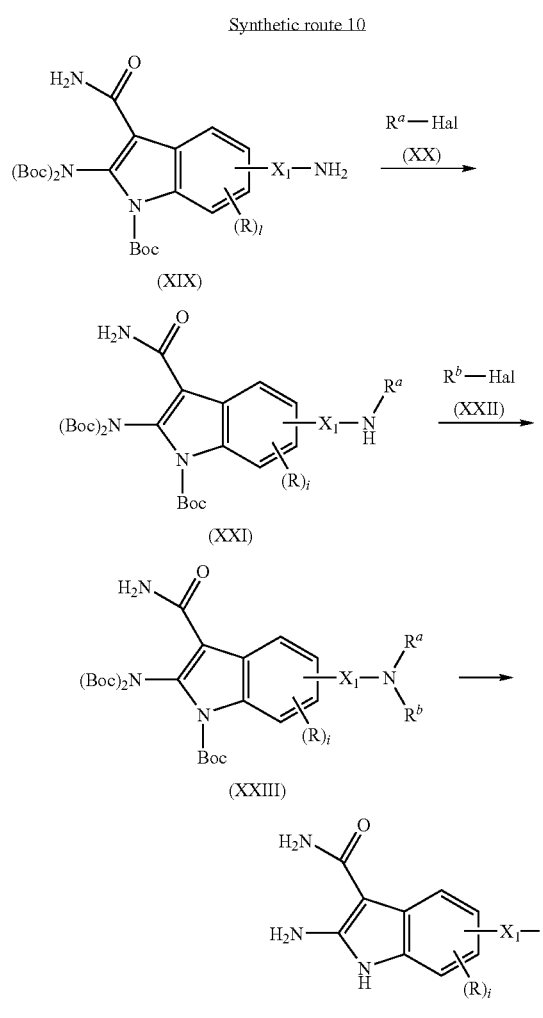

Compound (II)-(e) can be prepared according to synthetic route 11. Namely, compound (XXV) can be obtained by the reaction of compound (XIX) with acid chloride (XXIV) in an organic solvent such as ethyl acetate or dichloromethane in the presence of a base such as triethylamine or pyridine at 0° C. to 50° C. for 1 hour to 24 hours. Compound (II)-(e) can be obtained by the reaction of the given compound (XXV) in an organic solvent such as dichloromethane or 1,4-dioxane in the presence of an acid such as hydrochloric acid or trifluoroacetic acid at 0° C. to 50° C. for 1 hour to 24 hours.

Synthetic route 11

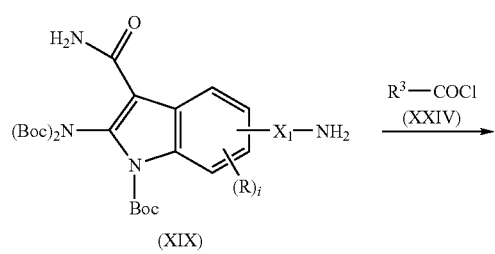

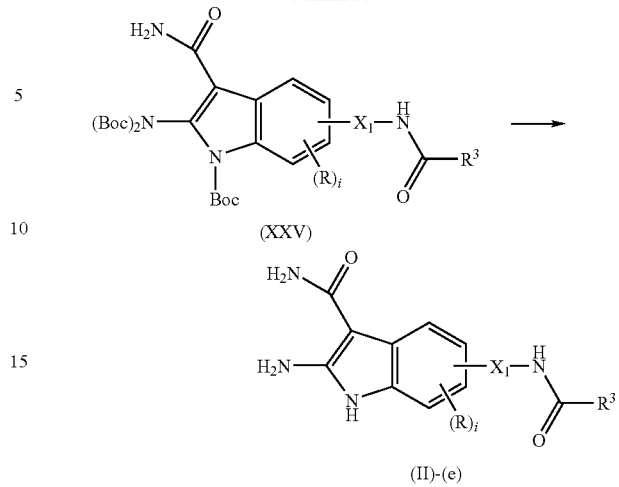

Compound (XIX) can be prepared according to synthetic route 12. Namely, compound (XXVII) can be obtained by the reaction of compound (XXVI) with di-tertbutyl dicarbonate in an organic solvent such as THF or dichloromethane in the presence of a base such as triethylamine or pyridine at 0° C. to 50° C. for 1 hour to 24 hours. Compound (XIX) can be obtained by the reaction of the given compound (XXVII) in an organic solvent such as methanol or DMF in the presence of palladium on activated carbon under hydrogen atmosphere at room temperature to 50° C. for 1 hour to 24 hours.

Synthetic route 12

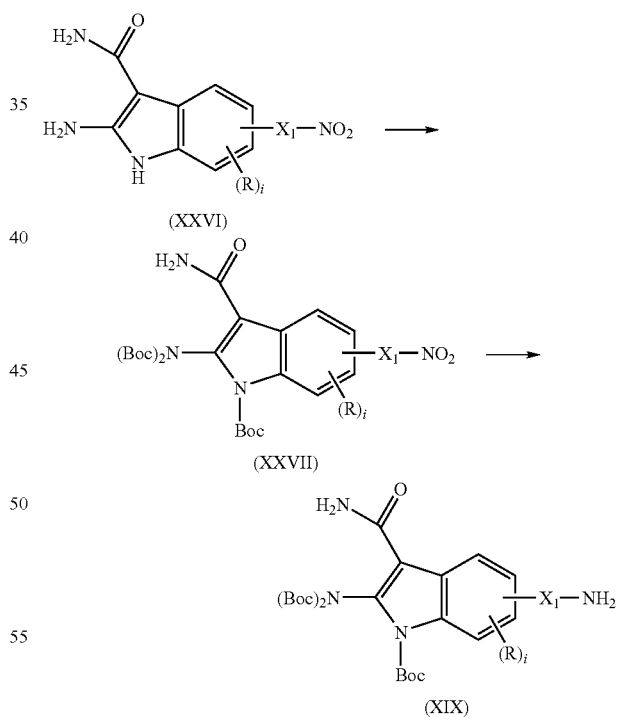

It is possible to modify each of the present compounds produced by the above synthetic routes into the above-described salt, hydrate, or solvate by a widely used technique.

The present compound exhibited excellent IKKβ inhibitory activity as a result of conducting an IKKβ inhibition assay by fluorescence polarization using IMAP™ IKKβ assay kit (manufactured by Molecular Devices Corporation, catalogue No. R8115) or IMAP™ FP Screening Express kit (manufactured by Molecular Devices Corporation, catalogue No. R8127), and details of the above will be described in [Pharmacological Test] in Examples described later in this specification.

As described above, IKKβ is involved in outbreak of various diseases, and the present compound having the excellent IKKβ inhibitory activity is useful as preventive and/or therapeutic agent for the diseases associated with IKKβ, particularly as preventive and/or therapeutic agent for inflammatory diseases, autoimmune diseases, allergic diseases, infectious diseases, degenerative diseases, vascular diseases, nerve/sensory organ diseases, endocrine/metabolic disease, neoplastic diseases, congenital diseases, traumatic diseases, and adverse reactions after organ transplantation, and more specific examples of such diseases include keratitis, conjunctivitis, uveitis, osteoarthritis, chronic obstructive pulmonary disease, bronchitis, pneumonia, hepatitis, pancreatitis, nephritis, sepsis, systemic inflammatory response syndrome, rheumatoid arthritis, psoriasis, multiple sclerosis, Crohn's disease, ulcerative colitis, systemic erythematosus, Sjogren's syndrome, multiple myositis, dermatomyositis, asthma, allergic rhinitis, hives, atopic dermatitis, age-related macular degeneration, retinopathy of prematurity, polypoidal choroidal vasculopathy, retinal vein occlusion, diabetes and its complication (diabetic retinopathy, diabetic macular edema, diabetic neuropathy, diabetic nephropathy), leukemia, multiple myeloma, malignant lymphoma, solid cancer, cachexia, Alzheimer's disease, Parkinson's syndrome, cerebral infarction, cerebral apoplexy, glaucoma, acquired immune deficiency syndrome, osteoporosis, obesity, fibrosis, gout, fever, headache, acute/chronic pain, hypertension, hyperlipidemia, arteriosclerosis, cardiac infarct, angina, dystrophia, acute respiratory distress syndrome, and the like.

The present compound can be administered either orally or parenterally. Examples of a dosage form include a tablet, a capsule, a granule, a powder, an injection, an eye drop, a suppository, a percutaneous absorption agent, an ointment, an airsol (including an inhalant), and the like, and these may be prepared by a widely used technique.

For example, an oral preparation such as a tablet, a capsule, a granule, or a powder can be prepared by optionally adding a necessary amount of an excipient such as lactose, mannitol, starch, crystalline cellulose, light silicic anhydride, calcium carbonate, or calcium hydrogen phosphate; a lubricant such as stearic acid, magnesium stearate, or talc; a binder such as starch, hydroxypropyl cellulose, hydroxypropylmethyl cellulose, or polyvinylpyrrolidone; a disintegrant such as carboxymethyl cellulose, low-substituted hydroxypropylmethyl cellulose, or calcium citrate; a coating agent such as hydroxypropylmethyl cellulose, macrogol, or a silicone resin; a stabilizer such as ethyl parahydroxybenzoate or benzyl alcohol; a corrigent such as a sweetener, a sour agent, or a flavor, or the like.

Further, a parenteral preparation such as an injection or an eye drop can be prepared by optionally adding a necessary amount of a tonicity agent such as sodium chloride, concentrated glycerin, propylene glycol, polyethylene glycol, potassium chloride, sorbitol, or mannitol; a buffer such as sodium phosphate, sodium hydrogen phosphate, sodium acetate, citric acid, glacial acetic acid, or trometamol; a surfactant such as polyosorbate 80, polyoxy 40 stearate, or polyoxyethylene hydrogenated castor oil 60; a stabilizer such as sodium citrate or sodium edetate; a preservative such as benzalkonium chloride, paraben, benzethonium chloride, parahydroxybenzoic acid ester, sodium benzoate, or chlorobutanol; a pH adjusting agent such as hydrochloric acid, citric acid, phosphoric acid, glacial acetic acid, sodium hydroxide, sodium carbonate, or sodium hydrogen carbonate; a soothing agent such as benzyl alcohol, or the like.

The present invention also relates to a method for inhibiting IKKβ comprising administering to a patient (human) in need thereof a pharmacologically effective amount of the present compound as well as to a method for preventing and/or treating a disease associated with IKKβ, comprising administering to a patient (human) in need thereof a therapeutically effective amount of the present compound.

The dose of the present compound can be appropriately selected depending on the symptoms, age, dosage form, or the like. For example, in the case of an oral preparation, it can be administered in an amount of generally from 0.01 to 1000 mg, preferably from 1 to 100 mg per day in a single dose or several divided doses. In the case of an eye drop, a preparation containing the present compound at a concentration of generally from 0.0001 to 10% (w/v), preferably from 0.01 to 5% (w/v) can be administered in a single dose or several divided doses.

Hereinafter, production examples of the present compound, preparation examples, and results of pharmacological tests will be described. However, these examples are described for the purpose of understanding the present invention better and are not meant to limit the scope of the present invention.

PRODUCTION EXAMPLE

Reference Example 1

2-(4-Bromo-2-nitrophenyl)-2-cyanoacetamide (Reference compound 1-1)

A solution of 2-cyanoacetamide (7.7 g, 91 mmol) in anhydrous N,N-dimethylformamide (20 mL) was added to a suspension of sodium hydride (purity 60%, 3.6 g, 91 mmol) in anhydrous N,N-dimethylformamide (50 mL) under ice-cooling, and the whole was stirred for 30 minutes. And then a solution of 5-bromo-2-fluoronitrobenzene (10 g, 46 mmol) in anhydrous N,N-dimethylformamide (20 mL) was added to the reaction mixture, and the mixture was stirred for 5.5 hours. The reaction mixture was poured into a solution of ice-water (200 mL) and 2 N hydrochloric acid (100 mL). The precipitated solid was filtered off, and dried under reduced pressure to give the title reference compound (11 g) as a slightly yellow solid (yield 85%).

| 2-(4-Bromo-2-nitrophenyl)-2-cyanoacetamide (Reference compound 1-1) 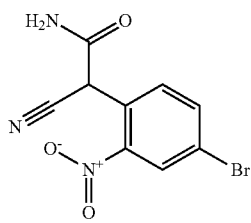 | $^1$H-NMR (400 MHz, DMSO-d$_6$) δ 5.65 (s, 1H), 7.67 (d, J = 8.4 Hz, 1H), 7.74 (s, 1H), 7.96 (s, 1H), 8.09 (dd, J = 8.4, 2.0 Hz, 1H), 8.36 (d, J = 2.0 Hz, 1H) |

As described below, Reference compound 1-2~1-7 were obtained according to the preparation method of Reference compound 1-1 by using commercially available reagents.

2-Cyano-2-(5-methyl-2-nitrophenyl)acetamide (Reference compound 1-2)

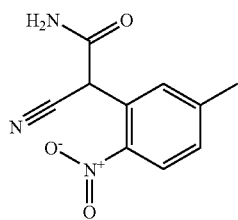

$^1$H-NMR (400 MHz, DMSO-$d_6$) δ 2.46 (s, 3H), 5.65 (s, 1H), 7.49-7.51 (m, 2H), 7.66 (s, 1H), 7.89 (s, 1H), 8.09 (dd, J = 7.8, 1.0 Hz, 1H)

2-Cyano-2-(4-methyl-2-nitrophenyl)acetamide (Reference compound 1-3)

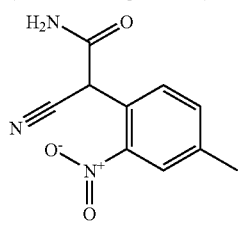

$^1$H-NMR (400 MHz, DMSO-$d_6$) δ 2.44 (s, 3H), 5.60 (s, 1H), 7.61 (d, J = 8.0 Hz, 1H), 7.67 (s, 1H), 7.68 (dd, J = 8.0, 1.0 Hz, 1H), 7.89 (s, 1H), 8.00 (d, J = 1.0 Hz, 1H)

2-Cyano-2-(2-nitro-4-trifluoromethylphenyl)acetamide (Reference compound 1-4)

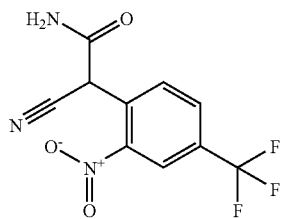

$^1$H-NMR (400 MHz, DMSO-$d_6$) δ 5.79 (s, 1H), 7.82 (s, 1H), 7.98 (d, J = 8.1 Hz, 1H), 8.08 (s, 1H), 8.28 (dd, J = 8.1, 1.5 Hz, 1H), 8.48 (d, J = 1.5 Hz, 1H)

2-Cyano-2-(4-methoxycarbonyl-2-nitrophenyl)acetamide (Reference compound 1-5)

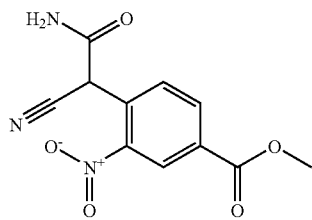

$^1$H-NMR (400 MHz, DMSO-$d_6$) δ 3.94 (s, 3H), 5.78 (s, 1H), 7.79 (s, 1H), 7.92 (d, J = 8.3 Hz, 1H), 8.06 (s, 1H), 8.39 (dd, J = 8.3, 2.0 Hz, 1H), 8.56 (d, J = 2.0 Hz, 1H)

2-(4-Chloro-2-nitrophenyl)-2-cyanoacetamide (Reference compound 1-6)

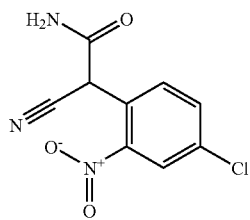

$^1$H-NMR (400 MHz, DMSO-$d_6$) δ 5.67 (s, 1H), 7.73 (s, 1H), 7.75 (d, J = 8.4 Hz, 1H), 7.96 (s, 1H), 7.97 (dd, J = 8.4, 2.3Hz, 1H), 8.26 (d, J = 2.3 Hz, 1H)

| | |
|---|---|
| 2-Cyano-2-(4-fluoro-2-nitrophenyl)acetamide (Reference compound 1-7) 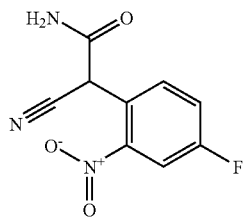 | $^1$H-NMR (400 MHz, DMSO-d$_6$) δ 5.66 (s, 1H), 7.73 (s, 1H), 7.78-7.79 (m, 2H) 7.94 (s, 1H), 8.12 (m, 1H) |

Reference Example 2

2-Amino-6-bromo-1-hydroxyindole-3-carboxamide (Reference compound 2-1)

2-Amino-6-bromoindole-3-carboxamide (Reference compound 2-2)

2-(4-Bromo-2-nitrophenyl)-2-cyanoacetamide (Reference compound 1-1, 0.60 g, 2.1 mmol) was dissolved in acetic acid (7.0 mL) and toluene (3.5 mL), and the whole was stirred at 90° C. Zinc powder (0.97 g, 15 mmol) was added portionwise to the solution while keeping at 90° C., and then the reaction mixture was stirred at room temperature for 45 minutes. Ice-water (30 mL) was added to the reaction mixture, and the whole was extracted with ethyl acetate (30 mL). The organic layer was washed with brine (30 mL), and dried over anhydrous magnesium sulfate. The solvent was evaporated under reduced pressure, and the residue was purified by silica gel column chromatography to give the mixture of the title reference compound (0.17 g) as a brown solid (yield 32%).

| | |
|---|---|
| 2-Amino-6-bromo-1-hydroxyindole-3-carboxamide (Reference compound 2-1) 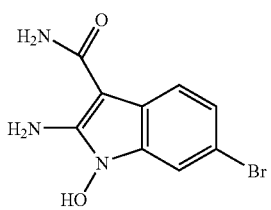 | $^1$H-NMR (400 MHz, DMSO-d$_6$) δ 6.58 (s, 2H), 7.02 (s, 2H), 7.06 (dd, J = 8.3, 2.0 Hz, 1H), 7.24 (d, J = 2.0 Hz, 1H), 7.53 (d, J = 8.3 Hz, 1H), 11.22 (s, 1H) |
| 2-Amino-6-bromoindole-3-carboxamide (Reference compound 2-2) 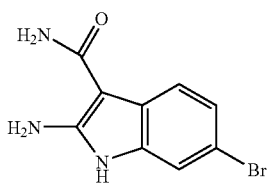 | $^1$H-NMR (400 MHz, DMSO-d$_6$) δ 6.50 (s, 2H), 6.90 (s, 2H), 7.03 (dd, J = 8.4, 1.8 Hz, 1H), 7.26 (d, J = 1.8 Hz, 1H), 7.48 (d, J = 8.4 Hz, 1H), 10.64 (s, 1H) |

As described below, Reference compound 2-3 and 2-4 were obtained according to the preparation method of Reference compound 2-1 by using Reference compound 1-2 or 1-3.

| | |
|---|---|
| 2-Amino-5-methylindole-3-carboxamide (Reference compound 2-3) 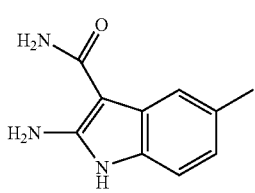 | $^1$H-NMR (500 MHz, DMSO-d$_6$) δ 2.32 (s, 3H), 6.38 (s, 2H), 6.66 (d, J = 7.6 Hz, 1H), 6.71 (s, 2H), 6.97 (d, J = 7.6 Hz, 1H), 7.33 (s, 1H), 10.40 (s, 1H) |

| 2-Amino-6-methylindole-3-carboxamide (Reference compound 2-4) 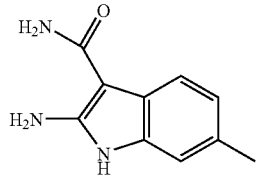 | ¹H-NMR (400 MHz, DMSO-d₆) δ 2.30 (s, 3H), 6.36 (s, 2H), 6.69 (s, 2H), 6.74 (d, J = 7.8 Hz, 1H), 6.90 (s, 1H), 7.38 (d, J = 7.8 Hz, 1H), 10.44 (s, 1H) |
|---|---|

Reference Example 3

2-(2-Amino-4-nitrophenyl)-2-cyanoacetamide (Reference compound 3-1)

Potassium tert-butoxide (36 g, 0.32 mol) was added to a solution of 2-cyanoacetamide (27 g, 0.32 mol) in anhydrous N,N-dimethylformamide (700 mL), and a solution of 2-fluoro-5-nitroaniline (25 g, 0.16 mol) in anhydrous N,N-dimethylformamide (80 mL) was added dropwise thereto under ice-cooling. After the reaction mixture was stirred at 5° C. for 18 hours, it was poured into a saturated ammonium chloride aqueous solution (1.0 L) under ice-cooling. The whole was extracted with ethyl acetate (1.0 L). The organic layer was washed with water (500 mL), brine (300 mL), and dried over anhydrous magnesium sulfate. After the solvent was evaporated under reduced pressure, toluene (100 mL) and dichloromethane (100 mL) were added to the residue. The precipitated solid was filtered off, and dried under reduced pressure to give the title reference compound (33 g) as a brown solid (yield 94%).

| 2-(2-Amino-4-nitrophenyl)-2-cyanoacetamide (Reference compound 3-1) 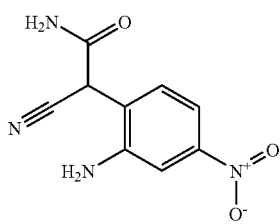 | ¹H-NMR (400 MHz, DMSO-d₆) δ 5.21 (s, 1H), 6.01 (s, 2H), 7.39 (d, J = 8.4 Hz, 1H), 7.43 (dd, J = 8.4, 2.4 Hz, 1H), 7.58 (d, J = 2.4 Hz, 1H), 7.72 (s, 1H), 7.86 (s, 1H) |
|---|---|

Reference Example 4

2-Amino-6-nitroindole-3-carboxamide (Reference compound 4-1)

Anhydrous N,N-dimethylformamide (1.0 L) was added to 2-(2-amino-4-nitrophenyl)-2-cyanoacetamide (Reference compound 3-1, 33 g, mol), and the solution was stirred at 85° C. for 17 hours. The reaction mixture was poured into ice-water (2.0 L), and precipitated solid was filtered off. The solid was washed with diethyl ether (30 mL), and dried under reduced pressure to give the title reference compound (13 g) as a red ocher solid (yield 41%).

| 2-Amino-6-nitroindole-3-carboxamide (Reference compound 4-1) 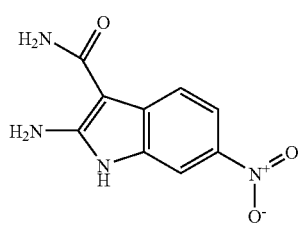 | ¹H-NMR (400 MHz, DMSO-d₆) δ 6.82 (s, 2H), 7.44 (s, 2H), 7.65 (d, J = 8.8 Hz, 1H), 7.85 (dd, J = 8.8, 2.2 Hz, 1H), 8.00 (d, J = 2.2 Hz, 1H), 11.07 (s, 1H) |
|---|---|

Reference Example 5

1-(tert-Butoxycarbonyl)-2-(di-tert-butoxycarbonyl)amino-6-nitroindole-3-carboxamide (Reference compound 5-1)

Di-tert-butyl dicarbonate (20 g, 91 mmol) and 4-(dimethylamino)pyridine (0.36 g, 3.0 mmol) were added to a solution of 2-amino-6-nitroindole-3-carboxamide (Reference compound 4-1, 5.0 g, 23 mmol) in tetrahydrofuran (100 mL) under ice-cooling, and the solution was stirred at room temperature for 18 hours. The reaction mixture was concentrated under reduced pressure, the residue was purified by silica gel column chromatography to give the title reference compound (7.7 g) as a yellow solid (yield 65%).

| | |
|---|---|
| 1-(tert-Butoxycarbonyl)-2-(di-tert-butoxycarbonyl)amino-6-nitroindole-3-carboxamide (Reference compound 5-1) 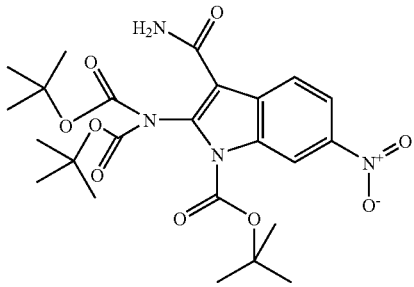 | $^1$H-NMR (500 MHz, DMSO-$d_6$) δ 1.33 (s, 18H), 1.62 (s, 9H), 7.60 (br s, 1H), 7.69 (br s, 1H), 8.06 (d, J = 8.8 Hz, 1H), 8.24 (dd, J = 8.8, 2.2 Hz, 1H), 9.03 (d, J = 2.2 Hz, 1H) |

Reference Example 6

6-Amino-1-(tert-butoxycarbonyl)-2-(di-tert-butoxycarbonyl)aminoindole-3-carboxamide (Reference compound 6-1)

5% Palladium-activated carbon (0.050 g) was added to a solution of 1-(tert-butoxycarbonyl)-2-(di-tert-butoxycarbonyl)amino-6-nitroindole-3-carboxamide (Reference compound 5-1, 0.34 g, 0.65 mmol) in methanol (7 mL), and the mixture was stirred at room temperature for 2.5 hours under hydrogen atmosphere. After the reaction mixture was filtered through Celite® pad, the filtrate was concentrated under reduced pressure to give the title reference compound (0.28 q) as a yellow solid (yield 87%).

Reference Example 7

6-Acetylamino-1-(tert-butoxycarbonyl)-2-(di-tert butoxycarbonyl)aminoindole-3-carboxamide (Reference compound 7-1)

Acetic anhydride (0.070 mL, 0.67 mmol) was added to a solution of 6-amino-1-(tert-butoxycarbonyl)-2-(di-tert-butoxycarbonyl)aminoindole-3-carboxamide (Reference compound 6-1, 0.29 g, 0.56 mmol) in pyridine (3 mL) under ice-cooling, and the mixture was stirred at room temperature for 3.5 hours. After the reaction mixture was concentrated under reduced pressure, the resultant solid was washed with diethyl ether (3 mL), and dried under reduced pressure to give the title reference compound (0.34 g) as a colorless solid quantitatively.

| | |
|---|---|
| 6-Amino-1-(tert-butoxycarbonyl)-2-(di-tert-butoxycarbonyl)aminoindole-3-carboxamide (Reference compound 6-1) 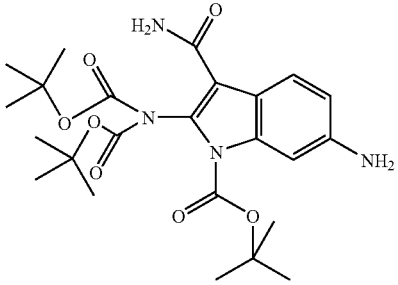 | $^1$H-NMR (400 MHz, DMSO-$d_6$) δ 1.33 (s, 18H), 1.55 (s, 9H), 5.29 (s, 2H), 6.61 (dd, J = 8.5, 2.0 Hz, 1H), 7.01 (br s, 1H), 7.36 (br s, 1H), 7.38 (d, J = 2.0 Hz, 1H), 7.45 (d, J = 8.5 Hz, 1H) |

| 6-Acetylamino-1-(tert-butoxycarbonyl)-2-(di-tert-butoxycarbonyl)aminoindole-3-carboxamide (Reference compound 7-1) 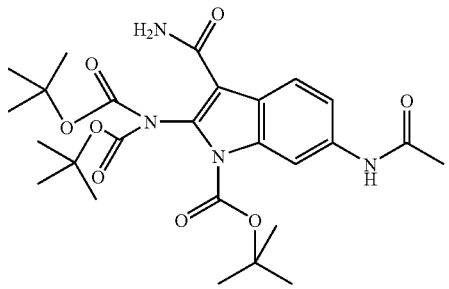 | ¹H-NMR (400 MHz, DMSO-d₆) δ 1.32 (s, 18H), 1.59 (s, 9H), 2.07 (s, 3H), 7.22 (br s, 1H), 7.43 (dd, J = 8.8, 2.0 Hz, 1H), 7.48 (br s, 1H), 7.73 (d, J = 8.8 Hz, 1H), 8.65 (d, J = 2.0 Hz, 1H), 10.09 (s, 1H) |

Reference Example 8

6-Benzoylamino-1-(tert-butoxycarbonyl)-2-(di-tert-butoxycarbonyl)aminoindole-3-carboxamide (Reference compound 8-1)

Triethylamine (0.10 mL, 0.73 mmol) and benzoylchloride (0.090 mL, 0.73 mmol) were added to a solution of 6-amino-1-(tert-butoxycarbonyl)-2-(di-tert-butoxycarbonyl)aminoindole-3-carboxamide (Reference compound 6-1, 0.30 g, 0.61 mmol) in ethyl acetate (4 mL). The mixture was stirred at room temperature for 2.5 hours. After the reaction mixture was concentrated under reduced pressure, the resultant solid was washed with water (3 mL) and diethyl ether (3 mL), and dried under reduced pressure to give the title reference compound (0.34 g) as a colorless solid (yield 94%).

| 6-Benzoylamino-1-(tert-butoxycarbonyl)-2-(di-tert-butoxycarbonyl)aminoindole-3-carboxamide (Reference compound 8-1) 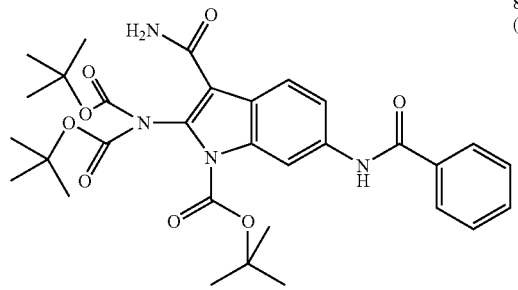 | ¹H-NMR (400 MHz, DMSO-d₆) δ 1.33 (s, 18H), 1.60 (s, 9H), 7.28 (br s, 1H), 7.52 (br s, 1H), 7.53-7.57 (m, 2H), 7.61 (tt, J = 7.2, 1.8 Hz, 1H), 7.70 (dd, J = 8.6, 2.0 Hz, 1H), 7.80 (d, J = 8.6 Hz, 1H), 7.98-8.00 (m, 2H), 8.84 (d, J = 2.0 Hz, 1H), 10.42 (s, 1H) |

Reference Example 9

1-(tert-butoxycarbonyl)-2-(di-tert-butoxycarbonyl)amino-6-(3-phenylureido)indole-3-carboxamide (Reference compound 9-1)

Phenyl isocyanate (0.12 mL, 1.0 mmol) was added to a solution of 6-amino-1-(tert-butoxycarbonyl)-2-(di-tert-butoxycarbonyl)aminoindole-3-carboxamide (Reference compound 6-1, 0.30 g, 0.61 mmol) in acetonitrile (4 mL), and the mixture was stirred at room temperature for 6.5 hours. After the reaction mixture was concentrated under reduced pressure, the resultant solid was washed with diethyl ether (3 mL), and dried under reduced pressure to give the title reference compound (0.31 g) as a colorless solid (yield 86%).

| 1-(tert-Butoxycarbonyl)-2-(di-tert-butoxycarbonyl)amino-6-(3-phenylureido)indole-3-carboxamide (Reference compound 9-1) 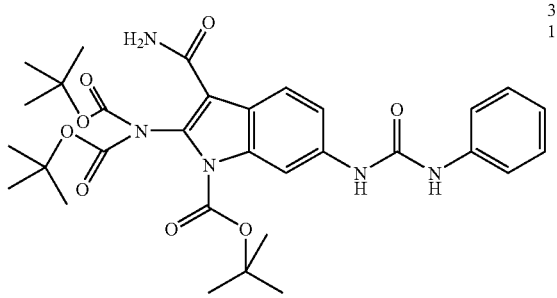 | ¹H-NMR (400 MHz, DMSO-d₆) δ 1.33 (s, 18H), 1.59 (s, 9H), 6.98 (tt, J = 7.3, 1.1 Hz, 1H), 7.22 (br s, 1H), 7.27-7.31 (m, 3H), 7.46-7.48 (m, 3H), 7.72 (d, J = 8.8 Hz, 1H), 8.54 (d, J = 1.7 Hz, 1H), 8.65 (s, 1H), 8.89 (s, 1H) |

Reference Example 10

1-(tert-butoxycarbonyl)-2-(di-tert-butoxycarbonyl)amino-6-dimethylaminoindole-3-carboxamide (Reference compound 10-1)

Potassium carbonate (0.16 g, 1.1 mmol) and methyl iodide (0.14 mL, 2.2 mmol) were added to a solution of 6-amino-1-(tert-butoxycarbonyl)-2-(di-tert-butoxycarbonyl)aminoindole-3-carboxamide (Reference compound 6-1, 0.50 g, 1.0 mmol) in N-methylpyrrolidone (5.0 mL), and the mixture was stirred at room temperature for 18 hours. The reaction mixture was poured into ice-water (50 mL), and the whole was extracted with ethyl acetate (80 mL). The organic layer was washed with water (50 mL) and brine (50 mL), and dried over anhydrous magnesium sulfate. After the solvent was evaporated under reduced pressure, the residue was purified by silica gel column chromatography to give the title reference compound (0.21 g) as a colorless solid (yield 39%).

| 1-(tert-Butoxycarbonyl)-2-(di-tert-butoxycarbonyl)amino-6-dimethylaminoindole-3-carboxamide (Reference compound 10-1) 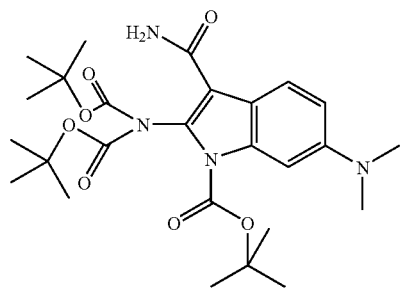 | ¹H-NMR (400 MHz, DMSO-d₆) δ 1.32 (s, 18H), 1.58 (s, 9H), 2.97 (s, 6H), 6.86 (dd, J = 8.8, 2.4 Hz, 1H), 7.08 (br s, 1H), 7.41(br s, 1H), 7.44 (d, J = 2.4 Hz, 1H), 7.63 (d, J = 8.8 Hz, 1H) |

Reference Example 11

1-(tert-Butoxycarbonyl)-2-(di-tert-butoxycarbonyl)amino-6-(pyrrolidin-1-yl)indole-3-carboxamide (Reference compound 11-1)

Potassium carbonate (0.16 g, 1.1 mmol) and 1,4-dibromobutane (0.13 mL, 1.1 mmol) were added to a solution of 6-amino-1-(tert-butoxycarbonyl)-2-(di-tert-butoxycarbonyl)aminoindole-3-carboxamide (Reference compound 6-1, 0.50 g, 1.0 mmol) in N-methylpyrrolidone (10 mL), and the mixture was stirred at 100° C. for 5 hours. The reaction mixture was poured into ice-water (100 mL), and the whole was extracted with ethyl acetate (100 mL×2). The organic layer was washed with water (50 mL) and brine (50 mL), and dried over anhydrous magnesium sulfate. After the solution was evaporated under reduced pressure, the residue was purified silica gel column chromatography to give the title reference compound (0.35 g) as a brown solid (yield 63%).

| 1-(tert-Butoxycarbonyl)-2-(di-tert-butoxycarbonyl)amino-6-(pyrrolidin-1-yl)indole-3-carboxamide (Reference compound 11-1) | $^1$H-NMR (500 MHz, CDCl$_3$) δ 1.39 (s, 18H), 1.65 (s, 9H), 2.03-2.05 (m, 4H), 3.36-3.38 (m, 4H), 5.54 (br s, 1H), 6.12 (br s, 1H), 6.67 (dd, J = 8.7, 2.3 Hz, 1H), 7.33 (d, J = 2.3 Hz, 1H), 7.98 (d, J = 8.7 Hz, 1H) |
|---|---|
| 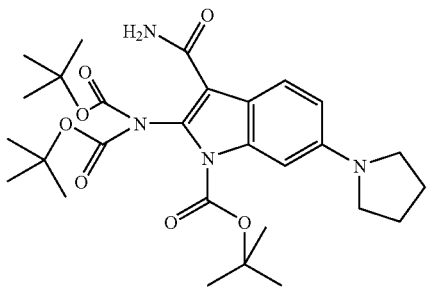 | |

Reference Example 12

1-(tert-butoxycarbonyl)-2-(di-tert-butoxycarbonyl)amino-6-(2-oxopyrrolidin-1-yl)indole-3-carboxamide (Reference compound 12-1)

4-Bromobutyryl chloride (0.13 mL, 1.1 mmol) was added to a solution of 6-amino-1-(tert-butoxycarbonyl)-2-(di-tert-butoxycarbonyl)aminoindole-3-carboxamide (Reference compound 6-1, 0.50 g, 1.0 mmol) in toluene (5.0 mL). The mixture was stirred at 60° C. for 3 hours. The reaction mixture was poured into water (20 mL), and the whole was extracted with ethyl acetate (30 mL). The organic layer was concentrated under reduced pressure. Acetonitrile (10 mL) and cesium carbonate (0.14 g, 0.44 mmol) were added to the resultant solid, and the mixture was stirred at room temperature for 6.5 hours. After the reaction mixture was concentrated under reduced pressure, water (50 mL) was added to the residue. The whole was extracted with ethyl acetate (50 mL). The organic layer was washed with water (50 mL) and brine (50 mL), and dried over anhydrous magnesium sulfate. After the solvent was evaporated under reduced pressure, the residue was purified by silica gel column chromatography to give the title reference compound (0.35 g) as a colorless solid (yield 63%).

| 1-(tert-Butoxycarbonyl)-2-(di-tert-butoxycarbonyl)amino-6-(2-oxopyrrolidin-1-yl)indole-3-carboxamide (Reference compound 12-1) | $^1$H-NMR (400 MHz, DMSO-d$_6$) δ 1.32 (s, 18H), 1.59 (s, 9H), 2.10 (m, 2H), 2.49-2.51 (m, 2H), 3.92 (t, J = 7.0 Hz, 2H), 7.27 (br s, 1H), 7.51 (br s, 1H), 7.60 (dd, J = 8.8, 2.0 Hz, 1H), 7.81 (d, J = 8.8 Hz, 1H), 8.53 (d, J = 2.0 Hz, 1H) |
|---|---|
| 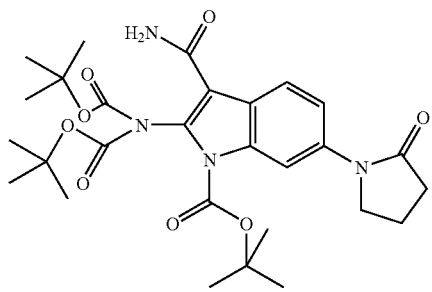 | |

Reference Example 13

1-(tert-butoxycarbonyl)-2-(di-tert-butoxycarbonyl)amino-6-(diphenylsulfonyl)aminoindole-3-carboxamide (Reference compound 13-1)

Triethylamine (0.19 mL, 1.4 mmol) and benzenesulfonyl chloride (0.18 mL, 1.4 mmol) were added to a solution of 6-amino-1-(tert-butoxycarbonyl)-2-(di-tert-butoxycarbonyl)aminoindole-3-carboxamide (Reference compound 6-1, 0.30 g, 0.61 mmol) in acetonitrile (4 mL). The mixture was stirred at room temperature for 6 hours. After the reaction mixture was concentrated under reduced pressure, water (20 mL) was added to the residue, and the whole was extracted with ethyl acetate (20 mL). The organic layer was washed with water (20 mL) and brine (20 mL), and dried over anhydrous magnesium sulfate. After the solvent was evaporated under reduced pressure, the residue was purified by silica gel column chromatography to give the title reference compound (0.26 g) as a colorless solid (yield 56%).

| 1-(tert-Butoxycarbonyl)-2-(di-tert-butoxycarbonyl)amino-6-(diphenylsulfonyl)aminoindole-3-carboxamide (Reference compound 13-1) 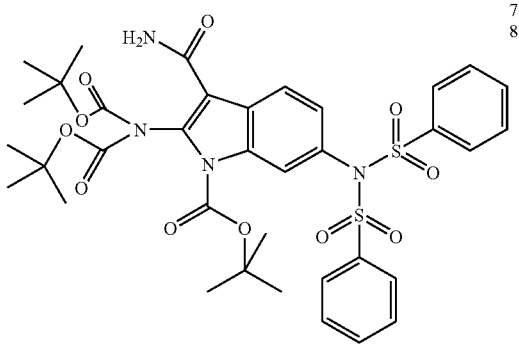 | ¹H-NMR (400 MHz, DMSO-d₆) δ 1.35 (s, 18H), 1.49 (s, 9H), 7.11 (dd, J = 8.5, 2.0 Hz, 1H), 7.47 (br s, 1H), 7.59 (br s, 1H), 7.63 (d, J = 2.0 Hz, 1H), 7.67-7.71 (m, 4H), 7.82-7.85 (m, 6H), 7.89 (d, J = 8.5 Hz, 1H) |

Reference Example 14

1-(tert-Butoxycarbonyl)-2-(di-tert-butoxycarbonyl)amino-6-(2,5-dimethylpyrrol-1-yl)indole-3-carboxamide (Reference compound 14-1)

p-Toluenesulfonic acid monohydrate (2.0 mg, 0.010 mmol) and 2,5-hexanedione (0.14 mL, 1.2 mmol) were added to a solution of 6-amino-1-(tert-butoxycarbonyl)-2-(di-tert-butoxycarbonyl)aminoindole-3-carboxamide (Reference compound 6-1, 0.50 g, 1.0 mmol) in toluene (2 mL), and the mixture was stirred at 110° C. for 3 hours. Saturated sodium hydrogen carbonate aqueous solution was added (20 mL) to the reaction mixture, and the whole was extracted ethyl acetate (30 mL). After the solvent was evaporated under reduced pressure, the residue was purified by silica gel column chromatography to give the title reference compound (0.24 g) as a colorless solid (yield 41%).

| 1-(tert-Butoxycarbonyl)-2-(di-tert-butoxycarbonyl)amino-6-(2,5-dimethylpyrrol-1-yl)indole-3-carboxamide (Reference compound 14-1) 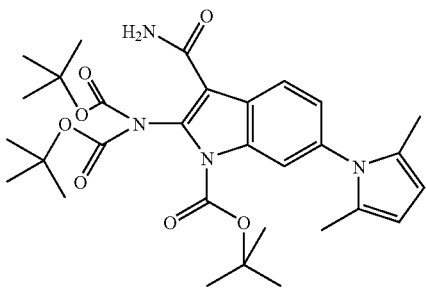 | ¹H-NMR (400 MHz, DMSO-d₆) δ 1.37 (s, 18H), 1.56 (s, 9H), 1.99 (s, 6H), 5.83 (S. 2H), 7.27 (dd, J = 8.3, 2.0 Hz, 1H), 7.46 (br s, 1H), 7.56 (br s, 1H), 7.93 (s, 1H), 7.94 (d, J = 8.3 Hz, 1H) |

Reference Example 15

6-Acetylamino-2-aminoindole-3-carboxamide (Reference compound 15-1)

Trifluoroacetic acid (0.67 mL, 9.0 mmol) was added to a solution of 6-acetylamino-1-(tert-butoxycarbonyl)-2-(di-tert-butoxycarbonyl)aminoindole-3-carboxamide (Reference compound 7-1, 0.32 g, 0.60 mmol) in dichloromethane (4 mL) under ice-cooling, and the mixture was stirred at room temperature for 18 hours. After the reaction mixture was concentrated under reduced pressure, water (3 mL) and 1 N sodium hydroxide aqueous solution (1.5 mL) were added to the residue under ice-cooling. The precipitated solid was washed with water (0.5 mL), and dried under reduced pressure to give the title reference compound (0.030 g) as a colorless solid (yield 24%).

| | |
|---|---|
| 6-Acetylamino-2-aminoindole-3-carboxamide (Reference compound 15-1) 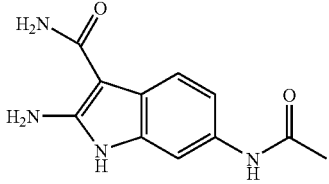 | $^1$H-NMR (400 MHz, DMSO-d$_6$) δ 2.01 (s, 3H), 6.39 (s, 2H), 6.73 (s, 2H), 6.97 (dd, J = 8.3, 2.0 Hz, 1H), 7.40 (d, J = 8.3 Hz, 1H), 7.62 (d, J = 2.0 Hz, 1H), 9.69 (s, 1H), 10.54 (s, 1H) |

As described below, Reference compound 15-2~15-8 were obtained according to the preparation method of Reference compound 15-1 by using Reference compound 8-1~14-1.

| | |
|---|---|
| 2-Amino-6-benzoylaminoindole-3-carboxamide (Reference compound 15-2) 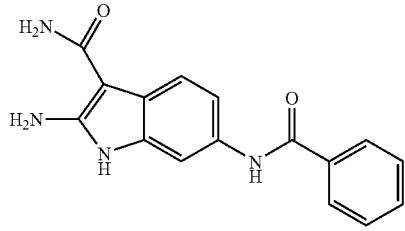 | $^1$H-NMR (500 MHz, DMSO-d$_6$) δ 6.43 (s, 2H), 6.76 (s, 2H), 7.24 (dd, J = 8.6, 1.8 Hz, 1H), 7.47 (d, J = 8.6 Hz, 1H), 7.51-7.53 (m, 2H), 7.57 (tt, J = 7.3, 1.8 Hz, 1H), 7.76 (d, J = 1.8 Hz, 1H), 7.95-7.96 (m, 2H), 10.05 (s, 1H), 10.62 (s, 1H) |
| 2-Amino-6-(3-phenylureido)indole-3-carboxamide (Reference compound 15-3) 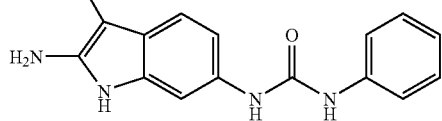 | $^1$H-NMR (400 MHz, DMSO-d$_6$) δ 6.38 (s, 2H), 6.71 (s, 2H), 6.84 (dd, J = 8.3, 2.0 Hz, 1H), 6.94 (t, J = 7.3 Hz, 1H), 7.26 (t, J = 7.3 Hz, 2H), 7.40 (d, J = 8.3 Hz, 1H), 7.45-7.47 (m, 3H), 8.41 (s, 1H), 8.52 (s, 1H), 10.50 (s, 1H) |
| 2-Amino-6-dimethylaminoindole-3-carboxamide (Reference compound 15-4) 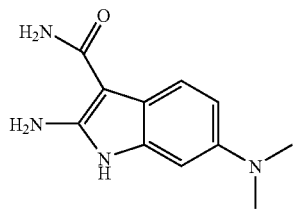 | $^1$H-NMR (500 MHz, DMSO-d$_6$) δ 2.81 (s, 6H), 6.27 (s, 2H), 6.48 (dd, J = 8.6, 2.4 Hz, 1H), 6.57 (d, J = 2.4 Hz, 1H), 6.58 (s, 2H), 7.34 (d, J = 8.6 Hz, 1H), 10.24 (s, 1H) |
| 2-Amino-6-(pyrrolidin-1-yl)indole-3-carboxamide (Reference compound 15-5) 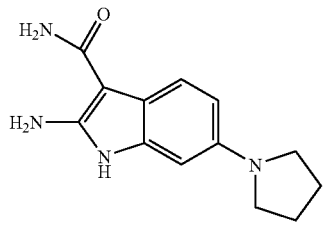 | $^1$H-NMR (400 MHz, DMSO-d$_6$) δ 1.93-1.96 (m, 4H), 3.18 (t, J = 6.1 Hz, 4H), 6.25 (s, 2H), 6.27 (dd, J = 8.3, 1.8 Hz, 1H), 6.35 (d, J = 1.8 Hz, 1H), 6.55 (s, 2H), 7.31 (d, J = 8.3 Hz, 1H), 10.27 (s, 1H) |

| | |
|---|---|
| 2-Amino-6-(2-oxopyrrolidin-1-yl)indole-3-carboxamide (Reference compound 15-6) 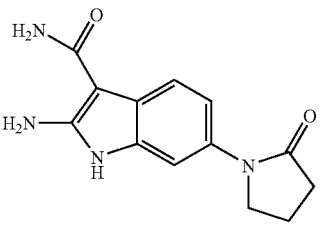 | ¹H-NMR (400 MHz, DMSO-d$_6$) δ 2.02-2.09 (m, 2H), 2.49-2.51 (m, 2H), 3.82 (t, J = 7.0 Hz, 2H), 6.80 (s, 2H), 6.44 (s, 2H), 7.06 (dd, J = 8.5, 2.2 Hz, 1H), 7.48 (d, J = 8.5 Hz, 1H), 7.56 (d, J = 2.2 Hz, 1H), 10.57 (s, 1H) |
| 2-Amino-6-(diphenylsulfonylamino)indole-3-carboxamide (Reference compound 15-7) 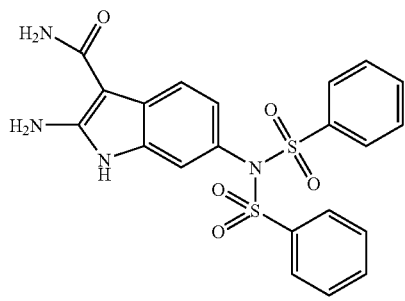 | ¹H-NMR (400 MHz, DMSO-d$_6$) δ 6.45 (dd, J = 8.5, 2.0 Hz, 1H), 6.56 (s, 2H), 6.74 (d, J = 2.0 Hz, 1H), 7.04 (br s, 2H), 7.47 (d, J = 8.5 Hz, 1H), 7.67-7.71 (m, 4H), 7.80-7.84 (m, 6H), 10.70 (s, 1H) |
| 2-Amino-6-(2,5-dimethylpyrrol-1-yl)indole-3-carboxamide (Reference compound 15-8) 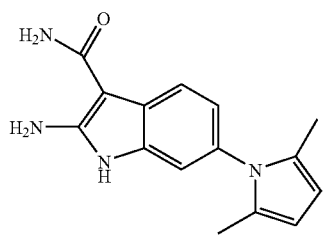 | ¹H-NMR (400 MHz, DMSO-d$_6$) δ 1.94 (s, 6H), 5.75 (s, 2H), 6.52 (s, 2H), 6.74 (dd, J = 8.1, 2.0 Hz, 1H), 6.90 (s, 2H), 6.93 (d, J = 2.0 Hz, 1H), 7.59 (d, J = 8.1 Hz, 1H), 10.65 (s, 1H) |

Reference Example 16

2-Amino-6-(pyrrole-1-yl)indole-3-carboxamide (Reference compound 16-1)

2,5-Dimethoxytetrahydrofuran (0.19 mL, 1.5 mmol) was added to a solution of 6-amino-1-(tert-butoxycarbonyl)-2-(di-tert-butoxycarbonyl)aminoindole-3-carboxamide (Reference compound 6-1, 0.60 g, 1.2 mmol) in acetic acid (2 mL), and the mixture was stirred at 110° C. for 8 hours. After the reaction mixture was concentrated under reduced pressure, 1 N sodium hydroxide aqueous solution (1.5 mL) was added to the residue. The precipitated solid was filtered off, and washed with water (1 mL). The resultant solid was purified by silica gel column chromatography to give the title Reference compound (0.11 g) as a colorless solid (yield 38%).

| | |
|---|---|
| 2-Amino-6-(pyrrol-1-yl)indole-3-carboxamide (Reference compound 16-1) 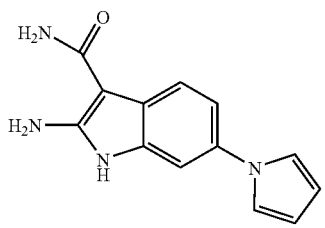 | ¹H-NMR (400 MHz, DMSO-d$_6$) δ 6.21 (t, J = 2.2 Hz, 2H), 6.51 (s, 2H), 6.85 (s, 2H), 7.08 (dd, J = 8.3, 2.2 Hz, 1H), 7.20-7.21 (m, 2H), 7.22 (d, J = 2.2 Hz, 1H), 7.57 (d, J = 8.3 Hz, 1H), 10.64 (s, 1H) |

Reference Example 17

2-(2-Benzoylaminophenyl)-2-cyanoacetamide (Reference compound 17-1)

After malononitrile (8.6 g, 0.13 mol) was added to a solution of N-benzoyl-N-phenylhydroxylamine (25 g, 0.12 mol) in chloroform (150 mL), triethylamine (4.0 mL, 0.030 mol) was added dropwise thereto for 5 minutes. After the mixture was stirred at room temperature for 3 hours, the reaction mixture was concentrated under reduced pressure, and diethyl ether (200 mL) was added to the residue. The precipitated solid was filtered off and was washed with diethyl ether (100 mL). The resultant solid was dried under reduced pressure to give the title reference compound (30 g) as a brown solid (yield 89%).

| 2-(2-Bezoylaminophenyl)-2-cyanoacetamide (Reference compound 17-1) 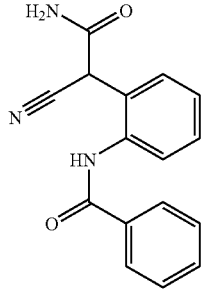 | $^1$H-NMR (500 MHz, DMSO-$d_6$) δ 5.25 (s, 1H), 7.35 (td, J = 7.5, 1.3 Hz, 1H), 7.46 (td, J = 7.8, 1.5 Hz, 1H), 7.56-7.57 (m, 3H), 7.61-7.64 (m, 2H), 7.75 (s, 1H), 7.98 (s, 1H), 8.02-8.03 (m, 2H), 10.51 (s, 1H) |
|---|---|

As described below, Reference compound 17-2 was obtained according to the preparation method of Reference compound 17-1 by using Reference compound 31-1.

| 2-Cyano-2-(2-acetylamino-4-bromo-3-methyl)phenyl-acetamide (Reference compound 17-2) 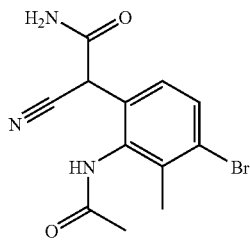 | $^1$H-NMR (400 MHz, DMSO-$d_6$) δ 2.10 (s, 3H), 2.24 (s, 3H), 5.08 (s, 1H), 7.29 (d, J = 8.5 Hz, 1H), 7.61 (s, 1H), 7.67 (d, J = 8.5 Hz, 1H), 7.70 (s, 1H), 9.68 (s, 1H) |
|---|---|

Reference Example 18

2-Aminoindole-3-carboxamide (Reference compound 18-1)

Sodium methylate methanol solution (28%, 96 g, 0.50 mol) was added to a solution of 2-(2-benzoylaminophenyl)-2-cyanoacetamide (Reference compound 17-1, 30 g, 0.11 mol) in anhydrous methanol (200 mL), and the mixture was stirred at 90° C. for 4.5 hours. The reaction mixture was concentrated by half in the volume under reduced pressure. After ice-water (500 mL) was added to the mixture, the whole was extracted with ethyl acetate (400 mL×2). The organic layer was washed with brine (300 mL), and dried over anhydrous magnesium sulfate. After the solvent was evaporated under reduced pressure, ethanol (400 mL) was added to the residue and the insoluble solid was removed by filtration. After the filtrate was concentrated under reduced pressure, chloroform (80 mL) was added to the residue and the precipitated solid was washed with diethyl ether (40 mL). The resultant solid was dried under reduced pressure to give the title reference compound (10 q) as a brown solid (yield 53%).

| | |
|---|---|
| 2-Aminoindole-3-carboxamide (Reference compound 18-1) 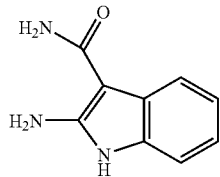 | $^1$H-NMR (400 MHz, DMSO-$d_6$) δ 6.44 (s, 2H), 6.78 (s, 2H), 6.84 (td, J = 7.6, 1.1 Hz, 1H), 6.92 (td, J = 7.6, 1.1 Hz, 1H), 7.10 (dd, J = 7.6, 1.1 Hz, 1H), 7.51 (d, J = 7.6 Hz, 1H), 10.55 (s, 1H) |

As described below, Reference compound 18-2 was obtained according to the preparation method of Reference compound 18-1 by using Reference compound 17-2.

| | |
|---|---|
| 2-Amino-6-bromo-7-methylindole-3-carboxamide (Reference compound 18-2) 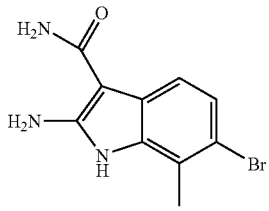 | $^1$H-NMR (400 MHz, DMSO-$d_6$) δ 2.39 (s, 3H), 6.52 (s, 2H), 6.60 (s, 2H), 7.09 (d, J = 8.4 Hz, 1H), 7.34 (d, J = 8.4 Hz, 1H), 10.78 (s, 1H) |

Reference Example 19

2-Amino-1-ethylindole-3-carboxamide (Reference compound 19-1)

A solution of 2-aminoindole-3-carboxamide (Reference compound 18-1, 0.40 g, 2.3 mmol) in anhydrous N,N-dimethylformamide (2 mL) and a solution of iodoethane (0.20 mL, 2.5 mmol) in anhydrous N,N-dimethylformamide (2 mL) were successively added to a suspension of sodium hydride (purity 60%, 0.10 g, 2.5 mmol) in anhydrous N,N-dimethylformamide (10 mL) under ice-cooling. The mixture was stirred at room temperature for 1 hour. The reaction mixture was poured into ice-water (30 mL), and the whole was extracted with ethyl acetate (50 mL×2). The organic layer was washed with brine (30 mL), and dried over anhydrous magnesium sulfate. After the solvent was evaporated under reduced pressure, the residue was purified by silica gel column chromatography to give the title reference compound (0.22 g) as a brown solid (yield 49%).

| | |
|---|---|
| 2-Amino-1-ethylindole-3-carboxamide (Reference compound 19-1) 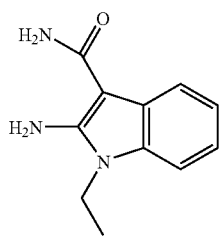 | $^1$H-NMR (400 MHz, DMSO-$d_6$) δ 1.14 (t, J = 7.1 Hz, 3H), 4.04 (q, J = 7.1 Hz, 2H), 6.48 (s, 2H), 6.92 (td, J = 7.5, 1.3 Hz, 1H), 6.97 (td, J = 7.5, 1.3 Hz, 1H), 7.18 (s, 2H), 7.20 (dd, J = 7.8, 0.7 Hz, 1H), 7.57 (dd, J = 7.8, 0.7 Hz, 1H) |

As described below, Reference compound 19-2 was obtained according to the preparation method of Reference compound 19-1 by using commercially available reagents and Reference compound 18-1.

| 2-Amino-1-benzylindole-3-carboxamide (Reference compound 19-2) 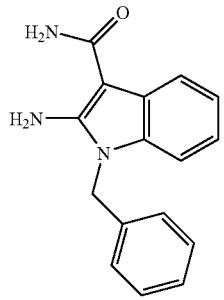 | $^1$H-NMR (400 MHz, DMSO-$d_6$) δ 5.32 (s, 2H), 6.56 (s, 2H), 6.85 (td, J = 7.6, 1.1 Hz, 1H), 6.97 (td, J = 7.6, 1.1 Hz, 1H), 7.09-7.13 (m, 3H), 7.23 (tt, J = 7.3, 1.6 Hz, 1H), 7.28-7.32 (m, 4H), 7.60 (d, J = 7.6 Hz, 1H) |
|---|---|

Reference Example 20
2-Amino-1-(4-nitrophenyl)indole-3-carboxamide (Reference compound 20-1)

A solution of 2-aminoindole-3-carboxamide (Reference compound 18-1, 0.20 g, 1.1 mmol) in anhydrous N,N-dimethylformamide (2 mL) and a solution of 4-fluoronitrobenzene (0.13 mL, 1.3 mmol) in anhydrous N,N-dimethylformamide (2 mL) were successively added to a suspension of sodium hydride (purity 60%, g, 1.3 mmol) in anhydrous N,N-dimethylformamide (3 mL) under ice-cooling, and the mixture was stirred at 85° C. for 3 hours. The reaction mixture was poured into ice-water (20 mL), the precipitated solid was washed with ethyl acetate (4 mL). The resultant solid was dried under reduced pressure to give the title reference compound (0.087 g) as a brown solid (yield 26%).

| 2-Amino-1-(4-nitrophenyl)indole-3-carboxamide (Reference compound 20-1) 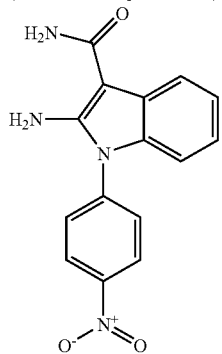 | $^1$H-NMR (400 MHz, DMSO-$d_6$) δ 6.76 (s, 2H), 6.92-6.93 (m, 2H), 7.05-7.09 (m, 3H), 7.71 (d, J = 7.8 Hz, 1H), 7.81 (dd, J = 7.0, 2.1 Hz, 2H), 8.47 (dd, J = 7.0, 2.1 Hz, 2H) |
|---|---|

As described below, Reference compound 20-2 was obtained according to the preparation method of Reference compound 20-1 by using commercially available reagents and Reference compound 18-1.

| 2-Amino-1-(2-nitrophenyl)indole-3-carboxamide (Reference compound 20-2) 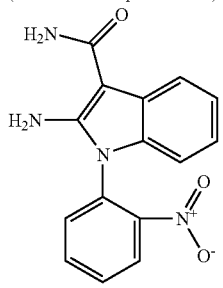 | $^1$H-NMR (400 MHz, DMSO-$d_6$) δ 6.61 (d, J = 8.0 Hz, 1H), 6.71 (s, 2H), 6.86 (td, J = 8.0, 1.0 Hz, 1H), 6.96 (s, 2H), 7.05 (td, J = 8.0, 1.0 Hz, 1H), 7.68 (d, J = 8.0 Hz, 1H), 7.73 (dd, J = 8.0, 1.5 Hz, 1H), 7.86 (td, J = 8.0, 1.5 Hz, 1H), 8.00 (td, J = 8.0, 1.5 Hz, 1H), 8.31 (dd, J = 8.0, 1.5 Hz, 1H) |
|---|---|

Reference Example 21

2-(2-Amino-4-trifluoromethylphenyl)-2-cyanoacetamide (Reference compound 21-1)

2-Cyano-2-(2-nitrophenyl-4-trifluoromethyl)acetamide (Reference compound 1-4, 2.5 g, 9.2 mmol) was added to a suspension of sodium hydrosulfite (8.0 g, 46 mmol) in 28% ammonia aqueous solution (180 mL) under ice-cooling, and the mixture was stirred for 1 hour. Water (50 mL) was added to the reaction mixture, and the whole was extracted with ethyl acetate (150 mL). The organic layer was washed with water (50 mL) and brine (50 mL), and dried over anhydrous magnesium sulfate. After the solvent was evaporated under reduced pressure, the precipitated solid was washed with chloroform (15 mL) and dried under reduced pressure to give the title reference compound (0.98 g) as a brown solid (yield 45%).

| | |
|---|---|
| 2-(2-Amino-4-trifluoromethylphenyl)-2-cyanoacetamide (Reference compound 21-1) 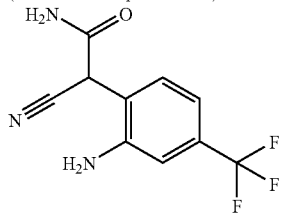 | $^1$H-NMR (400 MHz, DMSO-$d_6$) δ 5.14 (s, 1H), 5.79 (s, 2H), 6.91 (dd, J = 8.1, 1.5 Hz, 1H), 7.04 (d, J = 1.5 Hz, 1H), 7.34 (d, J = 8.1 Hz, 1H), 7.68 (s, 1H), 7.78 (s, 1H) |

As described below, Reference compound 21-2 and 21-3 were obtained according to the preparation method of Reference compound 21-1 by using Reference compound 1-6 or 1-7.

| | |
|---|---|
| 2-(2-Amino-4-chlorophenyl)-2-cyanoacetamide (Reference compound 21-2) 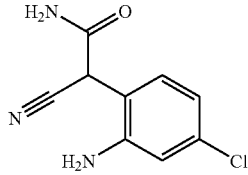 | $^1$H-NMR (400 MHz, DMSO-$d_6$) δ 5.03 (s, 1H), 5.62 (s, 2H), 6.63 (dd, J = 8.2, 2.3 Hz, 1H), 6.76 (d, J = 2.3 Hz, 1H), 7.13 (d, J = 8.2 Hz, 1H ), 7.62 (s, 1H), 7.71 (s, 1H) |
| 2-(2-Amino-4-fluorophenyl)-2-cyanoacetamide (Reference compound 21-3) 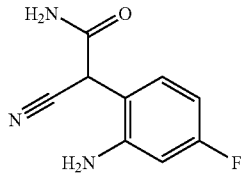 | $^1$H-NMR (400 MHz, DMSO-$d_6$) δ 5.02 (s, 1H), 5.63 (s, 2H), 6.40 (td, J = 8.5, 2.7 Hz, 1H), 6.48 (dd, J = 11.5, 2.7 Hz, 1H), 7.14 (dd, J = 8.5, 6.6 Hz, 1H), 7.60 (s, 1H), 7.69 (s, 1H) |

Reference Example 22

2-(2-Amino-4-methoxycarbonylphenyl)-2-cyanoacetamide (Reference compound 22-1)

5% Palladium-activated carbon (80 mg) was added to a solution of 2-cyano-2-(4-methoxycarbonyl-2-nitrophenyl)acetamide (Reference compound 1-5, 1.0 g, 3.8 mmol) in ethanol (10 mL), and the mixture was stirred at room temperature overnight under hydrogen atmosphere (3 kgf/cm$^2$). After the reaction mixture was filtered throught Celite®, the filtrate was concentrated under reduced pressure. The residue was purified by silica gel column chromatography to give the title reference compound (0.42 g) as a brown solid (yield 47%).

| | |
|---|---|
| 2-(2-Amino-4-methoxycarbonylphenyl)-2-cyanoacetamide (Reference compound 22-1) 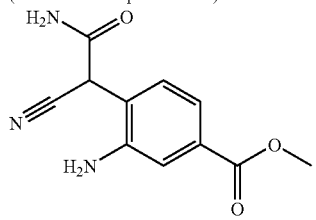 | $^1$H-NMR (400 MHz, DMSO-$d_6$) δ 3.82 (s, 3H), 5.13 (s, 1H), 5.63 (s, 2H), 7.19 (dd, J = 8.1, 1.8 Hz, 1H), 7.28 (d, J = 8.1 Hz, 1H), 7.37 (d, J = 1.8 Hz, 1H), 7.64 (s, 1H), 7.76 (s, 1H) |

Reference Example 23

2-Amino-6-trifluoromethylindole-3-carboxamide
(Reference compound 23-1)

1,4-Dioxane (40 mL) was added to 2-(2-amino-4-trifluoromethylphenyl)-2-cyanoacetamide (Reference compound 21-1, 0.98 g, 4.0 mmol), and the mixture was stirred at 100° C. for 36 hours. After the solvent was evaporated under reduced pressure, the residue was purified by silica gel column chromatography to give the title reference compound (0.50 q) as a brown solid (yield 51%).

| | |
|---|---|
| 2-Amino-6-trifluoromethylindole-3-carboxamide (Reference compound 23-1) 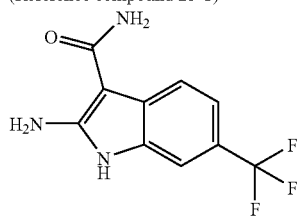 | $^1$H-NMR (400 MHz, DMSO-$d_6$) δ 6.64 (s, 2H), 7.10 (s, 2H), 7.20 (ddd, J = 8.3, 1.6, 0.7 Hz, 1H), 7.40 (dd, J = 1.6, 0.7 Hz, 1H), 7.69 (d, J = 8.3 Hz, 1H), 10.84 (s, 1H) |

As described below, Reference compound 23~23-4 were obtained according to the preparation method of Reference compound 23-1 by using Reference compound 21-2, 21-3 or 22-1.

| | |
|---|---|
| 2-Amino-6-methoxycarbonylindole-3-carboxamide (Reference compound 23-2) 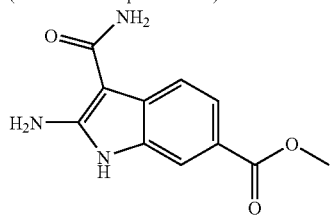 | $^1$H-NMR (400 MHz, DMSO-$d_6$) δ 3.81 (s, 3H), 6.63 (s, 2H), 7.13 (s, 2H), 7.57-7.60 (m, 2H), 7.72 (d, J = 0.7 Hz, 1H), 10.81 (s, 1H) |
| 2-Amino-6-chloroindole-3-carboxamide (Reference compound 23-3) 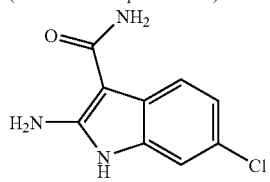 | $^1$H-NMR (400 MHz, DMSO-$d_6$) δ 6.51 (s, 2H), 6.90 (s, 2H), 6.91 (dd, J = 8.4, 2.1 Hz, 1H), 7.14 (d, J = 2.1 Hz, 1H), 7.52 (d, J = 8.4 Hz, 1H), 10.66 (s, 1H) |

| | |
|---|---|
| 2-Amino-6-fluoroindole-3-carboxamide (Reference compound 23-4)  | $^1$H-NMR (400 MHz, DMSO-$d_6$) δ 6.47 (s, 2H), 6.73 (ddd, J = 10.1, 8.3, 2.3 Hz, 1H), 6.80 (s, 2H), 6.92 (dd, J = 10.1, 2.3 Hz, 1H), 7.48 (dd, J = 8.3, 5.1 Hz, 1H), 10.63 (s, 1H) |

Reference Example 24

N-(5-Bromo-2-furoyl)-2-hydroxyethylamine (Reference compound 24-1)

O-(7-Azabenzotriazol-1-yl)-N,N,N',N'-tetramethyluronium hexafluorophosphate (0.66 g, 1.7 mmol), N,N-diisopropylethylamine (0.82 mL, 4.7 mmol) and 2-aminoethanol (0.14 mL, 2.4 mmol) were added to a solution of 5-bromo-2-furoic acid (0.30 g, 1.6 mmol) in dichloromethane (15 mL), and the mixture was stirred at room temperature overnight. After the reaction mixture was concentrated under reduced pressure, water (5 mL) was added thereto. The whole was extracted with ethyl acetate (10 mL), and the organic layer was washed with brine (5 mL) and dried over anhydrous magnesium sulfate. After the solvent was evaporated under reduced pressure, the residue was purified by silica gel column chromatography to give the title reference compound (0.18 g) as a colorless solid (yield 49%).

Reference Example 25

1-(3-Bromophenyl)cyclopropanecarbonitrile (Reference compound 25-1)

3-Bromophenylacetonitrile (5.0 g, 26 mmol) and 1,2-dibromoethane (6.6 mL, 77 mmol) were added to a solution of benzyltriethylammonium chloride (0.30 g, 1.3 mmol) in 50% sodium hydroxide aqueous solution (20 mL), and the mixture was stirred at room temperature overnight. Ice-water (70 mL) was added to the reaction mixture, and the whole was extracted with ethyl acetate (50 mL). The organic layer was washed with brine (30 mL), and dried over anhydrous magnesium sulfate. After the solvent was evaporated under reduced pressure, the residue was purified by silica gel column chromatography to give the title reference compound (5.4 q) as brown oil (yield 95%).

| | |
|---|---|
| N-(5-Bromo-2-furoyl)-2-hydroxyethylamine (Reference compound 24-1) 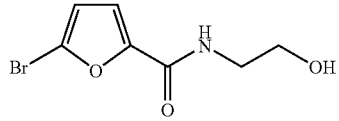 | $^1$H-NMR (400 MHz, CDCl$_3$) δ 2.37 (t, J =5.4 Hz, 1H), 3.60 (td, J =5.4, 4.8Hz, 2H), 3.83 (q, J = 4.8 Hz, 2H), 6.45 (d, J = 3.7 Hz, 1H), 6.72 (s, 1H), 7.08 (d, J = 3.7 Hz, 1H) |

As described below, Reference compound 24-2 and 24-3 were obtained according to the preparation method of Reference compound 24-1 by using commercially available reagents.

| | |
|---|---|
| N-(5-Bromo-2-furoyl)-2-methoxyethylamine (Reference compound 24-2) 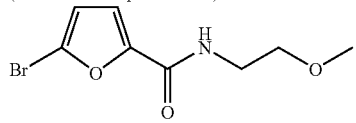 | $^1$H-NMR (500 MHz, CDCl$_3$) δ 3.40 (s, 3H), 3.54-3.56 (m, 2H), 3.59-3.63 (m, 2H), 6.43 (d, J = 3.7 Hz, 1H), 6.66 (s, 1H), 7.06 (d, J = 3.7 Hz, 1H) |
| N-(5-Bromo-2-furoyl)-2-morpholinoethylamine (Reference compound 24-3) 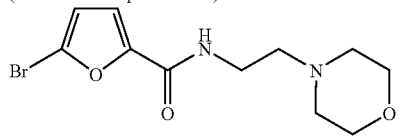 | $^1$H-NMR (400 MHz, CDCl$_3$) δ 2.50 (t, J = 4.8 Hz, 4H), 2.58 (t, J = 6.1 Hz, 2H), 3.48-3.53 (m, 2H), 3.74 (t, J = 4.8 Hz, 4H); 6.44 (d, J = 3.7 Hz, 1H), 6.79 (s, 1H), 7.05 (d, J = 3.7 Hz, 1H) |

| 1-(3-Bromophenyl)cyclopropanecarbonitrile (Reference compound 25-1) 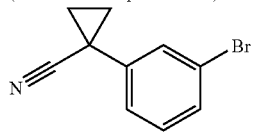 | $^1$H-NMR (400 MHz, CDCl$_3$) δ 1.40-1.43 (m, 2H), 1.74-1.77 (m, 2H), 7.20-7.28 (m, 2H), 7.40-7.44 (m, 2H) |
|---|---|

As described below, Reference compound 25-2 was obtained according to the preparation method of Reference compound 25-1 by using commercially available reagents.

| 1-(4-Bromophenyl)cyclopropanecarbonitrile (Reference compound 25-2) 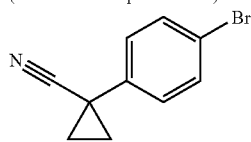 | $^1$H-NMR (500 MHz, CDCl$_3$) δ 1.37-1.40 (m, 2H), 1.73-1.76 (m, 2H), 7.17 (dd, J = 6.7, 2.1 Hz, 2H), 7.48 (dd, J = 6.7, 2.1 Hz, 2H) |
|---|---|

Reference Example 26

1-(3-Bromophenyl)cyclopropanecarboxylic acid (Reference compound 26-1)

1-(3-Bromophenyl)cyclopropanecarbonitrile (Reference compound 25-1, 5.0 g, 23 mmol) and ethylene glycol (20 mL) were added to a solution of potassium hydroxide (3.7 g, 66 mmol) in water (20 mL). The mixture was stirred at 140° C. for 4 hours. The reaction mixture was poured into a solution mixture of ice-water mL) and 6 N hydrochloric acid (50 mL). The precipitated solid was separated by filtration and dried under reduced pressure to give the title reference compound (4.7 q) as a brown solid (yield 87%).

Reference Example 27 tert-Butyl N-[1-(3-bromophenyl)cyclopropyl]carbamate (Reference compound 26-1)

Diphenylphosphoryl azide (1.5 mL, 6.8 mmol) and triethylamine (0.95 mL, 6.8 mmol) were added to a solution of 1-(3-bromophenyl)cyclopropanecarboxylic acid (Reference compound 26-1, 1.5 g, 6.2 mmol) in tert-butylalcohol (30 mL), and the mixture was stirred at 95° C. overnight. After the reaction mixture was concentrated under reduced pressure, water (25 mL) was added thereto and the whole was extracted with ethyl acetate (25 mL). The organic layer was washed with a 10% citric acid aqueous solution (25 mL), water (25 mL), saturated sodium hydrogen carbonate aqueous solution (25 mL), water (25 mL), and brine (25 mL), and dried over anhydrous magnesium sulfate. After the solvent was evaporated under reduced pressure, the residue was purified by silica gel column chromatography to give the title reference compound (0.95 g) as a slightly brown oil (yield 50%).

| 1-(3-Bromophenyl)cyclopropanecarboxylic acid (Reference compound 26-1) 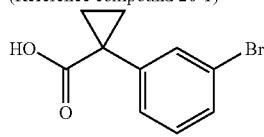 | $^1$H-NMR (400 MHz, CDCl$_3$) δ 1.26 (dd, J = 7.2, 4.3 Hz, 2H), 1.68 (dd, J = 7.2, 4.3 Hz, 2H), 7.18 (t, J = 7.8 Hz, 1H), 7.28 (ddd, J = 7.8, 1.7, 1.0 Hz, 1H), 7.39 (ddd, J = 7.8, 1.7, 1.0 Hz, 1H), 7.49 (t, J = 1.7 Hz, 1H) |
|---|---|

As described below, Reference compound 26-2 was obtained according to the preparation method of Reference compound 26-1 by using Reference compound 25-2.

| 1-(4-Bromophenyl)cyclopropanecarboxylic acid (Reference compound 26-2) 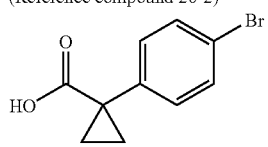 | $^1$H-NMR (500 MHz, CDCl$_3$) δ 1.23 (dd, J = 7.3, 4.0 Hz, 2H), 1.67 (dd, J = 7.3, 4.0 Hz, 2H), 7.22 (dd, J = 6.6, 1.8 Hz, 2H), 7.43 (dd, J = 6.6, 1.8 Hz, 2H) |
|---|---|

| | |
|---|---|
| tert-Butyl N-[1-(3-bromophenyl)cyclopropyl]carbamate (Reference compound 27-1) 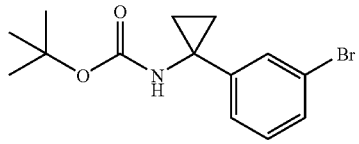 | $^1$H-NMR (500 MHz, CDCl$_3$) δ 1.22-1.29 (m, 4H), 1.44 (s, 9H), 5.25 (s, 1H), 7.13-7.15 (m, 2H), 7.31 (dt, J = 7.2, 1.7 Hz, 1H), 7.35 (s, 1H) |

As described below, Reference compound 27-2 was obtained according to the preparation method of Reference compound 27-1 by using Reference compound 26-2.

| | |
|---|---|
| tert-Butyl N[1-(4-bromophenyl)cyclopropyl]carbamate (Reference compound 27-2) 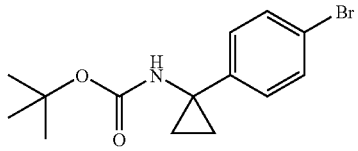 | $^1$H-NMR (400 MHz, CDCl$_3$) δ 1.18-1.20 (m, 2H), 1.25-1.28 (m, 2H), 1.43 (s, 9H), 5.23 (s, 1H), 7.10 (dd, J = 6.4, 2.0 Hz, 2H), 7.40 (dd, J = 6.4, 2.0 Hz, 2H) |

Reference Example 28 tert-Butyl N-[1-(3-bromophenyl)-1-methylethyl]carbamate (Reference compound 28-1)

Anhydrous tetrahydrofuran (60 mL) was added to cerium chloride (III) (13 g, 52 mmol), and the whole was stirred at room temperature overnight. 1 M Methyllithium in diethyl ether solution (52 mL, 52 mmol) was added to this suspension dropwise under dry ice/acetone cooling, and the mixture was stirred for 30 minutes. And then, a solution of 3-bromobenzonitrile (3.2 g, 17 mmol) in anhydrous tetrahydrofuran (30 mL) was added to the reaction mixture dropwise, and the whole was stirred for 4 hours under dry ice/acetone-cooling. 28% ammonia aqueous solution (50 mL) was added to the reaction mixture, and the whole was stirred at room temperature. The resultant insoluble solid was removed by filtration throught Celite® pad, the filtrate was extracted with ethyl acetate (40 mL). The organic layer was washed with water (50 mL) and brine (40 mL), and dried over anhydrous magnesium sulfate. After the solvent was evaporated under reduced pressure, a solution of di-tert-butyl dicarbonate (4.0 g, 18 mmol) in toluene (15 mL) was added to the residue, and the mixture was stirred at 100° C. for 1.5 hours. 10% Citric acid aqueous solution (20 mL) was added to the reaction mixture, and the whole was extracted with ethyl acetate (20 mL). The organic layer was washed with water (40 mL) and brine (30 mL), and dried over anhydrous magnesium sulfate. After the solvent was evaporated under reduced pressure, the residue was purified by silica gel column chromatography to give the title reference compound (4.6 g) as a yellow oil (yield 86%).

| | |
|---|---|
| tert-Butyl N-[1-(3-bromophenyl)-1-methylethyl]carbamate (Reference compound 28-1) 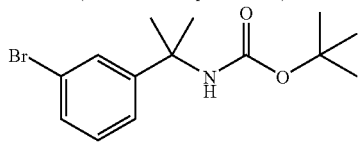 | $^1$H-NMR (400 MHz, CDCl$_3$) δ 1.39 (s, 9H), 1.59 (s, 6H), 4.93 (s, 1H), 7.18 (t, J = 7.9 Hz, 1H), 7.30-7.35 (m, 2H), 7.53 (t, J = 1.8 Hz, 1H) |

As described below, Reference compound 28-2 was obtained according to the preparation method of Reference compound 28-1 by using commercially available reagents.

| | |
|---|---|
| tert-Butyl N-[1-(4-bromophenyl)-1-methylethyl]carbamate (Reference compound 28-2) 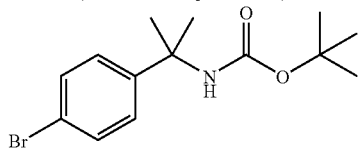 | $^1$H-NMR (400 MHz, DMSO-d$_6$) δ 1.33 (s, 9H), 1.46 (s, 6H), 7.07 (d, J = 8.0 Hz, 1H), 7.19 (d, J = 8.0 Hz, 1H), 7.23 (br s, 1H), 7.27 (d, J = 8.5 Hz, 1H), 7.46 (d, J = 8.5 Hz, 1H) |

Reference Example 29 tert-Butyl N-[1-(3-bromophenyl)ethyl]-N-cyclopropylcarbamate (Reference compound 29-1)

Cyclopropylamine (2.9 mL, 42 mmol) was added to a solution of 3-bromoacetophenone (2.0 g, 10 mmol) in anhydrous methanol (10 mL), and the mixture was stirred at 50° C. overnight. After the reaction mixture was concentrated under reduced pressure, sodium borohydride (0.57 g, 15 mmol) was added to a solution of the residue in anhydrous methanol (10 mL). The mixture was stirred at room temperature for 3 hours, and was concentrated under reduced pressure. Water (20 mL) was added to the residue, and the whole was extracted with ethyl acetate (20 mL). The organic layer was washed with water (20 mL), brine (20 mL), and dried over anhydrous magnesium sulfate. After the solvent was evaporated under reduced pressure, a solution of di-tert-butyl dicarbonate (2.2 g, 10 mmol) in tetrahydrofuran (10 mL) was added to the residue and the mixture was stirred at room temperature overnight. 10% Citric acid aqueous solution (20 mL) was added to the reaction mixture, and the whole was extracted with ethyl acetate (20 mL). The organic layer was washed with water (20 mL), saturated sodium hydrogen carbonate aqueous solution (20 mL), water (10 mL), brine (20 mL), and dried over anhydrous magnesium sulfate. The solvent was evaporated under reduced pressure to give the title reference compound (3.1 g) as a colorless oil (yield 92%).

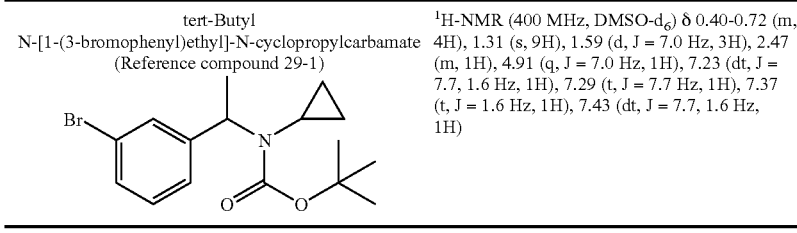

| tert-Butyl N-[1-(3-bromophenyl)ethyl]-N-cyclopropylcarbamate (Reference compound 29-1) | $^1$H-NMR (400 MHz, DMSO-$d_6$) δ 0.40-0.72 (m, 4H), 1.31 (s, 9H), 1.59 (d, J = 7.0 Hz, 3H), 2.47 (m, 1H), 4.91 (q, J = 7.0 Hz, 1H), 7.23 (dt, J = 7.7, 1.6 Hz, 1H), 7.29 (t, J = 7.7 Hz, 1H), 7.37 (t, J = 1.6 Hz, 1H), 7.43 (dt, J = 7.7, 1.6 Hz, 1H) |

As described below, Reference compound 29-2 was obtained according to the preparation method of Reference compound 29-1 by using commercially available reagents.

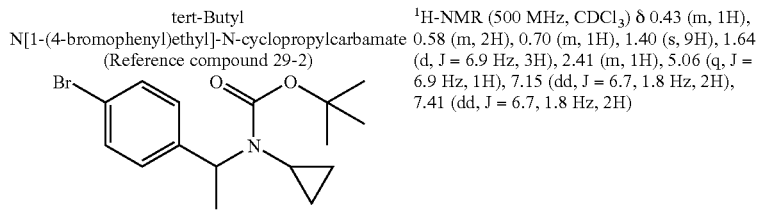

| tert-Butyl N[1-(4-bromophenyl)ethyl]-N-cyclopropylcarbamate (Reference compound 29-2) | $^1$H-NMR (500 MHz, CDCl$_3$) δ 0.43 (m, 1H), 0.58 (m, 2H), 0.70 (m, 1H), 1.40 (s, 9H), 1.64 (d, J = 6.9 Hz, 3H), 2.41 (m, 1H), 5.06 (q, J = 6.9 Hz, 1H), 7.15 (dd, J = 6.7, 1.8 Hz, 2H), 7.41 (dd, J = 6.7, 1.8 Hz, 2H) |

Reference Example 30 tert-Butyl N-[2-(4-bromophenyl)ethyl]carbamate (Reference compound 30-1)

A solution of di-tert-butyl dicarbonate (0.36 g, 1.6 mmol) in tetrahydrofuran (5 mL) was added to a solution of 4-bromophenethylamine (0.30 g, 1.5 mmol) in tetrahydrofuran (10 mL), and the mixture was stirred at room temperature for 1.5 hours. After the reaction mixture was concentrated, the resultant solid was washed with hexane (3 mL), and dried under reduced pressure to give the title Reference compound (0.23 g) as a colorless solid (yield 50%).

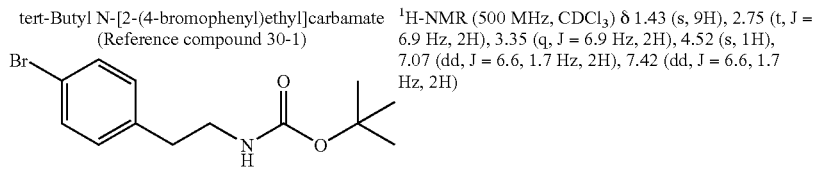

| tert-Butyl N-[2-(4-bromophenyl)ethyl]carbamate (Reference compound 30-1) | $^1$H-NMR (500 MHz, CDCl$_3$) δ 1.43 (s, 9H), 2.75 (t, J = 6.9 Hz, 2H), 3.35 (q, J = 6.9 Hz, 2H), 4.52 (s, 1H), 7.07 (dd, J = 6.6, 1.7 Hz, 2H), 7.42 (dd, J = 6.6, 1.7 Hz, 2H) |

As described below, Reference compound 30-2~30-5 were obtained according to the preparation method of Reference compound 30-1 by using commercially available reagents.

| Compound | NMR |
|---|---|
| 1-tert-Butoxycarbonyl-4-(4-bromophenyl)piperazine (Reference compound 30-2) 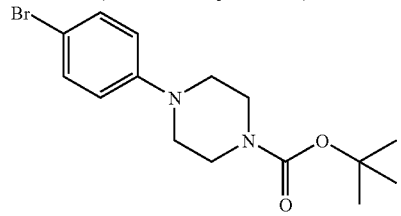 | ¹H-NMR (400 MHz, CDCl₃) δ 1.48 (s, 9H), 3.10 (t, J = 5.1 Hz, 4H), 3.57 (t, J = 5.1 Hz, 4H), 6.79 (dd, J = 7.0, 2.3 Hz, 2H), 7.35 (dd, J = 7.0, 2.3 Hz, 2H) |
| tert-Butyl N-(4-bromobenzyl)carbamate (Reference compound 30-3) 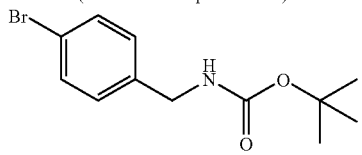 | ¹H-NMR (400 MHz, CDCl₃) δ 1.46 (s, 9H), 4.26 (d, J = 5.6 Hz, 2H), 4.84 (s, 1H), 7.16 (dd, J = 6.4, 2.0 Hz, 2H), 7.45 (dd, J = 6.4, 2.0 Hz, 2H) |
| tert-Butyl N-(3-bromobenzyl)carbamate (Reference compound 30-4) 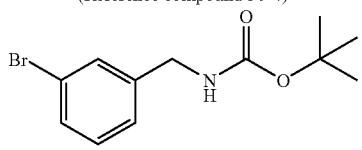 | ¹H-NMR (400 MHz, CDCl₃) δ 1.46 (s, 9H), 4.29 (d, J = 5.5 Hz, 2H), 4.86 (s, 1H), 7.18-7.21 (m, 2H), 7.39 (dt, J = 7.0, 1.7 Hz, 1H), 7.43 (t, J = 1.7 Hz, 1H) |
| tert-Butyl N[1-(4-bromophenyl)ethyl]carbamate (Reference compound 30-5) 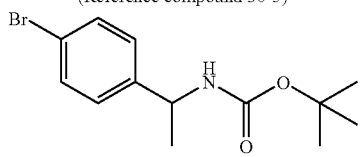 | ¹H-NMR (500 MHz, CDCl₃) δ 1.43-1.46 (m, 12H), 4.74-476 (m, 2H), 7.18 (dd, J = 6.6, 2.0 Hz, 2H), 7.45 (dd, J = 6.6, 2.0 Hz, 2H) |

Reference Example 31

N-Acetyl-N-(3-bromo2-methyl)phenylhydroxylamine (Reference compound 31-1)

Hydrazine monohydrate (4.9 mL, 100 mmol) was added to a solution mixture of 2-bromo-6-nitrotoluene (11 g, 50 mmol) and 10% palladium-activated carbon (0.24 g) in tetrahydrofuran and ethanol (1:1, 200 mL) under ice-cooling, and the mixture was stirred at room temperature for 10 hours. After the reaction mixture was filtered throught Celite® pad, the solvent was evaporated under reduced pressure. Acetyl chloride (5.4 mL, 76 mmol) was added to a suspension of the resultant residue and sodium hydrogen carbonate (13 g, 150 mmol) in N,N-dimethylformamide (50 mL) under ice-cooling, and the mixture was stirred at room temperature overnight. Water (200 mL) was added to the reaction mixture, and the whole was extracted with ethyl acetate (200 mL). The organic layer was washed with brine (100 mL), and dried over anhydrous magnesium sulfate. After the solvent was evaporated under reduced pressure, the residue was purified by silica gel column chromatography to give the title reference compound (6.5 g) as a orange color oil (yield 53%).

| Compound | NMR |
|---|---|
| N-Acetyl-N-(3-bromo-2-methyl)phenylhydroxylamine (Reference compound 31-1) 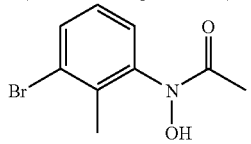 | ¹H-NMR (400 MHz, DMSO-d₆) δ 2.21 (s, 3H), 2.21 (s, 3H), 7.21 (t, J = 7.6 Hz, 1H), 7.32 (d, J = 7.6 Hz, 1H), 7.61 (d, J = 7.6 Hz, 1H), 10.67 (s, 1H) |

Example 1

2-Aminocarbonylamino-6-bromo-1-hydroxyindole-3-carboxamide (Compound 1-1)

Trichloroacetyl isocyanate (0.10 mL, 0.85 mmol) was added to a solution of 2-amino-6-bromo-1-hydroxyindole-3-carboxamide (Reference compound 2-1, 180 mg, 0.71 mmol) in acetonitrile (5 mL), and the mixture was stirred at room temperature for 5 hours. 2.0 M Ammonia in methanol solution (4.5 mL, 9.0 mmol) was added thereto, and the mixture was stirred at room temperature for 18 hours. The reaction mixture was concentrated under reduced pressure, 1 N hydrochloric acid (6 mL) and water (25 mL) was added to the residue and the whole was extracted with ethyl acetate (20 mL). The organic layer was washed with water (20 mL) and brine (20 mL), and dried over anhydrous magnesium sulfate. After the solvent was evaporated under reduced pressure, the resultant solid was washed with diethyl ether (10 mL), and dried under reduced pressure to give the title compound (90 mg) as a slightly brown solid (yield 42%).

Example 2

6-Acetylamino-2-aminocarbonylaminoindole-3-carboxamide (Compound 2-1)

Trichloroacetyl isocyanate (48 μL, 0.36 mmol) was added to a solution of 6-acetylamino-2-aminoindole-3-carboxamide (Reference compound 15-1, 26 mg, 0.11 mmol) in anhydrous tetrahydrofuran (1.5 mL), and the mixture was stirred at room temperature for 18 hours. 2.0 M Ammonia in methanol solution (2.0 mL, 4.0 mmol) was added thereto, and the mixture was stirred at room temperature for 6 hours. The precipitated solid was separated by filtration using methanol (0.5 mL), and dried under reduced pressure to give the title compound (13 mg) as a colorless solid (yield 43%).

| | |
|---|---|
| 2-Aminocarbonylamino-6-bromo-1-hydroxyindole-3-carboxamide (Compound 1-1) 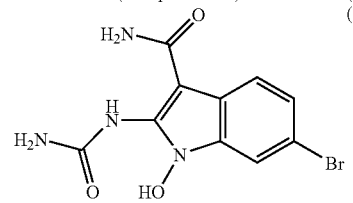 | $^1$H-NMR (400 MHz, DMSO-$d_6$) δ 6.98 (s, 2H), 7.17 (s, 2H), 7.24 (dd, J = 8.3, 1.7 Hz, 1H), 7.49 (d, J = 1.7 Hz, 1H), 7.88 (d, J = 8.3 Hz, 1H), 9.43 (s, 1H), 11.87 (s, 1H) |

As described below, Compound 1-2 and 1-3 were obtained according to the preparation method of Compound 1-1 by using Reference compound 2-3 or 2-4.

| | |
|---|---|
| 2-Aminocarbonylamino-5-methylindole-3-carboxamide (Compound 1-2) 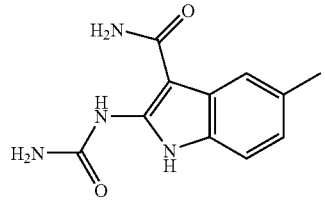 | $^1$H-NMR (400 MHz, DMSO-$d_6$) δ 2.35 (s, 3H), 6.80 (dd, J = 8.3, 1.0 Hz, 1H), 6.85 (s, 2H), 6.98 (br s, 2H), 7.37 (d, J = 8.3 Hz, 1H), 7.54 (s, 1H), 10.50 (s, 1H), 11.49 (s, 1H) |
| 2-Aminocarbonylamino-6-methylindole-3-carboxamide (Compound 1-3) 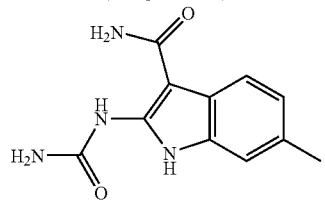 | $^1$H-NMR (400 MHz, DMSO-$d_6$) δ 2.34 (s, 3H), 6.83 (s, 2H), 6.86 (dd, J = 8.1, 1.2 Hz, 1H), 6.95 (br s, 2H), 7.30 (s, 1H), 7.61 (d, J = 8.1 Hz, 1H), 10.49 (s, 1H), 11.48 (s, 1H) |

| Compound | NMR |
|---|---|
| 6-Acetylamino-2-aminocarbonylaminoindole-3-carboxamide (Compound 2-1) 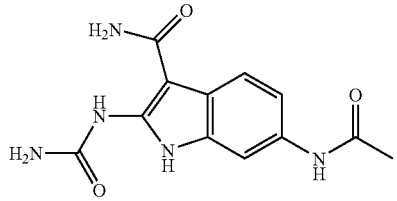 | ¹H-NMR (500 MHz, DMSO-d₆) δ 2.03 (s, 3H), 6.85 (s, 2H), 6.93 (br s, 2H), 7.21 (dd, J = 8.6, 1.8 Hz, 1H), 7.62 (d, J = 8.6 Hz, 1H), 7.82 (d, J = 1.8 Hz, 1H), 9.74 (s, 1H), 10.41 (s, 1H), 11.49 (s, 1H) |

As described below, Compound 2-2~2-19 were obtained according to the preparation method of Compound 2-1 by using Reference compound 15-2~15-8, 16-1, 18-1, 18-2, 19-1, 19-2, 20-1, 20-2 or 23-1~234.

| Compound | NMR |
|---|---|
| 2-Aminocarbonylamino-6-benzoylaminoindole-3-carboxamide (Compound 2-2) 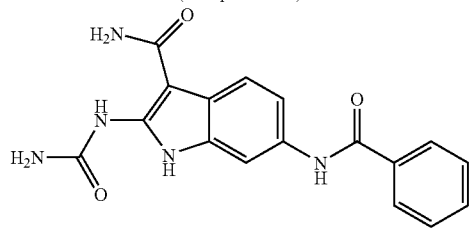 | ¹H-NMR (400 MHz, DMSO-d₆) δ 6.90 (s, 2H), 6.99 (br s, 2H), 7.37 (dd, J = 8.5, 2.0 Hz, 1H), 7.50-7.58 (m, 4H), 7.69 (d, J = 8.5 Hz, 1H), 7.95-8.00 (m, 2H), 10.16 (s, 1H), 10.50 (s, 1H), 11.63 (s, 1H) |
| 2-Aminocarbonylamino-6-(3-phenylureido)indole-3-carboxamide (Compound 2-3) 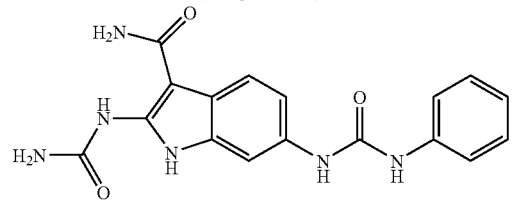 | ¹H-NMR (500 MHz, DMSO-d₆) δ 6.85 (s, 2H), 6.90 (br s, 2H), 6.95 (t, J = 7.3 Hz, 1H), 7.17 (dd, J = 8.6, 2.1 Hz, 1H), 7.27 (t, J = 7.3 Hz, 2H), 7.45 (d, J = 8.6 Hz, 2H), 7.60 (d, J = 2.1 Hz, 1H), 7.63 (d, J = 8.6 Hz, 1H), 8.49 (s, 1H), 8.54 (s, 1H), 10.47 (s, 1H), 11.52 (s, 1H) |
| 2-Aminocarbonylamino-6-dimethylaminoindole-3-carboxamide (Compound 2-4) 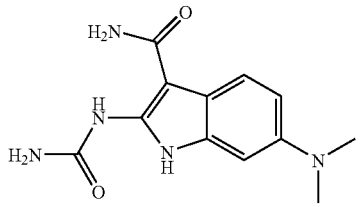 | ¹H-NMR (400 MHz, DMSO-d₆) δ 2.84 (s, 6H), 6.62 (dd, J = 8.5, 2.2 Hz, 1H), 6.76 (s, 2H), 6.93 (br s, 2H), 6.97 (d, J = 2.2 Hz, 1H), 7.55 (d, J = 8.5 Hz, 1H), 10.39 (s, 1H), 11.27 (s, 1H) |
| 2-Aminocarbonylamino-6-(pyrrolidin-1-yl)indole-3-carboxamide (Compound 2-5) 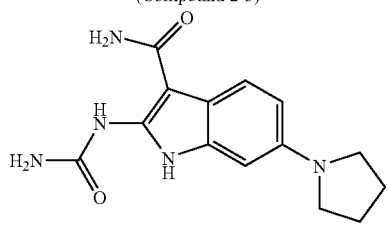 | ¹H-NMR (500 MHz, DMSO-d₆) δ 1.94-1.97 (m, 4H), 3.18-3.21 (m, 4H), 6.41 (dd, J = 8.6, 2.1 Hz, 1H), 6.72 (s, 2H), 6.75 (d, J = 2.1 Hz, 1H), 6.90 (br s, 2H), 7.52 (d, J = 8.6 Hz, 1H), 10.38 (s, 1H), 11.20 (s, 1H) |

| | |
|---|---|
| 2-Aminocarbonylamino-6-(2-oxopyrrolidin-1-yl)indole-3-carboxamide (Compound 2-6) 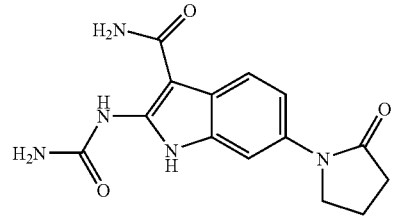 | $^1$H-NMR (400 MHz, DMSO-d$_6$) δ 2.03-2.11 (m, 2H), 2.49-2.51 (m, 2H), 3.83 (t, J = 7.1 Hz, 2H), 6.90 (s, 2H), 6.98 (br s, 2H), 7.35 (dd, J = 8.8, 2.0 Hz, 1H), 7.69 (d, J = 8.8 Hz, 1H), 7.76 (d, J = 2.0 Hz, 1H), 10.49 (s, 1H), 11.62 (s, 1H) |
| 2-Aminocarbonylamino-6-(diphenylsulfonylamino)indole-3-carboxamide (Compound 2-7) 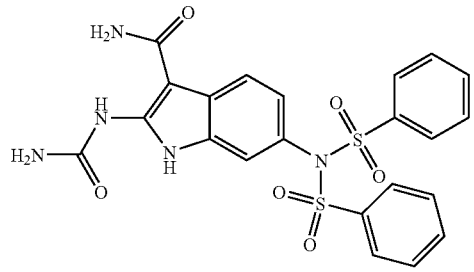 | $^1$H-NMR (500 MHz, DMSO-d$_6$) δ 6.56 (dd, J = 8.6, 2.1 Hz, 1H), 6.98-7.02 (m, 4H), 7.30 (d, J = 2.1 Hz, 1H), 7.68-7.71 (m, 5H), 7.79-7.85 (m, 6H), 10.55 (s, 1H), 11.87 (s, 1H) |
| 2-Aminocarbonylamino-6-(2,5-dimethylpyrrol-1-yl)indole-3-carboxamide (Compound 2-8) 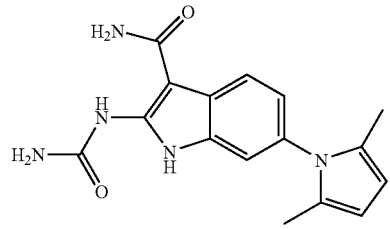 | $^1$H-NMR (500 MHz, DMSO-d$_6$) δ 1.94 (s, 6H), 5.77 (s, 2H), 6.86 (dd, J = 8.2, 1.8 Hz, 1H), 6.99 (s, 2H), 7.04 (br s, 2H), 7.37 (d, J = 1.8 Hz, 1H), 7.81 (d, J = 8.2 Hz, 1H), 10.54 (s, 1H), 11.78 (s, 1H) |
| 2-Aminocarbonylamino-6-(pyrrol-1-yl)indole-3-carboxamide (Compound 2-9) 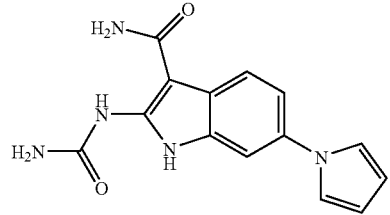 | $^1$H-NMR (400 MHz, DMSO-d$_6$) δ 6.24 (t, J = 2.2 Hz, 2H), 6.97 (s, 2H), 7.05 (br s, 2H), 7.20-7.21 (m, 2H), 7.23 (d, J = 2.2 Hz, 1H), 7.65 (d, J = 2.2 Hz, 1H), 7.80 (d, J = 8.8 Hz, 1H), 10.52 (s, 1H), 11.73 (s, 1H) |
| 2-Aminocarbonylaminoindole-3-carboxamide (Compound 2-10) 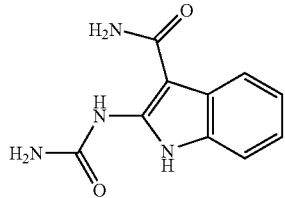 | $^1$H-NMR (500 MHz, DMSO-d$_6$) δ 6.89 (br s, 4H), 6.98 (td, J = 7.8, 1.2 Hz, 1H), 7.03 (td, J = 7.8, 1.2 Hz, 1H), 7.51 (d, J = 7.8 Hz, 1H), 7.72 (d, J = 7.8 Hz, 1H), 10.52 (s, 1H), 11.62 (s, 1H) |

| Compound | NMR |
|---|---|
| 2-Aminocarbonylamino-6-bromo-7-methylindole-3-carboxamide (Compound 2-11) 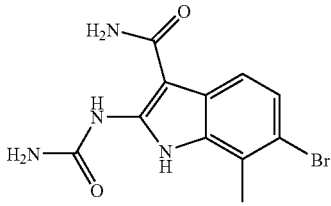 | $^1$H-NMR (500 MHz, DMSO-d$_6$) δ 2.46 (s, 3H), 7.01 (br s, 2H), 7.13 (br s, 2H), 7.24 (d, J = 8.6 Hz, 1H), 7.58 (d, J = 8.6 Hz, 1H), 10.38 (s, 1H), 11.29 (s, 1H) |
| 2-Aminocarbonylamino-1-ethylindole-3-carboxamide (Compound 2-12) 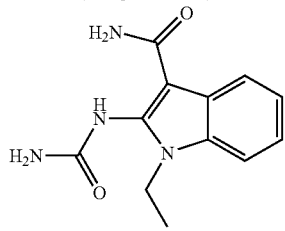 | $^1$H-NMR (400 MHz, DMSO-d$_6$) δ 1.26 (t, J = 7.0 Hz, 3H), 4.12 (q, J = 7.0 Hz, 2H), 6.46 (s, 2H), 7.02 (br s, 2H), 7.12 (td, J = 8.2, 1.2 Hz, 1H), 7.18 (td, J = 8.2, 1.2 Hz, 1H), 7.46 (d, J = 8.2 Hz, 1H), 7.96 (d, J = 8.2 Hz, 1H), 8.73 (s, 1H) |
| 2-Aminocarbonylamino-1-benzylindole-3-carboxamide (Compound 2-13) 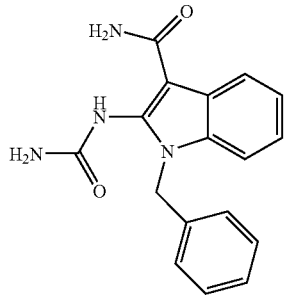 | $^1$H-NMR (400 MHz, DMSO-d$_6$) δ 5.36 (s, 2H), 6.50 (s, 2H), 7.09-7.12 (m, 6H), 7.20-7.29 (m, 3H), 7.34 (m, 1H), 7.97 (m, 1H), 8.87 (s, 1H) |
| 2-Aminocarbonylamino-1-(4-nitrophenyl)indole-3-carboxamide (Compound 2-14) 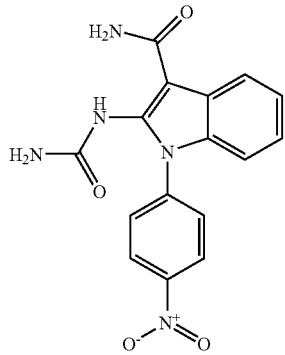 | $^1$H-NMR (500 MHz, DMSO-d$_6$) δ 6.32 (s, 2H), 7.18-7.25 (m, 5H), 7.72 (dd, J = 6.9, 2.0 Hz, 2H), 8.05 (dd, J = 8.2, 1.2 Hz, 1H), 8.43 (dd, J = 6.9, 2.0 Hz, 2H), 8.82 (s, 1H) |

| | |
|---|---|
| 2-Aminocarbonylamino-1-(2-nitrophenyl)indole-3-carboxamide (Compound 2-15) 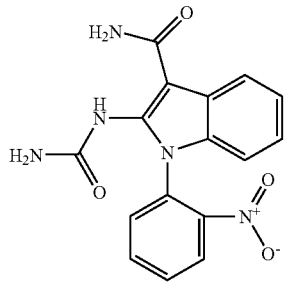 | $^1$H-NMR (500 MHz, DMSO-d$_6$) δ 6.25 (s, 2H), 6.94 (d, J = 7.9 Hz, 1H), 7.14 (td, J = 7.9, 1.2 Hz, 1H), 7.20 (td, J = 7.9, 1.2 Hz, 1H), 7.23 (br s, 2H), 7.63 (dd, J = 7.9, 1.2 Hz, 1H), 7.77 (td, J = 7.9, 1.2 Hz, 1H), 7.93 (td, J = 7.9, 1.2 Hz, 1H), 7.99 (d, J = 7.9 Hz, 1H), 8.24 (dd, J = 7.9, 1.2 Hz, 1H), 8.85 (s, 1H) |
| 2-Aminocarbonylamino-6-trifluoromethylindole-3-carboximide (Compound 2-16) 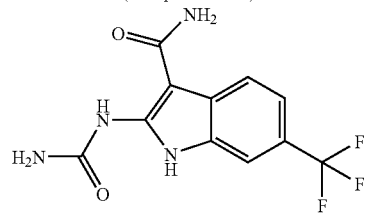 | $^1$H-NMR (500 MHz, DMSO-d$_6$) δ 7.09 (s, 2H), 7.11 (br s, 2H), 7.32 (dd, J = 8.2, 1.2 Hz, 1H), 7.90 (d, J = 1.2 Hz, 1H), 7.92 (d, J = 8.2 Hz, 1H), 10.58 (s, 1H), 12.04 (s, 1H) |
| 2-Aminocarbonylamino-6-methoxycarbonylindole-3-carboxamide (Compound 2-17) 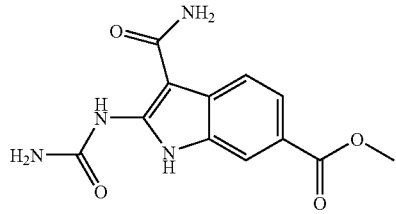 | $^1$H-NMR (400 MHz, DMSO-d$_6$) δ 3.83 (s, 3H), 7.07 (s, 2H), 7.13 (br s, 2H), 7.66 (dd, J = 8.3, 1.7 Hz, 1H), 7.82 (d, J = 8.3 Hz, 1H), 8.19 (d, J = 1.7 Hz, 1H), 10.61 (s, 1H), 11.99 (s, 1H) |
| 2-Aminocarbonylamino-6-chloroindole-3-carboxamide (Compound 2-18) 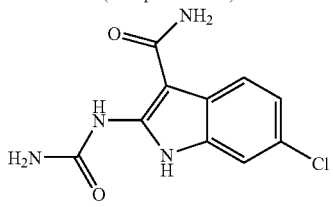 | $^1$H-NMR (400 MHz, DMSO-d$_6$) δ 6.98 (s, 2H), 7.00 br s, 2H), 7.04 (dd, J = 8.5, 2.0 Hz, 1H), 7.57 (d, J = 2.0 Hz, 1H), 7.74 (d, J = 8.5 Hz, 1H), 10.51 (s, 1H), 11.79 (s, 1H) |
| 2-Aminocarbonylamino-6-fluoroindole-3-carboxamide (Compound 2-19) 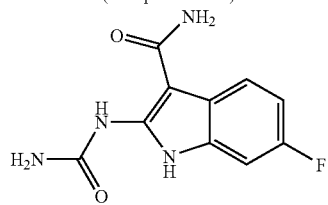 | $^1$H-NMR (500 MHz, DMSO-d$_6$) δ 6.87 (ddd, J = 10.3, 8.3, 2.2 Hz, 1H), 6.94 (s, 2H), 7.02 (br s, 2H), 7.33 (dd, J = 10.3, 2.2 Hz, 1H), 7.71 (dd, J = 8.3, 5.0 Hz, 1H), 10.48 (s, 1H), 11.73 (s, 1H) |

Example 3

2-Aminocarbonylamino-6-bromoindole-3-carboxamide (Compound 3-1)

N-Bromosuccinimide (4.8 g, 27 mmol) was added to a solution of 2-aminocarbonylaminoindole-3-carboxamide (Compound 2-10, 5.9 g, 27 mmol) in anhydrous N,N-dimethylformamide (180 mL) under ice-cooling, and the mixture was stirred at 50° C. for 6 hours. The reaction mixture was poured into ice-water (400 mL) and the whole was extracted with ethyl acetate (500 mL). The organic layer was washed with saturated sodium hydrogen carbonate aqueous solution (200 mL×2), 2 N sodium thiosulfate aqueous solution (200 mL×2), brine (150 mL), and dried over anhydrous magnesium sulfate. After the solvent was evaporated under reduced pressure, the resultant solid was washed with chloroform (40 mL) and dried under reduced pressure to give the title compound (5.4 g) as a slightly brown solid (yield 67%).

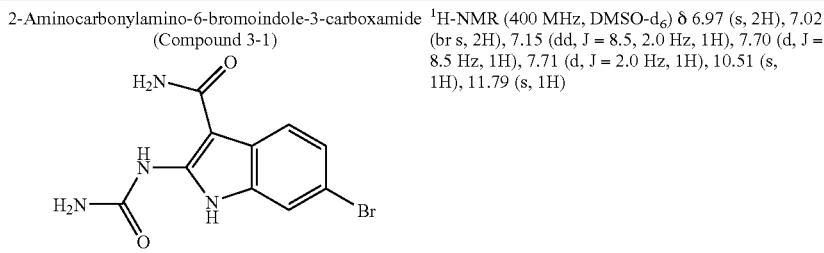

2-Aminocarbonylamino-6-bromoindole-3-carboxamide (Compound 3-1)

$^1$H-NMR (400 MHz, DMSO-$d_6$) δ 6.97 (s, 2H), 7.02 (br s, 2H), 7.15 (dd, J = 8.5, 2.0 Hz, 1H), 7.70 (d, J = 8.5 Hz, 1H), 7.71 (d, J = 2.0 Hz, 1H), 10.51 (s, 1H), 11.79 (s, 1H)

Example 4

2-Aminocarbonylamino-6-(4-fluorophenyl)indole-3-carboxamide (Compound 4-1)

A solution mixture of 2-aminocarbonylamino-6-bromoindole-3-carboxamide (Compound 3-1, 80 mg, 0.27 mmol), sodium hydrogen carbonate (57 mg, 0.68 mmol), 4-fluorophenylboronic acid (57 mg, 0.41 mmol) and tetrakis(triphenylphosphine)palladium (0) (16 mg, 0.014 mmol) in water and 1,4-dioxane (water/1,4-dioxane=1/3, 15 mL) was stirred at 100° C. for 1.5 hours. Brine (5 mL) was added to the reaction mixture, and the whole was extracted with ethyl acetate (5 mL). The organic layer was dried over anhydrous magnesium sulfate and filtered throught Celite® pad. After the solvent was evaporated under reduced pressure, the resultant solid was washed with a solution mixture of methanol and diethyl ether (methanol/diethyl ether=1/10, 2 mL), and dried under reduced pressure to give the title compound (42 mg) as slightly brown solid (yield 51%).

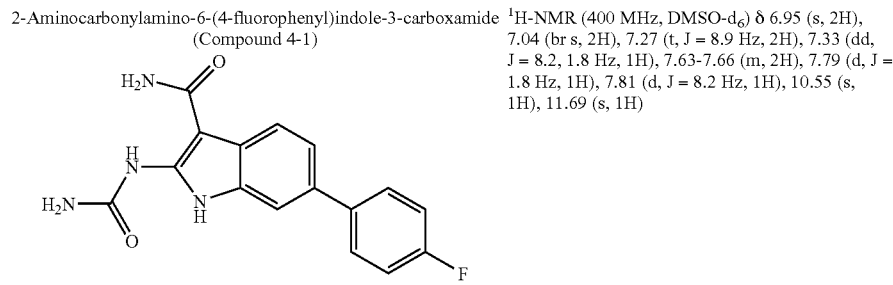

2-Aminocarbonylamino-6-(4-fluorophenyl)indole-3-carboxamide (Compound 4-1)

$^1$H-NMR (400 MHz, DMSO-$d_6$) δ 6.95 (s, 2H), 7.04 (br s, 2H), 7.27 (t, J = 8.9 Hz, 2H), 7.33 (dd, J = 8.2, 1.8 Hz, 1H), 7.63-7.66 (m, 2H), 7.79 (d, J = 1.8 Hz, 1H), 7.81 (d, J = 8.2 Hz, 1H), 10.55 (s, 1H), 11.69 (s, 1H)

As described below, Compound 4-2~4-86 were obtained according to the preparation method of Compound 4-1 by using commercially available reagents, Compound 2-11 and Compound 3-1.

| | |
|---|---|
| 2-Aminocarbonylamino-6-phenylindole-3-carboxamide (Compound 4-2) 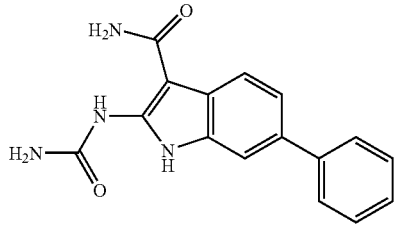 | $^1$H-NMR (500 MHz, DMSO-$d_6$) δ 6.96 (s, 2H), 7.09 (br s, 2H), 7.30 (tt, J = 7.5, 1.2 Hz, 1H), 7.36 (dd, J = 8.2, 1.7 Hz, 1H), 7.45 (t, J = 7.5 Hz, 2H), 7.62-7.65 (m, 2H), 7.82-7.83 (m, 2H), 10.55 (s, 1H), 11.70 (s, 1H) |
| 2-Aminocarbonylamino-6-(2-methoxyphenyl)indole-3-carboxamide (Compound 4-3) 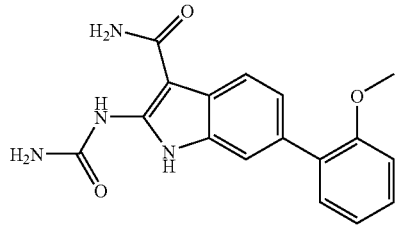 | $^1$H-NMR (400 MHz, DMSO-$d_6$) δ 3.76 (s, 3H), 6.91 (s, 2H), 6.93 (br s, 2H), 7.02 (td, J = 7.6, 1.1 Hz, 1H), 7.09 (d, J = 7.6 Hz, 1H), 7.16 (dd, J = 8.5, 1.5 Hz, 1H), 7.28-7.31 (m, 2H), 7.65 (d, J = 1.5 Hz, 1H), 7.73 (d, J = 8.5 Hz, 1H), 10.53 (s, 1H), 11.62 (s, 1H) |
| 2-Aminocarbonylamino-6-(3-methoxyphenyl)indole-3-carboxamide (Compound 4-4) 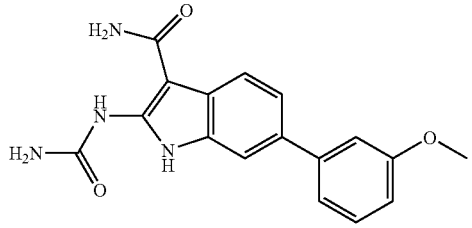 | $^1$H-NMR (400 MHz, DMSO-$d_6$) δ 3.83 (s, 3H), 6.88 (dd, J = 7.8, 2.2 Hz, 1H), 6.95 (s, 2H), 7.03 (s, 2H), 7.15 (t, J = 2.2 Hz, 1H), 7.20 (d, J = 7.8 Hz, 1H), 7.32-7.41 (m, 2H), 7.80 (d, J = 8.3 Hz, 1H), 7.84 (d, J = 1.5 Hz, 1H), 10.54 (s, 1H), 11.69 (s, 1H) |
| 2-Aminocarbonylamino-6-(4-methylphenyl)indole-3-carboxamide (Compound 4-5) 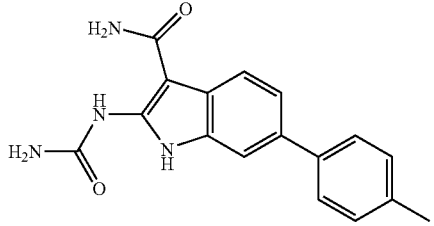 | $^1$H-NMR (400 MHz, DMSO-$d_6$) δ 2.34 (s, 3H), 6.94 (s, 2H), 7.03 (s, 2H), 7.25 (d, J = 8.1 Hz, 2H), 7.33 (dd, J = 8.4, 1.6 Hz, 1H), 7.52 (d, J = 8.1 Hz, 2H), 7.75-7.84 (m, 2H), 10.54 (s, 1H), 11.67 (s, 1H) |
| 2-Aminocarbonylamino-6-(4-methoxyphenyl)indole-3-carboxamide (Compound 4-6) 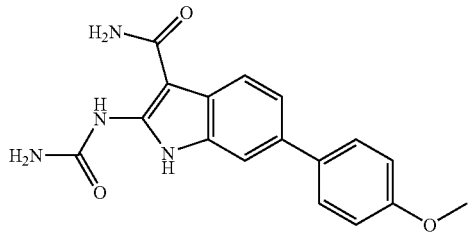 | $^1$H-NMR (400 MHz, DMSO-$d_6$) δ 3.79 (s, 3H), 6.93 (s, 2H), 7.02 (d, J = 9.0 Hz, 2H), 7.05 (br s, 2H), 7.30 (dd, J = 8.3, 1.6 Hz, 1H), 7.55 (d, J = 9.0 Hz, 2H), 7.76 (d, J = 1.6 Hz, 1H), 7.78 (d, J = 8.3 Hz, 1H), 10.53 (s, 1H), 11.64 (s, 1H) |

| | |
|---|---|
| 2-Aminocarbonylamino-6-(4-cyanophenyl)indole-3-carboxamide (Compound 4-7) 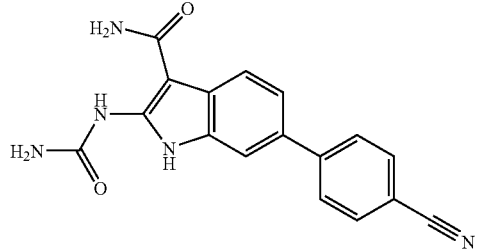 | ¹H-NMR (400 MHz, DMSO-d₆) δ 7.01 (s, 2H), 7.08 (br s, 2H), 7.46 (dd, J = 8.3, 1.7 Hz, 1H), 7.82-7.88 (m, 4H), 7.90 (d, J = 8.3 Hz, 1H), 7.93 (d, J = 1.7 Hz, 1H), 10.57 (s, 1H), 11.79 (s, 1H) |
| 2-Aminocarbonylamino-6-(thiophen-2-yl)indole-3-carboxamide (Compound 4-8) 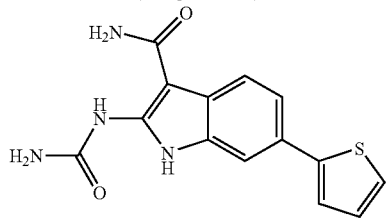 | ¹H-NMR (500 MHz, DMSO-d₆) δ 6.96 (s, 2H), 7.03 (br s, 2H), 7.10 (dd, J = 5.2, 3.7 Hz, 1H), 7.35 (dd, J = 3.7, 1.1 Hz, 1H), 7.36 (dd, J = 8.2, 1.8 Hz, 1H), 7.43 (dd, J = 5.2, 1.1 Hz, 1H), 7.76 (d, J = 8.2 Hz, 1H), 7.83 (d, J = 1.8 Hz, 1H), 10.53 (s, 1H), 11.72 (s, 1H) |
| 2-Aminocarbonylamino-6-(pyridin-3-yl)indole-3-carboxamide (Compound 4-9) 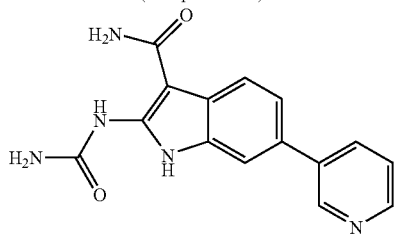 | ¹H-NMR (400 MHz, DMSO-d₆) δ 7.00 (s, 2H), 7.09 (br s, 2H), 7.41 (dd, J = 8.5, 1.7 Hz, 1H), 7.47 (ddd, J = 8.1, 4.6, 1.0 Hz, 1H), 7.87 (d, J = 8.5 Hz, 1H), 7.88 (s, 1H), 8.02 (ddd, J = 8.1, 2.4, 1.7 Hz, 1H), 8.51 (dd, J = 4.6, 1.7 Hz, 1H), 8.86 (dd, J = 2.4, 1.0 Hz, 1H), 10.56 (s, 1H), 11.76 (s, 1H) |
| 2-Aminocarbonylamino-6-(2-fluorophenyl)indole-3-carboxamide (Compound 4-10) 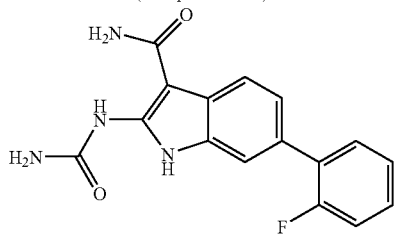 | ¹H-NMR (400 MHz, DMSO-d₆) δ 6.98 (s, 2H), 7.02 (br s, 2H), 7.23 (dt, J = 8.3, 1.5 Hz, 1H), 7.27-7.31 (m, 2H), 7.36 (m, 1H), 7.51 (td, J = 8.3, 1.5 Hz, 1H), 7.74 (t, J = 1.5 Hz, 1H), 7.83 (d, J = 8.3 Hz, 1H), 10.56 (s, 1H), 11.75 (s, 1H) |
| 2-Aminocarbonylamino-6-(3-fluorophenyl)indole-3-carboxamide (Compound 4-11) 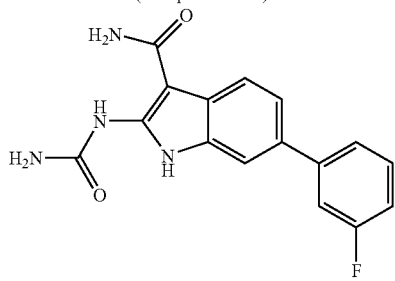 | ¹H-NMR (400 MHz, DMSO-d₆) δ 6.99 (s, 2H), 7.05 (br s, 2H), 7.13 (m, 1H), 7.39-7.44 (m, 2H), 7.48-7.51 (m, 2H), 7.83 (d, J = 8.3 Hz, 1H), 7.86 (d, J = 1.7 Hz, 1H), 10.56 (s, 1H), 11.73 (s, 1H) |

| | |
|---|---|
| 2-Aminocarbonylamino-6-(3-isopropyloxyphenyl)indole-3-carboxamide (Compound 4-12) 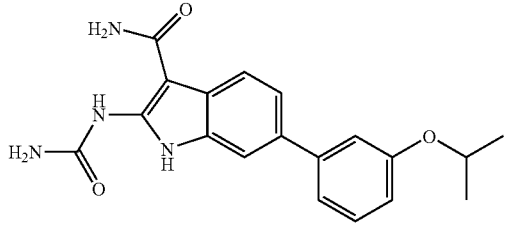 | $^1$H-NMR (500 MHz, DMSO-d$_6$) δ 1.31 (d, J = 6.1 Hz, 6H), 4.69 (m, 1H), 6.85 (dd, J = 8.2, 1.8 Hz, 1H), 6.95 (s, 2H), 7.02 (br s, 2H), 7.11 (m, 1H), 7.17 (d, J = 8.2 Hz, 1H), 7.33 (t, J = 8.2 Hz, 1H), 7.35 (dd, J = 8.2, 1.8 Hz, 1H), 7.80 (d, J = 8.2 Hz, 1H), 7.82 (d, J = 1.8 Hz, 1H), 10.54 (s, 1H), 11.68 (s, 1H) |
| 2-Aminocarbonylamino-6-(2-methylphenyl)indole-3-carboxamide (Compound 4-13) 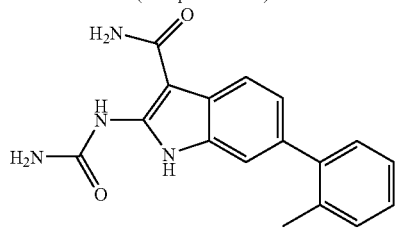 | $^1$H-NMR (500 MHz, DMSO-d$_6$) δ 2.26 (s, 3H), 6.94 (s, 2H), 7.01 (dd, J = 8.2, 1.5 Hz, 1H), 7.06 (br s, 2H), 7.21-7.24 (m, 3H), 7.28 (m, 1H), 7.50 (d, J = 1.5 Hz, 1H), 7.78 (d, J = 8.2 Hz, 1H), 10.55 (s, 1H), 11.67 (s, 1H) |
| 2-Aminocarbonylamino-6-(2-fluoro-4-methylphenyl)indole-3-carboxamide (Compound 4-14) 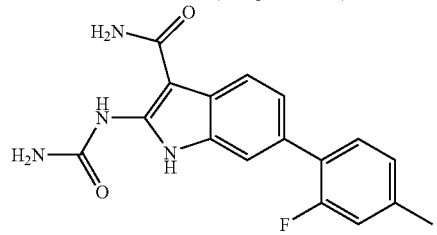 | $^1$H-NMR (500 MHz, DMSO-d$_6$) δ 2.36 (s, 3H), 6.96 (s, 2H), 7.09-7.13 (m, 4H), 7.20 (m, 1H), 7.39 (m, 1H), 7.71 (s, 1H), 7.80 (d, J = 8.2 Hz, 1H), 10.55 (s, 1H), 11.72 (s, 1H) |
| 2-Aminocarbonylamino-6-(3-cyanophenyl)indole-3-carboxamide (Compound 4-15) 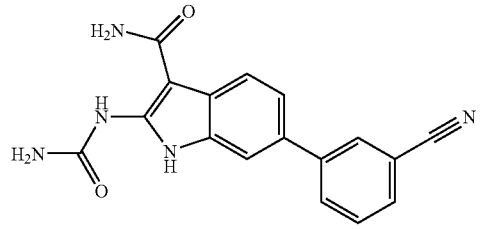 | $^1$H-NMR (400 MHz, DMSO-d$_6$) δ 7.01 (s, 2H), 7.08 (br s, 2H), 7.45 (dd, J = 8.3, 1.8 Hz, 1H), 7.66 (t, J = 7.6 Hz, 1H), 7.76 (dt, J = 7.6, 1.6 Hz, 1H), 7.86 (d, J = 8.3 Hz, 1H), 7.89 (d, J = 1.6 Hz, 1H), 7.97 (m, 1H), 8.07 (t, J = 1.8 Hz, 1H), 10.57 (s, 1H), 11.76 (s, 1H) |
| 2-Aminocarbonylamino-6-(3-nitrophenyl)indole-3-carboxamide (Compound 4-16) 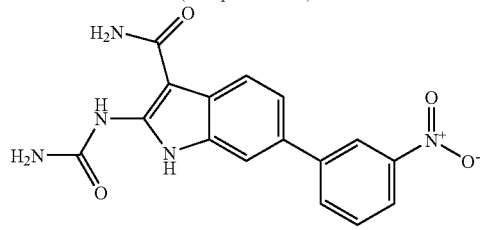 | $^1$H-NMR (500 MHz, DMSO-d$_6$) δ 7.02 (s, 2H), 7.05 (br s, 2H), 7.49 (dd, J = 8.2, 1.8 Hz, 1H), 7.75 (t, J = 8.2 Hz, 1H), 7.89 (d, J = 8.2 Hz, 1H), 7.98 (d, J = 1.8 Hz, 1H), 8.12-8.16 (m, 2H), 8.41 (t, J = 1.8 Hz, 1H), 10.55 (s, 1H), 11.80 (s, 1H) |

| Compound | 1H-NMR |
|---|---|
| 2-Aminocarbonylamino-6-(3-methylsulfonylaminophenyl)indole-3-carboxamide (Compound 4-17) 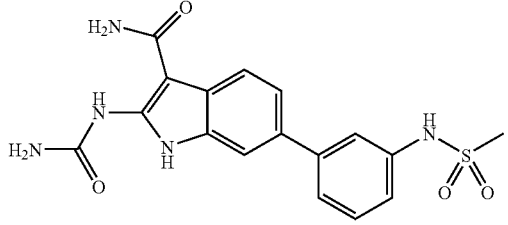 | $^1$H-NMR (400 MHz, DMSO-$d_6$) δ 3.04 (s, 3H), 6.97 (s, 2H), 7.03 (br s, 2H), 7.15 (dt, J = 8.0, 1.7 Hz, 1H), 7.30 (dd, J = 8.0, 1.7 Hz, 1H), 7.35-7.43 (m, 2H), 7.48 (t, J = 1.7 Hz, 1H), 7.81 (s, 1H), 7.82 (d, J = 8.0 Hz, 1H), 9.81 (s, 1H), 10.55 (s, 1H), 11.76 (s, 1H) |
| 2-Aminocarbonylamino-6-(thiophen-3-yl)indole-3-carboxamide (Compound 4-18) 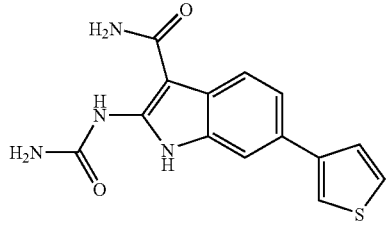 | $^1$H-NMR (500 MHz, DMSO-$d_6$) δ 6.95 (s, 2H), 7.03 (br s, 2H), 7.41 (dd, J = 8.2, 1.8 Hz, 1H), 7.47 (dd, J = 5.0, 1.5 Hz, 1H), 7.62 (dd, J = 5.0, 3.1 Hz, 1H), 7.67 (dd, J = 3.1, 1.5 Hz, 1H), 7.76 (d, J = 8.2 Hz, 1H), 7.83 (d, J = 1.8 Hz, 1H), 10.53 (s, 1H), 11.64 (s, 1H) |
| 2-Aminocarbonylamino-6-(furan-2-yl)indole-3-carboxamide (Compound 4-19) 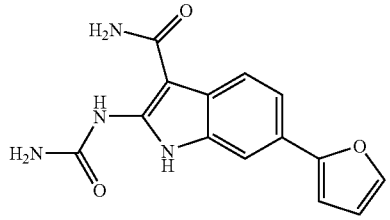 | $^1$H-NMR (500 MHz, DMSO-$d_6$) δ 6.56 (dd, J = 3.4, 1.6 Hz, 1H), 6.74 (dd, J = 3.4, 0.7 Hz, 1H), 6.97 (s, 2H), 7.03 (s, 2H), 7.41 (dd, J = 8.5, 1.7 Hz, 1H), 7.69 (dd, J = 1.6, 0.7 Hz, 1H), 7.77 (d, J = 8.5 Hz, 1H), 7.85 (d, J = 1.7 Hz, 1H), 10.54 (s, 1H), 11.73 (s, 1H) |
| 2-Aminocarbonylamino-6-(1-tert-butoxycarbonylpyrrol-2-yl)indole-3-carboxamide (Compound 4-20) 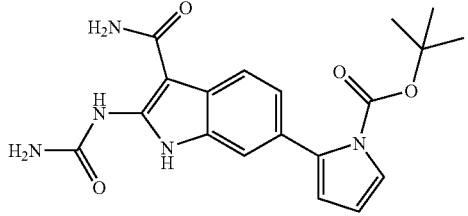 | $^1$H-NMR (400 MHz, DMSO-$d_6$) δ 1.28 (s, 9H), 6.16 (m, 1H), 6.25 (t, J = 3.2 Hz, 1H), 6.93 (s, 2H), 6.96 (br s, 2H), 6.99 (d, J = 8.1 Hz, 1H), 7.30 (m, 1H), 7.47 (s, 1H), 7.71 (d, J = 8.1 Hz, 1H), 10.56 (s, 1H), 11.68 (s, 1H) |
| 2-Aminocarbonylamino-6-(4-methylthiophen-3-yl)indole-3-carboxamide (Compound 4-21) 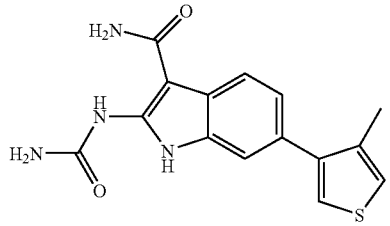 | $^1$H-NMR (500 MHz, DMSO-$d_6$) δ 2.25 (s, 3H), 6.93 (s, 2H), 7.01 (br s, 2H), 7.11 (dd, J = 8.2, 1.8 Hz, 1H), 7.25 (dd, J = 3.4, 0.9 Hz, 1H), 7.36 (d, J = 3.4 Hz, 1H), 7.61 (d, J = 1.8 Hz, 1H), 7.76 (d, J = 8.2 Hz, 1H), 10.54 (s, 1H), 11.67 (s, 1H) |
| 2-Aminocarbonylamino-6-(furan-3-yl)indole-3-carboxamide (Compound 4-22) 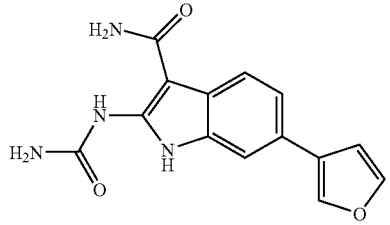 | $^1$H-NMR (500 MHz, DMSO-$d_6$) δ 6.84 (dd, J = 1.7, 0.9 Hz, 1H), 6.94 (s, 2H), 7.00 (br s, 2H), 7.31 (dd, J = 8.2, 1.5 Hz, 1H), 7.71 (d, J = 1.5 Hz, 1H), 7.72 (t, J = 1.7 Hz, 1H), 7.74 (d, J = 8.2 Hz, 1H), 8.04 (dd, J = 1.7, 0.9 Hz, 1H), 10.51 (s, 1H), 11.61 (s, 1H) |

2-Aminocarbonylamino-6-(2-chlorothiophen-3-yl)indole-3-carboxamide (Compound 4-23)

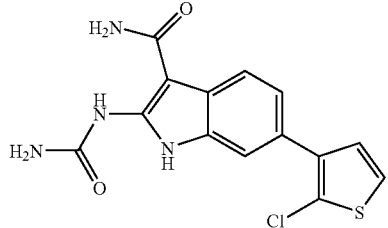

¹H-NMR (400 MHz, DMSO-$d_6$) δ 6.97 (s, 2H), 7.05 (br s, 2H), 7.21 (d, J = 5.6 Hz, 1H), 7.26 (dd, J = 8.4, 1.6 Hz, 1H), 7.54 (d, J = 5.6 Hz, 1H), 7.81 (d, J = 8.4 Hz, 1H), 7.82 (d, J = 1.6 Hz, 1H), 10.55 (s, 1H), 11.76 (s, 1H)

2-Aminocarbonylamino-6-(4-benzyloxyphenyl)indole-3-carboxamide (Compound 4-24)

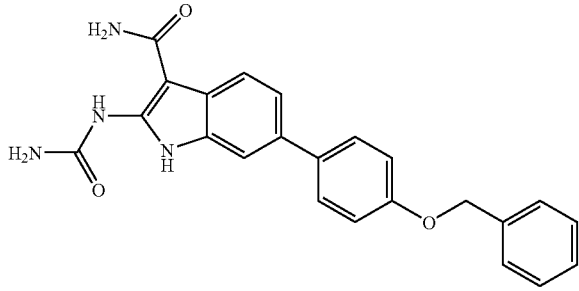

¹H-NMR (400 MHz, DMSO-$d_6$) δ 5.15 (s, 2H), 6.94 (s, 2H), 7.01 (br s, 2H), 7.09 (d, J = 8.8 Hz, 2H), 7.30 (dd, J = 8.5, 1.5 Hz, 1H), 7.34 (m, 1H), 7.41 (t, J = 7.4 Hz, 2H), 7.48 (d, J = 7.4 Hz, 2H), 7.55 (d, J = 8.8 Hz, 2H), 7.76 (d, J = 1.5 Hz, 1H), 7.78 (d, J = 8.5 Hz, 1H), 10.54 (s, 1H), 11.65 (s, 1H)

2-Aminocarbonylamino-6-(3-ethoxycarbonylphenyl)indole-3-carboxamide (Compound 4-25)

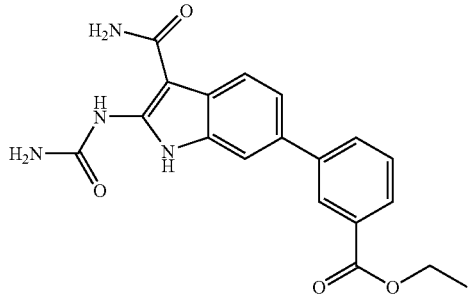

¹H-NMR (500 MHz, DMSO-$d_6$) δ 1.36 (t, J = 7.2 Hz, 3H), 4.36 (q, J = 7.2 Hz, 2H), 6.98 (s, 2H), 7.04 (br s, 2H), 7.40 (dd, J = 8.4, 1.7 Hz, 1H), 7.60 (t, J = 7.8 Hz, 1H), 7.85 (d, J = 8.4 Hz, 1H), 7.89 (dt, J = 7.8, 1.3 Hz, 1H), 7.91 (d, J = 1.7 Hz, 1H), 7.92 (m, 1H), 8.20 (m, 1H), 10.56 (s, 1H), 11.76 (s, 1H)

2-Aminocarbonylamino-6-(4-methylthiophen-2-yl)indole-3-carboxamide (Compound 4-26)

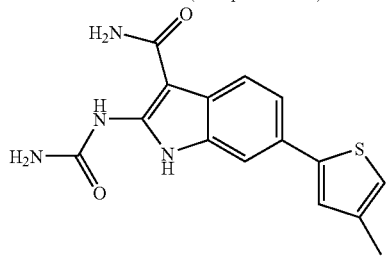

¹H-NMR (400 MHz, DMSO-$d_6$) δ 2.24 (s, 3H), 6.96 (s, 2H), 7.00 (m, 1H), 7.02 (br s, 2H), 7.17 (d, J = 1.2 Hz, 1H), 7.32 (dd, J = 8.3, 1.6 Hz, 1H), 7.74 (d, J = 8.3 Hz, 1H), 7.78 (d, J = 1.6 Hz, 1H), 10.53 (s, 1H), 11.70 (s, 1H)

2-Aminocarbonylamino-6-(3-methylphenyl)indole-3-carboxamide (Compound 4-27)

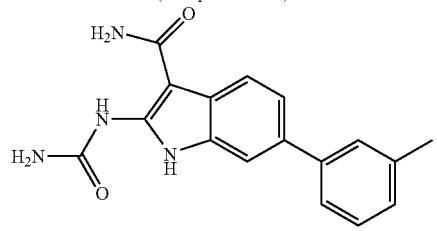

¹H-NMR (400 MHz, DMSO-$d_6$) δ 2.38 (s, 3H), 6.96 (s, 2H), 7.00 (br s, 2H), 7.11 (d, J = 7.3 Hz, 1H), 7.31-7.36 (m, 2H), 7.40-7.36 (m, 2H), 7.80 (d, J = 8.1 Hz, 1H), 7.81 (s, 1H), 10.55 (s, 1H), 11.68 (s, 1H)

| | |
|---|---|
| 2-Aminocarbonylamino-6-(3-acetylaminophenyl)indole-3-carboxamide (Compound 4-28) 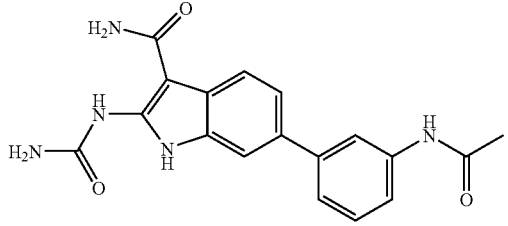 | ¹H-NMR (500 MHz, DMSO-d₆) δ 2.07 (s, 3H), 6.96 (s, 2H), 7.02 (br s, 2H), 7.26-7.31 (m, 2H), 7.36 (t, J = 7.6 Hz, 1H), 7.56 (d, J = 7.6 Hz, 1H), 7.80 (d, J = 1.5 Hz, 1H), 7.82 (d, J = 8.2 Hz, 1H), 7.90 (s, 1H), 10.00 (s, 1H), 10.54 (s, 1H), 11.73 (s, 1H) |
| 2-Aminocarbonylamino-6-(3-isopropylphenyl)indole-3-carboxamide (Compound 4-29) 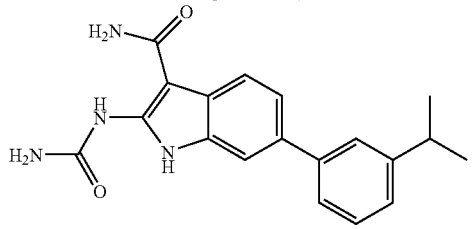 | ¹H-NMR (400 MHz, DMSO-d₆) δ 1.27 (d, J = 6.8 Hz, 6H), 2.96 (m, 1H), 6.96 (s, 2H), 7.03 (br s, 2H), 7.18 (dt, J = 7.6, 1.2 Hz, 1H), 7.34-7.38 (m, 2H), 7.43 (dt, J = 7.6, 1.2 Hz, 1H), 7.49 (t, J = 1.2 Hz, 1H), 7.81 (d, J = 8.3 Hz, 1H), 7.84 (d, J = 1.2 Hz, 1H), 10.54 (s, 1H), 11.69 (s, 1H) |
| 2-Aminocarbonylamino-6-(4-methylsulfonylphenyl)indole-3-carboxamide (Compound 4-30) 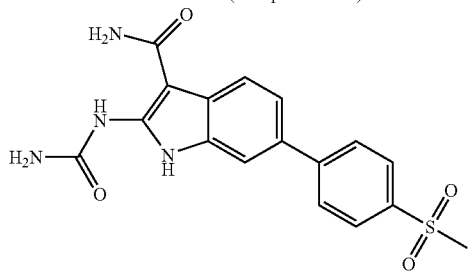 | ¹H-NMR (500 MHz, DMSO-d₆) δ 3.24 (s, 3H), 7.01 (s, 2H), 7.06 (br s, 2H), 7.46 (dd, J = 8.2, 1.5 Hz, 1H), 7.87 (d, J = 8.2 Hz, 1H), 7.89 (dd, J = 6.7, 1.8 Hz, 2H), 7.94 (d, J = 1.5 Hz, 1H), 7.98 (dd, J = 6.7, 1.8 Hz, 2H), 10.57 (s, 1H), 11.80 (s, 1H) |
| 2-Aminocarbonylamino-6-(2-methylsulfonylaminophenyl)indole-3-carboxamide (Compound 4-31) 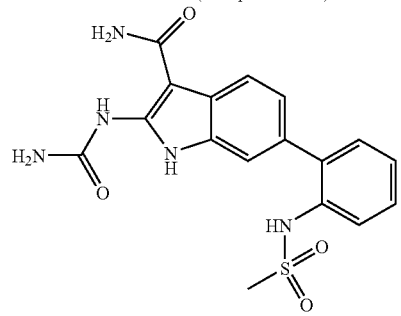 | ¹H-NMR (500 MHz, DMSO-d₆) δ 2.75 (s, 3H), 6.96 (s, 2H), 7.00 (br s, 2H), 7.16 (dd, J = 8.2, 1.5 Hz, 1H), 7.28-7.37 (m, 3H), 7.44 (dd, J = 7.6, 1.0 Hz, 1H), 7.57 (d, J = 1.5 Hz, 1H), 7.82 (d, J = 8.2 Hz, 1H), 8.66 (s, 1H), 10.57 (s, 1H), 11.71 (s, 1H) |
| 2-Aminocarbonylamino-6-(4-nitrophenyl)indole-3-carboxamide (Compound 4-32) 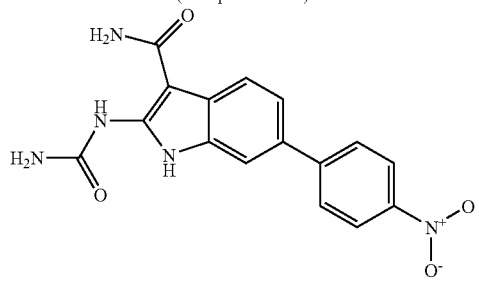 | ¹H-NMR (400 MHz, DMSO-d₆) δ 7.04 (s, 2H), 7.10 (br s, 2H), 7.49 (dd, J = 8.3, 1.5 Hz, 1H), 7.89 (d, J = 8.3 Hz, 1H), 7.92 (d, J = 9.0 Hz, 2H), 7.99 (d, J = 1.5 Hz, 1H), 8.30 (d, J = 9.0 Hz, 2H), 10.59 (s, 1H), 11.84 (s, 1H) |

| | |
|---|---|
| 2-Aminocarbonylamino-6-(3-propyloxyphenyl)indole-3-carboxamide (Compound 4-33) 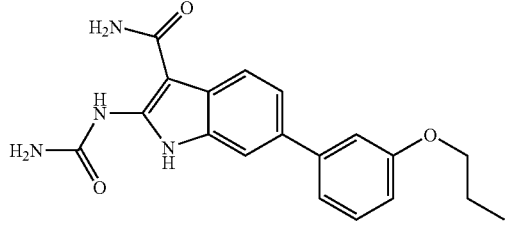 | $^1$H-NMR (400 MHz, DMSO-d$_6$) δ= 1.01 (t, J = 7.4 Hz, 3H), 1.75-1.78 (m, 2H), 4.00 (t, J = 6.6 Hz, 2H), 6.86 (ddd, J = 7.8, 2.2, 0.8 Hz, 1H), 6.96 (s, 2H), 7.04 (br s, 2H), 7.14 (m, 1H), 7.19 (ddd, J = 7.8, 1.5, 0.8 Hz, 1H), 7.34 (t, J = 7.8 Hz, 1H), 7.36 (dd, J = 8.3, 1.7 Hz, 1H), 7.80 (d, J = 8.3 Hz, 1H), 7.84 (d, J = 1.7 Hz, 1H), 10.55 (s, 1H), 11.68 (s, 1H) |
| 2-Aminocarbonylamino-6-(quinolin-5-yl)indole-3-carboxamide (Compound 4-34) 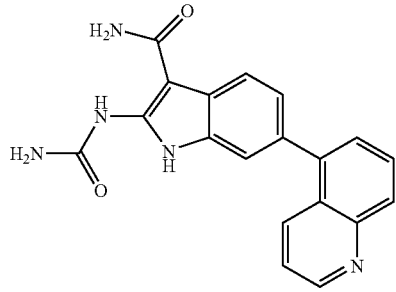 | $^1$H-NMR (500 MHz, DMSO-d$_6$) δ 7.01 (s, 2H), 7.06 (br s, 2H), 7.17 (dd, J = 8.2, 1.5 Hz, 1H), 7.51 (dd, J = 8.6, 4.3 Hz, 1H), 7.57 (dd, J = 7.3, 1.2 Hz, 1H), 7.67 (d, J = 1.5 Hz, 1H), 7.83 (dd, J = 8.6, 7.3 Hz, 1H), 7.91 (d, J = 8.2 Hz, 1H), 8.03 (d, J = 8.6 Hz, 1H), 8.31 (d, J = 8.6 Hz, 1H), 8.93 (dd, J = 4.3, 1.2 Hz, 1H), 10.59 (s, 1H), 11.79 (s, 1H) |
| 2-Aminocarbonylamino-6-(naphthalen-1-yl)indole-3-carboxamide (Compound 4-35) 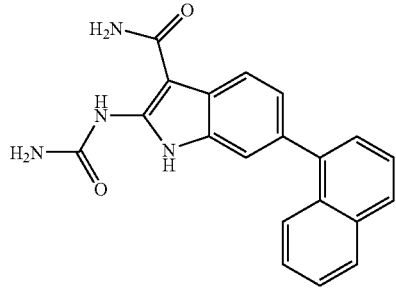 | $^1$H-NMR (500 MHz, DMSO-d$_6$) δ 6.99 (s, 2H), 7.03 (br s, 2H), 7.16 (dd, J = 8.2, 1.5 Hz, 1H), 7.44 (dd, J = 7.0, 1.2 Hz, 1H), 7.48 (m, 1H), 7.50-7.61 (m, 2H), 7.65 (d, J = 1.5 Hz, 1H), 7.88 (d, J = 8.2 Hz, 1H), 7.91 (d, J = 3.7 Hz, 1H), 7.93 (d, J = 3.7 Hz, 1H), 8.00 (d, J = 8.2 Hz, 1H), 10.58 (s, 1H), 11.75 (s, 1H) |
| 2-Aminocarbonylamino-6-(quinolin-3-yl)indole-3-carboxamide (Compound 4-36) 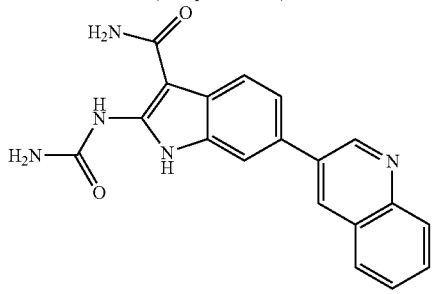 | $^1$H-NMR (400 MHz, DMSO-d$_6$) δ 7.04 (s, 2H), 7.09 (br s, 2H), 7.59 (dd, J = 8.3, 1.7 Hz, 1H), 7.64 (m, 1H), 7.74 (m, 1H), 7.93 (d, J = 8.3 Hz, 1H), 8.03-8.07 (m, 3H), 8.75 (d, J = 2.0 Hz, 1H), 9.36 (d, J = 2.0 Hz, 1H), 10.59 (s, 1H), 11.81 (s, 1H) |
| 2-Aminocarbonylamino-6-(2-cyanophenyl)indole-3-carboxamide (Compound 4-37) 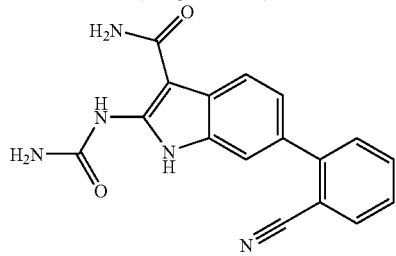 | $^1$H-NMR (400 MHz, DMSO-d$_6$) δ 7.02 (s, 2H), 7.05 (br s, 2H), 7.26 (dd, J = 8.3, 1.7 Hz, 1H), 7.53 (td, J = 7.6, 1.0 Hz, 1H), 7.62 (dd, J = 7.6, 1.0 Hz, 1H), 7.77 (dd, J = 7.6, 1.0 Hz, 1H), 7.79 (d, J = 1.7 Hz, 1H), 7.89 (d, J = 8.3 Hz, 1H), 7.93 (dd, J = 7.6, 1.0 Hz, 1H), 10.59 (s, 1H), 11.86 (s, 1H) |

| Compound | NMR |
|---|---|
| 2-Aminocarbonylamino-6-vinylindole-3-carboxamide (Compound 4-38) 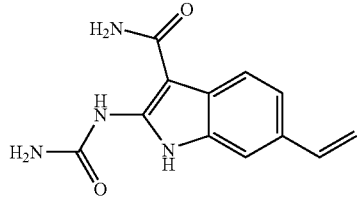 | ¹H-NMR (500 MHz, DMSO-$d_6$) δ 5.10 (dd, J = 10.8, 1.1 Hz, 1H), 5.66 (dd, J = 17.6, 1.1 Hz, 1H), 6.73 (dd, J = 17.6, 10.8 Hz, 1H), 6.93 (s, 2H), 7.03 (br s, 2H), 7.19 (dd, J = 8.3, 1.3 Hz, 1H), 7.59 (d, J = 1.3 Hz, 1H), 7.69 (d, J = 8.3 Hz, 1H), 10.52 (s, 1H), 11.63 (s, 1H) |
| 2-Aminocarbonylamino-6-(2-methoxy-4-trifluoromethoxyphenyl)indole-3-carboxamide (Compound 4-39) 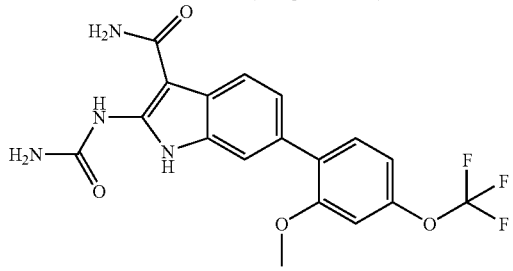 | ¹H-NMR (400 MHz, DMSO-$d_6$) δ 3.81 (s, 3H), 6.94 (s, 2H), 6.99 (br s, 2H), 7.02 (m, 1H), 7.09 (d, J = 2.4 Hz, 1H), 7.15 (dd, J = 8.4, 1.5 Hz, 1H), 7.38 (d, J = 8.4 Hz, 1H), 7.66 (d, J = 1.5 Hz, 1H), 7.76 (d, J = 8.4 Hz, 1H), 10.54 (s, 1H), 11.67 (s, 1H) |
| 2-Aminocarbonylamino-6-(4-trifluoromethoxyphenyl)indole-3-carboxamide (Compound 4-40) 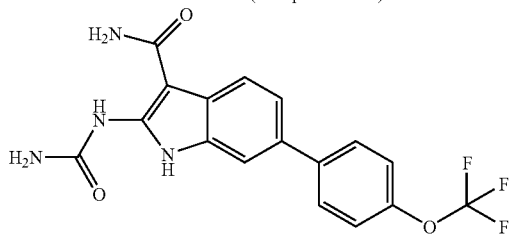 | ¹H-NMR (500 MHz, DMSO-$d_6$) δ 6.98 (s, 2H), 7.05 (br s, 2H), 7.37 (dd, J = 8.3, 1.8 Hz, 1H), 7.44 (d, J = 8.9 Hz, 2H), 7.74 (d, J = 8.9 Hz, 2H), 7.84 (d, J = 8.3 Hz, 1H), 7.84 (d, J = 1.8 Hz, 1H), 10.56 (s, 1H), 11.74 (s, 1H) |
| 2-Aminocarbonylamino-6-(4-benzoylphenyl)indole-3-carboxamide (Compound 4-41) 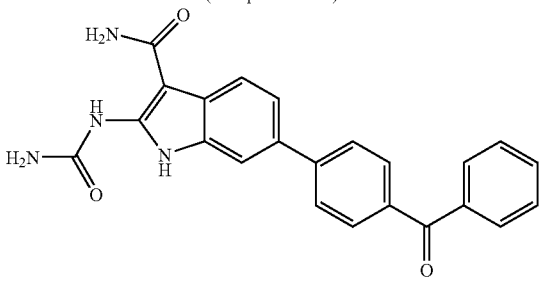 | ¹H-NMR (400 MHz, DMSO-$d_6$) δ 7.01 (s, 2H), 7.11 (br s, 2H), 7.49 (dd, J = 8.5, 1.7 Hz, 1H), 7.59 (t, J = 7.4 Hz, 2H), 7.70 (tt, J = 7.4, 1.5 Hz, 1H), 7.78-7.79 (m, 2H), 7.83-7.85 (m, 4H), 7.88 (d, J = 8.5 Hz, 1H), 7.97 (d, J = 1.7 Hz, 1H), 10.58 (s, 1H), 11.80 (s, 1H) |
| 2-Aminocarbonylamino-6-(4-ethoxycarbonylphenyl)indole-3-carboxamide (Compound 4-42) 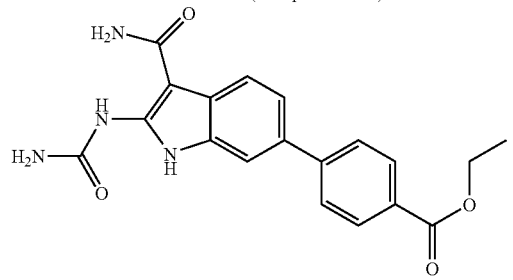 | ¹H-NMR (500 MHz, DMSO-$d_6$) δ 1.35 (t, J = 7.1 Hz, 3H), 4.34 (q, J = 7.1 Hz, 2H), 7.00 (s, 2H), 7.10 (br s, 2H), 7.45 (dd, J = 8.2, 1.5 Hz, 1H), 7.79 (d, J = 8.6 Hz, 2H), 7.86 (d, J = 8.2 Hz, 1H), 7.94 (d, J = 1.5 Hz, 1H), 8.03 (d, J = 8.6 Hz, 2H), 10.57 (s, 1H), 11.78 (s, 1H) |

| Compound | NMR |
|---|---|
| 2-Aminocarbonylamino-6-(2,4-dimethoxypyrimidin-5-yl)indole-3-carboxamide (Compound 4-43) 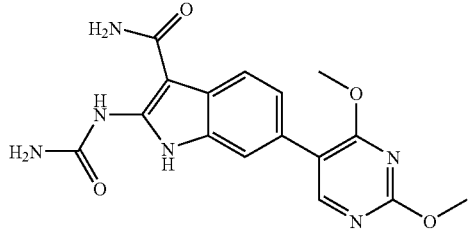 | $^1$H-NMR (400 MHz, DMSO-d$_6$) δ 3.95 (s, 6H), 6.95 (s, 2H), 7.02 (br s, 2H), 7.20 (dd, J = 8.3, 1.5 Hz, 1H), 7.70 (d, J = 1.5 Hz, 1H), 7.78 (d, J = 8.3 Hz, 1H), 8.33 (s, 1H), 10.54 (s, 1H), 11.69 (s, 1H) |
| 2-Aminocarbonylamino-6-(4-methoxypyridin-3-yl)indole-3-carboxamide (Compound 4-44) 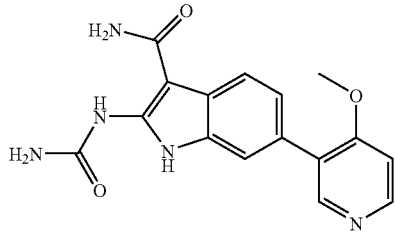 | $^1$H-NMR (400 MHz, DMSO-d$_6$) δ 3.90 (s, 3H), 6.98 (s, 2H), 7.06 (br s, 2H), 7.29 (dd, J = 8.3, 1.7 Hz, 1H), 7.34 (d, J = 4.9 Hz, 1H), 7.80 (d, J = 8.3 Hz, 1H), 7.83 (d, J = 1.7 Hz, 1H), 8.25 (d, J = 4.9 Hz, 1H), 8.43 (s, 1H), 10.56 (s, 1H), 11.74 (s, 1H) |
| 2-Aminocarbonylamino-6-(2,6-difluoropyridin-3-yl)indole-3-carboxamide (Compound 4-45) 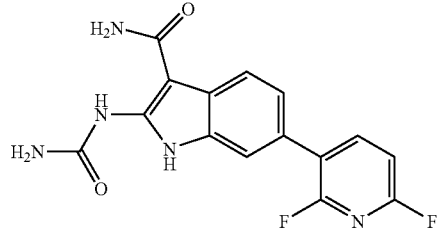 | $^1$H-NMR (400 MHz, DMSO-d$_6$) δ 7.00 (s, 2H), 7.05 (br s, 2H), 7.27-7.28 (m, 2H), 7.78 (s, 1H), 7.86 (d, J = 8.3 Hz, 1H), 8.28 (m, 1H), 10.57 (s, 1H), 11.81 (s, 1H) |
| 2-Aminocarbonylamino-6-[(E)-styryl]indole-3-carboxamide (Compound 4-46) 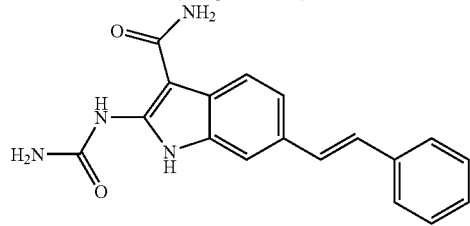 | $^1$H-NMR (400 MHz, DMSO-d$_6$) δ 6.96 (s, 2H), 6.98 (br s, 2H), 7.09 (d, J = 16.4 Hz, 1H), 7.23-7.29 (m, 2H), 7.35-7.37 (m, 3H), 7.59 (dd, J = 8.3, 1.2 Hz, 2H), 7.71 (d, J = 1.2 Hz, 1H), 7.74 (d, J = 8.3 Hz, 1H), 10.54 (s, 1H), 11.68 (s, 1H) |
| 2-Aminocarbonylamino-6-[(Z)-1-propenyl]indole-3-carboxamide (Compound 4-47) 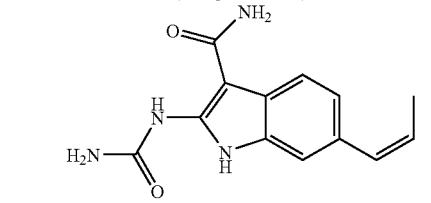 | $^1$H-NMR (500 MHz, DMSO-d$_6$) δ 1.91 (dd, J = 7.3, 1.8 Hz, 3H), 5.65 (m, 1H), 6.44 (dq, J = 11.6, 1.8 Hz, 1H), 6.90 (s, 2H), 6.91 (br s, 2H), 6.99 (dd, J = 8.3, 1.2 Hz, 1H), 7.59 (d, J = 1.2 Hz, 1H), 7.69 (d, J = 8.3 Hz, 1H), 10.52 (s, 1H), 11.62 (s, 1H) |
| 2-Aminocarbonylamino-6-[(E)-1-propenyl]indole-3-carboxamide (Compound 4-48) 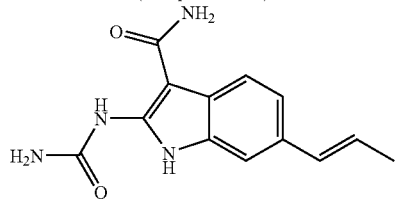 | $^1$H-NMR (400 MHz, DMSO-d$_6$) δ 1.85 (dd, J = 6.6, 1.6 Hz, 3H), 6.13 (dq, J = 15.6, 6.6 Hz, 1H), 6.41 (dq, J = 15.6, 1.6 Hz, 1H), 6.89 (s, 2H), 7.00 (br s, 2H), 7.09 (dd, J = 8.3, 1.2 Hz, 1H), 7.49 (d, J = 1.2 Hz, 1H), 7.65 (d, J = 8.3 Hz, 1H), 10.51 (s, 1H), 11.59 (s, 1H) |

| Compound | NMR |
|---|---|
| 2-Aminocarbonylamino-6-(1-triisopropylsilylpyrrol-3-yl)indole-3-carboxamide (Compound 4-49)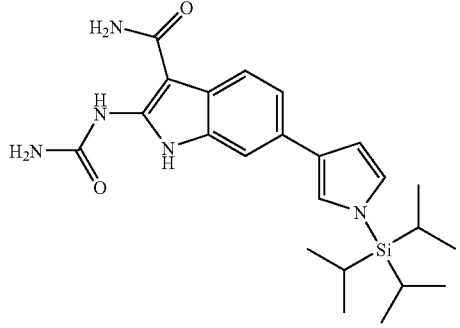 | ¹H-NMR (400 MHz, DMSO-d₆) δ 1.09 (d, J = 7.3 Hz, 18H), 1.49-1.57 (m, 3H), 6.55 (dd, J = 2.4, 1.7 Hz, 1H), 6.86 (dd, J = 2.4, 1.7 Hz, 1H), 6.88 (s, 2H), 7.00 (br s, 2H), 7.12 (t, J = 1.7 Hz, 1H), 7.28 (dd, J = 8.5, 1.5 Hz, 1H), 7.66 (d, J = 8.5 Hz, 1H), 7.70 (d, J = 1.5 Hz, 1H), 10.49 (s, 1H), 11.49 (s, 1H) |
| 2-Aminocarbonylamino-6-[(E)-2-cyclopropylvinyl]indole-3-carboxamide (Compound 4-50)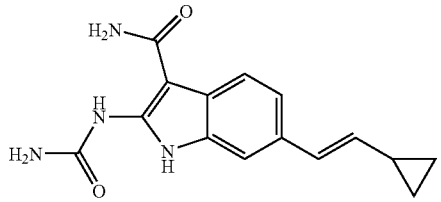 | ¹H-NMR (400 MHz, DMSO-d₆) δ 0.48 (dt, J = 7.9, 3.0 Hz, 2H), 0.77 (dt, J = 11.5, 3.0 Hz, 2H), 1.56 (m, 1H), 5.68 (dd, J = 15.9, 8.9 Hz, 1H), 6.46 (d, J = 15.9 Hz, 1H), 6.88 (s, 2H), 7.00 (br s, 2H), 7.07 (dd, J = 8.3, 1.2 Hz, 1H), 7.44 (d, J = 1.2 Hz, 1H), 7.63 (d, J = 8.3 Hz, 1H), 10.50 (s, 1H), 11.53 (s, 1H) |
| 2-Aminocarbonylamino-6-(cyclohexen-1-yl)indole-3-carboxamide (Compound 4-51)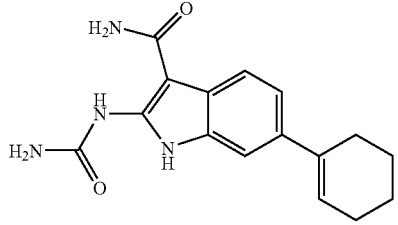 | ¹H-NMR (400 MHz, DMSO-d₆) δ 1.60-1.64 (m, 2H), 1.71-1.77 (m, 2H), 2.17-2.19 (m, 2H), 2.37-2.40 (m, 2H), 6.07 (m, 1H), 6.88 (s, 2H), 7.00 (br s, 2H), 7.13 (dd, J = 8.3, 1.5 Hz, 1H), 7.56 (d, J = 1.5 Hz, 1H), 7.65 (d, J = 8.3 Hz, 1H), 10.50 (s, 1H), 11.54 (s, 1H) |
| 2-Aminocarbonylamino-6-(3,5-difluorophenyl)indole-3-carboxamide (Compound 4-52)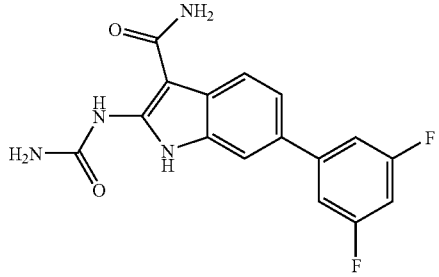 | ¹H-NMR (500 MHz, DMSO-d₆) δ 7.00 (s, 2H), 7.03 (br s, 2H), 7.14 (tt, J = 9.2, 2.1 Hz, 1H), 7.35 (dd, J = 9.2, 2.1 Hz, 2H), 7.44 (dd, J = 8.2, 1.8 Hz, 1H), 7.84 (d, J = 8.2 Hz, 1H), 7.88 (d, J = 1.8 Hz, 1H), 10.56 (s, 1H), 11.74 (s, 1H) |
| 2-Aminocarbonylamino-6-(3,5-dichlorophenyl)indole-3-carboxamide (Compound 4-53)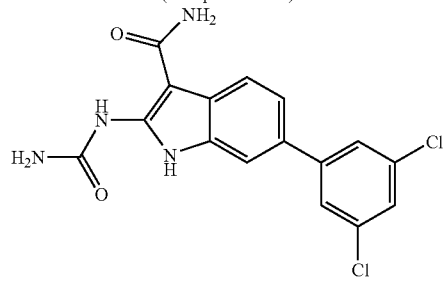 | ¹H-NMR (400 MHz, DMSO-d₆) δ 7.01 (br s, 2H), 7.11 (br s, 2H), 7.44 (dd, J = 8.5, 1.7 Hz, 1H), 7.52 (t, J = 2.0 Hz, 1H), 7.66 (d, J = 2.0 Hz, 2H), 7.85 (d, J = 8.5 Hz, 1H), 7.89 (d, J = 1.7 Hz, 1H), 10.57 (s, 1H), 11.74 (s, 1H) |

2-Aminocarbonylamino-6-(3,5-dimethoxyphenyl)indole-3-carboxamide (Compound 4-54)

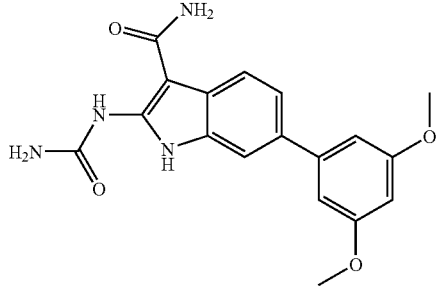

$^1$H-NMR (400 MHz, DMSO-$d_6$) δ 3.81 (s, 6H), 6.45 (t, J = 2.2 Hz, 1H), 6.76 (d, J = 2.2 Hz, 2H), 6.96 (s, 2H), 7.04 (br s, 2H), 7.36 (dd, J = 8.3, 1.5 Hz, 1H), 7.79 (d, J = 8.3 Hz, 1H), 7.84 (d, J = 1.5 Hz, 1H), 10.54 (s, 1H), 11.68 (s, 1H)

2-Aminocarbonylamino-6-(1-methylindol-5-yl)indole-3-carboxamide (Compound 4-55)

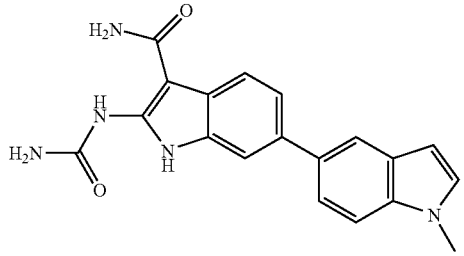

$^1$H-NMR (400 MHz, DMSO-$d_6$) δ 3.81 (s, 3H), 6.47 (d, J = 3.2 Hz, 1H), 6.93 (br s, 2H), 7.04 (br s, 2H), 7.34 (d, J = 3.2 Hz, 1H), 7.37 (dd, J = 8.5, 1.5 Hz, 1H), 7.43 (dd, J = 8.5, 1.5 Hz, 1H), 7.50 (d, J = 8.5 Hz, 1H), 7.76 (d, J = 1.5 Hz, 1H), 7.79 (d, J = 8.5 Hz, 1H), 7.82 (d, J = 1.5 Hz, 1H), 10.54 (s, 1H), 11.63 (s, 1H)

2-Aminocarbonylamino-(1-phenylvinyl)indole-3-carboxamide (Compound 4-56)

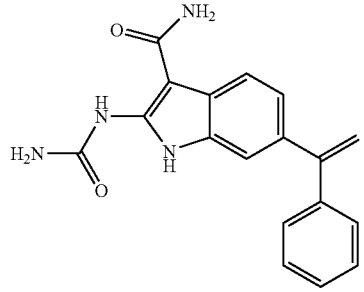

$^1$H-NMR (500 MHz, DMSO-$d_6$) δ 5.35 (d, J = 1.2 Hz, 1H), 5.43 (d, J = 1.2 Hz, 1H), 6.92 (s, 2H), 6.94 (br s, 2H), 7.00 (dd, J = 8.2, 1.5 Hz, 1H), 7.31-7.40 (m, 5H), 7.50 (d, J = 1.5 Hz, 1H), 7.71 (d, J = 8.2 Hz, 1H), 10.51 (s, 1H), 11.64 (s, 1H)

2-Aminocarbonylamino-6-[(E)-2-cyclohexylvinyl]indole-3-carboxamide (Compound 4-57)

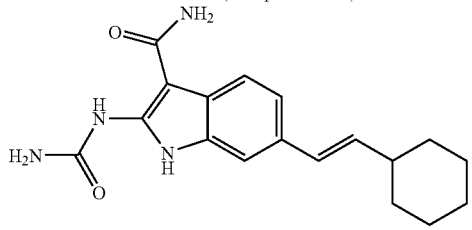

$^1$H-NMR (400 MHz, DMSO-$d_6$) δ 1.20-1.28 (m, 5H), 1.67-1.75 (m, 5H), 2.12 (m, 1H), 6.09 (dd, J = 16.0, 7.0 Hz, 1H), 6.35 (d, J = 16.0 Hz, 1H), 6.89 (s, 2H), 7.00 (br s, 2H), 7.10 (dd, J = 8.1, 1.0 Hz, 1H), 7.50 (d, J = 1.0 Hz, 1H), 7.65 (d, J = 8.1 Hz, 1H), 10.51 (s, 1H), 11.55 (s, 1H)

2-Aminocarbonylamino-6-[(E)-3-methoxy-1-propenyl]indole-3-carboxamide (Compound 4-58)

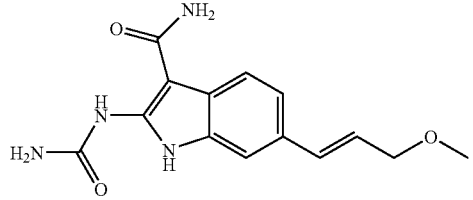

$^1$H-NMR (400 MHz, DMSO-$d_6$) δ 3.28 (s, 3H), 4.03 (dd, J = 6.2, 1.2 Hz, 2H), 6.18 (dt, J = 16.0, 6.2 Hz, 1H), 6.61 (d, J = 16.0 Hz, 1H), 6.92 (s, 2H), 7.02 (br s, 2H), 7.17 (dd, J = 8.3, 1.2 Hz, 1H), 7.57 (d, J = 1.2 Hz, 1H), 7.68 (d, J = 8.3 Hz, 1H), 10.52 (s, 1H), 11.62 (s, 1H)

| | |
|---|---|
| 2-Aminocarbonylamino-6-(benzothiophen-3-yl)indole-3-carboxamide (Compound 4-59) 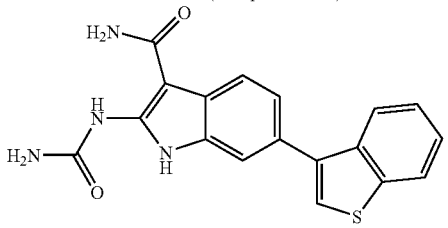 | $^1$H-NMR (400 MHz, DMSO-$d_6$) δ 6.95-7.10 (br s, 4H), 7.29 (dd, J = 8.3, 1.5 Hz, 1H), 7.40-7.48 (m, 2H), 7.71 (s, 1H), 7.84 (d, J = 1.5 Hz, 1H), 7.87 (d, J = 8.3 Hz, 1H), 7.98 (m, 1H), 8.07 (m, 1H), 10.57 (s, 1H), 11.77 (s, 1H) |
| 2-Aminocarbonylamino-6-(benzothiophen-2-yl)indole-3-carboxamide (Compound 4-60) 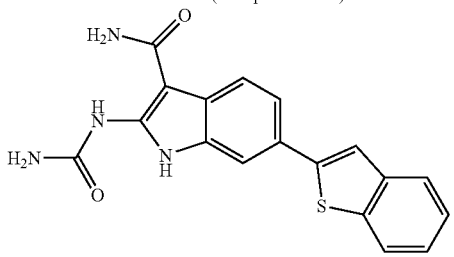 | $^1$H-NMR (400 MHz, DMSO-$d_6$) δ 6.95-7.19 (br s, 4H), 7.28-7.40 (m, 2H), 7.52 (dd, J = 8.3, 1.7 Hz, 1H), 7.70 (s, 1H), 7.79-7.86 (m, 2H), 7.92-7.97 (m, 2H), 10.56 (s, 1H), 11.82 (s, 1H) |
| 2-Aminocarbonylamino-6-(benzofuran-2-yl)indole-3-carboxamide (Compound 4-61) 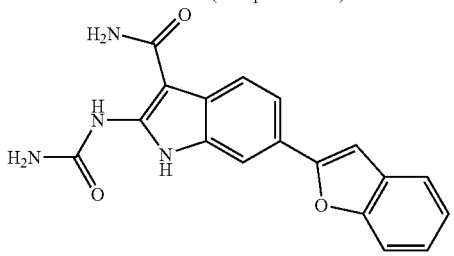 | $^1$H-NMR (400 MHz, DMSO-$d_6$) δ 7.03 (br s, 4H), 7.20-7.30 (m, 3H), 7.58-7.66 (m, 3H), 7.85 (d, J = 8.3 Hz, 1H), 8.08 (s, 1H), 10.57 (s, 1H), 11.84 (s, 1H) |
| 2-Aminocarbonylamino-6-(3,5-dimethylisoxazol-4-yl)indole-3-carboxamide (Compound 4-62) 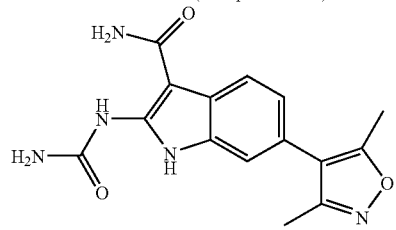 | $^1$H-NMR (400 MHz, DMSO-$d_6$) δ 2.24 (s, 3H), 2.41 (s, 3H), 6.96 (s, 2H), 7.03 (dd, J = 8.2, 1.5 Hz, 1H), 7.06 (br s, 2H), 7.56 (d, J = 1.5 Hz, 1H), 7.81 (d, J = 8.2 Hz, 1H), 10.53 (s, 1H), 11.69 (s, 1H) |
| 2-Aminocarbonylamino-6-[(E)-4-hydroxy-1-butenyl]indole-3-carboxamide (Compound 4-63) 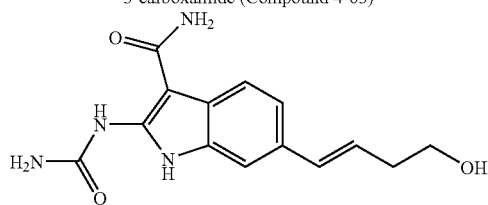 | $^1$H-NMR (400 MHz, DMSO-$d_6$) δ 2.32-2.35 (m, 2H), 3.49-3.54 (m, 2H), 4.57 (t, J = 5.2 Hz, 1H), 6.14 (dt, J = 15.9, 7.1 Hz, 1H), 6.43 (d, J = 15.9 Hz, 1H), 6.90 (s, 2H), 7.00 (br s, 2H), 7.11 (dd, J = 8.4, 1.2 Hz, 1H), 7.50 (d, J = 1.2 Hz, 1H), 7.65 (d, J = 8.4 Hz, 1H), 10.51 (s, 1H), 11.57 (s, 1H) |

| Compound | ¹H-NMR |
|---|---|
| 2-Aminocarbonylamino-6-(4-hydroxymethylphenyl)indole-3-carboxamide (Compound 4-64) 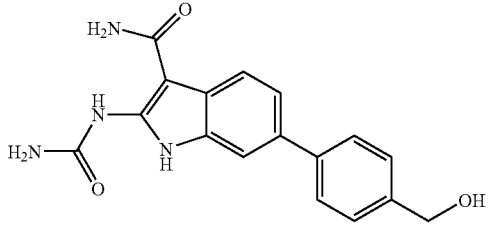 | ¹H-NMR (500 MHz, DMSO-d$_6$) δ 4.53 (d, J = 5.7 Hz, 2H), 5.17 (t, J = 5.7 Hz, 1H), 6.95 (br s, 4H), 7.35 (dd, J = 8.2, 1.5 Hz, 1H), 7.38 (d, J = 8.4 Hz, 2H), 7.58 (d, J = 8.4 Hz, 2H), 7.80 (d, J = 8.2 Hz, 1H), 7.82 (d, J = 1.5 Hz, 1H), 10.54 (s, 1H), 11.68 (s, 1H) |
| 2-Aminocarbonylamino-6-(indol-5-yl)indole-3-carboxamide (Compound 4-65) 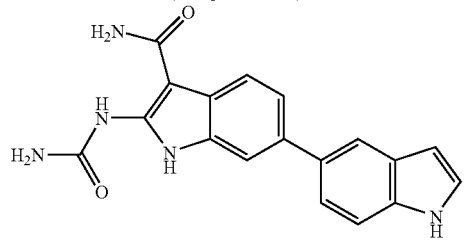 | ¹H-NMR (400 MHz, DMSO-d$_6$) δ 6.48 (m, 1H), 6.93 (s, 2H), 7.04 (br s, 2H), 7.34-7.39 (m, 3H), 7.46 (d, J = 8.5 Hz, 1H), 7.73-7.84 (m, 3H), 10.54 (s, 1H), 11.09 (s, 1H), 11.63 (s, 1H) |
| 2-Aminocarbonylamino-6-(3-chlorophenyl)indole-3-carboxamide (Compound 4-66) 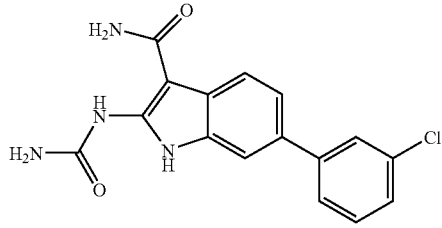 | ¹H-NMR (400 MHz, DMSO-d$_6$) δ 6.99 (br s, 4H), 7.33-7.42 (m, 2H), 7.49 (d, J = 7.8 Hz, 1H), 7.57-7.68 (m, 2H), 7.84 (d, J = 8.5 Hz, 1H), 7.86 (d, J = 1.7 Hz, 1H), 10.56 (s, 1H), 11.73 (s, 1H) |
| 2-Aminocarbonylamino-6-[(E)-1-pentenyl]indole-3-carboxamide (Compound 4-67) 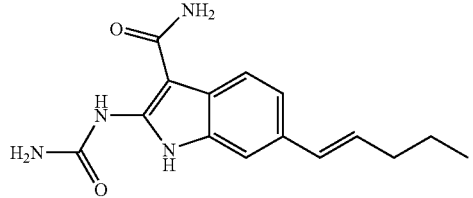 | ¹H-NMR (400 MHz, DMSO-d$_6$) δ 0.93 (t, J = 7.0 Hz, 3H), 1.46 (td, J = 14.6, 7.0 Hz, 2H), 2.13-2.19 (m, 2H), 6.13 (dt, J = 15.9, 7.0 Hz, 1H), 6.39 (d, J = 15.9 Hz, 1H), 6.90 (s, 2H), 7.01 (br s, 2H), 7.11 (dd, J = 8.3, 1.2 Hz, 1H), 7.50 (d, J = 1.2 Hz, 1H), 7.65 (d, J = 8.3 Hz, 1H), 10.51 (s, 1H), 11.56 (s, 1H) |
| 2-Aminocarbonylamino-6-[(E)-1-hexenyl]indole-3-carboxamide (Compound 4-68) 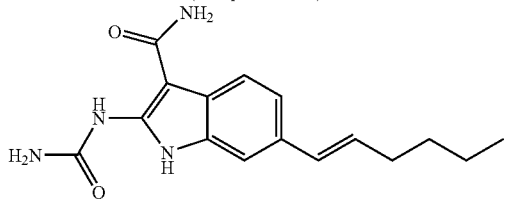 | ¹H-NMR (400 MHz, DMSO-d$_6$) δ 0.91 (t, J = 7.2 Hz, 3H), 1.30-1.46 (m, 4H), 2.19 (q, J = 6.8 Hz, 2H), 6.13 (dt, J = 15.6, 6.8 Hz, 1H), 6.39 (d, J = 15.6 Hz, 1H), 6.89 (s, 2H), 7.00 (br s, 2H), 7.10 (dd, J = 8.1, 1.2 Hz, 1H), 7.50 (d, J = 1.2 Hz, 1H), 7.65 (d, J = 8.1 Hz, 1H), 10.50 (s, 1H), 11.55 (s, 1H) |
| 2-Aminocarbonylamino-6-(3-formylphenyl)indole-3-carboxamide (Compound 4-69) 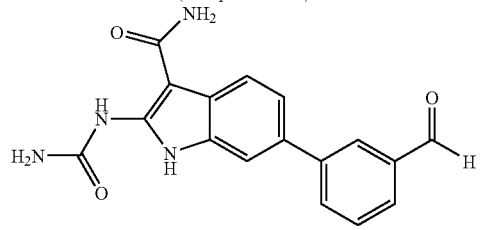 | ¹H-NMR (400 MHz, DMSO-d$_6$) δ 7.00 (s, 2H), 7.07 (br s, 2H), 7.45 (dd, J = 8.4, 1.8 Hz, 1H), 7.69 (t, J = 7.8 Hz, 1H), 7.84 (dt, J = 7.8, 1.5 Hz, 1H), 7.87 (d, J = 8.4 Hz, 1H), 7.93 (d, J = 1.8 Hz, 1H), 7.99 (dt, J = 7.8, 1.5 Hz, 1H), 8.17 (t, J = 1.5 Hz, 1H), 10.10 (s, 1H), 10.57 (s, 1H), 11.77 (s, 1H) |

| | |
|---|---|
| 2-Aminocarbonylamino-6-(2-dimethyiaminopyridin-5-yl)indole-3-carboxamide (Compound 4-70) 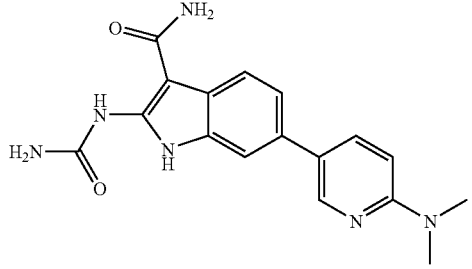 | $^1$H-NMR (400 MHz, DMSO-$d_6$) δ 3.06 (s, 6H), 6.73 (dd, J = 9.0, 0.6 Hz, 1H), 6.94 (s, 2H), 7.04 (br s, 2H), 7.28 (dd, J = 8.3, 1.7 Hz, 1H), 7.73 (d, J = 1.7 Hz, 1H), 7.76-7.78 (m, 2H), 8.38 (dd, J = 2.6, 0.6 Hz, 1H), 10.53 (s, 1H), 11.63 (s, 1H) |
| 2-Aminocarbonylamino-6-(2-aminopyridin-5-yl)indole-3-carboxamide (Compound 4-71) 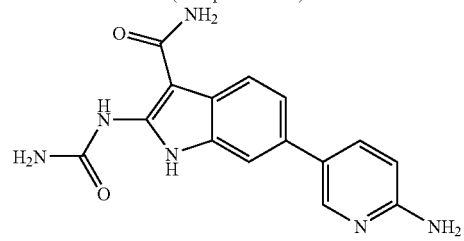 | $^1$H-NMR (400 MHz, DMSO-$d_6$) δ 5.94 (s, 2H), 6.52 (dd, J = 8.5, 0.5 Hz, 1H), 6.93 (s, 2H), 7.02 (br s, 2H), 7.24 (dd, J = 8.4, 1.8 Hz, 1H), 7.64 (dd, J = 8.5, 2.6 Hz, 1H), 7.69 (d, J = 1.8 Hz, 1H), 7.76 (d, J = 8.4 Hz, 1H), 8.19 (dd, J = 2.6, 0.5 Hz, 1H), 10.53 (s, 1H), 11.62 (s, 1H) |
| 2-Aminocarbonylamino-6-[2-(piperazin-1-yl)pyridin-5-yl]indole-3-carboxamide (Compound 4-72) 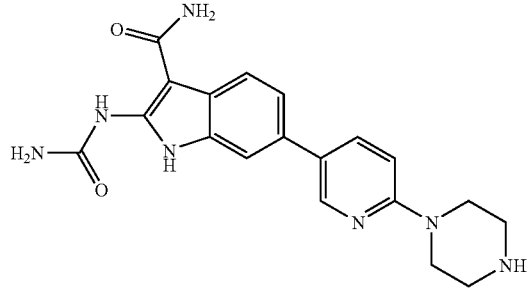 | $^1$H-NMR (400 MHz, DMSO-$d_6$) δ 2.81 (t, J = 5.0 Hz, 4H), 3.44 (t, J = 5.0 Hz, 4H), 6.89 (d, J = 8.6 Hz, 1H), 6.95 (s, 2H), 7.06 (br s, 2H), 7.30 (dd, J = 8.6, 1.5 Hz, 1H), 7.75 (d, J = 1.5 Hz, 1H), 7.78-7.80 (m, 2H), 8.40 (d, J = 2.4 Hz, 1H), 10.54 (s, 1H), 11.65 (s, 1H) |
| 2-Aminocarbonylamino-6-(2-morpholinopyridin-5-yl)indole-3-carboxamide (Compound 4-73) 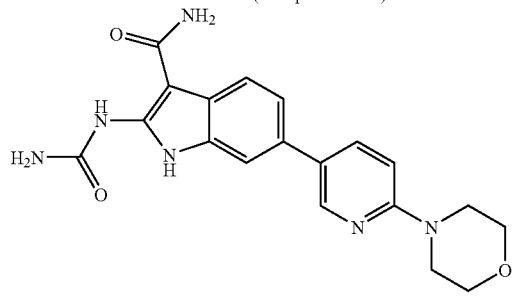 | $^1$H-NMR (500 MHz, DMSO-$d_6$) δ 3.47 (t, J = 4.7 Hz, 4H), 3.72 (t, J = 4.7 Hz, 4H), 6.93 (d, J = 8.9 Hz, 1H), 6.94 (s, 2H), 6.95 (br s, 2H), 7.31 (dd, J = 8.2, 1.8 Hz, 1H), 7.76 (d, J = 1.8 Hz, 1H), 7.79 (d, J = 8.2 Hz, 1H), 7.83 (dd, J = 8.9, 2.7 Hz, 1H), 8.43 (d, J = 2.7 Hz, 1H), 10.53 (s, 1H), 11.65 (s, 1H) |

| | |
|---|---|
| 2-Aminocarbonylamino-6-(5-formylfuran-2-yl)indole-3-carboxamide (Compound 4-74)<br>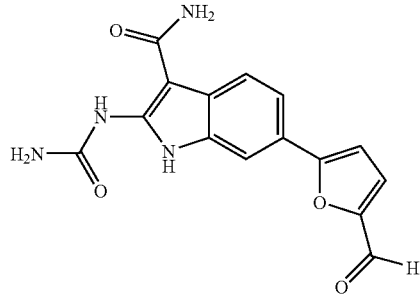 | $^1$H-NMR (400 MHz, DMSO-d$_6$) δ 7.06 (s, 2H), 7.09 (br s, 2H), 7.12 (d, J = 3.9 Hz, 1H), 7.59 (dd, J = 8.5, 1.7 Hz, 1H), 7.65 (d, J = 3.9 Hz, 1H), 7.86 (d, J = 8.5 Hz, 1H), 8.06 (d, J = 1.7 Hz, 1H), 9.55(s, 1H), 10.59 (s, 1H), 11.91 (s, 1H) |
| 2-Aminocarbonylamino-6-(5-formylthiophen-2-yl)indole-3-carboxamide (Compound 4-75)<br>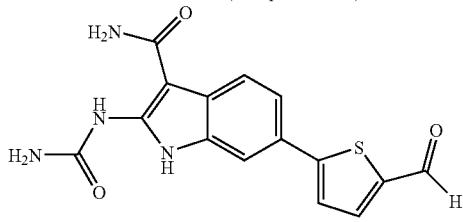 | $^1$H-NMR (400 MHz, DMSO-d$_6$) δ 7.05 (br s, 4H), 7.51 (dd, J = 8.5, 1.2 Hz, 1H), 7.60 (d, J = 3.9 Hz, 1H), 7.83 (d, J = 8.5 Hz, 1H), 7.98 (d, J = 1.2 Hz, 1H), 8.01 (d, J = 3.9 Hz, 1H), 9.87 (s, 1H), 10.57 (s, 1H), 11.86 (s, 1H) |
| 2-Aminocarbonylamino-6-(pyrimidin-5-yl)indole-3-carboxamide (Compound 4-76)<br>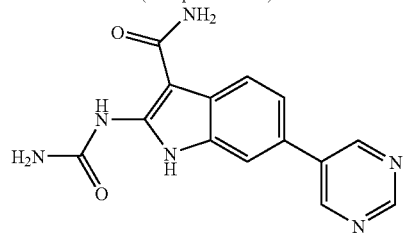 | $^1$H-NMR (500 MHz, DMSO-d$_6$) δ 7.03 (s, 2H), 7.04 (br s, 2H), 7.50 (dd, J = 8.4, 1.7 Hz, 1H), 7.91 (d, J = 8.4 Hz, 1H), 7.93 (d, J = 1.7 Hz, 1H), 9.09 (s, 2H), 9.12 (s, 1H), 10.58 (s, 1H), 11.82 (s, 1H) |
| 2-Aminocarbonylamino-6-(1-methylpyrazol-4-yl)indole-3 carboxamide (Compound 4-77)<br>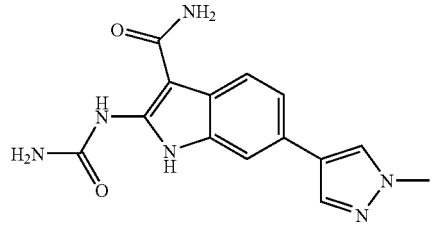 | $^1$H-NMR (400 MHz, DMSO-d$_6$) δ 3.87 (s, 3H), 6.91 (s, 2H), 7.03 (br s, 2H), 7.25 (dd, J = 8.3, 1.5 Hz, 1H), 7.66 (d, J = 1.5 Hz, 1H), 7.71 (d, J = 8.3 Hz, 1H), 7.72 (d, J = 0.7 Hz, 1H), 7.98 (d, J = 0.7 Hz, 1H), 10.50 (s, 1H), 11.57 (s, 1H) |
| 2-Aminocarbonylamino-6-(4-dimethylaminophenyl)indole-3-carboxamide (Compound 4-78)<br>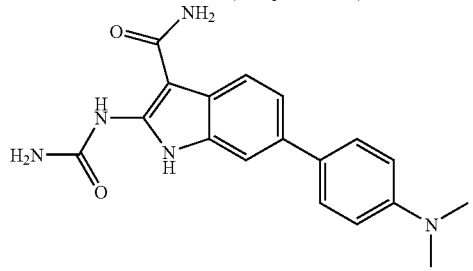 | $^1$H-NMR (400 MHz, DMSO-d$_6$) δ 2.93 (s, 6H), 6.81 (dd, J = 7.0, 2.2 Hz, 2H), 6.92 (s, 2H), 7.01 (br s, 2H), 7.28 (dd, J = 8.6, 2.0 Hz, 1H), 7.47 (dd, J = 7.0, 2.2 Hz, 2H), 7.73 (d, J = 2.0 Hz, 1H), 7.74 (d, J = 8.6 Hz, 1H), 10.53 (s, 1H), 11.60 (s, 1H) |

| Compound | NMR |
|---|---|
| 2-Aminocarbonylamino-6-(3-aminophenyl)indole-3-carboxamide (Compound 4-79) 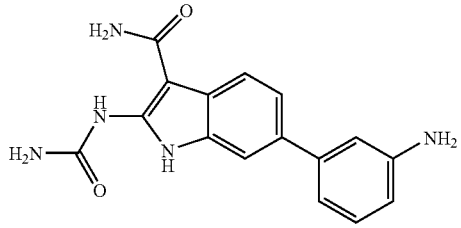 | $^1$H-NMR (500 MHz, DMSO-$d_6$) δ 5.11 (s, 2H), 6.50 (dd, J = 7.8, 1.2 Hz, 1H), 6.75 (dt, J = 7.8, 1.2 Hz, 1H), 6.83 (t, J = 1.5 Hz, 1H), 6.93 (s, 2H), 6.98 (br s, 2H), 7.07 (t, J = 7.8 Hz, 1H), 7.25 (dd, J = 8.2, 1.5 Hz, 1H), 7.73 (d, J = 1.5 Hz, 1H), 7.77 (d, J = 8.2 Hz, 1H), 10.54 (s, 1H), 11.67 (s, 1H) |
| 2-Aminocarbonylamino-7-methyl-6-vinylindole-3-carboxamide (Compound 4-80) 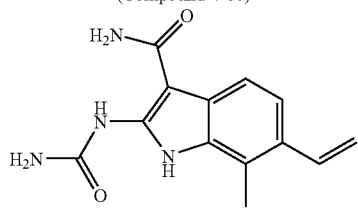 | $^1$H-NMR (500 MHz, DMSO-$d_6$) δ 2.39 (s, 3H), 5.21 (dd, J = 11.1, 1.2 Hz, 1H), 5.64 (dd, J = 17.4, 1.2 Hz, 1H), 6.96 (br s, 4H), 7.05 (dd, J = 17.4, 11.1 Hz, 1H), 7.31 (d, J = 8.5 Hz, 1H), 7.62 (d, J = 8.5 Hz, 1H), 10.39 (s, 1H), 11.19 (s, 1H) |
| 2-Aminocarbonylamino-6-(furan-3-yl)-7-methylindole-3-carboxamide (Compound 4-81) 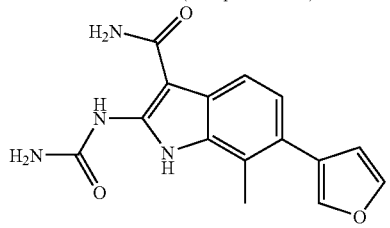 | $^1$H-NMR (500 MHz, DMSO-$d_6$) δ 2.43 (s, 3H), 6.75 (s, 1H), 6.97 (br s, 4H), 7.10 (d, J = 8.2 Hz, 1H), 7.66 (d, J = 8.2 Hz, 1H), 7.74 (s, 1H), 7.81 (s, 1H), 10.41 (s, 1H), 11.22 (s, 1H) |
| 2-Aminocarbonylamino-6-(4-chlorophenyl)indole-3-carboxamide (Compound 4-82) 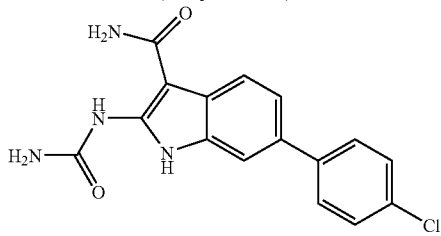 | $^1$H-NMR (400 MHz, DMSO-$d_6$) δ 6.98 (br s, 4H), 7.36 (dd, J = 8.4, 1.8 Hz, 1H), 7.50 (dd, J = 6.6, 2.0 Hz, 2H), 7.65 (dd, J = 6.6, 2.0 Hz, 2H), 7.80-7.86 (m, 2H), 10.56 (s, 1H), 11.73 (s, 1H) |
| 2-Aminocarbonylamino-6-(3-hydroxyphenyl)indole-3-carboxamide (Compound 4-83) 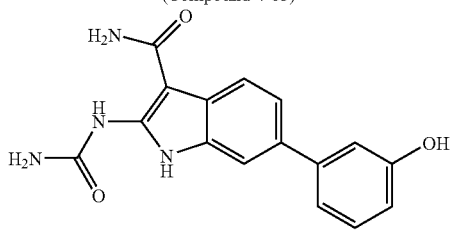 | $^1$H-NMR (400 MHz, DMSO-$d_6$) δ 6.70 (dd, J = 7.9, 2.3 Hz, 1H), 6.95 (br s, 4H), 6.98-7.08 (m, 2H), 7.23 (t, J = 7.9 Hz, 1H), 7.29 (dd, J = 8.3, 1.5 Hz, 1H), 7.77 (d, J = 1.5 Hz, 1H), 7.79 (d, J = 8.3 Hz, 1H), 9.45 (s, 1H), 10.55 (s, 1H), 11.69 (s, 1H) |

| | |
|---|---|
| 2-Aminocarbonylamino-7-methyl-6-phenylindole-3-carboxamide (Compound 4-84) 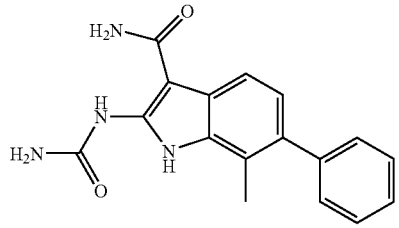 | $^1$H-NMR (400 MHz, DMSO-$d_6$) δ 2.34 (s, 3H), 6.84-7.08 (m, 5H), 7.29-7.40 (m, 3H), 7.40-7.50 (m, 2H), 7.70 (d, J = 8.0 Hz, 1H), 10.43 (s, 1H), 11.22 (s, 1H) |
| 2-Aminocarbonylamino-6-(3-cyanophenyl)-7-methylindole-3-carboxamide (Compound 4-85) 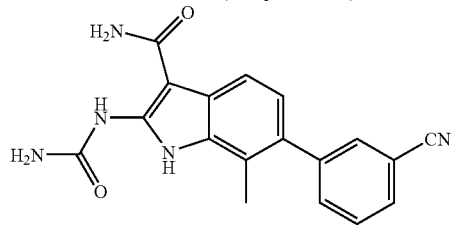 | $^1$H-NMR (400 MHz, DMSO-$d_6$) δ 2.35 (s, 3H), 7.02 (br s, 4H), 7.62-7.69 (m, 2H), 7.69-7.77 (m, 2H), 7.79-7.86 (m, 2H), 10.45 (s, 1H), 11.28 (s, 1H) |
| 2-Aminocarbonylamino-6-(3-methoxyphenyl)-7-methylindole-3-carboxamide (Compound 4-86) 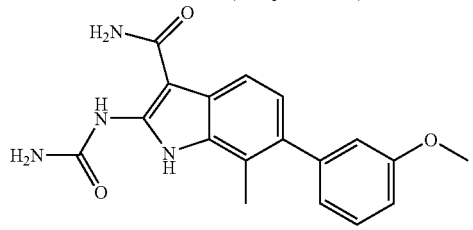 | $^1$H-NMR (500 MHz, DMSO-$d_6$) δ 2.34 (s, 3H), 3.79 (s, 3H), 6.85-6.95 (m, 3H), 6.98 (br s, 4H), 7.00 (d, J = 8.2 Hz, 1H), 7.35 (t, J = 7.9 Hz, 1H), 7.69 (d, J = 8.2 Hz, 1H), 10.42 (s, 1H), 11.22 (s, 1H) |

Example 5

2-Aminocarbonylamino-6-(pyrrol-2-yl)indole-3-carboxamide (Compound 5-1)

Trifluoroacetic acid (0.50 mL, 6.7 mmol) was added to a solution of 2-aminocarbonylamino-6-(1-tert-butoxycarbonylpyrrol-2-yl)indole-3-carboxamide (Compound 4-20, 28 mg, 0.073 mmol) in dichloromethane (0.5 mL) under ice-cooling, and the mixture was stirred for 30 minutes. 2 N Sodium hydroxide aqueous solution (3.5 mL) and water (10 mL) were added to the reaction mixture, and the whole was extracted with ethyl acetate (15 mL). The organic layer was washed with water (5 mL), brine (5 mL), and dried over anhydrous magnesium sulfate. The solvent was evaporated under reduced pressure to give the title compound (6.0 mg) as an off-white solid (yield 29%).

| | |
|---|---|
| 2-Aminocarbonylamino-6-(pyrrol-2-yl)indole-3-carboxamide (Compound 5-1) 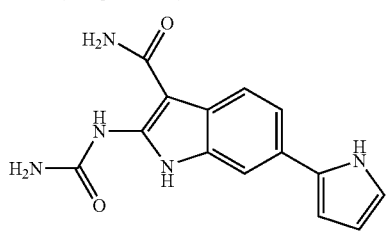 | $^1$H-NMR (500 MHz, DMSO-$d_6$) δ 6.08 (dd, J = 5.5, 2.4 Hz, 1H), 6.32 (m, 1H), 6.77 (m, 1H), 6.91 (s, 2H), 7.00 (br s, 2H), 7.34 (dd, J = 8.2, 1.5 Hz, 1H), 7.69 (d, J = 1.5 Hz, 1H), 7.71 (d, J = 8.2 Hz, 1H), 10.51 (s, 1H), 11.11 (s, 1H), 11.56 (s, 1H) |

As described below, Compound 5-2 was obtained according to the preparation method of Compound 5-1 by using Compound 4-49.

| 2-Aminocarbonylamino-6-(pyrrol-3-yl)indole-3-carboxamide (Compound 5-2) 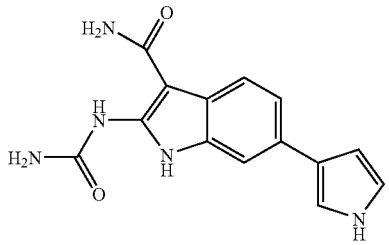 | $^1$H-NMR (500 MHz, DMSO-d$_6$) δ 6.36 (m, 1H), 6.77 (m, 1H), 6.85 (s, 2H), 6.99 (br s, 2H), 7.08 (m, 1H), 7.25 (dd, J = 8.6, 1.8 Hz, 1H), 7.64 (d, J = 8.6 Hz, 1H), 7.64 (d, J = 1.8 Hz, 1H), 10.48 (s, 1H), 10.79 (s, 1H), 11.46 (s, 1H) |
|---|---|

Example 6

2-Aminocarbonylamino-3-carbamoylindole-6-boronic acid pinacol ester (Compound 6-1)

A solution mixture of 2-aminocarbonylamino-6-bromoindole-3-carboxamide (Compound 3-1, 5.3 g, 18 mmol), potassium acetate (5.3 g, 54 mmol), bis(pinacolato)diboron (5.0 g, 20 mmol) and tetrakis(triphenylphosphine)palladium (0) (1.0 g, 0.90 mmol) in water-1,4-dioxane (1:3, 300 mL) was stirred at 100° C. for 2 hours. Brine (100 mL) was added to the reaction mixture, and the whole was extracted with ethyl acetate (100 mL). The organic layer was dried over anhydrous magnesium sulfate and was filtered throught Celite® pad. After the solvent was evaporated under reduced pressure, the resultant solid was washed with ethyl acetate (20 mL), and dried under reduced pressure to give the title compound (2.6 g) as a slightly brown solid (yield 43%).

| 2-Aminocarbonylamino-3-carbamoylindole-6-boronic acid pinacol ester (Compound 6-1) 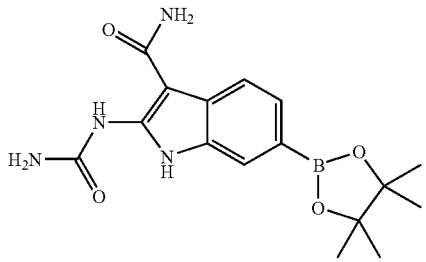 | $^1$H-NMR (400 MHz, DMSO-d$_6$) δ 1.30 (s, 12H), 6.96 (s, 2H), 7.01 (br s, 2H), 7.36 (dd, J = 8.0, 0.5 Hz, 1H), 7.73 (d, J = 8.0 Hz, 1H), 7.84 (s, 1H), 10.58 (s, 1H), 11.69 (s, 1H) |
|---|---|

Example 7

2-Aminocarbonylamino-6-(4-hydroxymethylpyridin-2-yl)indole-3-carboxamide (Compound 7-1)

A solution mixture of 2-aminocarbonylamino-3-carbamoylindole-6-boronic acid pinacol ester (Compound 6-1, 90 mg, 0.26 mmol), sodium hydrogen carbonate (55 mg, 0.65 mmol), 2-bromopyridine-4-methanol (58 mg, 0.31 mmol) and tetrakis(triphenylphosphine)palladium (0) (15 mg, 0.013 mmol) in water-1,4-dioxane (1:3, 15 mL) was stirred at 100° C. for 6 hours. Brine (5 mL) was added to the reaction mixture, and the whole was extracted with ethyl acetate (5 mL). The organic layer was dried over anhydrous magnesium sulfate, and was filtered throught Celite® pad. After the solvent was evaporated under reduced pressure, the resultant solid was washed with ethanol (2 mL), and dried under reduced pressure to give the title compound (20 mg) as a brown solid (yield 23%).

| | |
|---|---|
| 2-Aminocarbonylamino-6-(4-hydroxymethylpyridin-2-yl)indole-3-carboxamide (Compound 7-1) 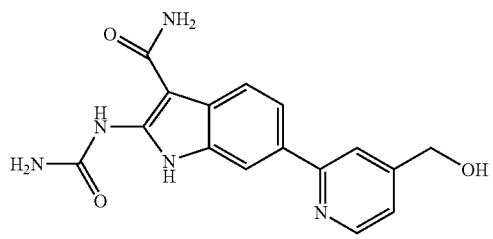 | $^1$H-NMR (400 MHz, DMSO-d$_6$) δ 4.61 (d, J = 5.9 Hz, 2H), 5.47 (t, J = 5.9 Hz, 1H), 7.00 (s, 2H), 7.04 (br s, 2H), 7.19 (dd, J = 5.0, 1.3 Hz, 1H), 7.79-7.84 (m, 3H), 8.28 (d, J = 1.3 Hz, 1H), 8.54 (dd, J = 5.0, 0.5 Hz, 1H), 10.57 (s, 1H), 11.77 (s, 1H) |

As described below, Compound 7-2~7-47 were obtained according to the preparation method of Compound 7-1 by using commercially available reagents, Reference compound 24-1~24-3, 25-1, 25-2, 27-1, 27-2, 28-1, 28-2, 29-1, 29-2 or 30-1~30-5 and Compound 6-1.

| | |
|---|---|
| 2-Aminocarbonylamino-6-(5-aminopyridin-2-yl)indole-3-carboxamide (Compound 7-2) 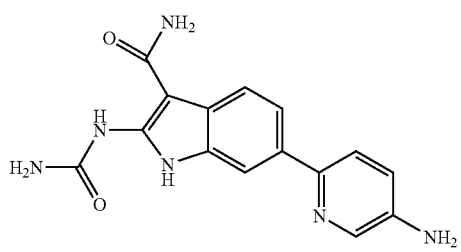 | $^1$H-NMR (500 MHz, DMSO-d$_6$) δ 5.31 (s, 2H), 6.92 (s, 2H), 6.95 (br s, 2H), 6.99 (dd, J = 8.6, 2.7 Hz, 1H), 7.53 (d, J = 8.4 Hz, 1H), 7.64 (dd, J = 8.4, 1.7 Hz, 1H), 7.73 (d, J = 8.6 Hz, 1H), 8.00 (d, J = 2.7 Hz, 1H), 8.05 (d, J = 1.7 Hz, 1H), 10.53 (s, 1H), 11.61 (s, 1H) |
| 2-Aminocarbonylamino-6-(pyridin-2-yl)indole-3-carboxamide (Compound 7-3) 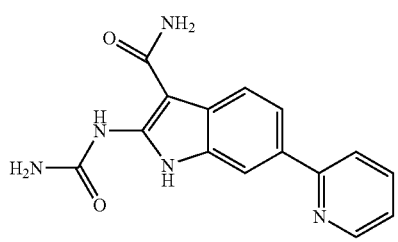 | $^1$H-NMR (500 MHz, DMSO-d$_6$) δ 6.99 (s, 2H), 7.02 (br s, 2H), 7.26 (m, 1H), 7.82-7.87 (m, 4H), 8.26 (s, 1H), 8.62 (td, J = 3.0, 1.8 Hz, 1H), 10.58 (s, 1H), 11.76 (s, 1H) |
| 2-Aminocarbonylamino-6-[4-(2-hydroxyethyl)phenyl]indole-3-carboxamide (Compound 7-4) 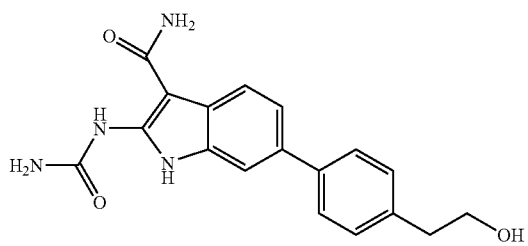 | $^1$H-NMR (500 MHz, DMSO-d$_6$) δ 2.75 (t, J = 7.2 Hz, 2H), 3.63 (td, J = 7.2, 5.2 Hz, 2H), 4.66 (t, J = 5.2 Hz, 1H), 6.95 (s, 2H), 6.96 (br s, 2H), 7.29 (dd, J = 6.4, 1.8 Hz, 2H), 7.33 (dd, J = 8.4, 1.7 Hz, 1H), 7.53 (dd, J = 6.4, 1.8 Hz, 2H), 7.79-7.80 (m, 2H), 10.54 (s, 1H), 11.68 (s, 1H) |

2-Aminocarbonylamino-6-[3-(2-hydroxyethyl)phenyl]indole-3-carboxamide (Compound 7-5)

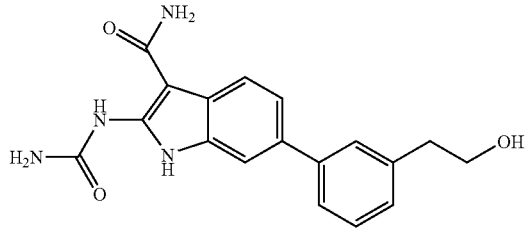

$^1$H-NMR (400 MHz, DMSO-d$_6$) δ 2.79 (t, J = 7.0 Hz, 2H), 3.66 (td, J = 7.0, 5.3 Hz, 2H), 4.67 (t, J = 5.3 Hz, 1H), 6.96 (s, 2H), 7.05 (br s, 2H), 7.15 (dt, J = 7.5, 1.5 Hz, 1H), 7.33-7.34 (m, 2H), 7.36-7.36 (m, 2H), 7.81 (d, J = 8.3 Hz, 1H), 7.83 (d, J = 1.5 Hz, 1H), 10.55 (s, 1H), 11.69 (s, 1H)

2-Aminocarbonylamino-6-(4-morpholinophenyl)indole-3-carboxamide (Compound 7-6)

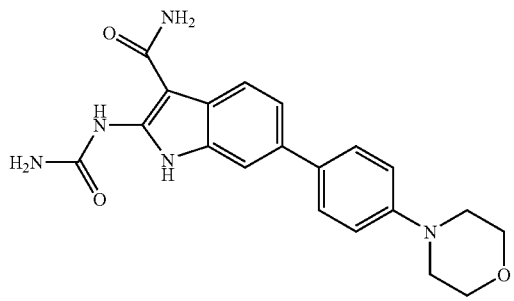

$^1$H NMR (400 MHz, DMSO-d$_6$) δ 3.14 (t, J = 4.9 Hz, 4H), 3.76 (t, J = 4.9 Hz, 4H), 6.93 (s, 2H), 6.99 (br s, 2H), 7.02 (dd, J = 6.8, 2.0 Hz, 2H), 7.30 (dd, J = 8.4, 1.6 Hz, 1H), 7.51 (dd, J = 6.8, 2.0 Hz, 2H), 7.75-7.77 (m, 2H), 10.53 (s, 1H), 11.63 (s, 1H)

2-Aminocarbonylamino-6-[2-(2-hydroxyethyl)phenyl]indole-3-carboxamide (Compound 7-7)

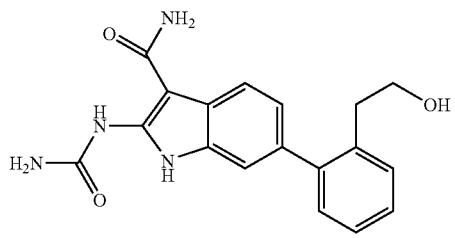

$^1$H-NMR (400 MHz, DMSO-d$_6$) δ 2.74 (t, J = 7.4 Hz, 2H), 3.46 (td, J = 7.4, 5.5 Hz, 2H), 4.55 (t, J = 5.5 Hz, 1H), 6.95 (s, 2H), 6.98 (dd, J = 8.2, 1.6 Hz, 1H), 7.04 (br s, 2H), 7.17 (dd, J = 7.3, 1.7 Hz, 1H), 7.23-7.27 (m, 2H), 7.33 (dd, J = 7.3, 1.7 Hz, 1H), 7.47 (d, J = 1.6 Hz, 1H), 7.78 (d, J = 8.2 Hz, 1H), 10.55 (s, 1H), 11.68 (s, 1H)

2-Aminocarbonylamino-6-[4-(1-hydroxyethyl)phenyl]indole-3-carboxamide (Compound 7-8)

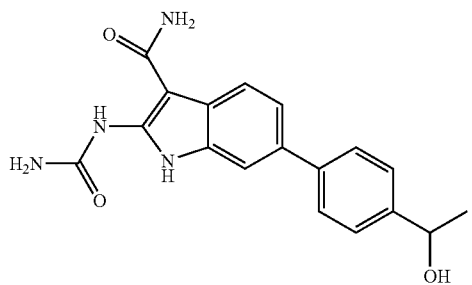

$^1$H-NMR (400 MHz, DMSO-d$_6$) δ 1.36 (d, J = 6.3 Hz, 3H), 4.76 (m, 1H), 5.15 (d, J = 4.2 Hz, 1H), 6.95 (s, 2H), 7.04 (br s, 2H), 7.34 (dd, J = 8.3, 1.3 Hz, 1H), 7.41 (dd, J = 6.2, 2.0 Hz, 2H), 7.57 (dd, J = 6.2, 2.0 Hz, 2H), 7.80 (d, J = 8.3 Hz, 1H), 7.81 (d, J = 1.3 Hz, 1H), 10.54 (s, 1H), 11.68 (s, 1H)

2-Aminocarbonylamino-6-(pyridin-4-yl)indole-3-carboxamide (Compound 7-9)

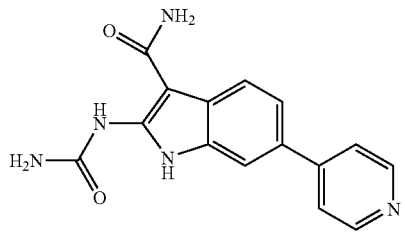

$^1$H-NMR (400 MHz, DMSO-d$_6$) δ 7.02 (s, 2H), 7.09 (br s, 2H), 7.51 (dd, J = 8.3, 1.5 Hz, 1H), 7.65 (dd, J = 4.5, 1.6 Hz, 2H), 7.88 (d, J = 8.3 Hz, 1H), 7.99 (d, J = 1.5 Hz, 1H), 8.59 (dd, J = 4.5, 1.6 Hz, 2H), 10.58 (s, 1H), 11.81 (s, 1H)

| | |
|---|---|
| 2-Aminocarbonylamino-6-[3-(1-hydroxyethyl)phenyl]indole-3-carboxamide (Compound 7-10) 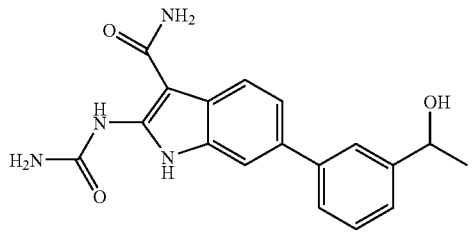 | $^1$H-NMR (400 MHz, DMSO-$d_6$) δ 1.38 (d, J = 6.3 Hz, 3H), 4.79 (m, 1H), 5.21 (d, J = 4.2 Hz, 1H), 6.96 (s, 2H), 7.03 (br s, 2H), 7.26 (dt, J = 7.6, 1.3 Hz, 1H), 7.35 (dd, J = 8.3, 1.8 Hz, 1H), 7.38 (t, J = 7.6 Hz, 1H), 7.47 (dt, J = 7.6, 1.3 Hz, 1H), 7.62 (t, J = 1.3 Hz, 1H), 7.81 (d, J = 8.3 Hz, 1H), 7.85 (d, J = 1.8 Hz, 1H), 10.55 (s, 1H), 11.70 (s, 1H) |
| 2-Aminocarbonylamino-6-(3-dimethylaminophenyl)indole-3-carboxamide (Compound 7-11) 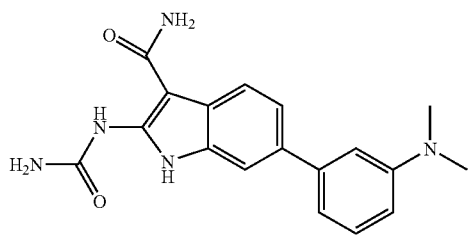 | $^1$H-NMR (400 MHz, DMSO-$d_6$) δ 2.96 (s, 6H), 6.69 (m, 1H), 6.91-6.92 (m, 4H), 6.94 (br s, 2H), 7.24 (t, J = 8.3 Hz, 1H), 7.34 (dd, J = 8.3, 1.7 Hz, 1H), 7.78 (d, J = 8.3 Hz, 1H), 7.83 (d, J = 1.7 Hz, 1H), 10.53 (s, 1H), 11.66 (s, 1H) |
| 2-Aminocarbonylamino-6-(thiazol-2-yl)indole-3-carboxamide (Compound 7-12) 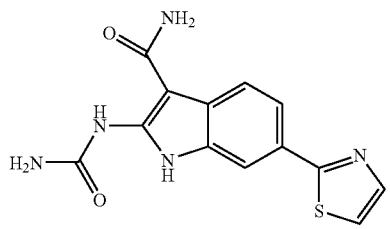 | $^1$H-NMR (500 MHz, DMSO-$d_6$) δ 7.02 (s, 2H), 7.03 (br s, 2H), 7.64-7.65 (m, 2H), 7.82 (d, J = 8.2 Hz, 1H), 7.84 (d, J = 3.4 Hz, 1H), 8.17 (d, J = 1.5 Hz, 1H), 10.57 (s, 1H), 11.88 (s, 1H) |
| 2-Aminocarbonylamino-6-(4-chloro-3-hydroxymethylphenyl)indole-3-carboxamide (Compound 7-13) 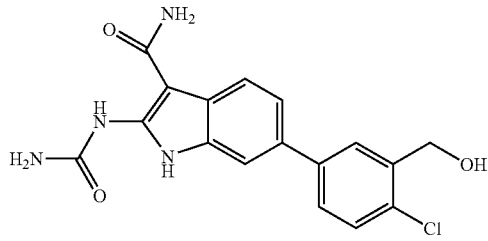 | $^1$H-NMR (500 MHz, DMSO-$d_6$) δ 4.63 (d, J = 5.7 Hz, 2H), 5.47 (t, J = 5.7 Hz, 1H), 6.97 (s, 2H), 6.99 (br s, 2H), 7.36 (dd, J = 8.4, 2.0 Hz, 1H), 7.46 (d, J = 8.2 Hz, 1H), 7.53 (dd, J = 8.2, 1.8 Hz, 1H), 7.82-7.84 (m, 2H), 7.87 (d, J = 1.8 Hz, 1H), 10.55 (s, 1H), 11.74 (s, 1H) |
| 2-Aminocarbonylamino-6-(4-hydroxymethyl-3-methoxyphenyl)indole-3-carboxamide (Compound 7-14) 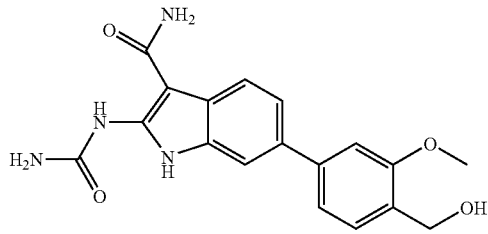 | $^1$H-NMR (400 MHz, DMSO-$d_6$) δ 3.87 (s, 3H), 4.52 (d, J = 5.7 Hz, 2H), 4.98 (t, J = 5.7 Hz, 1H), 6.96 (s, 2H), 7.03 (br s, 2H), 7.16 (d, J = 1.2 Hz, 1H), 7.20 (dd, J = 7.8, 1.2 Hz, 1H), 7.39 (dd, J = 8.5, 1.7 Hz, 1H), 7.42 (d, J = 7.8 Hz, 1H), 7.80 (d, J = 8.5 Hz, 1H), 7.86 (d, J = 1.7 Hz, 1H), 10.54 (s, 1H), 11.68 (s, 1H) |

2-Aminocarbonylamino-6-(3-hydroxymethyl-4-methoxyphenyl)indole-3-carboxamide (Compound 7-15)

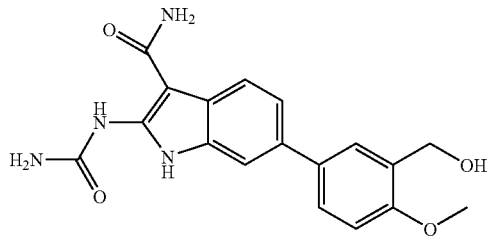

$^1$H-NMR (500 MHz, DMSO-$d_6$) δ 3.81 (s, 3H), 4.55 (d, J = 5.8 Hz, 2H), 5.07 (t, J = 5.8 Hz, 1H), 6.93 (s, 2H), 6.98 (br s, 2H), 7.02 (d, J = 8.6 Hz, 1H), 7.31 (dd, J = 8.2, 1.5 Hz, 1H), 7.47 (dd, J = 8.6, 2.4 Hz, 1H), 7.68 (d, J = 2.4 Hz, 1H), 7.78 (d, J = 8.2 Hz, 1H), 7.79 (d, J = 1.5 Hz, 1H), 10.53 (s, 1H), 11.66 (s, 1H)

2-Aminocarbonylamino-6-(6-aminopyridin-2-yl)indole-3-carboxamide (Compound 7-16)

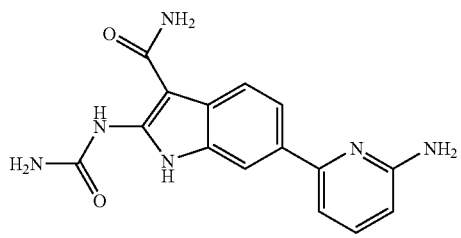

$^1$H-NMR (500 MHz, DMSO-$d_6$) δ 5.86 (s, 2H), 6.35 (dd, J = 7.9, 0.6 Hz, 1H), 6.94 (s, 2H), 6.95 (br s, 2H), 6.97 (dd, J = 7.9, 0.6 Hz, 1H), 7.42 (t, J = 7.9 Hz, 1H), 7.72 (dd, J = 8.3, 1.2 Hz, 1H), 7.76 (d, J = 8.3 Hz, 1H), 8.10 (d, J = 1.2 Hz, 1H), 10.54 (s, 1H), 11.68 (s, 1H)

2-Aminocarbonylamino-6-(3-morpholinophenyl)indole-3-carboxamide (Compound 7-17)

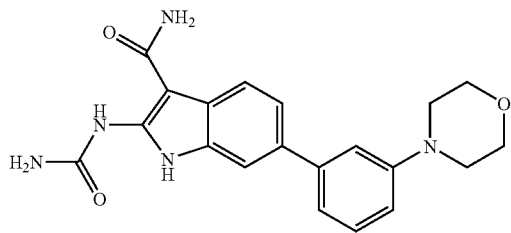

$^1$H-NMR (400 MHz, DMSO-$d_6$) δ 3.18 (t, J = 4.8 Hz, 4H), 3.77 (t, J = 4.8 Hz, 4H), 6.96-6.99 (m, 5H), 7.08 (dt, J = 7.5, 1.4 Hz, 1H), 7.15 (t, J = 1.4 Hz, 1H), 7.29 (t, J = 7.5 Hz, 1H), 7.35 (dd, J = 8.3, 1.5 Hz, 1H), 7.79 (d, J = 8.3 Hz, 1H), 7.83 (d, J = 1.5 Hz, 1H), 10.54 (s, 1H), 11.66 (s, 1H)

2-Aminocarbonylamino-6-(5-aminopyridin-3-yl)indole-3-carboxamide (Compound 7-18)

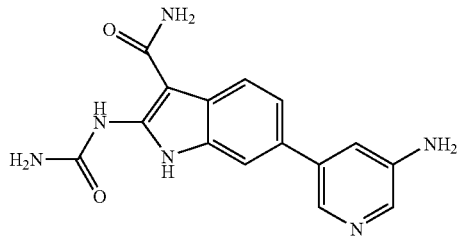

$^1$H-NMR (400 MHz, DMSO-$d_6$) δ 5.37 (s, 2H), 6.96 (s, 2H), 7.00 (br s, 2H), 7.12 (t, J = 2.3 Hz, 1H), 7.28 (dd, J = 8.3, 1.5 Hz, 1H), 7.77 (d, J = 1.5 Hz, 1H), 7.82 (d, J = 8.3 Hz, 1H), 7.87 (d, J = 2.3 Hz, 1H), 8.01 (d, J = 2.3 Hz, 1H), 10.55 (s, 1H), 11.73 (s, 1H)

2-Aminocarbonylamino-6-(5-aminosulfonylthiophen-2-yl)indole-3-carboxamide (Compound 7-19)

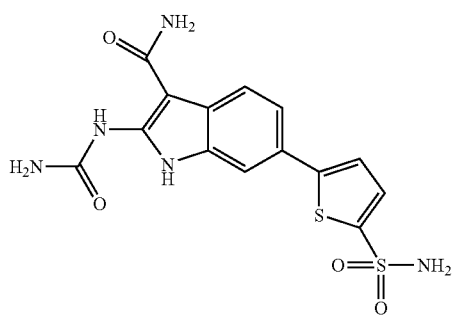

$^1$H-NMR (400 MHz, DMSO-$d_6$) δ 7.01 (s, 2H), 7.03 (br s, 2H), 7.36 (d, J = 3.9 Hz, 1H), 7.40 (dd, J = 8.3, 1.7 Hz, 1H), 7.51 (d, J = 3.9 Hz, 1H), 7.67 (s, 2H), 7.81 (d, J = 8.3 Hz, 1H), 7.86 (d, J = 1.7 Hz, 1H), 10.55 (s, 1H), 11.81 (s, 1H)

| | |
|---|---|
| 2-Aminocarbonylamino-6-(6-morpholinopyridin-2-yl)indole-3-carboxamide (Compound 7-20)<br/>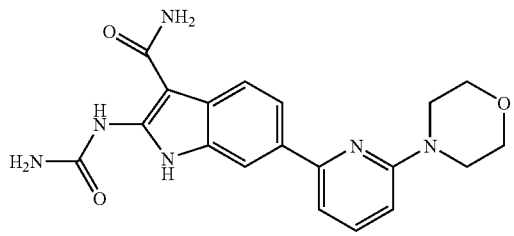 | ¹H-NMR (400 MHz, DMSO-d₆) δ 3.56 (t, J = 4.8 Hz, 4H), 3.76 (t, J = 4.8 Hz, 4H), 6.71 (d, J = 8.3 Hz, 1H), 6.96 (s, 2H), 7.04 (br s, 2H), 7.22 (d, J = 7.6 Hz, 1H), 7.61 (t, J = 7.6 Hz, 1H), 7.74-7.77 (m, 2H), 8.32 (s, 1H), 10.54 (s, 1H), 11.74 (s, 1H) |
| 2-Aminocarbonylamino-6-(5-cyanothiophen-2-yl)indole-3-carboxamide (Compound 7-21)<br/>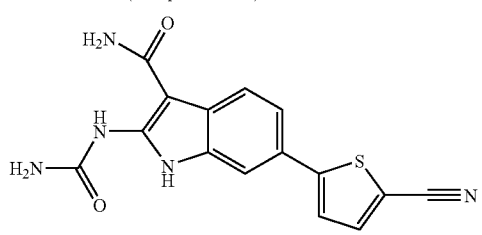 | ¹H-NMR (400 MHz, DMSO-d₆) δ 7.04 (s, 2H), 7.07 (br s, 2H), 7.46 (dd, J = 8.4, 1.8 Hz, 1H), 7.52 (d, J = 3.9 Hz, 1H), 7.82 (d, J = 8.4 Hz, 1H), 7.92 (d, J = 1.8 Hz, 1H), 7.94 (d, J = 3.9 Hz, 1H), 10.56 (s, 1H), 11.85 (s, 1H) |
| 2-Aminocarbonylamino-6-(2,6-diaminopyridin-4-yl)indole-3-carboxamide (Compound 7-22)<br/>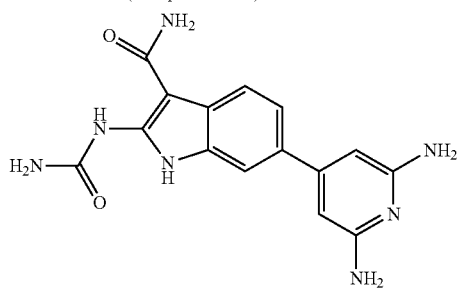 | ¹H-NMR (500 MHz, DMSO-d₆) δ 5.39 (s, 4H), 5.92 (s, 2H), 6.94 (s, 2H), 7.00 (br s, 2H), 7.23 (dd, J = 8.2, 1.8 Hz, 1H), 7.73 (d, J = 1.8 Hz, 1H), 7.77 (d, J = 8.2 Hz, 1H), 10.53 (s, 1H), 11.67 (s, 1H) |
| 2-Aminocarbonylamino-6-(6-hydroxymethylpyridin-2-yl)indole-3-carboxamide (Compound 7-23)<br/>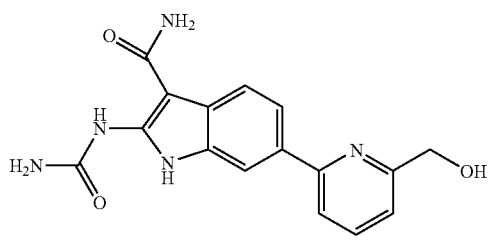 | ¹H-NMR (400 MHz, DMSO-d₆) δ 4.64 (d, J = 5.9 Hz, 2H), 5.41 (t, J = 5.9 Hz, 1H), 6.98 (s, 2H), 7.00 (br s, 2H), 7.35 (d, J = 7.8 Hz, 1H), 7.72 (d, J = 7.8 Hz, 1H), 7.80-7.81 (m, 2H), 7.84 (t, J = 7.8 Hz, 1H), 8.27 (s, 1H), 10.56 (s, 1H), 11.76 (s, 1H) |
| 2-Aminocarbonylamino-6-(1-methylimidazol-2-yl)indole-3-carboxamide (Compound 7-24)<br/>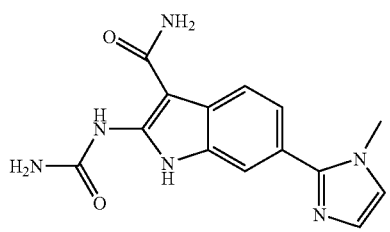 | ¹H-NMR (400 MHz, DMSO-d₆) δ 3.74 (s, 3H), 6.94 (d, J = 1.0 Hz, 1H), 6.98 (s, 2H), 7.02 (br s, 2H), 7.20 (d, J = 1.0 Hz, 1H), 7.37 (dd, J = 8.3, 1.5 Hz, 1H), 7.81 (d, J = 8.3 Hz, 1H), 7.84 (d, J = 1.5 Hz, 1H), 10.56 (s, 1H), 11.76 (s, 1H) |

| | |
|---|---|
| 2-Aminocarbonylamino-6-[3-(1-hydroxy-1-methylethyl)phenyl]indole-3-carboxamide (Compound 7-25)<br>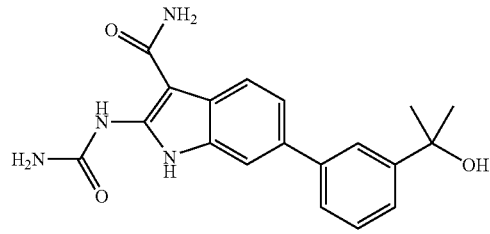 | ¹H-NMR (500 MHz, DMSO-d₆) δ 1.48 (s, 6H), 5.05 (s, 1H), 6.94 (s, 2H), 6.96 (br s, 2H), 7.34-7.39 (m, 3H), 7.44 (dt, J = 6.7, 1.8 Hz, 1H), 7.75 (t, J = 1.8 Hz, 1H), 7.81 (d, J = 8.2 Hz, 1H), 7.85 (d, J = 1.8 Hz, 1H), 10.54 (s, 1H), 11.69 (s, 1H) |
| 2-Aminocarbonylamino-6-(2-chloropyridin-4-yl)indole-3-carboxamide (Compound 7-26)<br>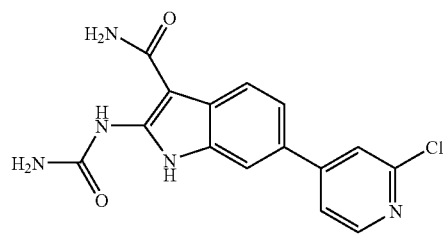 | ¹H-NMR (500 MHz, DMSO-d₆) δ 7.04 (br s, 4H), 7.57 (dd, J = 8.6, 1.8 Hz, 1H), 7.69 (dd, J = 5.2, 1.5 Hz, 1H), 7.75 (d, J = 1.5 Hz, 1H), 7.88 (d, J = 8.6 Hz, 1H), 8.02 (d, J = 1.8 Hz, 1H), 8.41 (d, J = 5.2 Hz, 1H), 10.58 (s, 1H), 11.83 (s, 1H) |
| 2-Aminocarbonylamino-6-(2-formylfuran-4-yl)indole-3-carboxamide (Compound 7-27)<br>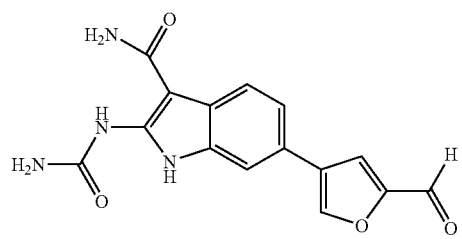 | ¹H-NMR (400 MHz, DMSO-d₆) δ 6.99 (s, 2H), 7.10 (br s, 2H), 7.40 (dd, J = 8.3, 1.7 Hz, 1H), 7.77-7.83 (m, 2H), 7.89 (d, J = 0.7 Hz, 1H), 8.49 (s, 1H), 9.67 (d, J = 0.7 Hz, 1H), 10.54 (s, 1H), 11.71 (s, 1H) |
| 2-Aminocarbonylamino-6-[5-(2-hydroxyethylaminocarbonyl)furan-2-yl]indole-3-carboxamide (Compound 7-28)<br>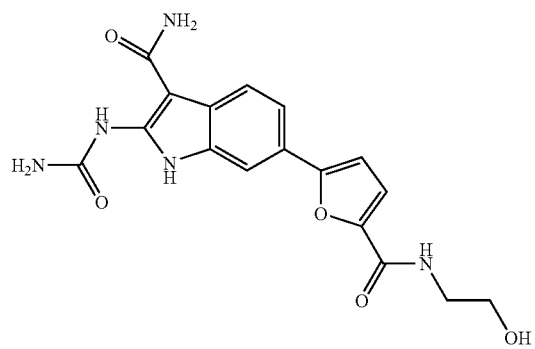 | ¹H-NMR (400 MHz, DMSO-d₆) δ 3.34-3.35 (m, 2H), 3.51-3.53 (m, 2H), 4.78 (t, J = 5.5 Hz, 1H), 6.85 (d, J = 3.4 Hz, 1H), 7.02 (s, 2H), 7.04 (br s, 2H), 7.16 (d, J = 3.4 Hz, 1H), 7.61(dd, J = 8.3, 1.5 Hz, 1H), 7.81 (d, J = 8.3 Hz, 1H), 7.97 (d, J = 1.5 Hz, 1H), 8.30 (t, J = 5.7 Hz, 1H), 10.55 (s, 1H), 11.77 (s, 1H) |

2-Aminocarbonylamino-6-[5-(2-methoxyethylamino-carbonyl)furan-2-yl]indole-3-carboxamide (Compound 7-29)

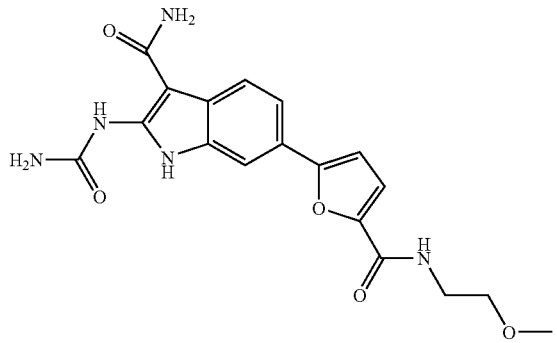

$^1$H-NMR (500 MHz, DMSO-d$_6$) δ 3.28 (s, 3H), 3.43 (t, J = 5.3 Hz, 2H), 3.46-3.48 (m, 2H), 6.84 (d, J = 3.7 Hz, 1H), 7.02 (s, 2H), 7.03 (br s, 2H), 7.17 (d, J = 3.7 Hz, 1H), 7.61 (dd, J = 8.2, 1.5 Hz, 1H), 7.81 (d, J = 8.2 Hz, 1H), 7.97 (d, J = 1.5 Hz, 1H), 8.39 (t, J = 5.3 Hz, 1H), 10.55 (s, 1H), 11.77 (s, 1H)

2-Aminocarbonylamino-6-[5-(2-morpholinoethylamino-carbonyl)furan-2-yl]indole-3-carboxamide (Compound 7-30)

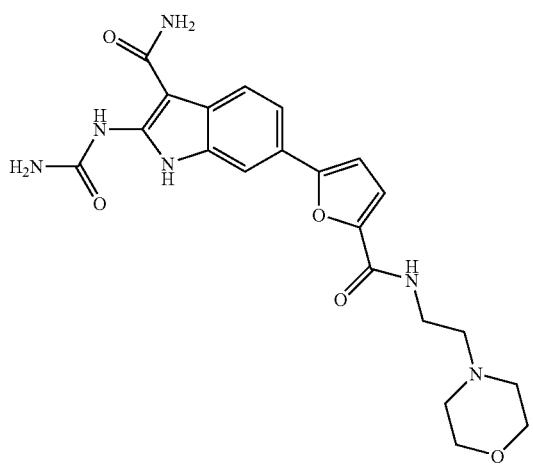

$^1$H-NMR (500 MHz, DMSO-d$_6$) δ 2.43 (t, J = 4.6 Hz, 4H), 2.48 (t, J = 6.3 Hz, 2H), 3.39 (q, J = 6.3 Hz, 2H), 3.58 (t, J = 4.6 Hz, 4H), 6.84 (d, J = 3.7 Hz, 1H), 7.02 (s, 2H), 7.03 (br s, 2H), 7.14 (d, J = 3.7 Hz, 1H), 7.61 (dd, J = 8.6, 1.5 Hz, 1H), 7.82 (d, J = 8.6 Hz, 1H), 7.96 (d, J = 1.5 Hz, 1H), 8.29 (t, J = 6.3 Hz, 1H), 10.55 (s, 1H), 11.76 (s, 1H)

2-Aminocarbonylamino-6-[4-(1-cyanocyclopropyl)phenyl]indole-3-carboxamide (Compound 7-31)

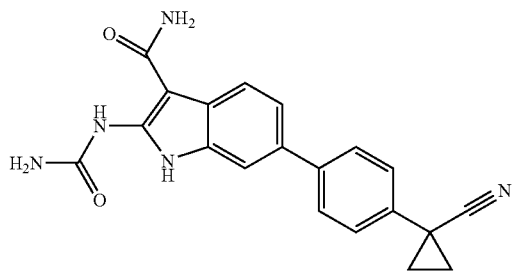

$^1$H-NMR (400 MHz, DMSO-d$_6$) δ 1.54 (dd, J = 7.7, 4.8 Hz, 2H), 1.77 (dd, J = 7.7, 4.8 Hz, 2H), 6.96 (s, 2H), 6.99 (br s, 2H), 7.36 (dd, J = 8.6, 1.7 Hz, 1H), 7.40 (dd, J = 6.6, 2.0 Hz, 2H), 7.65 (dd, J = 6.6, 2.0 Hz, 2H), 7.82 (d, J = 8.6 Hz, 1H), 7.83 (d, J = 1.7 Hz, 1H), 10.55 (s, 1H), 11.71 (s, 1H)

2-Aminocarbonylamino-6-[3-(1-cyanocyclopropyl)phenyl]indole-3-carboxamide (Compound 7-32)

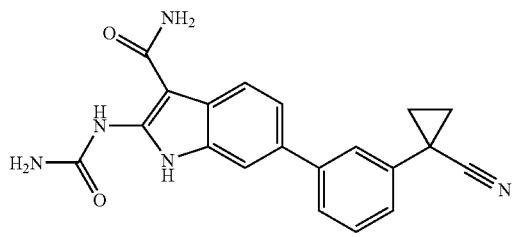

$^1$H-NMR (500 MHz, DMSO-d$_6$) δ 1.60 (dd, J = 7.9, 5.2 Hz, 2H), 1.79 (dd, J = 7.9, 5.2 Hz, 2H), 6.96 (s, 2H), 6.98 (br s, 2H), 7.25 (dt, J = 7.7, 1.3 Hz, 1H), 7.38 (dd, J = 8.2, 1.8 Hz, 1H), 7.46 (t, J = 7.7 Hz, 1H), 7.55 (t, J = 1.3 Hz, 1H), 7.57 (dt, J = 7.7, 1.3 Hz, 1H), 7.83 (d, J = 8.2 Hz, 1H), 7.87 (d, J = 1.8 Hz, 1H), 10.54 (s, 1H), 11.72 (s, 1H)

| | |
|---|---|
| 2-Aminocarbonylamino-6-[4-(2-tert-butoxycarbonylamino-ethyl)phenyl]indole-3-carboxamide (Compound 7-33)<br />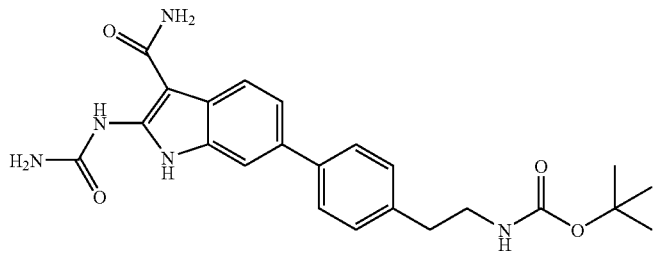 | $^1$H-NMR (500 MHz, DMSO-d$_6$) δ 1.38 (s, 9H), 2.72 (t, J = 7.3 Hz, 2H), 3.16-3.18 (m, 2H), 6.91 (t, J = 5.5 Hz, 1H), 6.95 (s, 2H), 6.98 (br s, 2H), 7.26 (dd, J = 6.4, 1.8 Hz, 2H), 7.33 (dd, J = 8.4, 1.4 Hz, 2H), 7.54 (dd, J = 6.4, 1.8 Hz, 2H), 7.79-7.80 (m, 2H), 10.54 (s, 1H), 11.68 (s, 1H) |
| 2-Aminocarbonylamino-6-[4-(4-tert-butoxycarbonylpiper-azin-1-yl)phenyl]indole-3-carboxamide (Compound 7-34)<br />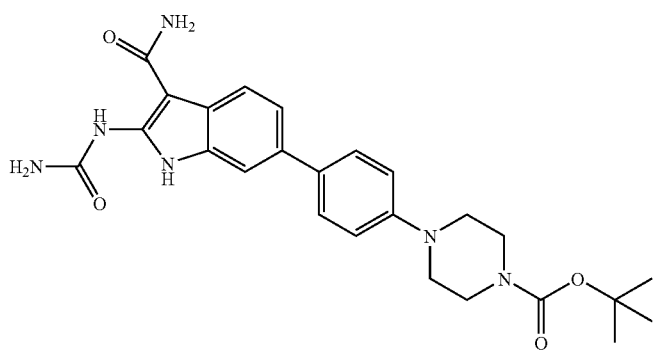 | $^1$H-NMR (500 MHz, DMSO-d$_6$) δ 1.43 (s, 9H), 3.14 (t, J = 5.0 Hz, 4H), 3.48 (t, J = 5.0 Hz, 4H), 6.92 (s, 2H), 6.95 (br s, 2H), 7.03 (dd, J = 6.9, 2.0 Hz, 2H) 7.30 (dd, J = 8.4, 1.7 Hz, 1H), 7.50 (dd, J = 6.9, 2.0 Hz, 2H), 7.76-7.77 (m, 2H), 10.53 (s, 1H), 11.62 (s, 1H) |
| 2-Aminocarbonylamino-6-[4-(tert-butoxycarbonylamino methyl)phenyl]indole-3-carboxamide (Compound 7-35)<br />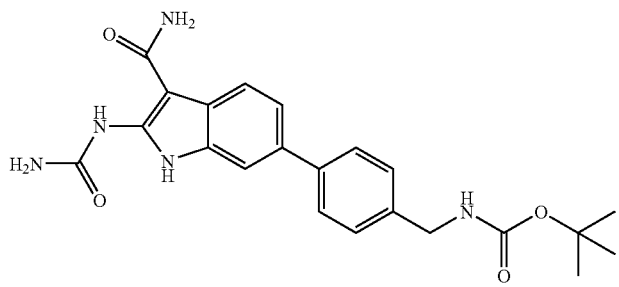 | $^1$H-NMR (500 MHz, DMSO-d$_6$) δ 1.41 (s, 9H), 4.15 (d, J = 6.0 Hz, 2H), 6.95 (s, 2H), 7.00 (br s, 2H), 7.30 (d, J = 8.2 Hz, 2H), 7.34 (dd, J = 8.2, 1.8 Hz, 1H), 7.41 (t, J = 6.0 Hz, 1H), 7.57 (d, J = 8.2 Hz, 2H), 7.79-7.81 (m, 2H), 10.54 (s, 1H), 11.68 (s, 1H) |
| 2-Aminocarbonylamino-6-[3-(tert-butoxycarbonylamino methyl)phenyl]indole-3-carboxamide (Compound 7-36)<br />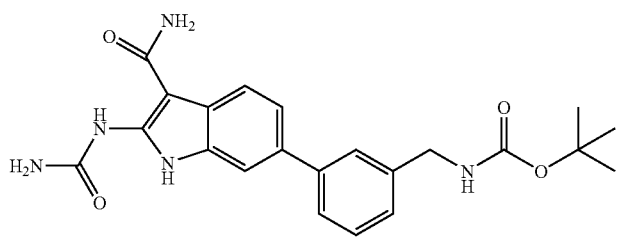 | $^1$H-NMR (500 MHz, DMSO-d$_6$) δ 1.41 (s, 9H), 4.20 (d, J = 6.0 Hz, 2H), 6.95 (s, 2H), 6.98 (br s, 2H), 7.16 (d, J = 7.6 Hz, 1H), 7.33 (dd, J = 8.2, 1.5 Hz, 1H), 7.38 (t, J = 7.6 Hz, 1H), 7.44 (t, J = 6.0 Hz, 1H), 7.48 (d, J = 7.6 Hz, 1H), 7.51 (s, 1H), 7.81-7.82 (m, 2H), 10.55 (s, 1H), 11.71 (s, 1H) |

| | |
|---|---|
| 2-Aminocarbonylamino-6-[4-(1-tert-butoxycarbonylamino-ethyl)phenyl]indole-3-carboxamide (Compound 7-37) 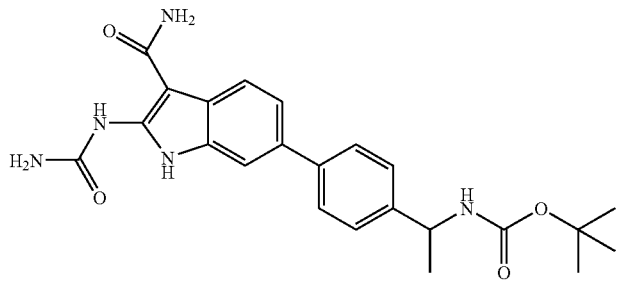 | $^1$H-NMR (500 MHz, DMSO-d$_6$) δ 1.34 (d, J = 7.0 Hz, 3H), 1.38 (s, 9H), 4.64 (m, 1H), 6.94 (s, 2H) 6.98 (br s, 2H), 7.33 (d, J = 1.8 Hz, 1H), 7.36 (dd, J = 6.4, 1.8 Hz, 2H), 7.40 (d, J = 8.2 Hz, 1H), 7.56 (dd, J = 6.4, 1.8 Hz, 2H), 7.80 (d, J = 8.2 Hz, 1H), 7.81 (s, 1H), 10.54 (s, 1H), 11.68 (s, 1H) |
| 2-Aminocarbonylamino-6-[4-(1-tert-butoxycarbonylamino-1-methylethyl)phenyl]indole-3-carboxamide (Compound 7-38) 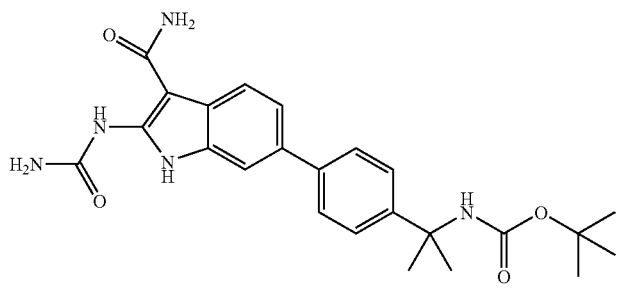 | $^1$H-NMR (500 MHz, DMSO-d$_6$) δ 1.36 (s, 9H), 1.53 (s, 6H), 6.94 (s, 2H), 6.98 (br s, 2H), 7.19 (s, 1H), 7.35 (dd, J = 8.2, 1.5 Hz, 1H), 7.39 (dd, J = 6.4, 1.8 Hz, 2H), 7.54 (dd, J = 6.4, 1.8 Hz, 2H), 7.80 (d, J = 8.2 Hz, 1H), 7.82 (d, J = 1.5 Hz, 1H), 10.54 (s, 1H), 11.68 (s, 1H) |
| 2-Aminocarbonylamino-6-[3-[1-(N-tert-butoxycarbonyl-N-cyclopropylamino)ethyl]phenyl]indole-3-carboxamide (Compound 7-39) 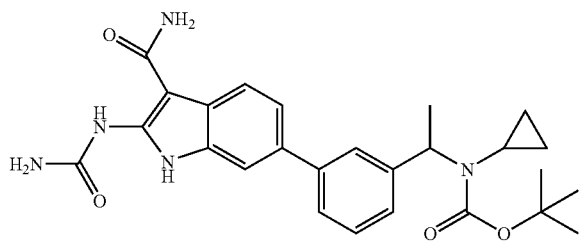 | $^1$H-NMR (400 MHz, DMSO-d$_6$) δ 0.54-0.64 (m, 4H), 1.33 (s, 9H), 1.67 (d, J = 7.0 Hz, 3H), 2.50 (m, 1H), 5.05 (q, J = 7.0 Hz, 1H), 6.96 (s, 2H), 7.00 (br s, 2H), 7.17 (d, J = 7.5 Hz, 1H), 7.31 (dd, J = 8.3, 1.2 Hz, 1H), 7.39 (t, J = 7.5 Hz, 1H), 7.47-7.49 (m, 2H), 7.81-7.82 (m, 2H), 10.55 (s, 1H), 11.72 (s, 1H) |
| 2-Aminocarbonylamino-6-[4-(1-tert-butoxycarbonylamino-cyclopropyl)phenyl]indole-3-carboxamide (Compound 7-40) 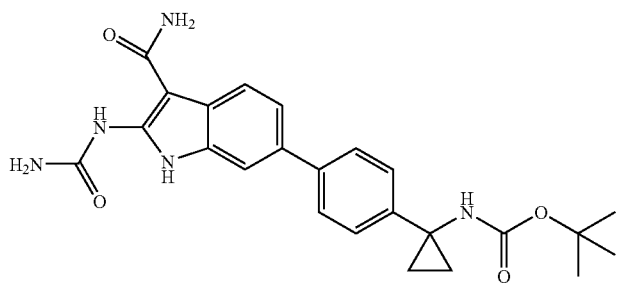 | $^1$H-NMR (400 MHz, DMSO-d$_6$) δ 1.13-1.15 (m, 4H), 1.40 (s, 9H), 6.94 (s, 2H), 7.00 (br s, 2H), 7.20 (d, J = 8.3 Hz, 2H), 7.34 (d, J = 8.5 Hz, 1H), 7.53 (d, J = 8.3 Hz, 2H), 7.72 (s, 1H), 7.79-7.82 (m, 2H), 10.54 (s, 1H), 11.67 (s, 1H) |

| | |
|---|---|
| 2-Aminocarbonylamino-6-[4-[1-(N-tert-butoxycarbonyl-N-cyclopropylamino)ethyl]phenyl]indole-3-carboxamide (Compound 7-41) 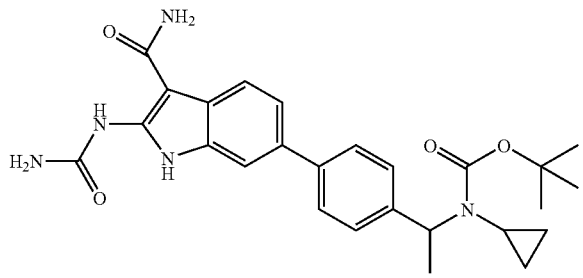 | ¹H-NMR (500 MHz, DMSO-d₆) δ 0.45 (m, 1H), 0.57-0.59 (m, 2H), 0.68 (m, 1H), 1.36 (s, 9H), 1.64 (d, J = 7.3 Hz, 3H), 2.44 (m, 1H), 5.04 (q, J = 7.3 Hz, 1H), 6.94 (s, 2H), 6.96 (br s, 2H), 7.31 (d, J = 8.3 Hz, 2H), 7.36 (dd, J = 8.2, 1.2 Hz, 1H), 7.59 (d, J = 8.3 Hz, 2H), 7.80 (d, J = 8.2 Hz, 1H), 7.82 (d, J = 1.2 Hz, 1H), 10.54 (s, 1H), 11.68 (s, 1H) |
| 2-Aminocarbonylamino-6-[3-(1-tert-butoxycarbonylamino-cyclopropyl)phenyl]indole-3-carboxamide (Compound 7-42) 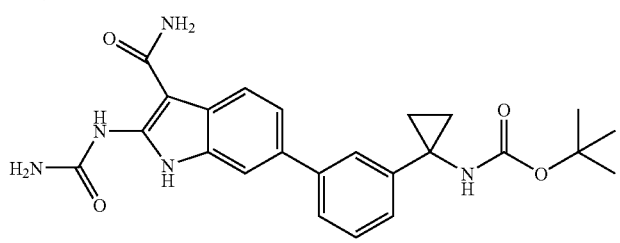 | ¹H-NMR (400 MHz, DMSO-d₆) δ 1.07-1.07 (m, 2H), 1.17-1.18 (m, 2H), 1.40 (s, 9H), 6.96 (s, 2H), 7.00 (br s, 2H), 7.06 (d, J = 7.3 Hz, 1H), 7.30-7.38 (m, 4H), 7.74 (s, 1H), 7.80-7.82 (m, 2H), 10.55 (s, 1H), 11.70 (s, 1H) |
| 2-Aminocarbonylamino-6-[3-(1-tert-butoxycarbonylamino-1-methylethyl)phenyl]indole-3-carboxamide (Compound 7-43) 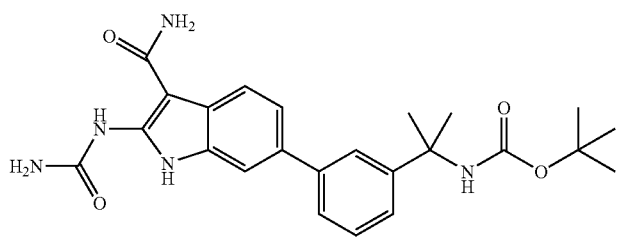 | ¹H-NMR (500 MHz, DMSO-d₆) δ 1.36 (s, 9H), 1.55 (s, 6H), 6.95 (s, 2H), 6.98 (br s, 2H), 7.22 (s, 1H), 7.26 (dt, J = 7.6, 1.5 Hz, 1H), 7.31 (dd, J = 8.2, 1.5 Hz, 1H), 7.35 (t, J = 7.6 Hz, 1H), 7.42 (dt, J = 7.6, 1.5 Hz, 1H), 7.58 (t, J = 1.5 Hz, 1H), 7.81 (d, J = 8.2 Hz, 1H), 7.82 (d, J = 1.5 Hz, 1H), 10.54 (s, 1H), 11.70 (s, 1H) |
| 2-Aminocarbonylamino-6-[(1R)-3-(1-hydroxyethyl)phenyl]indole-3-carboxamide (Compound 7-44) 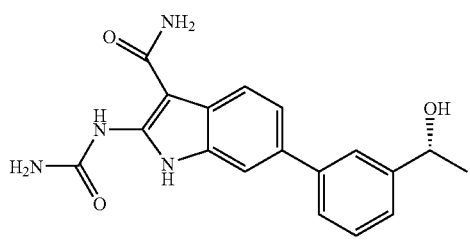 | ¹H-NMR (400 MHz, DMSO-d₆) δ 1.38 (d, J = 6.3 Hz, 3H), 4.79 (m, 1H), 5.20 (d, J = 4.1 Hz, 1H), 6.95 (s, 2H), 7.05 (br s, 2H), 7.26 (dt, J = 7.6, 1.5 Hz, 1H), 7.36 (dd, J = 8.2, 1.8 Hz, 1H), 7.38 (t, J = 7.6 Hz, 1H), 7.47 (dt, J = 7.6, 1.5 Hz, 1H), 7.62 (t, J = 1.5 Hz, 1H), 7.81 (d, J = 8.2 Hz, 1H), 7.85 (d, J = 1.8 Hz, 1H), 10.55 (s, 1H), 11.70 (s, 1H) |

| | |
|---|---|
| 2-Aminocarbonylamino-6-[(1S)-3-(1-hydroxyethyl)phenyl]indole-3-carboxamide (Compound 7-45)<br>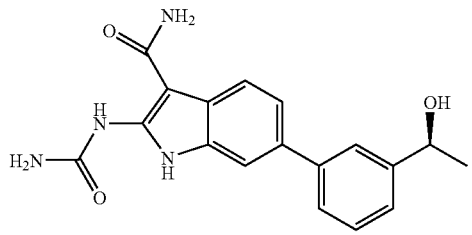 | $^1$H-NMR (400 MHz, DMSO-d$_6$) δ 1.38 (d, J = 6.6 Hz, 3H), 4.79 (m, 1H), 5.20 (d, J = 4.1 Hz, 1H), 6.95 (s, 2H), 7.05 (br s, 2H), 7.26 (dt, J = 7.7, 1.6 Hz, 1H), 7.35 (dd, J = 8.3, 1.5 Hz, 1H), 7.38 (t, J = 7.6 Hz, 1H), 7.47 (dt, J = 7.7, 1.6 Hz, 1H), 7.62 (t, J = 1.6 Hz, 1H), 7.81 (d, J = 8.3 Hz, 1H), 7.85 (d, J = 1.5 Hz, 1H), 10.54 (s, 1H), 11.70 (s, 1H) |
| 2-Aminocarbonylamino-6-(2-cyanopyridin-4-yl)indole-3-carboxamide (Compound 7-46)<br>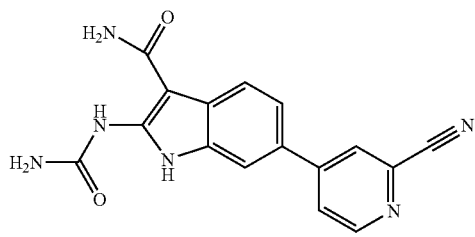 | $^1$H-NMR (400 MHz, DMSO-d$_6$) δ 7.07 (br s, 4H), 7.64 (dd, J = 8.4, 1.7 Hz, 1H), 7.91 (d, J = 8.4 Hz, 1H), 7.98 (dd, J = 5.2, 1.8 Hz, 1H), 8.06 (d, J = 1.8 Hz, 1H), 8.34 (d, J = 1.7 Hz, 1H), 8.74 (d, J = 5.2 Hz, 1H), 10.60 (s, 1H), 11.87 (s, 1H) |
| 2-Aminocarbonylamino-6-(4-acetylaminomethylphenyl)indole-3-carboxamide (Compound 7-47)<br>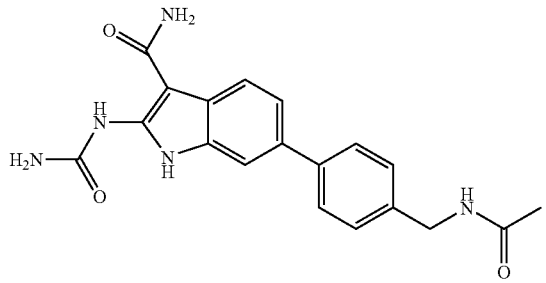 | $^1$H-NMR (400 MHz, DMSO-d$_6$) δ 1.89 (s, 3H), 4.28 (d, J = 5.9 Hz, 2H), 6.96 (s, 2H), 7.02 (br s, 2H), 7.32-7.34 (m, 3H), 7.57 (dd, J = 6.5, 1.8 Hz, 2H), 7.80-7.81 (m, 2H), 8.36 (t, J = 5.9 Hz, 1H), 10.55 (s, 1H), 11.69 (s, 1H) |

Example 8

2-Aminocarbonylamino-6-[4-(2-aminoethyl)phenyl]indole-3-carboxamide hydrochloride (Compound 8-1)

4 N Hydrogene chloride dioxane solution (15 mL) was added to 2-aminocarbonylamino-6-[4-(2-tert-butoxycarbonylaminoethyl)phenyl]indole-3-c arboxamide (Compound 7-33, 65 mg, 0.15 mmol) under ice-cooling, and the mixture was stirred at room temperature overnight. After the reaction mixture was concentrated under reduced pressure, the precipitated solid was washed with ethyl acetate (3 mL), and dried under reduced pressure to give the title compound (56 mg) quantitatively as a slightly yellow solid.

| | |
|---|---|
| 2-Aminocarbonylamino-6-[4-(2-aminoethyl)phenyl]indole-3-carboxamide hydrochloride (Compound 8-1)<br>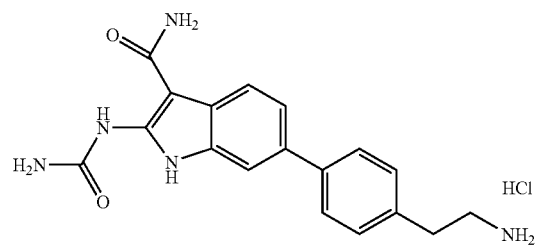 | $^1$H-NMR (400 MHz, DMSO-d$_6$) δ 2.90-2.95 (m, 2H), 3.06-3.08 (m, 2H), 6.98 (br s, 4H), 7.34-7.36 (m, 3H), 7.60 (dd, J = 6.3, 2.0 Hz, 2H), 7.79-7.82 (m, 2H), 8.01 (s, 3H), 10.55 (s, 1H), 11.69 (s, 1H) |

As described below, Compound 8-2~8-11 were obtained according to the preparation method of Compound 8-1 by using Compound 7-34~7-43.

2-Aminocarbonylamino-6-[4-(piperazin-1-yl)phenyl]indole-3-carboxamide hydrochloride (Compound 8-2)

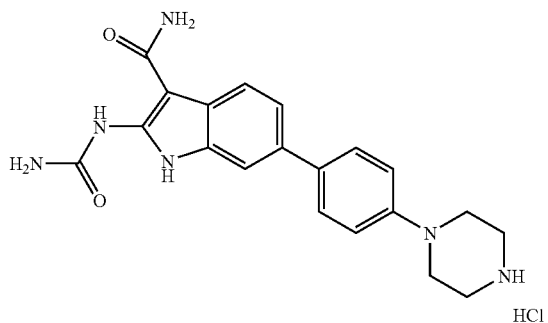

$^1$H-NMR (400 MHz, DMSO-$d_6$) δ 3.24 (t, J = 5.2 Hz, 4H), 3.40 (t, J = 5.2 Hz, 4H), 6.95 (s, 2H), 7.01 (br s, 2H), 7.08 (dd, J = 7.0, 2.1 Hz, 2H), 7.31 (dd, J = 8.4, 1.6 Hz, 1H), 7.54 (dd, J = 7.0, 2.1 Hz, 2H), 7.77 (d, J = 1.6 Hz, 1H), 7.78 (d, J = 8.4 Hz, 1H), 9.06 (s, 2H), 10.54 (s, 1H), 11.64 (s, 1H)

2-Aminocarbonylamino-6-(4-aminomethylphenyl)indole-3-carboxamide hydrochloride (Compound 8-3)

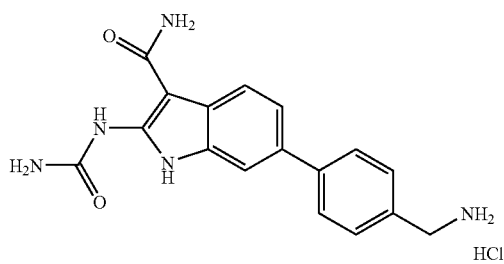

$^1$H-NMR (500 MHz, DMSO-$d_6$) δ 4.05-4.07 (m, 2H), 6.99 (s, 2H), 7.03 (br s, 2H), 7.38 (dd, J = 8.2, 1.5 Hz, 1H), 7.55 (dd, J = 6.4, 1.8 Hz, 2H), 7.68 (dd, J = 6.4, 1.8 Hz, 2H), 7.83 (d, J = 8.2 Hz, 1H), 7.85 (d, J = 1.5 Hz, 1H), 8.33 (s, 3H), 10.55 (s, 1H), 11.71 (s, 1H)

2-Aminocarbonylamino-6-(3-aminomethylphenyl)indole-3-carboxamide hydrochloride (Compound 8-4)

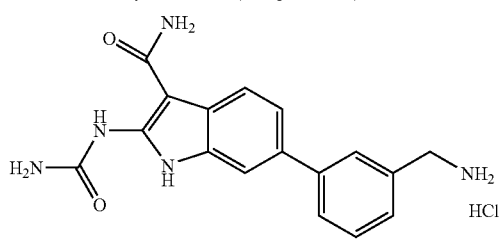

$^1$H-NMR (500 MHz, DMSO-$d_6$) δ 4.10-4.12 (m, 2H), 6.98 (s, 2H), 7.02 (br s, 2H), 7.39-7.42 (m, 2H), 7.50 (t, J = 7.6 Hz, 1H), 7.64 (d, J = 7.6 Hz, 1H), 7.79 (s, 1H), 7.85-7.86 (m, 2H), 8.32 (s, 3H), 10.56 (s, 1H), 11.73 (s, 1H)

2-Aminocarbonylamino-6-[4-(1-aminoethyl)phenyl]indole-3-carboxamide hydrochloride (Compound 8-5)

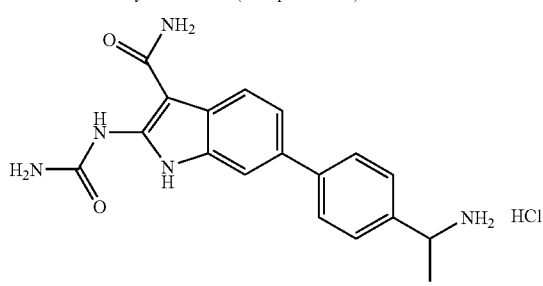

$^1$H-NMR (400 MHz, DMSO-$d_6$) δ 1.55 (d, J = 6.8 Hz, 3H), 4.44 (m, 1H), 6.98 (s, 2H), 7.03 (br s, 2H), 7.38 (dd, J = 8.3, 1.7 Hz, 1H), 7.57 (dd, J = 6.6, 2.0 Hz, 2H), 7.69 (dd, J = 6.6, 2.0 Hz, 2H), 7.83 (d, J = 8.3 Hz, 1H), 7.85 (d, J = 1.7 Hz, 1H), 8.40 (s, 3H), 10.55 (s, 1H), 11.71 (s, 1H)

| | |
|---|---|
| 2-Aminocarbonylamino-6-[4-(1-amino-1-methylethyl)phenyl]indole-3-carboxamide hydrochloride (Compound 8-6) 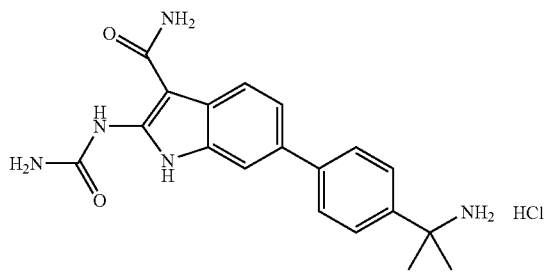 | $^1$H-NMR (400 MHz, DMSO-$d_6$) δ 1.68 (s, 6H), 6.99 (s, 2H), 7.05 (br s, 2H), 7.39 (dd, J = 8.5, 1.7 Hz, 1H), 7.63 (dd, J = 6.6, 2.0 Hz, 2H), 7.69 (dd, J = 6.6, 2.0 Hz, 2H), 7.83 (d, J = 8.5 Hz, 1H), 7.85 (d, J = 1.7 Hz, 1H), 8.65 (s, 3H), 10.55 (s, 1H), 11.71 (s, 1H) |
| 2-Aminocarbonylamino-6-[3-(1-N-cyclopropylamino-ethyl)phenyl]indole-3-carboxamide hydrochloride (Compound 8-7) 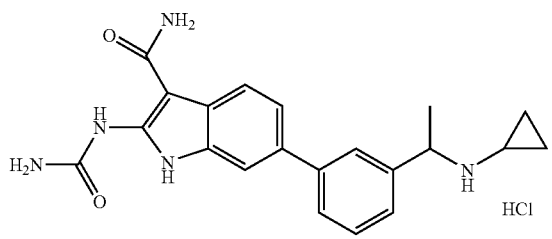 | $^1$H-NMR (500 MHz, DMSO-$d_6$) δ 0.66-0.93 (m, 4H), 1.66 (d, J = 6.4 Hz, 3H), 2.50 (m, 1H), 4.52 (q, J = 6.4 Hz, 1H), 6.98 (s, 2H), 7.02 (br s, 2H), 7.42 (dd, J = 8.2, 1.5 Hz, 1H), 7.47 (dt, J = 7.8, 1.3 Hz, 1H), 7.53 (t, J = 7.8 Hz, 1H), 7.66 (dt, J = 7.8, 1.3 Hz, 1H), 7.84 (s, 1H), 7.86-7.87 (m, 2H), 9.25 (s, 1H), 9.44 (s, 1H), 10.56 (s, 1H), 11.73 (s, 1H) |
| 2-Aminocarbonylamino-6-[4-(1-aminocyclopropyl)phenyl]indole-3-carboxamide hydrochloride (Compound 8-8) 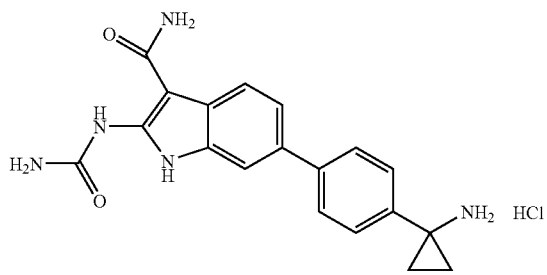 | $^1$H-NMR (500 MHz, DMSO-$d_6$) δ 1.24 (t, J = 6.6 Hz, 2H), 1.40 (t, J = 6.6 Hz, 2H), 6.97 (s, 2H), 7.00 (br s, 2H), 7.38 (dd, J = 8.4, 1.7 Hz, 1H), 7.50 (dd, J = 6.6, 2.0 Hz, 2H), 7.67 (dd, J = 6.6, 2.0 Hz, 2H), 7.82 (d, J = 8.4 Hz, 1H), 7.84 (d, J = 1.7 Hz, 1H), 8.82 (s, 3H), 10.55 (s, 1H), 11.71 (s, 1H) |
| 2-Aminocarbonylamino-6-[4-(1-N-cyclopropylamino-ethyl)phenyl]indole-3-carboxamide hydrochloride (Compound 8-9) 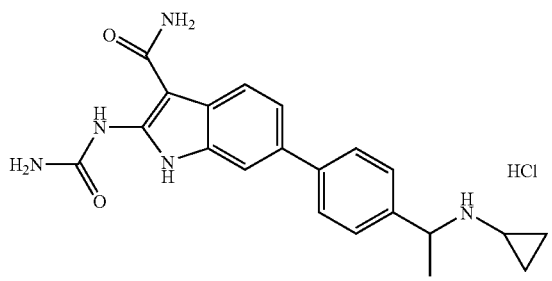 | $^1$H-NMR (500 MHz, DMSO-$d_6$) δ 0.67-0.71 (m, 2H), 0.84 (m, 1H), 0.94 (m, 1H), 1.64 (d, J = 6.7 Hz, 3H), 2.44 (m, 1H), 4.46 (m, 1H), 6.97 (s, 2H), 6.98 (br s, 2H), 7.39 (dd, J = 8.2, 1.7 Hz, 1H), 7.65 (dd, J = 6.6, 2.0 Hz, 2H), 7.71 (dd, J = 6.6, 2.0 Hz, 2H), 7.83 (d, J = 8.2 Hz, 1H), 7.86 (d, J = 1.7 Hz, 1H), 9.39 (s, 1H), 9.66 (s, 1H), 10.55 (s, 1H), 11.71 (s, 1H) |

| | |
|---|---|
| 2-Aminocarbonylamino-6-[3-(1-aminocyclopropyl)phenyl]indole-3-carboxamide hydrochloride (Compound 8-10)<br>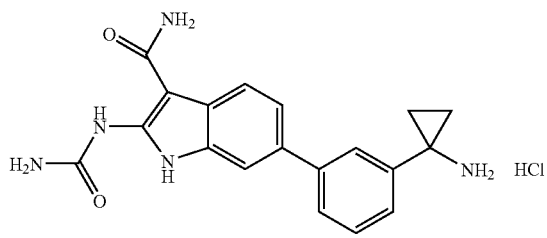 | $^1$H-NMR (500 MHz, DMSO-$d_6$) δ 1.28 (t, J = 6.6 Hz, 2H), 1.42 (t, J = 6.6 Hz, 2H), 6.98 (s, 2H), 7.00 (br s, 2H), 7.34 (dt, J = 7.9, 1.5 Hz, 1H), 7.44 (dd, J = 8.4, 1.7 Hz, 1H), 7.48 (t, J = 7.9 Hz, 1H), 7.61 (dt, J = 7.9, 1.5 Hz, 1H), 7.73 (t, J = 1.5 Hz, 1H), 7.84 (d, J = 8.4 Hz, 1H), 7.87 (d, J = 1.7 Hz, 1H), 8.90 (s, 3H), 10.55 (s, 1H), 11.71 (s, 1H) |
| 2-Aminocarbonylamino-6-[3-(1-amino-1-methylethyl)phenyl]indole-3-carboxamide hydrochloride (Compound 8-11)<br>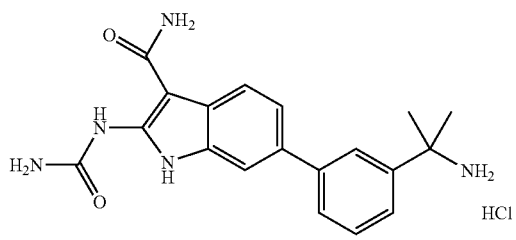 | $^1$H-NMR (400 MHz, DMSO-$d_6$) δ 1.70 (s, 6H), 6.99 (s, 2H), 7.06 (br s, 2H), 7.44 (dd, J = 8.3, 1.7 Hz, 1H), 7.47 (dt, J = 7.4, 1.3 Hz, 1H), 7.52 (t, J = 7.4 Hz, 1H), 7.62 (dt, J = 7.4, 1.3 Hz, 1H), 7.83 (t, J = 1.3 Hz, 1H), 7.85 (d, J = 8.3 Hz, 1H), 7.89 (d, J = 1.7 Hz, 1H), 8.59 (s, 3H), 10.56 (s, 1H), 11.72 (s, 1H) |

Example 9

2-Aminocarbonylamino-6-phenylethynylindole-3-carboxamide (Compound 9-1)

A solution mixture of 2-aminocarbonylamino-6-bromoindole-3-carboxamide (Compound 3-1, 50 mg, 0.17 mmol), potassium carbonate (36 mg, 0.26 mmol), copper (I) iodide (3.0 mg, 0.017 mmol), phenylacetylene (22 μL, 0.20 mmol) and tetrakis(triphenylphosphine)palladium (0) (20 mg, 0.017 mmol) in water-1,4-dioxane (1:3, 5 mL) was stirred at 100° C. for 3.5 hours. Brine (5 mL) was added to the reaction mixture, and the whole was extracted with ethyl acetate (5 mL). The organic layer was dried over anhydrous magnesium sulfate and was filtered throught Celite® pad. After the solvent was evaporated under reduced pressure, the resultant solid was washed with a solution mixture of ethanol and chloroform (ethanol/chloroform=1/2, 3 mL), and dried under reduced pressure to give the title compound (23 mg) as a slightly brown solid (yield 43%).

| | |
|---|---|
| 2-Aminocarbonylamino-6-phenylethynylindoLe-3-carboxamide (Compound 9-1)<br>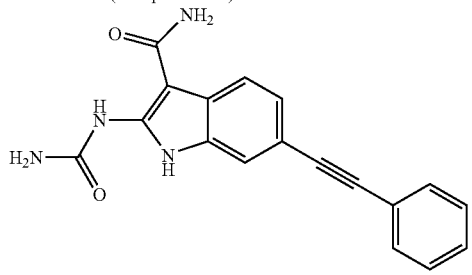 | $^1$H-NMR (500 MHz, DMSO-$d_6$) δ 7.01 (s, 2H), 7.02 (br s, 2H), 7.22 (dd, J = 8.2, 1.5 Hz, 1H), 7.39-7.44 (m, 3H), 7.54 (dt, J = 6.4, 1.8 Hz, 2H), 7.70 (d, J = 1.5 Hz, 1H), 7.78 (d, J = 8.2 Hz, 1H), 10.57 (s, 1H), 11.82 (s, 1H) |

As described below, Compound 9-2~9-18 were obtained according to the preparation method of Compound 9-1 by using commercially available reagents and Compound 3-1.

2-Aminocarbonylamino-6-(3-hydroxy-1-propynyl)indole-3-carboxamide (Compound 9-2)

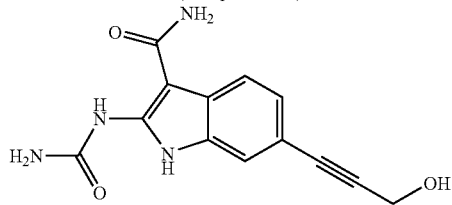

$^1$H-NMR (500 MHz, DMSO-$d_6$) δ 4.30 (d, J = 6.0 Hz, 2H), 5.26 (t, J = 6.0 Hz, 1H), 6.96 (s, 2H), 6.98 (br s, 2H), 7.08 (dd, J = 8.2, 1.2 Hz, 1H), 7.59 (d, J = 1.2 Hz, 1H), 7.71 (d, J = 8.2 Hz, 1H), 10.54 (s, 1H), 11.76 (s, 1H)

2-Aminocarbonylamino-6-(4-hydroxy-1-butynyl)indole-3-carboxamide (Compound 9-3)

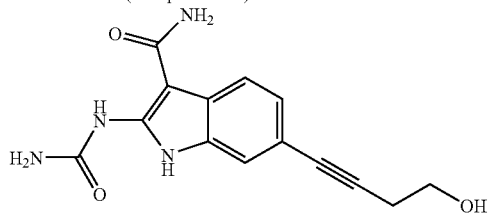

$^1$H-NMR (500 MHz, DMSO-$d_6$) δ 2.55 (t, J = 6.9 Hz, 2H), 3.58 (td, J = 6.9, 5.5 Hz, 2H), 4.87 (t, J = 5.5 Hz, 1H), 6.95 (s, 2H), 6.96 (br s, 2H), 7.05 (dd, J = 8.2, 1.2 Hz, 1H), 7.54 (d, J = 1.2 Hz, 1H), 7.68 (d, J = 8.2 Hz, 1H), 10.54 (s, 1H), 11.71 (s, 1H)

2-Aminocarbonylamino-6-(3-trifluoromethylphenylethynyl)indole-3-carboxamide (Compound 9-4)

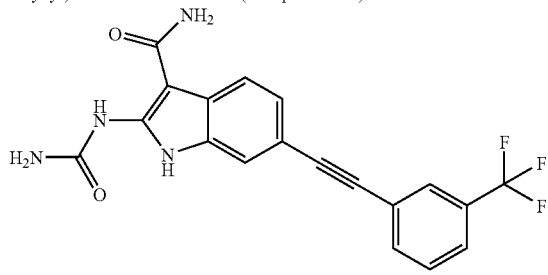

$^1$H-NMR (400 MHz, DMSO-$d_6$) δ 7.03 (s, 2H), 7.09 (br s, 2H), 7.27 (dd, J = 8.3, 1.5 Hz, 1H), 7.66 (t, J = 7.8 Hz, 1H), 7.71-7.75 (m, 2H), 7.80 (d, J = 8.3 Hz, 1H), 7.85 (d, J = 7.8 Hz, 1H), 7.89 (s, 1H), 10.58 (s, 1H), 11.86 (s, 1H)

2-Aminocarbonylamino-6-(1-octynyl)indole-3-carboxamide (Compound 9-5)

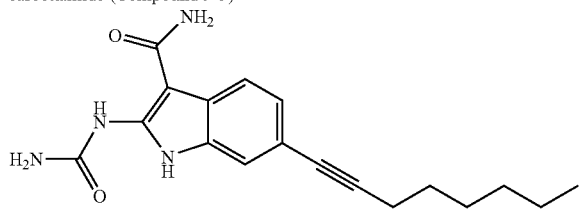

$^1$H-NMR (400 MHz, DMSO-$d_6$) δ 0.89 (t, J = 7.0 Hz, 3H), 1.23-1.32 (m, 4H), 1.39-1.46 (m, 2H), 1.50-1.58 (m, 2H), 2.41 (t, J = 7.0 Hz, 2H), 6.94 (s, 2H), 7.00 (br s, 2H), 7.03 (dd, J = 8.3, 1.5 Hz, 1H), 7.53 (d, J = 1.5 Hz, 1H), 7.68 (d, J = 8.3 Hz, 1H), 10.53 (s, 1H), 11.70 (s, 1H)

2-Aminocarbonylamino-6-(3-hydroxy-1-pentynyl)indole-3-carboxamide (Compound 9-6)

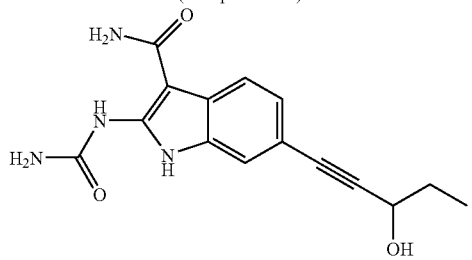

$^1$H-NMR (400 MHz, DMSO-$d_6$) δ 0.98 (t, J = 7.4 Hz, 3H), 1.62-1.70 (m, 2H), 4.37 (q, J = 5.9 Hz, 1H), 5.36 (d, J = 5.9 Hz, 1H), 6.97 (s, 2H), 7.03 (br s, 2H), 7.06 (dd, J = 8.3, 1.5 Hz, 1H), 7.58 (d, J = 1.5 Hz, 1H), 7.71 (d, J = 8.3 Hz, 1H), 10.54 (s, 1H), 11.75 (s, 1H)

| | |
|---|---|
| 2-Aminocarbonylamino-6-(4-aminophenylethynyl) indole-3-carboxamide (Compound 9-7) 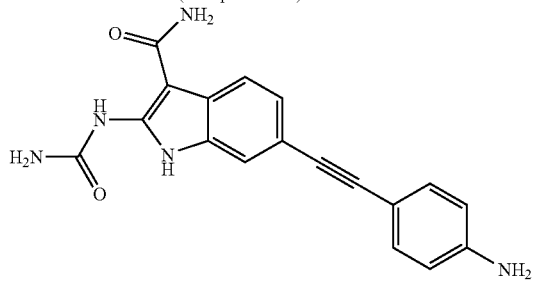 | $^1$H-NMR (500 MHz, DMSO-d$_6$) δ 5.48 (s, 2H), 6.55 (d, J = 8.5 Hz, 2H), 6.97 (s, 2H), 6.99 (br s, 2H), 7.13 (dd, J = 8.2, 1.2 Hz, 1H), 7.18 (d, J = 8.5 Hz, 2H), 7.60 (d, J = 1.2 Hz, 1H), 7.72 (d, J = 8.2 Hz, 1H), 10.55 (s, 1H), 11.74 (s, 1H) |
| 2-Aminocarbonylamino-6-(4-hydroxy-1-pentynyl) indole-3-carboxamide (Compound 9-8) 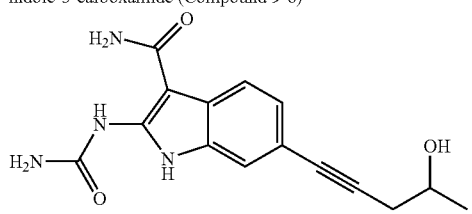 | $^1$H-NMR (400 MHz, DMSO-d$_6$) δ 1.20 (d, J = 6.1 Hz, 3H), 2.39-2.43 (m, 2H), 3.83 (m, 1H), 4.82 (d, J = 4.6 Hz, 1H), 6.95 (s, 2H), 7.00 (br s, 2H), 7.05 (dd, J = 8.3, 1.5 Hz, 1H), 7.54 (d, J = 1.5 Hz, 1H), 7.68 (d, J = 8.3 Hz, 1H), 10.53 (s, 1H), 11.70 (s, 1H) |
| 2-Aminocarbonylamino-6-(4-trifluoromethylphenyl-ethynyl)indole-3-carboxamide (Compound 9-9) 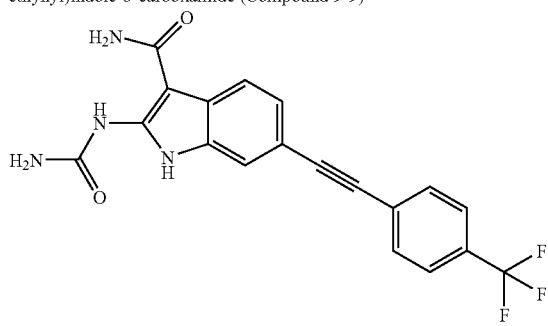 | $^1$H-NMR (400 MHz, DMSO-d$_6$) δ 7.03 (s, 2H), 7.08 (br s, 2H), 7.27 (dd, J = 8.3, 1.5 Hz, 1H), 7.74 (d, J = 1.5 Hz, 1H), 7.76-7.77 (m, 4H), 7.80 (d, J = 8.3 Hz, 1H), 10.58 (s, 1H), 11.87 (s, 1H) |
| 2-Aminocarbonylamino-6-(3-hydroxyphenylethynyl) indole-3-carboxamide (Compound 9-10) 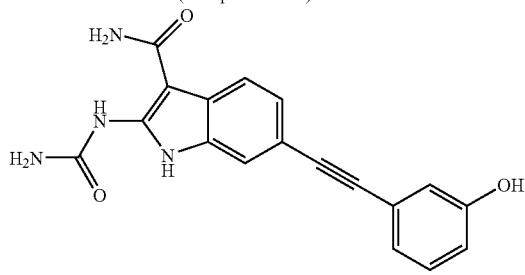 | $^1$H-NMR (400 MHz, DMSO-d$_6$) δ 6.79 (ddd, J = 8.0, 2.4, 1.2 Hz, 1H), 6.89 (t, J = 1.2 Hz, 1H), 6.95 (dt, J = 8.0, 1.2 Hz, 1H), 7.01 (s, 2H), 7.04 (br s, 2H), 7.20-7.21 (m, 2H), 7.68 (d, J = 1.5 Hz, 1H), 7.76 (d, J = 8.3 Hz, 1H), 9.65 (s, 1H), 10.57 (s, 1H), 11.81 (s, 1H) |
| 2-Aminocarbonylamino-6-(3-cyclohexyl-1-propynyl) indole-3-carboxamide (Compound 9-11) 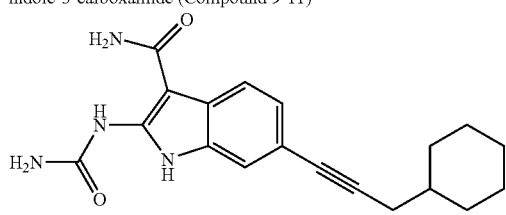 | $^1$H-NMR (400 MHz, DMSO-d$_6$) δ 1.11-1.20 (m, 5H), 1.51 (m, 1H), 1.63 (m, 1H), 1.69-1.72 (m, 2H), 1.81-1.84 (m, 2H), 2.31 (d, J = 6.8 Hz, 2H), 6.94 (s, 2H), 7.00 (br s, 2H), 7.03 (dd, J = 8.3, 1.3 Hz, 1H), 7.54 (d, J = 1.3 Hz, 1H), 7.67 (d, J = 8.3 Hz, 1H), 10.53 (s, 1H), 11.69 (s, 1H) |

2-Aminocarbonylamino-6-(pyridin-2-ylethynyl)indole-3-carboxamide (Compound 9-12)

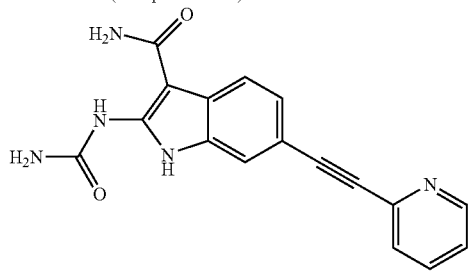

¹H-NMR (400 MHz, DMSO-$d_6$) δ 7.04 (s, 2H), 7.06 (br s, 2H), 7.26 (dd, J = 8.3, 1.2 Hz, 1H), 7.38 (ddd, J = 7.9, 4.9, 1.0 Hz, 1H), 7.62 (dt, J = 7.9, 1.0 Hz, 1H), 7.76 (d, J = 1.2 Hz, 1H), 7.79-7.85 (m, 2H), 8.59 (m, 1H), 10.58 (s, 1H), 11.88 (s, 1H)

2-Aminocarbonylamino-6-(3-hydroxy-1-butynyl)indole-3-carboxamide (Compound 9-13)

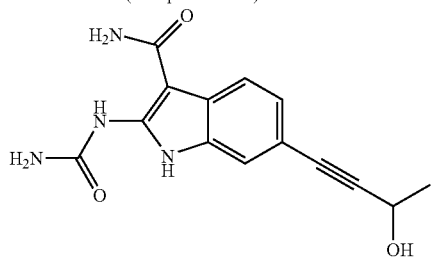

¹H-NMR (500 MHz, DMSO-$d_6$) δ 1.38 (d, J = 6.7 Hz, 3H), 4.59 (m, 1H), 5.39 (d, J = 5.2 Hz, 1H), 6.96 (s, 2H), 7.01 (br s, 2H), 7.06 (dd, J = 8.2, 1.2 Hz, 1H), 7.56 (d, J = 1.2 Hz, 1H), 7.71 (d, J = 8.2 Hz, 1H), 10.54 (s, 1H), 11.75 (s, 1H)

2-Aminocarbonylamino-6-(5-hydroxy-1-pentynyl)indole-3-carboxamide (Compound 9-14)

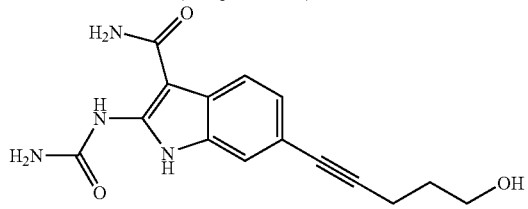

¹H-NMR (400 MHz, DMSO-$d_6$) δ 1.65-1.72 (m, 2H), 2.45 (t, J = 7.1 Hz, 2H), 3.53 (q, J = 5.1 Hz, 2H), 4.53 (t, J = 5.1 Hz, 1H), 6.95 (s, 2H), 7.04 (dd, J = 8.3, 1.5 Hz, 1H), 7.07 (br s, 2H), 7.53 (d, J = 1.5 Hz, 1H), 7.68 (d, J = 8.3 Hz, 1H), 10.53 (s, 1H), 11.70 (s, 1H)

2-Aminocarbonylamino-6-triisopropylsilylethynylindole-3-carboxamide (Compound 9-15)

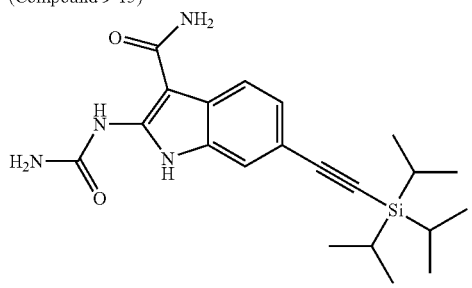

¹H-NMR (400 MHz, DMSO-$d_6$) δ 1.11 (m, 21H), 6.99 (s, 2H), 7.06 (br s, 2H), 7.10 (dd, J = 8.3, 1.5 Hz, 1H), 7.66 (d, J = 1.5 Hz, 1H); 7.72 (d, J = 8.3 Hz, 1H), 10.55 (s, 1H), 11.77 (s, 1H)

2-Aminocarbonylamino-6-(5-methoxycarbonyl-1-pentynyl)indole-3-carboxamide (Compound 9-16)

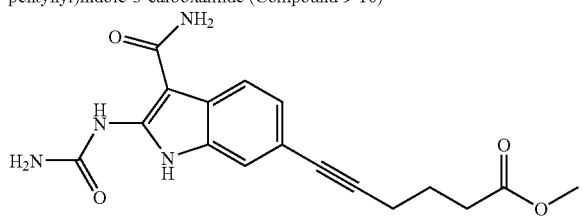

¹H-NMR (400 MHz, DMSO-$d_6$) δ 1.68-1.89 (m, 2H), 2.41-2.49 (m, 4H), 3.62 (s, 3H), 6.95 (s, 2H), 7.01 (br s, 2H), 7.04 (dd, J = 8.3, 1.5 Hz, 1H), 7.54 (d, J = 1.5 Hz, 1H), 7.68 (d, J = 8.3 Hz, 1H), 10.53 (s, 1H), 11.71 (s, 1H)

-continued

| | |
|---|---|
| 2-Aminocarbonylamino-6-(3-diethylamino-1-propynyl)indole-3-carboxamide (Compound 9-17)<br>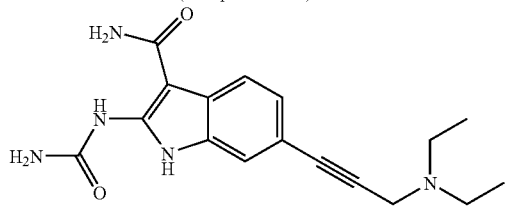 | ¹H-NMR (400 MHz, DMSO-d$_6$) δ 1.03 (t, J = 7.2 Hz, 6H), 2.55 (q, J = 7.2 Hz, 4H), 3.58 (s, 2H), 6.96 (s, 2H), 7.02 (br s, 2H), 7.06 (dd, J = 8.3, 1.5 Hz, 1H), 7.58 (d, J = 1.5 Hz, 1H), 7.69 (d, J = 8.3 Hz, 1H), 10.53 (s, 1H), 11.72 (s, 1H) |
| 2-Aminocarbonylamino-6-(3-dimethylamino-1-propynyl)indole-3-carboxamide (Compound 9-18)<br>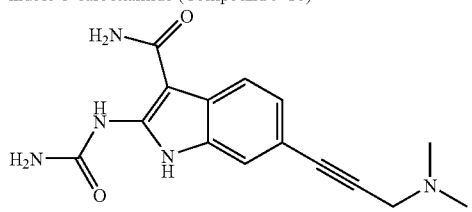 | ¹H-NMR (400 MHz, DMSO-d$_6$) δ 2.25 (s, 6H), 3.43 (s, 2H), 6.97 (s, 2H), 7.05 (br s, 2H), 7.09 (dd, J = 8.3, 1.5 Hz, 1H), 7.60 (d, J = 1.5 Hz, 1H), 7.71 (d, J = 8.3 Hz, 1H), 10.54 (s, 1H), 11.74 (s, 1H) |

Example 10

2-Aminocarbonylamino-6-ethynylindole-3-carboxamide (Compound 10-1)

1.0 M Tetrabutylammonium fluoride tetrahydrofuran solution (15 mL, 15 mmol) was added to a solution of 2-aminocarbonylamino-6-triisopropylsilylethynylindole-3-carboxamide (Compound 9-15, 4.0 g, 10 mmol) in anhydrous tetrahydrofuran (180 mL), and the mixture was stirred at 75° C. for 2.5 hours. Water (180 mL) was added to the reaction mixture, and the whole was extracted with ethyl acetate (180 mL). The organic layer was washed with brine (180 mL), and dried over anhydrous magnesium sulfate. After the solvent was evaporated under reduced pressure, the resultant solid was washed with a solution mixture of ethanol and chloroform (ethanol/chloroform=1/3, 55 mL) and dried under reduced pressure to give the title compound (2.2 g) as a slightly brown solid (yield 90%).

| | |
|---|---|
| 2-Aminocarbonylamino-6-ethynylindole-3-carboxamide (Compound 10-1)<br>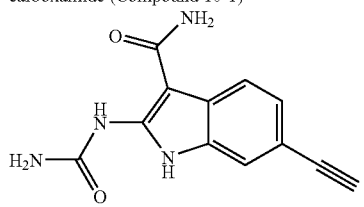 | ¹H-NMR (500 MHz, DMSO-d$_6$) δ 3.96 (s, 1H), 6.98 (s, 2H), 7.06 (br s, 2H), 7.12 (dd, J = 8.2, 1.5 Hz, 1H), 7.64 (d, J = 1.5 Hz, 1H), 7.72 (d, J = 8.2 Hz, 1H), 10.54 (s, 1H), 11.78 (s, 1H) |

Example 11

2-Aminocarbonylamino-6-ethylindole-3-carboxamide (Compound 11-1)

5% Palladium-activated carbon (19 mg) was added to a solution of 2-aminocarbonylamino-6-vinylindole-3-carboxamide (Compound 4-38, 18 mg, 0.073 mmol) in methanol (3 mL), and was stirred at room temperature for 4 hours under hydrogen atmosphere. After the reaction mixture was filtered throught Celite® pad, the filtrate was concentrated under reduced pressure to give the title compound (9.3 mg) as an off-white solid (yield 52%).

2-Aminocarbonylamino-6-ethylindole-3-carboxamide (Compound 11-1)

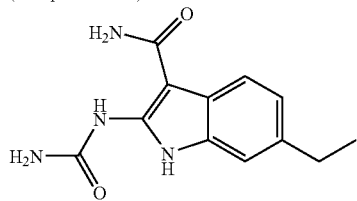

$^1$H-NMR (400 MHz, DMSO-d$_6$) δ 1.23 (t, J = 7.6 Hz, 3H), 2.66 (q, J = 7.6 Hz, 2H), 6.88 (s, 2H), 6.93 (dd, J = 8.2, 1.5 Hz, 1H), 6.99 (br s, 2H), 7.37 (d, J = 1.5 Hz, 1H), 7.66 (d, J = 8.2 Hz, 1H), 10.51 (s, 1H), 11.52 (s, 1H)

As described below, Compound 11-2~11-12 were obtained according to the preparation method of Compound 11-1 by using Compound 4-46, 4-48, 4-50, 4-51, 4-56, 4-58, 4-63, 4-68, 4-80, 9-17 and 9-18.

2-Aminocarbonylamino-6-propylindole-3-carboxamide (Compound 11-2)

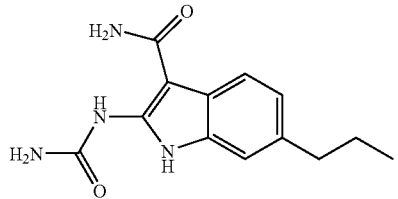

$^1$H-NMR (500 MHz, DMSO-d$_6$) δ 0.90 (t, J = 7.3 Hz, 3H), 1.58-1.61 (m, 2H), 2.57 (t, J = 7.3 Hz, 2H), 6.84 (s, 2H), 6.88 (d, J = 8.0 Hz, 1H), 6.97 (br s, 2H), 7.32 (s, 1H), 7.62 (d, J = 8.0 Hz, 1H), 10.47 (s, 1H), 11.47 (s, 1H)

2-Aminocarbonylamino-6-(2-phenylethyl)indole-3-carboxamide (Compound 11-3)

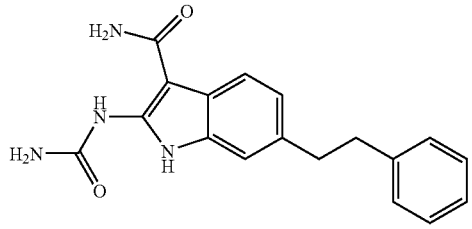

$^1$H-NMR (400 MHz, DMSO-d$_6$) δ 2.89-2.90 (m, 4H), 6.85 (s, 2H), 6.93 (dd, J = 8.3, 1.5 Hz, 1H), 6.96 (br s, 2H), 7.16 (tt, J = 6.8, 2.0 Hz, 1H), 7.23-7.27 (m, 4H), 7.35 (d, J = 1.5 Hz, 1H), 7.62 (d, J = 8.3 Hz, 1H), 10.48 (s, 1H), 11.49 (s, 1H)

2-Aminocarbonylamino-6-cyclohexylindole-3-carboxamide (Compound 11-4)

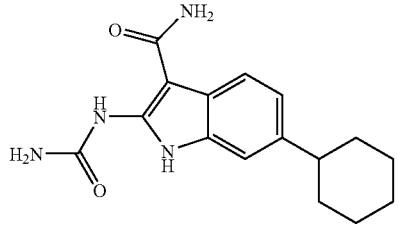

$^1$H-NMR (400 MHz, DMSO-d$_6$) δ 1.31-1.41 (m, 5H), 1.63-1.81 (m, 5H), 2.50 (m, 1H), 6.83 (s, 2H), 6.92 (dd, J = 8.1, 1.2 Hz, 1H), 6.95 (br s, 2H), 7.35 (d, J = 1.2 Hz, 1H), 7.62 (d, J = 8.1 Hz, 1H), 10.46 (s, 1H), 11.46 (s, 1H)

2-Aminocarbonylamino-6-(2-cyclopropylethyl)indole-3-carboxamide (Compound 11-5)

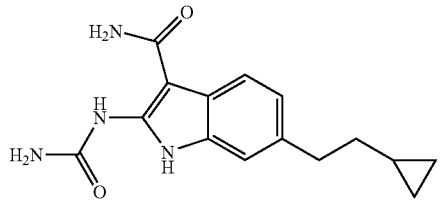

$^1$H-NMR (400 MHz, DMSO-d$_6$) δ 0.05 (td, J = 5.1, 4.0 Hz, 2H), 0.39-0.40 (m, 2H), 0.70 (m, 1H), 1.47 (dt, J = 8.1, 7.4 Hz, 2H), 2.68 (t, J = 7.4 Hz, 2H), 6.84 (s, 2H), 6.89 (dd, J = 8.2, 1.3 Hz, 1H), 6.97 (br s, 2H), 7.33 (d, J = 1.3 Hz, 1H), 7.61 (d, J = 8.2 Hz, 1H), 10.48 (s, 1H), 11.47 (s, 1H)

| | |
|---|---|
| 2-Aminocarbonylamino-6-(4-hydroxybutyl)indole-3-carboxamide (Compound 11-6) 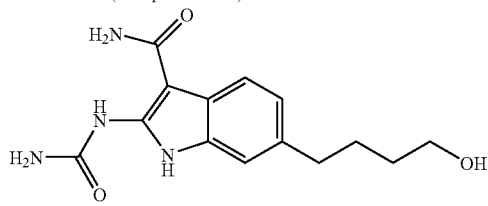 | $^1$H-NMR (500 MHz, DMSO-$d_6$) δ 1.41-1.47 (m, 2H), 1.56-1.62 (m, 2H), 2.59 (t, J = 7.5 Hz, 2H), 3.39-3.41 (m, 2H), 4.34 (t, J = 4.9 Hz, 1H), 6.84 (s, 2H), 6.88 (d, J = 7.9 Hz, 1H), 6.98 (br s, 2H), 7.32 (s, 1H), 7.62 (d, J = 7.9 Hz, 1H), 10.47 (s, 1H), 11.47 (s, 1H) |
| 2-Aminocarbonylamino-6-(3-diethylaminopropyl)indole-3-carboxamide (Compound 11-7) 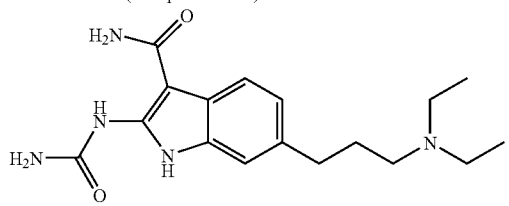 | $^1$H-NMR (400 MHz, DMSO-$d_6$) δ 0.92 (t, J = 7.3 Hz, 6H), 1.64-1.71 (m, 2H), 2.37 (t, J = 7.3 Hz, 2H), 2.44 (q, J = 7.3 Hz, 4H), 2.59 (t, J = 7.3 Hz, 2H), 6.84 (s, 2H), 6.89 (d, J = 8.3 Hz, 1H), 6.98 (br s, 2H), 7.33 (s, 1H), 7.61 (d, J = 8.3 Hz, 1H), 10.48 (s, 1H), 11.48 (s, 1H) |
| 2-Aminocarbonylamino-6-(3-dimethylaminopropyl)indole-3-carboxamide (Compound 11-8) 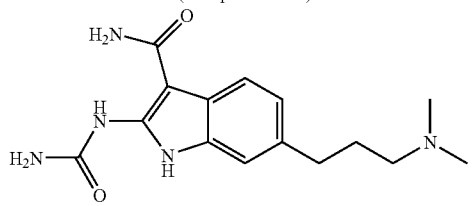 | $^1$H-NMR (400 MHz, DMSO-$d_6$) δ 1.73-1.80 (m, 2H), 2.32 (s, 6H), 2.46-2.54 (m, 2H), 2.62 (t, J = 7.4 Hz, 2H), 6.86 (s, 2H), 6.90 (dd, J = 8.1, 1.2 Hz, 1H), 6.99 (br s, 2H), 7.33 (d, J = 1.2 Hz, 1H), 7.64 (d, J = 8.1 Hz, 1H), 10.48 (s, 1H), 11.50 (s, 1H) |
| 2-Aminocarbonylamino-6-(1-phenylethyl)indole-3-carboxamide (Compound 11-9) 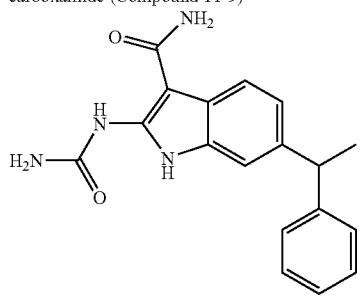 | $^1$H-NMR (500 MHz, DMSO-$d_6$) δ 1.59 (d, J = 7.0 Hz, 3H), 4.16 (q, J = 7.0 Hz, 1H), 6.84 (s, 2H), 6.93 (dd, J = 8.4, 1.5 Hz, 1H), 6.99 (br s, 2H), 7.14 (m, 1H), 7.23-7.28 (m, 4H), 7.44 (d, J = 1.5 Hz, 1H), 7.61 (d, J = 8.4 Hz, 1H), 10.45 (s, 1H), 11.51 (s, 1H) |
| 2-Aminocarbonylamino-6-(3-methoxypropyl)indole-3-carboxamide (Compound 11-10) 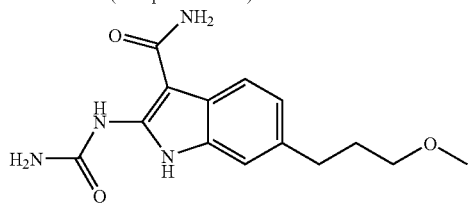 | $^1$H-NMR (400 MHz, DMSO-$d_6$) δ 1.78-1.80 (m, 2H), 2.63 (t, J = 7.7 Hz, 2H), 3.23 (s, 3H), 3.30-3.31 (m, 2H), 6.85 (s, 2H), 6.88 (dd, J = 8.1, 1.3 Hz, 1H), 6.98 (br s, 2H), 7.32 (d, J = 1.3 Hz, 1H), 7.63 (d, J = 8.1 Hz, 1H), 10.48 (s, 1H), 11.49 (s, 1H) |
| 2-Aminocarbonylamino-6-(1-hexyl)indole-3-carboxamide (Compound 11-11) 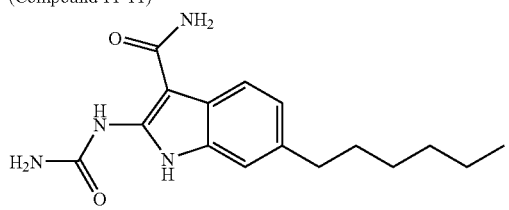 | $^1$H-NMR (500 MHz, DMSO-$d_6$) δ 0.85 (t, J = 6.9 Hz, 3H), 1.22-1.32 (m, 6H), 1.54-1.60 (m, 2H), 2.59 (t, J = 7.6 Hz, 2H), 6.84 (s, 2H), 6.87 (d, J = 7.9 Hz, 1H), 6.98 (br s, 2H), 7.31 (s, 1H), 7.61 (d, J = 7.9 Hz, 1H), 10.47 (s, 1H), 11.47 (s, 1H) |

| | |
|---|---|
| 2-Aminocarbonylamino-6-ethyl-7-methylindole-3-carboxamide (Compound 11-12)<br>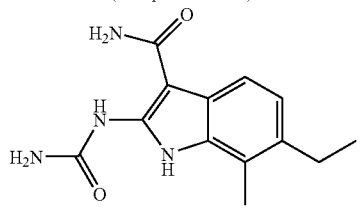 | $^1$H-NMR (400 MHz, DMSO-d$_6$) δ 1.15 (t, J = 7.4 Hz, 3H), 2.34 (s, 3H), 2.67 (q, J = 7.4 Hz, 2H), 6.88 (br s, 2H), 6.91 (d, J = 8.1 Hz, 1H), 7.08 (br s, 2H), 7.54 (d, J = 8.1 Hz, 1H), 10.37 (s, 1H), 11.07 (s, 1H) |

Example 12

2-Aminocarbonylamino-6-(3-hydroxymethylphenyl)indole-3-carboxamide (Compound 12-1)

Sodium borohydride (0.23 g, 6.2 mmol) was added to a solution mixture of 2-aminocarbonylamino-6-(3-formylphenyl)indole-3-carboxamide (Compound 4-69, 1.0 g, 3.1 mmol) in anhydrous methanol and anhydrous tetrahydrofuran (methanol/tetrahydrofuran=1/1, 60 mL) under ice-cooling, and the mixture was stirred at room temperature overnight. After the reaction mixture was concentrated under reduced pressure, the precipitated solid was washed with water (30 mL), ethyl acetate (30 mL), and dried under reduced pressure to give the title compound (0.59 g) as a brown solid (yield 58%).

| | |
|---|---|
| 2-Aminocarbonylamino-6-(3-hydroxymethylphenyl)indole-3-carboxamide (Compound 12-1)<br>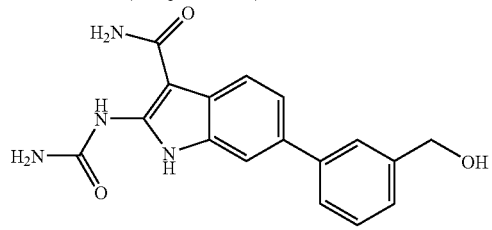 | $^1$H-NMR (400 MHz, DMSO-d$_6$) δ 4.57 (d, J = 5.7 Hz, 2H), 5.24 (t, J = 5.7 Hz, 1H), 6.96 (br s, 4H), 7.24 (d, J = 7.7 Hz, 1H), 7.36 (dd, J = 8.3, 1.6 Hz, 1H), 7.40 (t, J = 7.7 Hz, 1H), 7.49 (d, J = 7.7 Hz, 1H), 7.60 (s, 1H), 7.82 (d, J = 8.3 Hz, 1H), 7.84 (d, J = 1.6 Hz, 1H), 10.55 (s, 1H), 11.70 (s, 1H) |

As described below, Compound 12-2~12-4 were obtained according to the preparation method of Compound 12-1 by using Compound 4-74, 4-75 and 7-27.

| | |
|---|---|
| 2-Aminocarbonylamino-6-(5-hydroxymethylfuran-2-yl)indole-3-carboxamide (Compound 12-2)<br>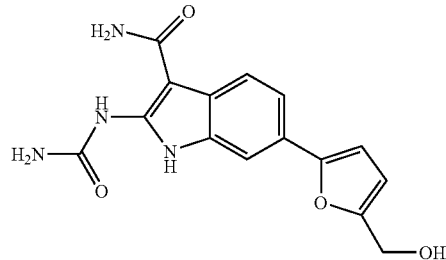 | $^1$H-NMR (400 MHz, DMSO-d$_6$) δ 4.45 (d, J = 5.7 Hz, 2H), 5.23 (t, J = 5.7 Hz, 1H), 6.36 (d, J = 3.3 Hz, 1H), 6.65 (d, J = 3.3 Hz, 1H), 6.97 (br s, 4H), 7.39 (dd, J = 8.3, 1.5 Hz, 1H), 7.76 (d, J = 8.3 Hz, 1H), 7.83 (d, J = 1.5 Hz, 1H), 10.53 (s, 1H), 11.72 (s, 1H) |
| 2-Aminocarbonylamino-6-(2-hydroxymethylfuran-4-yl)indole-3-carboxamide (Compound 12-3)<br>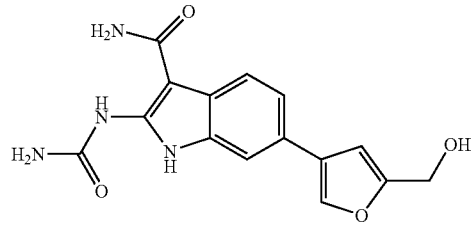 | $^1$H-NMR (400 MHz, DMSO-d$_6$) δ 4.42 (d, J = 5.8 Hz, 2H), 5.25 (t, J = 5.8 Hz, 1H), 6.64 (s, 1H), 6.94 (s, 2H), 7.00 (br s, 2H), 7.28 (dd, J = 8.3, 1.6 Hz, 1H), 7.68 (d, J = 1.6 Hz, 1H), 7.73 (d, J = 8.3 Hz, 1H), 7.95 (s, 1H), 10.51 (s, 1H), 11.61 (s, 1H) |

| 2-Aminocarbonylamino-6-(5-hydroxymethylthiophen-2-yl)indole-3-carboxamide (Compound 12-4) 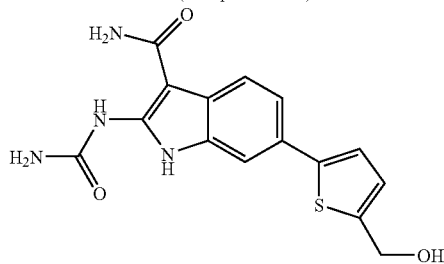 | ¹H-NMR (500 MHz, DMSO-d₆) δ 4.61 (d, J = 6.1 Hz, 2H), 5.44 (t, J = 6.1 Hz, 1H), 6.92 (d, J = 3.7 Hz, 1H), 6.95 (br s, 4H), 7.17 (d, J = 3.7 Hz, 1H), 7.32 (dd, J = 8.2, 1.7 Hz, 1H), 7.74 (d, J = 8.2 Hz, 1H), 7.78 (d, J = 1.7 Hz, 1H), 10.52 (s, 1H), 11.70 (s, 1H) |

Example 13

2-Aminocarbonylamino-6-(5-methylaminomethylfuran-2-yl)indole-3-carboxamide (Compound 13-1)

A solution of 40% methylamine in methanol (49 μL, 0.48 mmol) was added to a solution of 2-aminocarbonylamino-6-(5-formylfuran-2-yl)indole-3-carboxamide (Compound 4-74, 0.10 g, 0.32 mmol) in anhydrous methanol (2 mL), and the mixture was stirred at 60° C. for 6 hours in a sealed tube. The reaction mixture was concentrated under reduced pressure, and the residue was dissolved in a solution mixture of methanol and tetrahydrofuran (methanol/tetrahydrofuran=1/2, 3 mL). Sodium borohydride (0.024 g, 0.64 mmol) was added to the solution mixture under ice-cooling, and the mixture was stirred at room temperature overnight. After the reaction mixture was concentrated under reduced pressure, the precipitated solid was washed with H₂O (5 mL) and dried under reduced pressure to give the title compound (0.077 g) as a slightly brown solid (yield 74%).

| 2-Aminocarbonylamino-6-(5-methylaminomethylfuran-2-yl)indole-3-carboxamide (Compound 13-1) 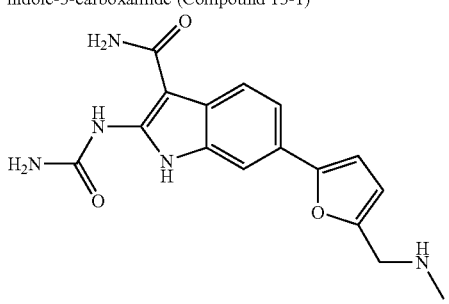 | ¹H-NMR (400 MHz, DMSO-d₆) δ 2.32 (s, 3H), 3.67 (s, 2H), 6.30 (d, J = 3.2 Hz, 1H), 6.63 (d, J = 3.2 Hz, 1H), 6.95 (br s, 4H), 7.37 (dd, J = 8.3, 1.5 Hz, 1H), 7.75 (d, J = 8.3 Hz, 1H), 7.82 (d, J = 1.5 Hz, 1H), 10.52 (s, 1H), 11.69 (s, 1H) |

As described below, Compound 13-2~13-24 were obtained according to the preparation method of Compound 13-1 by using commercially available reagents, Compound 4-69, 4-74 and 4-75.

| 2-Aminocarbonylamino-6-[3-(2-dimethylaminoethylaminomethyl)phenyl]indole-3-carboxamide (Compound 13-2) 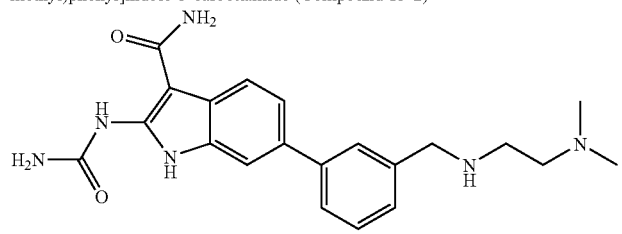 | ¹H-NMR (400 MHz, DMSO-d₆) δ 2.11 (s, 6H), 2.33 (t, J = 6.4 Hz, 2H), 2.59 (t, J = 6.4 Hz, 2H), 3.76 (s, 2H), 6.96 (s, 2H), 7.03 (br s, 2H), 7.24 (dt, J = 7.6, 1.6 Hz, 1H), 7.35 (dd, J = 8.1, 1.3 Hz, 1H), 7.37 (t, J = 7.6 Hz, 1H), 7.48 (dt, J = 7.6, 1.6 Hz, 1H), 7.59 (t, J =1.6 Hz, 1H), 7.81 (d, J = 8.1 Hz, 1H), 7.83 (d, J = 1.3 Hz, 1H), 10.55 (s, 1H), 11.70 (s, 1H) |

2-Aminocarbonylamino-6-[3-(2-morpholinoethylamino-methyl)phenyl]indole-3-carboxamide (Compound 13-3)

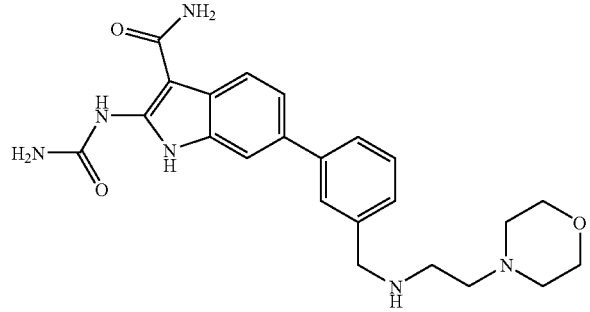

$^1$H-NMR (400 MHz, DMSO-d$_6$) δ 2.33 (t, J = 4.1 Hz, 4H), 2.40 (t, J = 6.5 Hz, 2H), 2.62 (t, J = 6.5 Hz, 2H), 3.54 (t, J = 4.1 Hz, 4H), 3.77 (s, 2H), 6.96 (s, 2H), 7.04 (br s, 2H), 7.24 (d, J = 7.6 Hz, 1H), 7.34-7.39 (m, 2H), 7.48 (dt, J = 7.6, 1.5 Hz, 1H), 7.59 (t, J = 1.5 Hz, 1H), 7.81 (d, J = 8.3 Hz, 1H), 7.83 (d, J = 1.2 Hz, 1H), 10.55 (s, 1H), 11.70 (s, 1H)

2-Aminocarbonylamino-6-[3-(2-ethoxyethylaminomethyl) phenyl]indole-3-carboxamide (Compound 13-4)

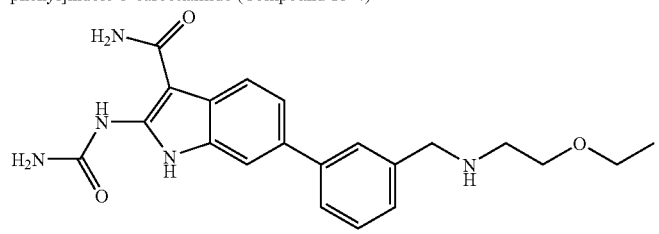

$^1$H-NMR (500 MHz, DMSO-d$_6$) δ 1.10 (t, J = 7.0 Hz, 3H), 2.68 (t, J = 5.8 Hz, 2H), 3.42 (q, J = 7.0 Hz, 2H), 3.45 (t, J = 5.8 Hz, 2H), 3.78 (s, 2H), 6.95 (br s, 4H), 7.24 (d, J = 7.6 Hz, 1H), 7.36 (dd, J = 8.6 Hz, 1.5 Hz 1H), 7.38 (t, J = 7.6 Hz, 1H), 7.48 (d, J = 7.6 Hz, 1H), 7.59 (s, 1H), 7.81 (d, J = 8.6 Hz, 1H), 7.84 (d, J = 1.5 Hz, 1H), 10.54 (s, 1H), 11.69 (s, 1H)

2-Aminocarbonylamino-6-(3-isopropylaminomethylphenyl) indole-3-carboxamide (Compound 13-5)

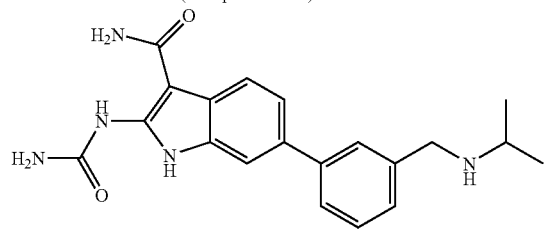

$^1$H-NMR (500 MHz, DMSO-d$_6$) δ 1.03 (d, J = 6.1 Hz, 6H), 2.74 (m, 1H), 3.75 (s, 2H), 6.96 (br s, 4H), 7.25 (d, J = 7.6 Hz, 1H), 7.34-7.39 (m, 2H), 7.47 (d, J = 7.6 Hz, 1H), 7.61 (s, 1H), 7.81 (d, J = 8.2 Hz, 1H), 7.84 (d, J = 1.2 Hz, 1H), 10.55 (s, 1H), 11.70 (s, 1H)

2-Aminocarbonylamino-6-(3-ethylaminomethylphenyl) indole-3-carboxamide (Compound 13-6)

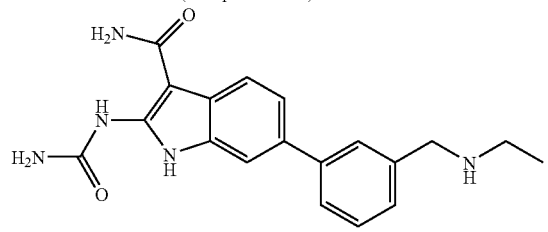

$^1$H-NMR (400 MHz, DMSO-d$_6$) δ 1.06 (t, J = 7.1 Hz, 3H), 2.57 (q, J = 7.1 Hz, 2H), 3.76 (s, 2H), 6.97 (br s, 4H), 7.25 (d, J = 7.7 Hz, 1H), 7.33-7.41 (m, 2H), 7.48 (d, J = 7.7 Hz, 1H), 7.60 (s, 1H), 7.81 (d, J = 8.3 Hz, 1H), 7.84 (d, J = 1.5 Hz, 1H), 10.55 (s, 1H), 11.70 (s, 1H)

2-Aminocarbonylamino-6-[3-(2-methoxyethylaminomethyl) phenyl]indole-3-carboxamide (Compound 13-7)

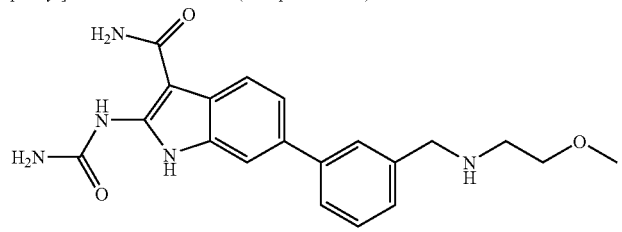

$^1$H-NMR (400 MHz, DMSO-d$_6$) δ 2.68 (t, J = 5.7 Hz, 2H), 3.24 (s, 3H), 3.42 (t, J = 5.7 Hz, 2H), 3.77 (s, 2H), 6.97 (br s, 4H), 7.24 (d, J = 7.9 Hz, 1H), 7.34-7.38 (m, 2H), 7.48 (d, J = 7.9 Hz, 1H), 7.60 (s, 1H), 7.81 (d, J = 8.3 Hz, 1H), 7.84 (d, J = 1.5 Hz, 1H), 10.55 (s, 1H), 11.70 (s, 1H)

| | |
|---|---|
| 2-Aminocarbonylamino-6-[3-(1-methylpiperidin-4-ylaminomethyl)phenyl]indole-3-carboxamide (Compound 13-8) 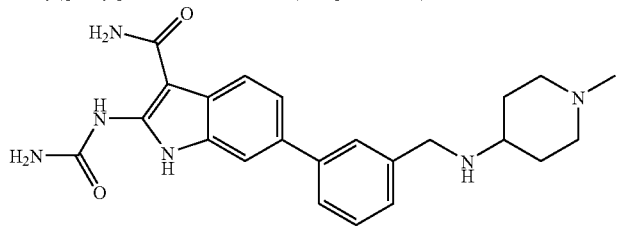 | $^1$H-NMR (500 MHz, DMSO-d$_6$) δ 1.23-1.35 (m, 2H), 1.75-1.88 (m, 4H), 2.11 (s, 3H), 2.42-2.75 (m, 3H), 3.77 (s, 2H), 6.96 (br s, 4H), 7.25 (t, J = 7.5 Hz, 1H), 7.32-7.39 (m, 2H), 7.47 (d, J = 7.5 Hz, 1H), 7.60 (s, 1H), 7.81 (d, J = 8.6 Hz, 1H), 7.83 (d, J = 1.2 Hz, 1H), 10.55 (s, 1H), 11.70 (s, 1H) |
| 2-Aminocarbonylamino-6-]3-(tetrahydropyran-4-ylaminomethyl)phenyl]indole-3-carboxamide (Compound 13-9) 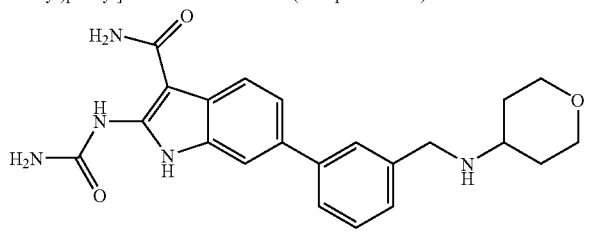 | $^1$H-NMR (400 MHz, DMSO-d$_6$) δ 1.21-1.40 (m, 2H), 1.72-1.88 (m, 2H), 2.63 (m, 1H), 3.22-3.35 (m, 3H), 3.79 (s, 2H), 3.83 (dt, J = 11.6, 3.6 Hz, 1H), 6.96 (br s, 4H), 7.26 (d, J = 7.8 Hz, 1H), 7.31-7.42 (m, 2H), 7.47 (d, J = 7.8 Hz, 1H), 7.62 (s, 1H), 7.81 (d, J = 8.5 Hz, 1H), 7.83 (d, J = 1.5 Hz, 1H), 10.55 (s, 1H), 11.70 (s, 1H) |
| 2-Aminocarbonylamino-6-(3-cyclopropylaminomethylphenyl)indole-3-carboxamide (Compound 13-10) 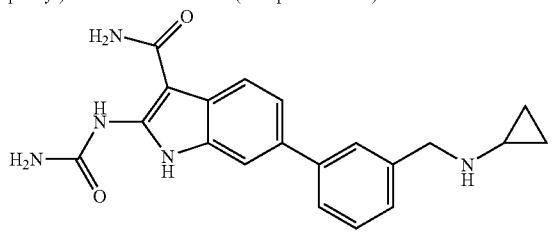 | $^1$H-NMR (400 MHz, DMSO-d$_6$) δ 0.25-0.30 (m, 2H), 0.34-0.40 (m, 2H), 2.08 (m, 1H), 3.78 (s, 2H), 6.96 (br s, 4H), 7.24 (d, J = 7.6 Hz, 1H), 7.34-7.40 (m, 2H), 7.47 (d, J = 7.6 Hz, 1H), 7.59 (s, 1H), 7.81 (d, J = 8.5 Hz, 1H), 7.83 (d, J = 1.7 Hz, 1H), 10.55 (s, 1H), 11.70 (s, 1H) |
| 2-Aminocarbonylamino-6-(3-tert-butylaminomethylphenyl)indole-3-carboxamide (Compound 13-11) 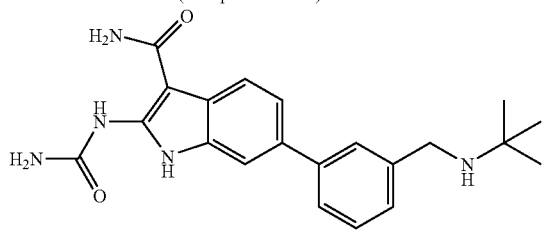 | $^1$H-NMR (400 MHz, DMSO-d$_6$) δ 1.12 (s, 9H), 3.73 (s, 2H), 6.96 (br s, 4H), 7.26 (d, J = 7.7 Hz, 1H), 7.33-7.38 (m, 2H), 7.46 (d, J = 7.7 Hz, 1H), 7.62 (s, 1H), 7.81 (d, J = 8.5 Hz, 1H), 7.84 (d, J = 1.5 Hz, 1H), 10.55 (s, 1H), 11.70 (s, 1H) |
| 2-Aminocarbonylamino-6-(3-cyclopentylaminomethylphenyl)indole-3-carboxamide (Compound 13-12) 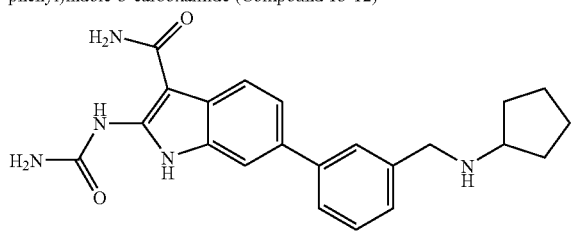 | $^1$H-NMR (400 MHz, DMSO-d$_6$) δ 1.33-1.50 (m, 4H), 1.58-1.79 (m, 4H), 3.04 (m, 1H), 3.74 (s, 2H), 6.96 (br s, 4H), 7.25 (d, J = 7.8 Hz, 1H), 7.34-7.39 (m, 2H), 7.47 (d, J = 8.3 Hz, 1H), 7.60 (s, 1H), 7.81 (d, J = 8.3 Hz, 1H), 7.83 (d, J = 1.5 Hz, 1H), 10.55 (s, 1H), 11.70 (s, 1H) |

| | |
|---|---|
| 2-Aminocarbonylamino-6-[3-(2-hydroxyethylaminomethyl)phenyl]indole-3-carboxamide (Compound 13-13) 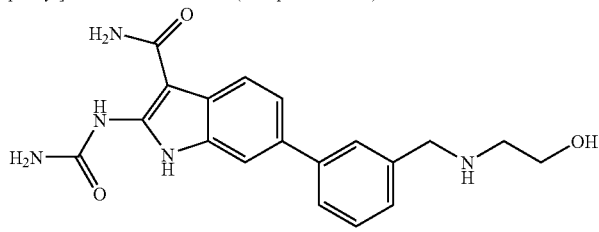 | ¹H-NMR (400 MHz, DMSO-d₆) δ 2.61 (t, J = 5.6 Hz, 2H), 3.49 (q, J = 5.6 Hz, 2H), 3.77 (s, 2H), 4.48 (t, J = 5.6 Hz, 1H), 6.96 (br s, 4H), 7.24 (d, J = 7.8 Hz, 1H), 7.33-7.41 (m, 2H), 7.48 (d, J = 7.8 Hz, 1H), 7.60 (s, 1H), 7.81 (d, J = 8.2 Hz, 1H), 7.84 (d, J = 1.2 Hz, 1H), 10.55 (s, 1H), 11.70 (s, 1H) |
| 2-Aminocarbonylamino-6-(3-methylaminomethylphenyl)indole-3-carboxamide (Compound 13-14) 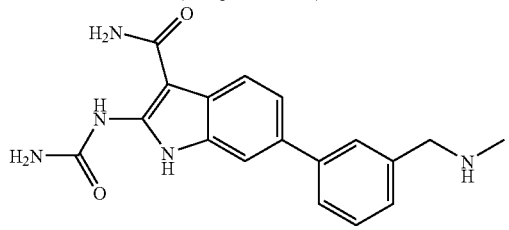 | ¹H-NMR (400 MHz, DMSO-d₆) δ 2.30 (s, 3H), 3.71 (s, 2H), 6.95 (br s, 4H), 7.23 (d, J = 7.6 Hz, 1H), 7.33-7.41 (m, 2H), 7.48 (d, J = 7.6 Hz, 1H), 7.59 (s, 1H), 7.81 (d, J = 8.3 Hz, 1H), 7.84 (d, J = 1.5 Hz, 1H), 10.54 (s, 1H), 11.69 (s, 1H) |
| 2-Aminocarbonylamino-6-(5-cyclopropylaminomethylfuran-2-yl)indole-3-carboxamide (Compound 13-15) 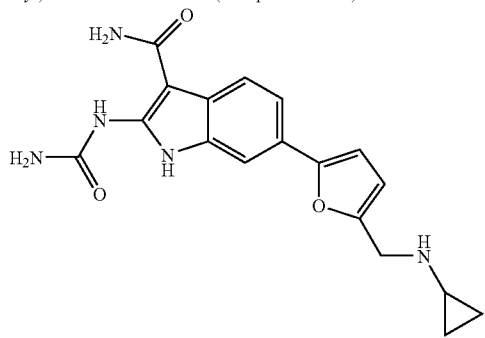 | ¹H-NMR (400 MHz, DMSO-d₆) δ 0.24-0.29 (m, 2H), 0.36-0.42 (m, 2H), 2.16 (m, 1H), 3.75 (s, 2H), 6.30 (d, J = 3.3 Hz, 1H), 6.63 (d, J = 3.3 Hz, 1H), 6.95 (br s, 4H), 7.38 (dd, J = 8.3, 1.6 Hz, 1H), 7.74 (d, J = 8.3 Hz, 1H), 7.82 (d, J = 1.6 Hz, 1H), 10.52 (s, 1H), 11.69 (s, 1H) |
| 2-Aminocarbonylamino-6-(5-isopropylaminomethylfuran-2-yl)indole-3-carboxamide (Compound 13-16) 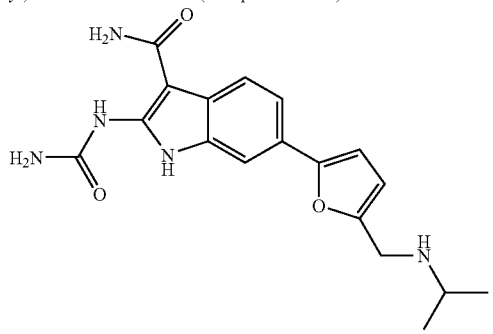 | ¹H-NMR (400 MHz, DMSO-d₆) δ 1.02 (d, J = 6.3 Hz, 6H), 2.79 (m, 1H), 3.73 (s, 2H), 6.30 (d, J = 3.3 Hz, 1H), 6.63 (d, J = 3.3 Hz, 1H), 6.96 (br s, 4H), 7.38 (m, 1H), 7.74 (m, 1H), 7.82 (m, 1H), 10.53 (s, 1H), 11.70 (s, 1H) |

| | |
|---|---|
| 2-Aminocarbonylamino-6-(5-cyclopentylaminomethylfuran-2-yl)indole-3-carboxamide (Compound 13-17) 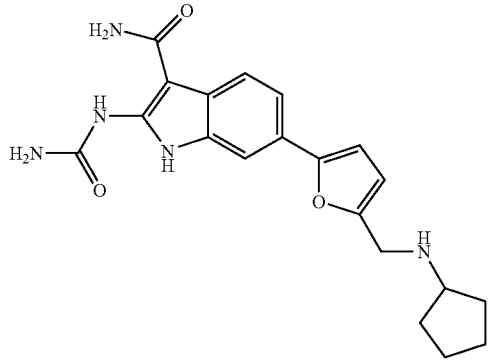 | $^1$H-NMR (400 MHz, DMSO-d$_6$) δ 1.28-1.40 (m, 2H), 1.41-1.53 (m, 2H), 1.57-1.67 (m, 2H), 1.68-1.78 (m, 2H), 3.07 (m, 1H), 3.71 (s, 2H), 6.30 (d, J = 3.2 Hz, 1H), 6.63 (d, J = 3.2 Hz, 1H), 6.95 (br s, 4H), 7.37 (dd, J = 8.3, 1.2 Hz, 1H), 7.74 (d, J = 8.3 Hz, 1H), 7.82 (d, J = 1.2 Hz, 1H), 10.52 (s, 1H), 11.69 (s, 1H) |
| 2-Aminocarbonylamino-6-[5-(2-hydroxyethylaminomethyl)furan-2-yl]indole-3-carboxamide (Compound 13-18) 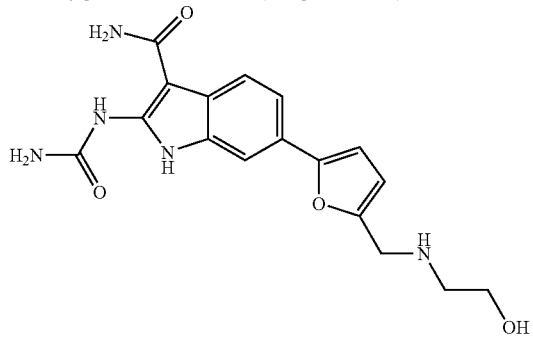 | $^1$H-NMR (400 MHz, DMSO-d$_6$) δ 2.65 (t, J = 5.7 Hz, 2H), 3.48 (q, J = 5.7 Hz, 2H), 3.74 (s, 2H), 4.49 (t, J = 5.4 Hz, 1H), 6.31 (d, J = 3.2 Hz, 1H), 6.64 (d, J = 3.2 Hz, 1H), 6.95 (br s, 4H), 7.37 (dd, J = 8.3, 1.4 Hz, 1H), 7.75 (d, J = 8.3 Hz, 1H), 7.82 (d, J = 1.4 Hz, 1H), 10.53 (s, 1H), 11.70 (s, 1H) |
| 2-Aminocarbonylamino-6-[5-(tetrahydropyran-4-ylamino-methyl)furan-2-yl]indole-3-carboxamide (Compound 13-19) 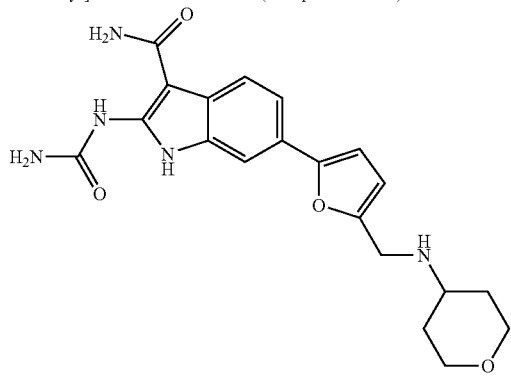 | $^1$H-NMR (500 MHz, DMSO-d$_6$) δ 1.23-1.32 (m, 2H), 1.72-1.84 (m, 2H), 2.67 (m, 1H), 3.25-3.32 (m, 2H), 3.77 (s, 2H), 3.80-3.86 (m, 2H), 6.31 (d, J = 3.3 Hz, 1H), 6.63 (d, J = 3.3 Hz, 1H), 6.95 (br s, 4H), 7.37 (dd, J = 8.4, 1.4 Hz, 1H), 7.75 (d, J = 8.4 Hz, 1H), 7.81 (d, J = 1.4 Hz, 1H), 10.52 (s, 1H), 11.69 (s, 1H) |
| 2-Aminocarbonylamino-6-[5-(2-methoxyethylaminomethyl)furan-2-yl]indole-3-carboxamide (Compound 13-20) 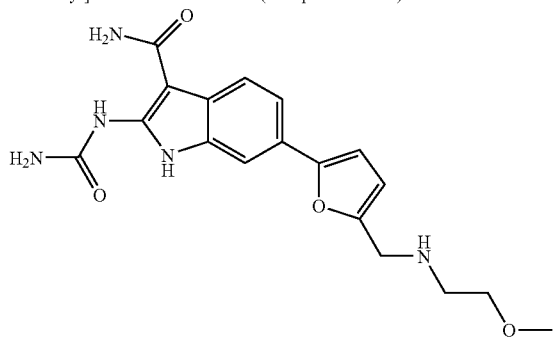 | $^1$H-NMR (400 MHz, DMSO-d$_6$) δ 2.72 (t, J = 5.7 Hz, 2H), 3.24 (s, 3H), 3.41 (t, J = 5.7 Hz, 2H), 3.74 (s, 2H), 6.31 (d, J = 3.2 Hz, 1H), 6.63 (d, J = 3.2 Hz, 1H), 6.95 (br s, 4H), 7.37 (dd, J = 8.3, 1.3 Hz, 1H), 7.75 (d, J = 8.3 Hz, 1H), 7.82 (d, J = 1.3 Hz, 1H), 10.53 (s, 1H), 11.70 (s, 1H) |

| Compound | Structure | ¹H-NMR |
|---|---|---|
| 2-Aminocarbonylamino-6-(5-tert-butylaminomethylfuran-2-yl)indole-3-carboxamide hydrochloride (Compound 13-21) | 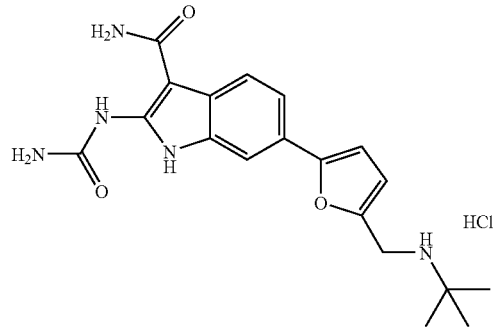 | ¹H-NMR (400 MHz, DMSO-d₆) δ 1.37 (s, 9H), 4.25 (s, 2H), 6.72 (d, J = 3.3 Hz, 1H), 6.78 (d, J = 3.3 Hz, 1H), 6.99 (br s, 4H), 7.47 (dd, J = 8.3, 1.4 Hz, 1H), 7.80 (d, J = 8.3 Hz, 1H), 7.89 (d, J = 1.4 Hz, 1H), 9.05 (br s, 2H), 10.54 (s, 1H), 11.79 (s, 1H) |
| 2-Aminocarbonylamino-6-(5-ethylaminomethylthiophen-2-yl)indole-3-carboxamide (Compound 13-22) | 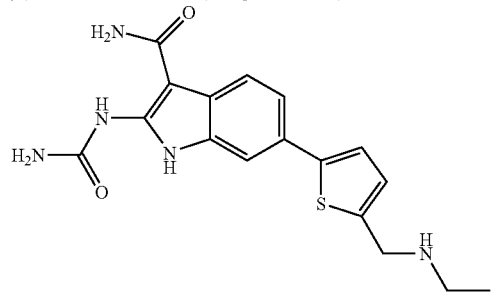 | ¹H-NMR (400 MHz, DMSO-d₆) δ 1.04 (t, J = 7.1 Hz, 3H), 2.58 (q, J = 7.1 Hz, 2H), 3.85 (s, 2H), 6.90 (d, J = 3.7 Hz, 1H), 6.95 (br s, 4H), 7.15 (d, J = 3.7 Hz, 1H), 7.30 (dd, J = 8.3, 1.3 Hz, 1H), 7.65-7.82 (m, 2H), 10.52 (s, 1H), 11.68 (s, 1H) |
| 2-Aminocarbonylamino-6-(3-dimethylaminomethylphenyl)indole-3-carboxamide (Compound 13-23) | 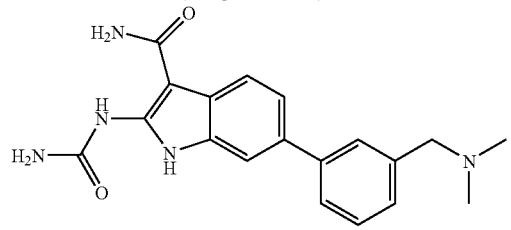 | ¹H-NMR (400 MHz, DMSO-d₆) δ 2.19 (s, 6H), 3.45 (s, 2H), 6.95 (br s, 4H), 7.21 (d, J = 7.7 Hz, 1H), 7.35 (dd, J = 8.3, 1.5 Hz, 1H), 7.39 (t, J = 7.7 Hz, 1H), 7.51 (d, J = 7.7 Hz, 1H), 7.56 (s, 1H), 7.81 (d, J = 8.3 Hz, 1H), 7.85 (d, J = 1.5 Hz, 1H), 10.54 (s, 1H), 11.70 (s, 1H) |
| 2-Aminocarbonylamino-6-(5-methylaminomethylthiophen-2-yl)indole-3-carboxamide (Compound 13-24) | 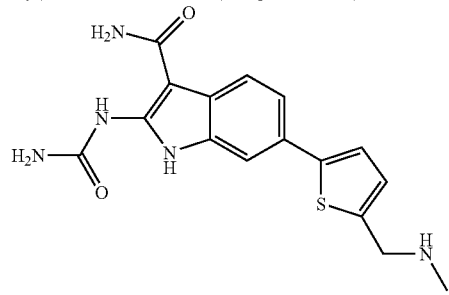 | ¹H-NMR (500 MHz, DMSO-d₆) δ 2.31 (s, 3H), 3.80 (s, 2H), 6.90 (d, J = 3.7 Hz, 1H), 6.94 (br s, 4H), 7.16 (d, J = 3.7 Hz, 1H), 7.31 (dd, J = 8.2, 1.5 Hz, 1H), 7.73 (d, J = 8.2 Hz, 1H), 7.76 (d, J = 1.5 Hz, 1H), 10.52 (s, 1H), 11.68 (s, 1H) |

Example 14

6-Acetyl-2-aminocarbonylaminoindole-3-carboxamide (Compound 14-1)

Water (6 μL, 0.25 mmol) and trifluoroacetic acid (150 μL, 2.0 mmol) were added to a solution of 2-aminocarbonylamino-6-ethynylindole-3-carboxamide (Compound 10-1, 20 mg, 0.083 mmol) in 1,4-dioxane (2 mL), the mixture was stirred at 95° C. for 5 hours. 1 N Sodium hydroxide aqueous solution (2 mL) was added to the reaction mixture under ice-cooling, and the whole was extracted with ethyl acetate (20 mL). The organic layer was washed with brine (10 mL), and dried over anhydrous magnesium sulfate. After the solvent was evaporated under reduced pressure, the resultant solid was washed with diethyl ether (2 mL) and dried under reduced pressure to give the title compound (12 mg) as a colorless solid (yield 57%).

| | |
|---|---|
| 6-Acetyl-2-aminocarbonylaminoindole-3-carboxamide (Compound 14-1) 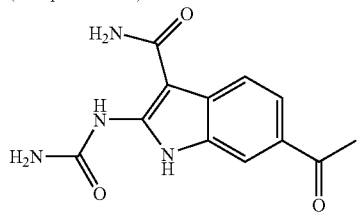 | 1H-NMR (400 MHz, DMSO-d$_6$) δ 2.55 (s, 3H), 7.08 (s, 2H), 7.15 (br s, 2H), 7.68 (dd, J = 8.5, 1.5 Hz, 1H), 7.82 (d, J = 8.5 Hz, 1H), 8.18 (d, J = 1.5 Hz, 1H), 10.61 (s, 1H), 11.96 (s, 1H) |

Example 15

2-Aminocarbonylamino-6-(1-hydroxyethyl)indole-3-carboxamide (Compound 15-1)

Sodium borohydride (10 mg, 0.26 mmol) was added to a solution of 6-acetyl-2-aminocarbonylaminoindole-3-carboxamide (Compound 14-1, 14 mg, 0.054 mmol) in anhydrous tetrahydrofuran (2 mL) under ice-cooling, and the mixture was stirred at room temperature for 1 hour. Water (5 mL) was added to the reaction mixture, and the whole was extracted with ethyl acetate (20 mL). The organic layer was washed with brine (5 mL), and dried over anhydrous magnesium sulfate. After the solvent was evaporated under reduced pressure, the resultant solid was washed with diethyl ether (2 mL) and dried under reduced pressure to give the title compound (3 mg) as a colorless solid (yield 22%).

| | |
|---|---|
| 2-Aminocarbonylamino-6-(1-hydroxyethyl)indole-3-carboxamide (Compound 15-1) 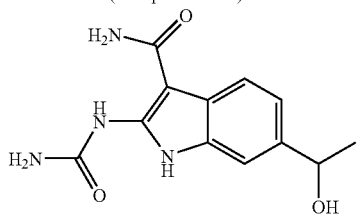 | 1H-NMR (400 MHz, DMSO-d$_6$) δ 1.33 (d, J = 6.3 Hz, 3H), 4.74 (m, 1H), 5.00 (d, J = 3.9 Hz, 1H), 6.86 (s, 2H), 6.98 (br s, 2H), 7.03 (dd, J = 8.3, 1.5 Hz, 1H), 7.48 (d, J = 1.5 Hz, 1H), 7.65 (d, J = 8.3 Hz, 1H), 10.49 (s, 1H), 11.54 (s, 1H) |

Example 16

2-Aminocarbonylamino-6-hydroxymethylindole-3-carboxamide (Compound 16-1)

1.0 M Diisobutylaluminium hydride hexane solution (68 mL, 68 mmol) was added to a solution of 2-aminocarbonylamino-6-methoxycarbonylindole-3-carboxamide (Compound 2-17, 4.0 g, 15 mmol) in anhydrous tetrahydrofuran (50 mL) under ice-cooling, and the mixture was stirred at room temperature for 3.5 hours. Water (2 mL) and methanol (20 mL) were added to the reaction mixture, and the mixture was filtered throught Celite® pad with methanol (200 mL) and 1,4-dioxane (200 mL). After the solvent was evaporated under reduced pressure, the resultant solid was washed with diethyl ether (10 mL) and dried under reduced pressure to give the title compound (2.3 g) as a yellow solid (yield 63%).

| | |
|---|---|
| 2-Aminocarbonylamino-6-hydroxymethylindole-3-carboxamide (Compound 16-1) 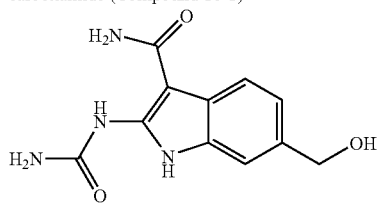 | 1H-NMR (400 MHz, DMSO-d$_6$) δ 4.50 (d, J = 5.6 Hz, 2H), 5.02 (t, J = 5.6 Hz, 1H), 6.88 (s, 2H), 6.96 (br s, 2H), 7.00 (dd, J = 8.3, 1.5 Hz, 1H), 7.46 (d, J = 1.5 Hz, 1H), 7.67 (d, J = 8.3 Hz, 1H), 10.52 (s, 1H), 11.57 (s, 1H) |

Example 17

2-Aminocarbonylamino-6-formylindole-3-carboxamide (Compound 17-1)

2-Iodoxybenzoic acid (1.8 g, 6.4 mmol) was added to a solution of 2-aminocarbonylamino-6-hydroxymethylindole-3-carboxamide (Compound 16-1, 1.4 g, 5.8 mmol) in dimethyl sulfoxide (100 mL), and the mixture was stirred at room temperature for 30 minutes. Water (100 mL) was added to the reaction mixture under ice-cooling, and the precipitated solid was separated by filtration. The resultant solid was washed with 0.25 N sodium hydroxide aqueous solution-(5 mL) and water (5 mL) and dried under reduced pressure to give the title compound (1.1 g) as a brown solid (yield 74%).

| 2-Aminocarbonylamino-6-formylindole-3-carboxamide (Compound 17-1) 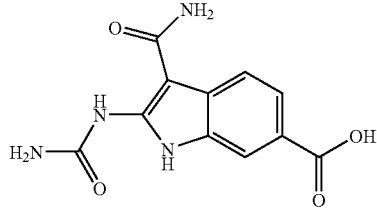 | $^1$H-NMR (400 MHz, DMSO-$d_6$) δ 7.13 (s, 2H), 7.24 (br s, 2H), 7.59 (dd, J = 8.3, 1.5 Hz, 1H), 7.90 (d, J = 8.3 Hz, 1H), 8.05 (d, J = 1.5 Hz, 1H), 9.90 (s, 1H), 10.65 (s, 1H), 12.10 (s, 1H) |

Example 18

2-Aminocarbonylamino-3-carbamoylindole-6-carboxylic acid (Compound 18-1)

Lithium hydroxide monohydrate (1.5 g, 36 mmol) was added to a solution mixture of 2-aminocarbonylamino-6-methoxycarbonylindole-3-carboxamide (Compound 2-17, 1.0 g, 3.6 mmol) in tetrahydrofuran, methanol and water (tetrahydrofuran/methanol/water=3/1/1, 50 mL), and the mixture was stirred at 65° C. for 7 hours. After the reaction mixture was concentrated under reduced pressure, 6 N hydrochloric acid (4 mL) was added to the residue under ice-cooling. The precipitated solid was washed with water (20 mL), chloroform (20 mL), and dried under reduced pressure to give the title compound (0.94 g) as a colorless solid (yield 99%).

Example 19

2-Aminocarbonylamino-6-cyanoindole-3-carboxamide (Compound 19-1)

Hydroxylamine hydrochloride (28 mg, 0.40 mmol) was added to a solution of 2-aminocarbonylamino-6-formylindole-3-carboxamide (Compound 17-1, 40 mg, 0.16 mmol) in anhydrous ethanol (2 mL), the mixture was stirred at 70° C. for 2.5 hours. Water (5 mL) was added to the reaction mixture, and the whole was extracted with ethyl acetate (10 mL). The organic layer was washed with brine (5 mL), and dried over anhydrous magnesium sulfate. After the solvent was evaporated under reduced pressure, the resultant solid was washed with diethyl ether (2 mL), and dried under reduced pressure. Acetic anhydride (18 µL, 0.19 mmol) was added to a solution of the resultant solid in anhydrous pyridine (1 mL), and the mixture was stirred at 100° C. for 4 hours. Water (3 mL) was added to the reaction mixture, and the whole was extracted with ethyl acetate (10 mL). The organic layer was washed with brine (5 mL), and dried over anhydrous magnesium sulfate. After the solvent was evaporated under reduced pressure, the resultant solid was washed with diethyl ether (2 mL) and dried under reduced pressure to give the title compound (5.0 mg) as a brown solid (yield 12%)

| 2-Aminocarbonylamino-3-carbamoylindole-6-carboxylic acid (Compound 18-1) 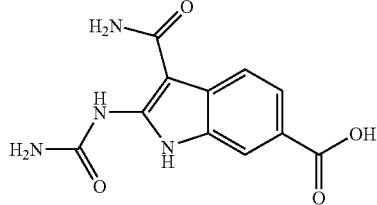 | $^1$H-NMR (400 MHz, DMSO-$d_6$) δ 7.04 (s, 2H), 7.11 (br s, 2H), 7.65 (dd, J = 8.5, 1.6 Hz, 1H), 7.79 (d, J = 8.5 Hz, 1H), 8.15 (d, J = 1.6 Hz, 1H), 10.60 (s, 1H), 11.94 (s, 1H), 12.44 (br s, 1H) |

| 2-Aminocarbonylamino-6-yanoindole-3-carboxamide (Compound 19-1) | $^1$H-NMR (400 MHz, DMSO-d$_6$) δ 7.13 (s, 2H), 7.20 (br s, 2H), 7.40 (dd, J = 8.1, 1.5 Hz, 1H), 7.89 (d, J = 8.1 Hz, 1H), 7.90 (d, J = 1.5 Hz, 1H), 10.60 (s, 1H), 12.10 (s, 1H) |
|---|---|
| 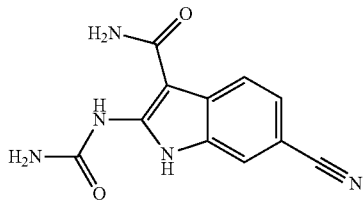 | |

Example 20

2-Aminocarbonylamino-6-(1,3-dithiolan-2-yl)indole-3-carboxamide (Compound 20-1)

1,2-Ethanedithiol (100 μL, 1.2 mmol) and boron trifluoride diethyl ether complex (8 μL, 0.065 mmol) were added to a solution of 2-aminocarbonylamino-6-formylindole-3-carboxamide (Compound 17-1, 50 mg, 0.20 mmol) in acetonitrile (2 mL), and the mixture was stirred at 50° C. for 3.5 hours. Water (30 mL) was added to the reaction mixture, and the whole was extracted with ethyl acetate (30 mL). The organic layer was washed with brine (30 mL), and dried over anhydrous magnesium sulfate. After the solvent was evaporated under reduced pressure, the resultant solid was washed with diethyl ether (2 mL) and dried under reduced pressure to give the title compound (27 ma) as a red solid (yield 41%).

| 2-Aminocarbonylamino-6-(1,3-dithiolan-2-yl)indole-3-carboxamide (Compound 20-1) | $^1$H-NMR (400 MHz, DMSO-d$_6$) δ 3.34-3.36 (m, 2H), 3.49-3.56 (m, 2H), 5.78 (s, 1H), 6.91 (s, 2H), 7.00 (br s, 2H), 7.21 (dd, J = 8.4, 1.6 Hz, 1H), 7.66 (d, J = 8.4 Hz, 1H), 7.69 (d, J = 1.6 Hz, 1H), 10.49 (s, 1H), 11.64 (s, 1H) |
|---|---|
| 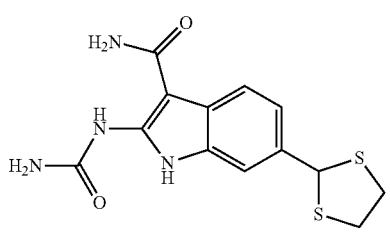 | |

Example 21

2-Aminocarbonylamino-6-[(E)-2-cyanoethenyl]indole-3-carboxamide (Compound 21-1)

Cyanomethylenetriphenylphosphorane (62 mg, 0.26 mmol) was added to a suspension of 2-aminocarbonylamino-6-formylindole-3-carboxamide (Compound 17-1, 30 mg, 0.12 mmol) in anhydrous tetrahydrofuran (2 mL), and the mixture was stirred at room temperature for 22 hours. After the reaction mixture was concentrated under reduced pressure, the residue was purified by silica gel column chromatography to give the title compound (3.0 mg) as a yellow solid (yield 16%)

| 2-Aminocarbonylamino-6-[(E)-2-cyanoethenyl]indole-3-carboxamide (Compound 21-1) | $^1$H-NMR (400 MHz, DMSO-d$_6$) δ 6.19 (d, J = 16.6 Hz, 1H), 7.04 (s, 2H), 7.12 (br s, 2H), 7.40 (dd, J = 8.5, 1.5 Hz, 1H), 7.62 (d, J = 16.6 Hz, 1H), 7.72 (d, J = 1.5 Hz, 1H), 7.78 (d, J = 8.5 Hz, 1H), 10.57 (s, 1H), 11.87 (s, 1H) |
|---|---|
| 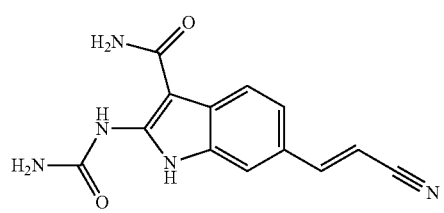 | |

Example 22

2-Aminocarbonylamino-6-(2-phenylethylaminocarbonyl)indole-3-carboxamide (Compound 22-1)

N,N-Diisopropylethylamine (0.20 mL, 1.14 mmol) and 2-phenethylamine (48 μL, 0.38 mmol) were added to a solution of 2-aminocarbonylamino-3-carbamoylindole-6-carboxylic acid (Compound 18-1, 0.10 g, 0.38 mmol) and O-(7-azabenzotriazol-1-yl)-N,N,N',N'-tetramethyluronium hexafluorophosphate g, 0.38 mmol) in anhydrous N,N-dimethylformamide (4 mL), and the mixture was stirred at room temperature for 2.5 hours. After the reaction mixture was concentrated under reduced pressure, the precipitated solid was washed with saturated sodium hydrogen carbonate aqueous solution (20 mL), water (20 mL), and dried under reduced pressure to give the title compound (0.11 g) as a slightly yellow solid (yield 77%).

| 2-Aminocarbonylamino-6-(2-phenylethylaminocarbonyl)indole-3-carboxamide (Compound 22-1) 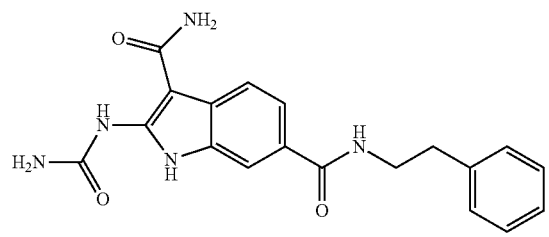 | $^1$H-NMR (400 MHz, DMSO-$d_6$) δ 2.85 (t, J = 7.4 Hz, 2H), 3.46-3.50 (m, 2H), 7.01 (s, 2H), 7.03 (br s, 2H), 7.20 (t, J = 7.0 Hz, 1H), 7.25-7.32 (m, 4H), 7.54 (dd, J = 8.4, 1.7 Hz, 1H), 7.76 (d, J = 8.4 Hz, 1H), 8.01 (d, J = 1.7 Hz, 1H), 8.35 (t, J = 5.9 Hz, 1H), 10.59 (s, 1H), 11.83 (s, 1H) |
|---|---|

As described below, Compound 22-2~22-16 were obtained according to the preparation method of Compound 22-1 by using commercially available reagents and Compound 18-1.

| 2-Aminocarbonylamino-6-(pyrrolidin-1-ylcarbonyl)indole-3-carboxamide (Compound 22-2) 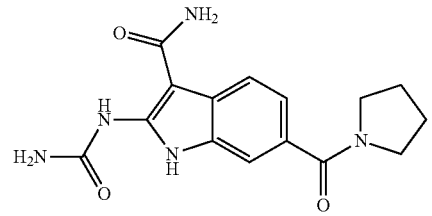 | $^1$H-NMR (400 MHz, DMSO-$d_6$) δ 1.82-1.86 (m, 4H), 3.47 (t, J = 6.5 Hz, 4H), 6.98 (s, 2H), 7.04 (br s, 2H), 7.24 (dd, J = 8.4, 1.3 Hz, 1H), 7.74-7.75 (m, 2H), 10.56 (s, 1H), 11.79 (s, 1H) |
|---|---|
| 2-Aminocarbonylamino-6-cyclopropylaminocarbonylindole-3-carboxamide (Compound 22-3) 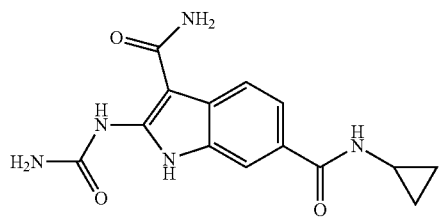 | $^1$H-NMR (400 MHz, DMSO-$d_6$) δ 0.55-0.59 (m, 2H), 0.67-0.68 (m, 2H), 2.84 (m, 1H), 7.01 (s, 2H), 7.07 (br s, 2H), 7.53 (dd, J = 8.3, 1.5 Hz, 1H), 7.74 (d, J = 8.3 Hz, 1H), 7.99 (d, J = 1.5 Hz, 1H), 8.23 (d, J = 4.2 Hz, 1H), 10.58 (s, 1H), 11.81 (s, 1H) |

2-Aminocarbonylamino-6-cyclopentylaminocarbonylindole-3-carboxamide (Compound 22-4)

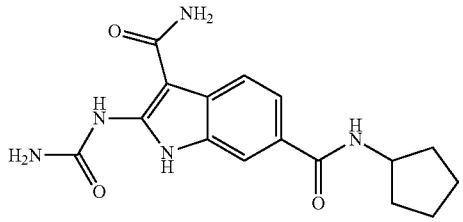

$^1$H-NMR (400 MHz, DMSO-d$_6$) δ 1.53-1.54 (m, 4H), 1.69-1.71 (m, 2H), 1.87-1.89 (m, 2H), 4.23 (m, 1H), 7.01 (s, 2H), 7.04 (br s, 2H), 7.57 (dd, J = 8.3, 1.4 Hz, 1H), 7.75 (d, J = 8.3 Hz, 1H), 8.00 (d, J = 1.4 Hz, 1H), 8.06 (d, J = 7.3 Hz, 1H), 10.58 (s, 1H), 11.80 (s, 1H)

2-Aminocarbonylamino-6-phenylaminocarbonylindole-3-carboxamide (Compound 22-5)

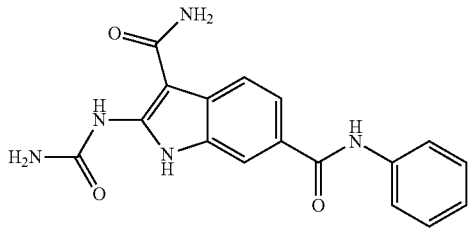

$^1$H-NMR (500 MHz, DMSO-d$_6$) δ 7.06-7.08 (m, 5H), 7.34 (t, J = 7.6 Hz, 2H), 7.71 (dd, J = 8.4, 1.7 Hz, 1H), 7.79 (d, J = 7.6 Hz, 2H), 7.84 (d, J = 8.4 Hz, 1H), 8.12 (d, J = 1.7 Hz, 1H), 10.08 (s, 1H), 10.62 (s, 1H), 11.91 (s, 1H)

2-Aminocarbonylamino-6-(pyridin-3-ylaminocarbonyl)indole-3-carboxamide (Compound 22-6)

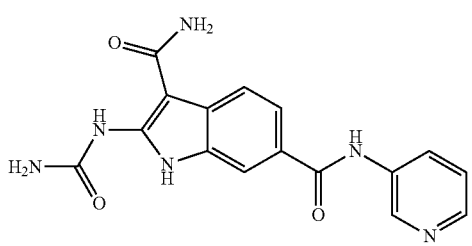

$^1$H-NMR (400 MHz, DMSO-d$_6$) δ 7.08 (s, 2H), 7.11 (br s, 2H), 7.38 (dd, J = 8.4, 4.8 Hz, 1H), 7.74 (dd, J = 8.5, 1.5 Hz, 1H), 7.86 (d, J = 8.5 Hz, 1H), 8.15 (d, J = 1.5 Hz, 1H), 8.21 (m, 1H), 8.28 (dd, J = 4.8, 1.3 Hz, 1H), 8.95 (m, 1H), 10.29 (s, 1H), 10.63 (s, 1H), 11.95 (s, 1H)

2-Aminocarbonylamino-6-(3-methoxyphenylaminocarbonyl)indole-3-carboxamide (Compound 22-7)

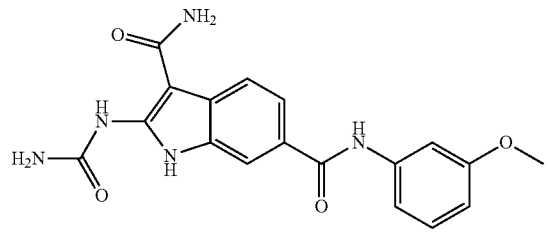

$^1$H-NMR (500 MHz, DMSO-D$_6$) δ 3.76 (s, 3H), 6.65 (dd, J = 8.2, 2.0 Hz, 1H), 7.06 (s, 2H), 7.07 (br s, 2H), 7.23 (t, J = 8.2 Hz, 1H), 7.39 (dd, J = 8.2, 2.0 Hz, 1H), 7.51 (t, J = 2.0 Hz, 1H), 7.71 (dd, J = 8.2, 1.5 Hz, 1H), 7.84 (d, J = 8.2 Hz, 1H), 8.12 (d, J = 1.5 Hz, 1H), 10.05 (s, 1H), 10.62 (s, 1H), 11.92 (s, 1H)

2-Aminocarbonylamino-6-(3-dimethylaminophenylaminocarbonyl)indole-3-carboxamide (Compound 22-8)

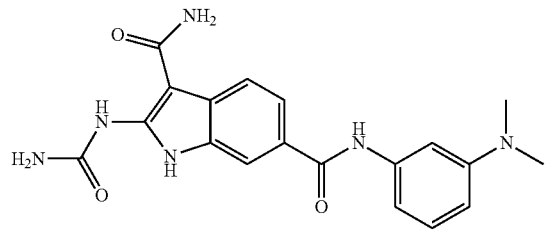

$^1$H-NMR (400 MHz, DMSO-d$_6$) δ 2.90 (s, 6H), 6.46 (ddd, J = 8.1, 2.0, 1.0 Hz, 1H), 7.06 (s, 2H), 7.07 (br s, 2H), 7.12 (t, J = 8.1 Hz, 1H), 7.18 (ddd, J = 8.1, 2.0, 1.0 Hz, 1H), 7.24 (t, J = 2.0 Hz, 1H), 7.70 (dd, J = 8.3, 1.5 Hz, 1H), 7.83 (d, J = 8.3 Hz, 1H), 8.11 (d, J = 1.5 Hz, 1H), 9.87 (s, 1H), 10.62 (s, 1H), 11.90 (s, 1H)

2-Aminocarbonylamino-6-benzylaminocarbonylindole-3-carboxamide (Compound 22-9)

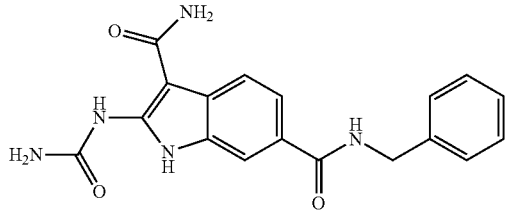

$^1$H-NMR (400 MHz, DMSO-$d_6$) δ 4.48 (d, J = 6.1 Hz, 2H), 7.02 (s, 2H), 7.04 (br s, 2H), 7.23 (m, 1H), 7.32-7.33 (m, 4H), 7.63 (dd, J = 8.5, 1.5 Hz, 1H), 7.78 (d, J = 8.5 Hz, 1H), 8.06 (d, J = 1.5 Hz, 1H), 8.84 (t, J = 6.1 Hz, 1H), 10.59 (s, 1H), 11.85 (s, 1H)

2-Aminocarbonylamino-6-(pyridin-4-ylmethylaminocarbonyl)indole-3-carboxamide (Compound 22-10)

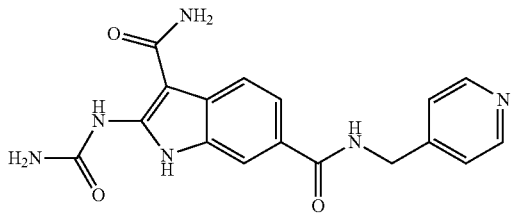

$^1$H-NMR (500 MHz, DMSO-$d_6$) δ 4.50 (d, J = 6.0 Hz, 2H), 7.02 (s, 2H), 7.03 (br s, 2H), 7.31 (dd, J = 4.4, 1.5 Hz, 2H), 7.64 (dd, J = 8.2, 1.5 Hz, 1H), 7.80 (d, J = 8.2 Hz, 1H), 8.08 (d, J = 1.5 Hz, 1H), 8.50 (dd, J = 4.4, 1.5 Hz, 2H), 8.92 (t, J = 6.0 Hz, 1H), 10.60 (s, 1H), 11.87 (s, 1H)

2-Aminocarbonylamino-6-(adamantan-1-ylaminocarbonyl)indole-3-carboxamide (Compound 22-11)

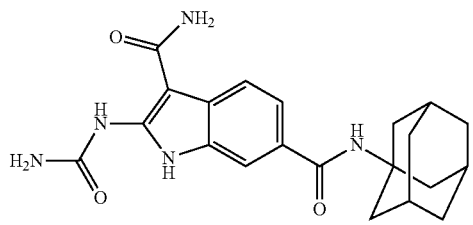

$^1$H-NMR (400 MHz, DMSO-$d_6$) δ 1.66 (t, J = 2.5 Hz, 6H), 2.06 (s, 3H), 2.09 (d, J = 2.5 Hz, 6H), 6.99 (s, 2H), 7.05 (br s, 2H), 7.33 (s, 1H), 7.51 (dd, J = 8.3, 1.5 Hz, 1H), 7.73 (d, J = 8.3 Hz, 1H), 7.94 (d, J = 1.5 Hz, 1H), 10.58 (s, 1H), 11.78 (s, 1H)

2-Aminocarbonylamino-6-[(1-methylpiperidin-4-yl)aminocarbonyl]indole-3-carboxamide (Compound 22-12)

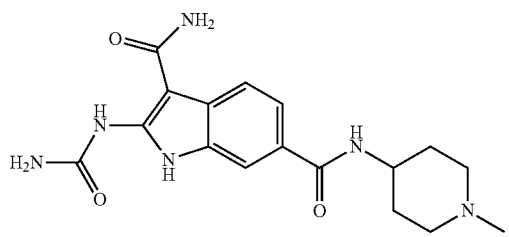

$^1$H-NMR (400 MHz, DMSO-$d_6$) δ 1.57-1.64 (m, 2H), 1.77 (dt, J = 11.0, 2.6 Hz, 2H), 2.01 (m, 2H), 2.20 (s, 3H), 2.80 (dt, J = 11.0, 2.6 Hz, 2H), 3.75 (m, 1H), 7.01 (s, 2H), 7.06 (br s, 2H), 7.57 (dd, J = 8.5, 1.5 Hz, 1H), 7.75 (d, J = 8.5 Hz, 1H), 8.01 (d, J = 1.5 Hz, 1H), 8.03 (d, J = 7.8 Hz, 1H), 10.58 (s, 1H), 11.81 (s, 1H)

2-Aminocarbonylamino-6-(2-cyanoethylaminocarbonyl)indole-3-carboxamide (Compound 22-13)

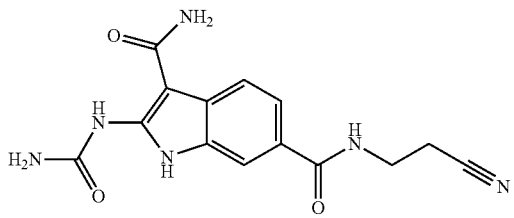

$^1$H-NMR (500 MHz, DMSO-$d_6$) δ 2.78 (t, J = 6.6 Hz, 2H), 3.49-3.50 (m, 2H), 7.02 (s, 2H), 7.03 (br s, 2H), 7.57 (dd, J = 8.6, 1.0 Hz, 1H), 7.79 (d, J = 8.6 Hz, 1H), 8.04 (d, J = 1.0 Hz, 1H), 8.62 (t, J = 5.5 Hz, 1H), 10.60 (s, 1H), 11.87 (s, 1H)

| | |
|---|---|
| 2-Aminocarbonylamino-6-propylaminocarbonylindole-3-carboxamide (Compound 22-14)<br>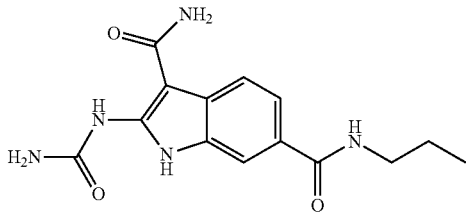 | $^1$H-NMR (400 MHz, DMSO-$d_6$) δ 0.90 (t, J = 7.4 Hz, 3H), 1.52-1.56 (m, 2H), 3.18-3.22 (m, 2H), 7.00 (s, 2H), 7.07 (br s, 2H), 7.56 (dd, J = 8.3, 1.5 Hz, 1H), 7.76 (d, J = 8.3 Hz, 1H), 8.01 (d, J = 1.5 Hz, 1H), 8.24 (t, J = 5.7 Hz, 1H), 10.58 (s, 1H), 11.82 (s, 1H) |
| 2-Aminocarbonylamino-6-[2-(3-methoxyphenyl)ethylaminocarbonyl]indole-3-carboxamide (Compound 22-15)<br>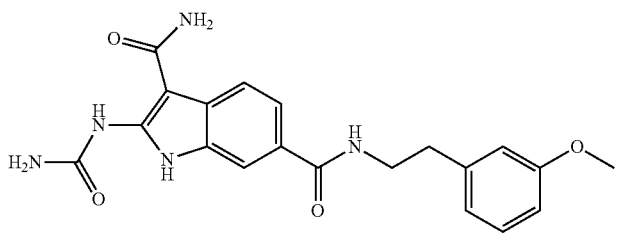 | $^1$H-NMR (500 MHz, DMSO-$d_6$) δ 2.83 (t, J = 7.3 Hz, 2H), 3.47-3.49 (m, 2H), 3.73 (s, 3H), 6.77-6.82 (m, 3H), 7.01 (s, 2H), 7.03 (br s, 2H), 7.21 (t, J = 7.9 Hz, 1H), 7.55 (dd, J = 8.6, 1.5 Hz, 1H), 7.76 (d, J = 8.6 Hz, 1H), 8.01 (d, J = 1.5 Hz, 1H), 8.33 (t, J = 5.7 Hz, 1H), 10.59 (s, 1H), 11.83 (s, 1H) |
| 2-Aminocarbonylamino-6-ethoxycarbonylmethylaminocarbonylindole-3-carboxamide (Compound 22-16)<br>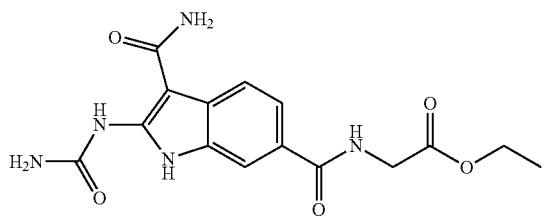 | $^1$H-NMR (500 MHz, DMSO-$d_6$) δ 1.21 (t, J = 7.1 Hz, 3H), 3.98 (d, J = 5.9 Hz, 2H), 4.12 (q, J = 7.1 Hz, 2H), 7.02 (s, 2H), 7.05 (br s, 2H), 7.60 (dd, J = 8.6, 1.5 Hz, 1H), 7.79 (d, J = 8.6 Hz, 1H), 8.04 (d, J = 1.5 Hz, 1H), 8.69 (t, J = 5.9 Hz, 1H), 10.60 (s, 1H), 11.88 (s, 1H) |

Example 23

2-Aminocarbonylamino-6-(N-benzylaminomethyl)indole-3-carboxamide (Compound 23-1)

Benzylamine (0.18 mL, 1.6 mmol) was added to a suspension of 2-aminocarbonylamino-6-formylindole-3-carboxamide (Compound 17-1, 0.10 g, 0.41 mmol) in anhydrous ethanol (3 mL), and the mixture was stirred at 80° C. overnight. After the reaction mixture was concentrated under reduced pressure, sodium borohydride (24 mg, 63 mmol) was added to a solution mixture of the residue in anhydrous methanol and anhydrous tetrahydrofuran (methanol/tetrahydrofuran=1/1, 2 mL), and the mixture was stirred at room temperature for 7 hours. Water (10 mL) was added to the reaction mixture under ice-cooling, and the whole was extracted with ethyl acetate (10 mL). The organic layer was washed with brine (10 mL), and dried over anhydrous magnesium sulfate. After evaporating the solvent under reduced pressure, the resultant solid was washed with chloroform (3 mL), diethyl ether (2 mL), and dried under reduced pressure to give the title compound (0.072 g) as a yellow solid (yield 59%)

| | |
|---|---|
| 2-Aminocarbonylamino-6-(N-benzylaminomethyl)indole-3-carboxamide (Compound 23-1)<br>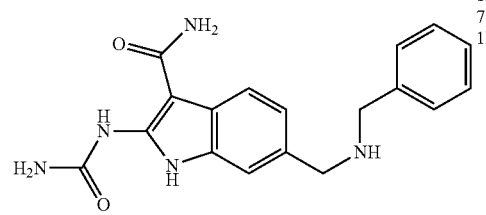 | $^1$H-NMR (500 MHz, DMSO-$d_6$) δ 3.68 (s, 2H), 3.71 (s, 2H), 6.86 (s, 2H), 6.95 (br s, 2H), 7.04 (dd, J = 8.2, 1.4 Hz, 1H), 7.23 (tt, J = 7.2, 1.7 Hz, 1H), 7.30-7.37 (m, 4H), 7.48 (d, J = 1.4 Hz, 1H), 7.66 (d, J = 8.2 Hz, 1H), 10.50 (s, 1H), 11.54 (s, 1H) |

As described below, Compound 23-2~23-6 were obtained according to the preparation method of Compound 23-1 by using commercially available reagents and Compound 17-1.

2-Aminocarbonylamino-6-(N-cyclopropylaminomethyl)indole-3-carboxamide (Compound 23-2)

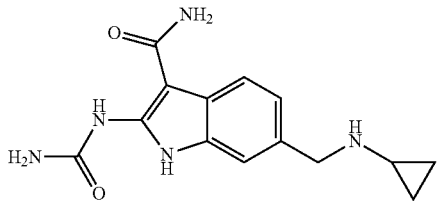

$^1$H-NMR (400 MHz, DMSO-$d_6$) δ 0.23-0.26 (m, 2H), 0.32-0.36 (m, 2H), 2.05 (m, 1H), 3.73 (s, 2H), 6.86 (s, 2H), 6.95 (br s, 2H), 7.02 (d, J = 7.6 Hz, 1H), 7.43 (s, 1H), 7.65 (d, J = 7.6 Hz, 1H), 10.49 (s, 1H), 11.52 (s, 1H)

2-Aminocarbonylamino-6-(N-cyclopentylaminomethyl)indole-3-carboxamide (Compound 23-3)

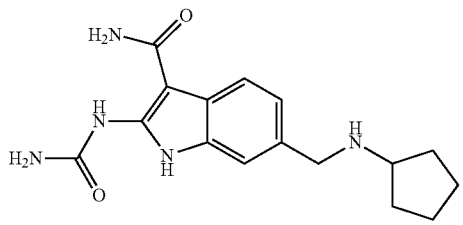

$^1$H-NMR (400 MHz, DMSO-$d_6$) δ 1.31-1.37 (m, 2H), 1.44-1.46 (m, 2H), 1.65-1.69 (m, 4H), 2.99 (m, 1H), 3.68 (s, 2H), 6.85 (s, 2H), 6.98 (br s, 2H), 7.02 (d, J = 8.3 Hz, 1H), 7.44 (s, 1H), 7.64 (d, J = 8.3 Hz, 1H), 10.49 (s, 1H), 11.51 (s, 1H)

2-Aminocarbonylamino-6-(N-methylaminomethyl)indole-3-carboxamide (Compound 23-4)

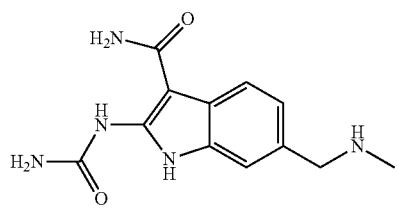

$^1$H-NMR (500 MHz, DMSO-$d_6$) δ 2.53 (s, 3H), 4.11 (s, 2H), 6.97 (s, 2H), 7.03 (br s, 2H), 7.20 (d, J = 8.2 Hz, 1H), 7.57 (s, 1H), 7.80 (d, J = 8.2 Hz, 1H), 10.56 (s, 1H), 11.80 (s, 1H)

2-Aminocarbonylamino-6-(N-phenylaminomethyl)indole-3-carboxamide (Compound 23-5)

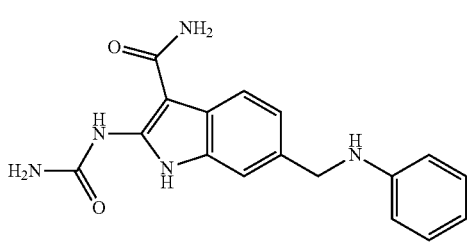

$^1$H-NMR (400 MHz, DMSO-$d_6$) δ 4.26 (d, J = 5.7 Hz, 2H), 6.13 (t, J = 5.7 Hz, 1H), 6.48 (tt, J = 7.2, 1.1 Hz, 1H), 6.58 (dt, J = 7.2, 1.1 Hz, 2H), 6.87 (s, 2H), 6.97 (br s, 2H), 7.00-7.03 (m, 2H), 7.06 (dd, J = 8.2, 1.0 Hz, 1H), 7.50 (d, J = 1.0 Hz, 1H), 7.67 (d, J = 8.2 Hz, 1H), 10.49 (s, 1H), 11.56 (s, 1H)

2-Aminocarbonylamino-6-(N-pyridin-3-ylaminomethyl)indole-3-carboxamide (Compound 23-6)

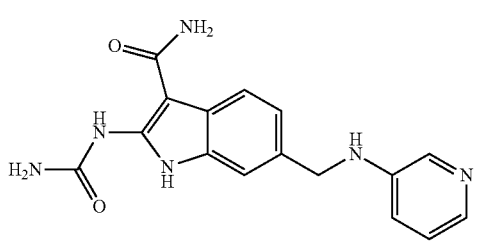

$^1$H-NMR (400 MHz, DMSO-$d_6$) δ 4.30 (d, J = 5.7 Hz, 2H), 6.43 (t, J = 5.7 Hz, 1H), 6.87 (ddd, J = 8.3, 2.9, 1.5 Hz, 1H), 6.87 (s, 2H), 6.97 (br s, 2H), 7.01 (dd, J = 8.3, 4.4 Hz, 1H), 7.06 (dd, J = 8.3, 1.5 Hz, 1H), 7.50 (d, J = 1.5 Hz, 1H), 7.68 (d, J = 8.3 Hz, 1H), 7.71 (dd, J = 4.4, 1.5 Hz, 1H), 7.98 (d, J = 2.9 Hz, 1H), 10.48 (s, 1H), 11.58 (s, 1H)

Example 24

2-Aminocarbonylamino-6-thiomorpholinomethylindole-3-carboxamide (Compound 24-1)

Acetic acid (0.060 mL), thiomorpholine (0.12 mL, 1.2 mmol) and sodium cyanoborohydride (0.077 g, 1.2 mmol) were added to a solution of 2-aminocarbonylamino-6-formylindole-3-carboxamide (Compound 17-1, 0.10 g, 0.41 mmol) in anhydrous N,N-dimethylformamide (6 mL), and the mixture was stirred at room temperature overnight. Saturated sodium hydrogen carbonate aqueous solution (5 mL) and water (20 mL) were added to the reaction mixture, and the whole was extracted with ethyl acetate (30 mL). The organic layer was washed with brine (20 mL), and dried over anhydrous magnesium sulfate. After the solvent was evaporated under reduced pressure, the resultant solid was washed with chloroform (2 mL), diethyl ether (2 mL), and dried under reduced pressure to give the title compound (0.062 g) as a colorless solid (yield 45%).

2-Aminocarbonylamino-6-thiomorpholinomethylindole-3-carboxamide (Compound 24-1)

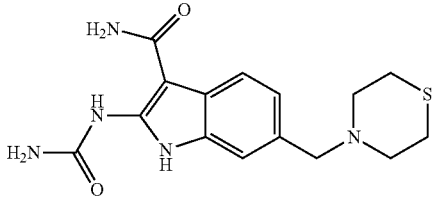

$^1$H-NMR (400 MHz, DMSO-$d_6$) δ 2.59-2.61 (m, 8H), 3.51 (s, 2H), 6.87 (s, 2H), 6.94 (br s, 2H), 6.97 (dd, J = 8.1, 1.5 Hz, 1H), 7.43 (d, J = 1.5 Hz, 1H), 7.65 (d, J = 8.1 Hz, 1H), 10.48 (s, 1H), 11.55 (s, 1H)

As described below, Compound 24-2~24-4 were obtained according to the preparation method of Compound 24-1 by using commercially available reagents and Compound 17-1.

2-Aminocarbonylamino-6-(pyrrolidin-1-ylmethyl)indole-3-carboxamide (Compound 24-2)

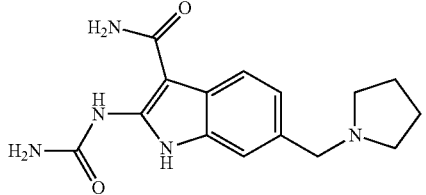

$^1$H-NMR (400 MHz, DMSO-$d_6$) δ 1.66-1.69 (m, 4H), 2.39-2.42 (m, 4H), 3.57 (s, 2H), 6.87 (s, 2H), 6.94 (br s, 2H), 6.98 (dd, J = 8.2, 1.6 Hz, 1H), 7.43 (s, 1H), 7.64 (d, J = 8.2 Hz, 1H), 10.49 (s, 1H), 11.53 (s, 1H)

2-Aminocarbonylamino-6-(morpholinomethyl)indole-3-carboxamide (Compound 24-3)

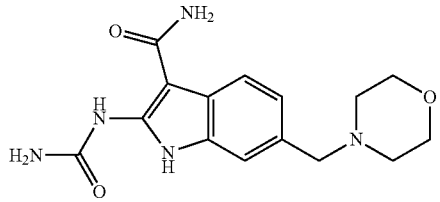

$^1$H-NMR (400 MHz, DMSO-$d_6$) δ 2.33-2.35 (m, 4H), 3.47 (s, 2H), 3.56-3.57 (m, 4H), 6.87 (s, 2H), 6.94 (br s, 2H), 6.99 (dd, J = 8.0, 1.0 Hz, 1H), 7.44 (d, J = 1.0 Hz, 1H), 7.66 (d, J = 8.0 Hz, 1H), 10.49 (s, 1H), 11.56 (s, 1H)

2-Aminocarbonylamino-6-(N-methoxy-N-methylaminomethyl)indole-3-carboxamide (Compound 24-4)

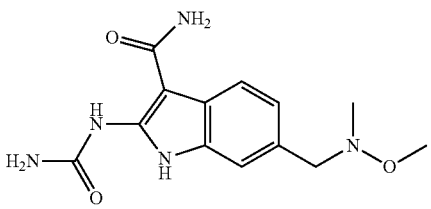

$^1$H-NMR (500 MHz, DMSO-$d_6$) δ 2.50 (s, 3H), 3.28 (s, 3H), 3.76 (s, 2H), 6.87 (s, 2H), 6.96 (br s, 2H), 7.02 (dd, J = 8.2, 1.2 Hz, 1H), 7.47 (d, J = 1.2 Hz, 1H), 7.66 (d, J = 8.2 Hz, 1H), 10.50 (s, 1H), 11.57 (s, 1H)

Example 25

2-Aminocarbonylamino-6-cyclohexylthiomethylindole-3-carboxamide (Compound 25-1)

A solution of 2-aminocarbonylamino-6-formylindole-3-carboxamide (Compound 17-1, 30 mg, 0.12 mmol) in trifluoroacetic acid (2 mL) was added to a solution of cyclohexanethiol (16 µL, 0.13 mmol) in anhydrous dichloromethane (1 mL) under ice-cooling. The mixture was stirred for 5 minutes, then borane-pyridine complex (14 µL, 0.13 mmol) was added thereto. After the mixture was stirred for 5 minutes, the reaction mixture was concentrated under reduced pressure. 1 N Sodium hydroxide aqueous solution (3 mL) and water (10 mL) were added to the residue, and the whole was extracted with ethyl acetate (15 mL). The organic layer was washed with brine (10 mL), and dried over anhydrous magnesium sulfate. After the solvent was evaporated under reduced pressure, the resultant solid was washed with diethyl ether (2 mL) and dried under reduced pressure to give the title compound (15 mg) as a yellow solid (yield 36%).

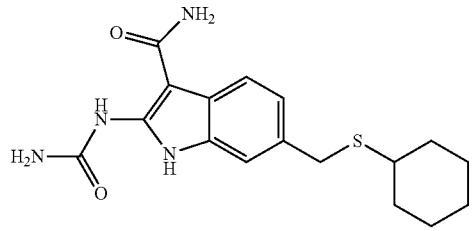

2-Aminocarbonylamino-6-cyclohexylthiomethylindole-3-carboxamide (Compound 25-1)

$^1$H-NMR (500 MHz, DMSO-$d_6$) δ 1.20-1.28 (m, 5H), 1.54-1.67 (m, 3H), 1.89-1.91 (m, 2H), 2.50 (m, 1H), 3.78 (s, 2H), 6.88 (s, 2H), 6.95 (br s, 2H), 6.99 (dd, J = 8.2, 1.5 Hz, 1H), 7.45 (d, J = 1.5 Hz, 1H), 7.65 (d, J = 8.2 Hz, 1H), 10.49 (s, 1H), 11.58 (s, 1H)

As described below, Compound 25-2~25-9 were obtained according to the preparation method of Compound 25-1 by using commercially available reagents and Compound 17-1.

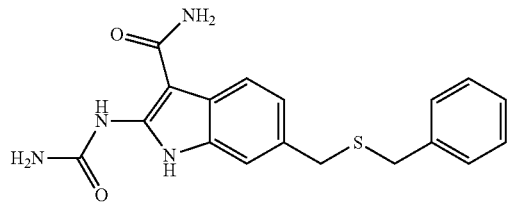

2-Aminocarbonylamino-6-benzylthiomethylindole-3-carboxamide (Compound 25-2)

$^1$H-NMR (400 MHz, DMSO-$d_6$) δ 3.64 (s, 2H), 3.68 (s, 2H), 6.89 (s, 2H), 6.95 (br s, 2H), 6.98 (dd, J = 8.1, 1.5 Hz, 1H), 7.25 (m, 1H), 7.32-7.35 (m, 4H), 7.47 (d, J = 1.5 Hz, 1H), 7.67 (d, J = 8.1 Hz, 1H), 10.50 (s, 1H), 11.62 (s, 1H)

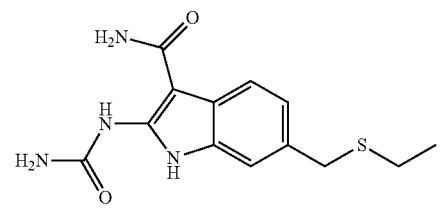

2-Aminocarbonylamino-6-ethylthiomethylindole-3-carboxamide (Compound 25-3)

$^1$H-NMR (400 MHz, DMSO-$d_6$) δ 1.17 (t, J = 7.4 Hz, 3H), 2.39 (q, J = 7.4 Hz, 2H), 3.77 (s, 2H), 6.88 (s, 2H), 6.96 (br s, 2H), 7.00 (dd, J = 8.3, 1.2 Hz, 1H), 7.45 (d, J = 1.2 Hz, 1H), 7.66 (d, J = 8.3 Hz, 1H), 10.49 (s, 1H), 11.58 (s, 1H)

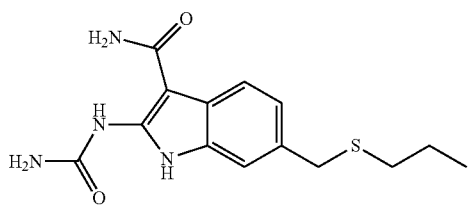

2-Aminocarbonylamino-6-propylthiomethylindole-3-carboxamide (Compound 25-4)

$^1$H-NMR (500 MHz, DMSO-$d_6$) δ 0.90 (t, J = 7.2 Hz, 3H), 1.51-1.54 (m, 2H), 2.37 (t, J = 7.2 Hz, 2H), 3.75 (s, 2H), 6.88 (s, 2H), 6.95 (br s, 2H), 6.99 (dd, J = 8.2, 1.4 Hz, 1H), 7.44 (d, J = 1.4 Hz, 1H), 7.65 (d, J = 8.2 Hz, 1H), 10.49 (s, 1H), 11.58 (s, 1H)

-continued

2-Aminocarbonylamino-6-(2,2,2-trifluoroethylthiomethyl) indole-3-carboxamide (Compound 25-5)

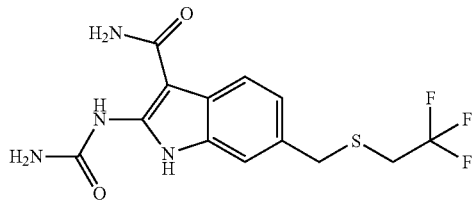

$^1$H-NMR (500 MHz, DMSO-$d_6$) δ 3.30-3.33 (m, 2H), 3.94 (s, 2H), 6.90 (s, 2H), 6.97 (br s, 2H), 7.01 (dd, J = 8.2, 1.5 Hz, 1H), 7.47 (d, J = 1.5 Hz, 1H), 7.70 (d, J = 8.2 H, 1H), 10.50 (s, 1H), 11.65 (s, 1H)

2-Aminocarbonylamino-6-isopropylthiomethylindole-3-carboxamide (Compound 25-6)

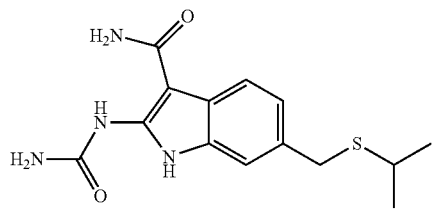

$^1$H-NMR (400 MHz, DMSO-$d_6$) δ 1.20 (d, J = 6.8 Hz, 6H), 2.77 (m, 1H), 3.79 (s, 2H), 6.88 (s, 2H), 6.95 (br s, 2H), 7.00 (dd, J = 8.3, 1.5 Hz, 1H), 7.46 (d, J = 1.5 Hz, 1H), 7.65 (d, J = 8.3 Hz, 1H), 10.49 (s, 1H), 11.58 (s, 1H)

2-Aminocarbonylamino-6-allylthiomethylindole-3-carboxamide (Compound 25-7)

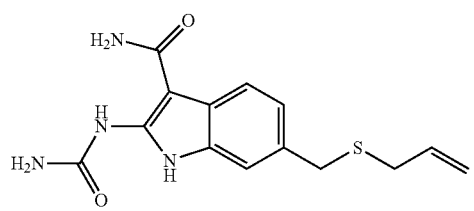

$^1$H-NMR (500 MHz, DMSO-$d_6$) δ 3.05 (d, J = 7.0 Hz, 2H), 3.70 (s, 2H), 5.11-5.19 (m, 2H), 5.80 (m, 1H), 6.88 (s, 2H), 6.95 (br s, 2H), 6.98 (dd, J = 8.1, 1.2 Hz, 1H), 7.44 (d, J = 1.2 Hz, 1H), 7.66 (d, J = 8.1 Hz, 1H), 10.50 (s, 1H), 11.60 (s, 1H)

2-Aminocarbonylamino-6-methylthiomethylindole-3-carboxamide (Compound 25-8)

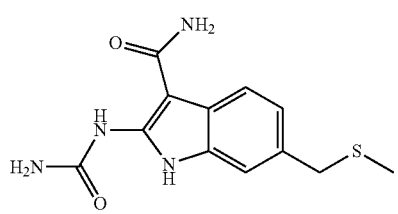

$^1$H-NMR (500 MHz, DMSO-$d_6$) δ 1.95 (s, 3H), 3.73 (s, 2H), 6.88 (s, 2H), 6.95 (br s, 2H), 6.99 (d, J = 7.8 Hz, 1H), 7.44 (s, 1H), 7.66 (d, J = 7.8 Hz, 1H), 10.49 (s, 1H), 11.58 (s, 1H)

2-Aminocarbonylamino-6-(2-hydroxyethylthiomethyl) indole-3-carboxamide (Compound 25-9)

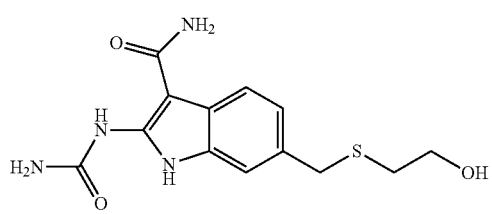

$^1$H-NMR (500 MHz, DMSO-$d_6$) δ 2.47 (t, J = 6.7 Hz, 2H), 3.48-3.52 (m, 2H), 3.78 (s, 2H), 4.73 (t, J = 5.7 Hz, 1H), 6.88 (s, 2H), 6.95 (br s, 2H), 7.00 (dd, J = 8.2, 1.5 Hz, 1H), 7.45 (d, J = 1.5 Hz, 1H), 7.66 (d, J = 8.2 Hz, 1H), 10.49 (s, 1H), 11.58 (s, 1H)

Example 26

6-[(2)-1-(1-Acetyl-2-hydroxy)propenyl]-2-aminocarbonylaminoindole-3-carboxamide (Compound 26-1)

A solution mixture of 2-aminocarbonylamino-6-(3,5-dimethylisoxazol-4-yl)indole-3-carboxamide (Compound 4-62, 8.6 mg, 0.027 mmol) and hexacarbonylmolybdenum (22 mg, 0.083 mmol) in acetonitrile and water (acetonitrile/water=10/1, 1.7 mL) was stirred at 85° C. for 17.5 hours. Water (20 mL) was added to the reaction mixture, and the whole was extracted with ethyl acetate (20 mL). The organic layer was washed with brine (20 mL), and dried over anhydrous magnesium sulfate. After the solvent was evaporated under reduced pressure, the resultant solid was washed with a solution mixture of diethyl ether and hexane (diethyl ether/hexane=1/1, 4 mL), and dried under reduced pressure to give the title compound (5.5 mg) as a yellow solid (yield 65%)

| 6-[(Z)-1-(1-Acetyl-2-hydroxy)propenyl]-2-aminocarbonylaminoindole-3-carboxamide (Compound 26-1) 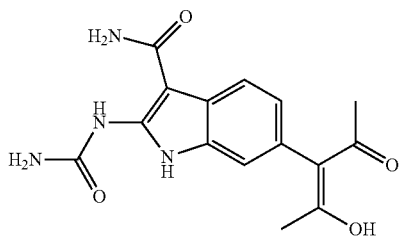 | $^1$H-NMR (400 MHz, DMSO-$d_6$) δ 1.86 (s, 6H), 6.91 (dd, J = 8.4, 1.5 Hz, 1H), 6.95 (s, 2H), 7.05 (br s, 2H), 7.35 (d, J = 1.5 Hz, 1H), 7.77 (d, J = 8.4 Hz, 1H), 10.52 (s, 1H), 11.65 (s, 1H), 16.80 (s, 1H) |
|---|---|

Example 27

2-Aminocarbonylamino-6-[3-(2,4-dihydroxy)pentyl]indole-3-carboxamide (Compound 27-1)

Sodium borohydride (11 mg, 0.29 mmol) was added to a solution of 6-[(2)-1-(1-acetyl-2-hydroxy)propenyl]-2-aminocarbonylaminoindole-3-carboxamide (Compound 26-1, 15 mg, 0.047 mmol) in anhydrous tetrahydrofuran (3 mL) under ice-cooling, and the mixture stirred at room temperature for 4.5 hours. Water (1 mL) was added to the reaction mixture, and precipitated solid was separated by filtration. The resultant solid was washed with a solution mixture of acetone and chloroform (acetone/chloroform=1/1, 4 mL), and dried under reduced pressure to give the title compound (4.5 mg) as an off-white solid (yield 30%)

Example 28

2-Aminocarbonylamino-6-azidomethylindole-3-carboxamide (Compound 28-1)

Diphenylphosphoryl azide (42 μL, 0.19 mmol) and 1,8-diazabicyclo[5.4.0]undec-7-ene (29 μL, 0.19 mmol) were added to a solution of 2-aminocarbonylamino-6-hydroxymethylindole-3-carboxamide (Compound 16-1, 40 mg, 0.16 mmol) in anhydrous tetrahydrofuran (5 mL) under ice-cooling, the mixture was stirred at room temperature overnight. Water (10 mL) was added to the reaction mixture, and the whole was extracted with ethyl acetate (10 mL). The organic layer was washed with brine (20 mL) and dried over anhydrous magnesium sulfate. The solvent was evaporated under reduced pressure, and the residue was purified by silica gel column chromatography to give the title compound (5.0 mg) as a yellow solid (yield 11%).

| 2-Aminocarbonylamino-6-[3-(2,4-dihydroxy)pentyl]indole-3-carboxamide (Compound 27-1) 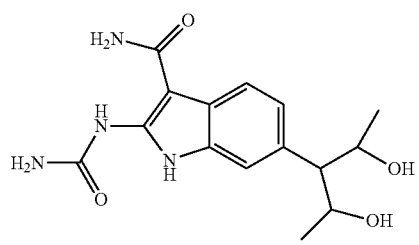 | $^1$H-NMR (400 MHz, DMSO-$d_6$) δ 0.99 (d, J = 6.1 Hz, 6H), 2.27 (t, J = 5.4 Hz, 1H), 4.09-4.13 (m, 2H), 4.27 (d, J = 4.2 Hz, 2H), 6.84 (s, 2H), 6.93 (br s, 2H), 7.02 (dd, J = 8.3, 1.3 Hz, 1H), 7.41 (s, 1H), 7.58 (d, J = 8.3 Hz, 1H), 10.47 (s, 1H), 11.42 (s, 1H) |
|---|---|

| 2-Aminocarbonylamino-6-azidomethylindole-3-carboxamide (Compound 28-1) | $^1$H-NMR (400 MHz, DMSO-$d_6$) δ 4.43 (s, 2H), 6.95 (s, 2H), 7.02 (br s, 2H), 7.06 (dd, J = 8.1, 1.3 Hz, 1H), 7.52 (s, 1H), 7.75 (d, J = 8.1 Hz, 1H), 10.53 (s, 1H), 11.73 (s, 1H) |
|---|---|

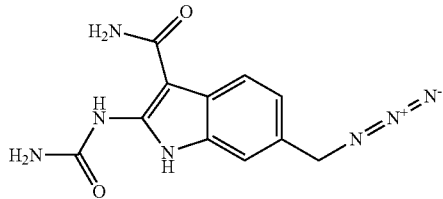

Example 29

6-(3-Acetoxymethylphenyl)-2-aminocarbonylaminoindole-3-carboxamide (Compound 29-1)

Pyridine (4 mL) and acetic anhydride (61 μL, 0.65 mmol) were added to 2-aminocarbonylamino-6-(3-hydroxymethylphenyl)indole-3-carboxamide (Compound 12-1, 0.18 g, 0.55 mmol), and the mixture was stirred at room temperature overnight. The reaction mixture was concentrated under reduced pressure, and water (10 mL) was added to the residue. The precipitated solid was separated by filtration. The resultant solid was washed with water (10 mL) and dried under reduced pressure to give the title compound (0.17 g) as a slightly brown solid (yield 87%).

A tablet of the above-mentioned formulation is coated using 3 mg of a coating agent (for example, a conventional coating agent such as hydroxypropylmethyl cellulose, macrogol, or a silicone resin), whereby an objective tablet can be obtained. In addition, a desired tablet can be obtained by appropriately changing the type and/or amount of the present compound and additives.

| 2) Capsule (in 150 mg) | |
|---|---|
| Present compound | 5 mg |
| Lactose | 135 mg |

| 6-(3-Acetoxymethylphenyl)-2-aminocarbonylaminoindole-3-carboxamide (Compound 29-1) | $^1$H-NMR (500 MHz, DMSO-$d_6$) δ 2.10 (s, 3H), 5.15 (s, 2H), 6.97 (s, 2H), 7.02 (br s, 2H), 7.30 (dt, J = 7.6, 1.3 Hz, 1H), 7.36 (dd, J = 8.4, 1.5 Hz, 1H), 7.45 (t, J = 7.6 Hz, 1H), 7.59 (dt, J = 7.6, 1.3 Hz, 1H), 7.62 (t, J = 1.3 Hz, 1H), 7.83 (d, J = 8.4 Hz, 1H), 7.84 (d, J = 1.5 Hz, 1H), 10.55 (s, 1H), 11.72 (s, 1H) |
|---|---|

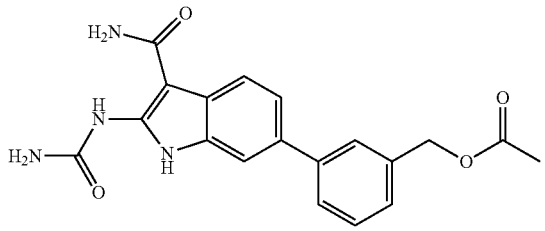

In addition, commercially available reagents are compounds which listed on product catalogs from 2006 to 2008 published by Sigma-Aldrich, Wako Pure Chemical Industries, Ltd., Kanto Chemical Co., Inc., Tokyo Chemical Industry Co., Ltd., Nacalai Tesque, Inc., etc.

Preparation Examples

Hereinafter, typical preparation examples of the present compound will be described.

| -continued | |
|---|---|
| 2) Capsule (in 150 mg) | |
| Carboxymethylcellulose Calcium | 4.5 mg |
| Hydroxypropyl Cellulose | 4 mg |
| Magnesium Stearate | 1.5 mg |

A desired capsule can be obtained by appropriately changing the type and/or amount of the present compound and additives.

| 1) Tablet (in 150 mg) | |
|---|---|
| Present compound | 1 mg |
| Lactose | 100 mg |
| Cornstarch | 40 mg |
| Carxboxymethyl cellulose calcium | 4.5 mg |
| Hydroxypropyl cellulose | 4 mg |
| Magnesium stearate | 0.5 mg |

| 3) Eye drop (in 100 ml) | |
|---|---|
| Present compound | 100 mg |
| Sodium chloride | 900 mg |
| Polysorbate 80 | 500 mg |
| Sodium hydroxide | q.s. |
| Hydrochloric acid | q.s. |
| Sterile purified water | q.s. |

A desired eye drop can be obtained by appropriately changing the type and/or amount of the present compound and additives.

[Pharmacological Test]

1. IKKβ Inhibitory Activity Measurement Test

In order to evaluate IKKβ inhibitory activity of the present compounds, an IKKβ inhibition assay by the fluorescence polarization method was conducted.

The assay was conducted using IMAP™ IKKβ assay kit (manufactured by Molecular Devices Corporation, catalogue No. R8115) or IMAP™ FP Screening Express kit (manufactured by Molecular Devices Corporation, catalogue No. R8127) and in accordance with the protocol attached to each kit. The specific methods are described below.

(Preparation of Reagents)

1) Complete Reaction Buffer: a complete reaction buffer was so prepared as to obtain a final concentration of 10 mM Tris-HCL (pH 7.2), 10 mM magnesium chloride, 0.1% bovine serum albumin, and 1 mM dithiothreitol.

2) Substrate Working Solution: 400 nM of a substrate working solution was prepared by dissolving and diluting a fluorescein-labeled IKKβ substrate peptide (amino acid sequence: GRHDSGLDSMK) with the complete reaction buffer.

3) Enzyme Working Solution: 0.2 units/mL of an enzyme working solution was prepared by diluting IKKβ solution (manufactured by Upstate Biotechnology Inc., catalogue No. 14-485) with the complete reaction buffer.

4) ATP Working Solution: 8 μM of an ATP working solution was prepared by dissolving ATP into ultrapure water followed by diluting it with the complete reaction buffer.

5) IMAP binding solution: After diluting an IMAP binding buffer with ultrapure water, an IMAP binding solution was prepared by diluting an IMAP binding reagent with the diluted IMAP binding buffer.

(Preparation of Test Compound Solution)

A test compound was dissolved in dimethylsulfoxide followed by diluting it with the complete reaction buffer to prepare 4 μM of a test compound solution.

(Test Method and Measurement Method)

1) To a 384-well plate, the test compound solution, the enzyme working solution, the substrate working solution, and the ATP working solution were added in an amount of 5 μL per well.

2) Incubation was performed at a room temperature for 60 minutes under light shielding.

3) The IMAP binding solution was added in an amount of 60 μL per well.

4) Incubation was performed at a room temperature for 30 minutes under light shielding.

5) Fluorescence polarization value of each well was measured by using Analyst™ HT (multimode plate reader manufactured by Molecular Devices Corporation) and Criterion Host Software v2.00 (manufactured by Molecular Devices Corporation).

6) Operations were performed in the same manner as in 1) to 5) except for changing the test compound to 0.4% dimethylsulfoxide. The obtained result was designated as a control.

7) Operations were performed in the same manner as in 1) to 5) except for changing the test compound and the enzyme working solution to 0.4% dimethylsulfoxide and the complete reaction buffer, respectively. The obtained result was designated as a background.

(Calculation Equation for IKKβ Inhibition Rate)

An IKKβ inhibition rate (%) was calculated by the following equation.

IKKβ inhibition rate (%)=100×{1−(fluorescence polarization value of test compound−fluorescence polarization value of background)/(fluorescence polarization value of control−fluorescence polarization value of background)}

(Evaluation Results)

As examples of evaluation results, IKKβ inhibition rates (%) of the test compounds (compounds 1-1, 1-2, 2-1, 2-2, 2-3, 24, 2-5, 2-9, 2-10, 2-11, 2-16, 2-17, 3-1, 4-1, 4-2, 4-4, 4-8, 4-9, 4-10, 4-11, 4-15, 4-16, 4-17, 4-18, 4-19, 4-22, 4-23, 4-36, 4-38, 4-58, 4-65, 4-67, 4-78, 4-81, 5-1, 7-5, 7-9, 7-14, 7-26, 7-44, 7-45, 8-3, 8-5, 8-6, 9-1, 9-2, 9-18, 10-1, 11-1, 11-4, 11-6, 11-8, 11-10, 12-1, 12-2, 13-5, 13-13, 13-15, 13-24, 16-1, 20-1, 22-2, 22-9, 24-2, and 25-3) at 1 μM are shown in Table I.

TABLE I

|  | IKKβ Inhibition Rate (%) |
|---|---|
| Compound 1-1 | 86 |
| Compound 1-2 | 55 |
| Compound 2-1 | 80 |
| Compound 2-2 | 49 |
| Compound 2-3 | 56 |
| Compound 2-4 | 95 |
| Compound 2-5 | 86 |
| Compound 2-9 | 100 |
| Compound 2-10 | 75 |
| Compound 2-11 | 96 |
| Compound 2-16 | 95 |
| Compound 2-17 | 100 |
| Compound 3-1 | 100 |
| Compound 4-1 | 97 |
| Compound 4-2 | 100 |
| Compound 4-4 | 98 |
| Compound 4-8 | 100 |
| Compound 4-9 | 100 |
| Compound 4-10 | 100 |
| Compound 4-11 | 100 |
| Compound 4-15 | 100 |
| Compound 4-16 | 100 |
| Compound 4-17 | 100 |
| Compound 4-18 | 98 |
| Compound 4-19 | 100 |
| Compound 4-22 | 100 |
| Compound 4-23 | 100 |
| Compound 4-36 | 99 |
| Compound 4-38 | 100 |
| Compound 4-58 | 99 |
| Compound 4-65 | 100 |
| Compound 4-67 | 94 |
| Compound 4-78 | 95 |
| Compound 4-81 | 96 |
| Compound 5-1 | 95 |
| Compound 7-5 | 97 |
| Compound 7-9 | 98 |
| Compound 7-14 | 100 |
| Compound 7-26 | 98 |
| Compound 7-44 | 100 |
| Compound 7-45 | 98 |
| Compound 8-3 | 100 |
| Compound 8-5 | 100 |
| Compound 8-6 | 99 |
| Compound 9-1 | 87 |
| Compound 9-2 | 95 |
| Compound 9-18 | 94 |
| Compound 10-1 | 100 |
| Compound 11-1 | 95 |
| Compound 11-4 | 100 |
| Compound 11-6 | 98 |
| Compound 11-8 | 95 |
| Compound 11-10 | 94 |
| Compound 12-1 | 100 |

TABLE I-continued

| | IKKβ Inhibition Rate (%) |
|---|---|
| Compound 12-2 | 99 |
| Compound 13-5 | 100 |
| Compound 13-13 | 100 |
| Compound 13-15 | 100 |
| Compound 13-24 | 98 |
| Compound 16-1 | 78 |
| Compound 20-1 | 100 |
| Compound 22-2 | 70 |
| Compound 22-9 | 100 |
| Compound 24-2 | 100 |
| Compound 25-3 | 100 |

IKKβ inhibition rate exceeding 100% is indicated as 100%.

As shown in Table 1, the present compounds exhibited the excellent IKKβ inhibition rates. Therefore, the present compounds can be used as an IKKβ inhibitor and useful as preventive and/or therapeutic agent for the diseases associated with IKKβ, such as inflammatory diseases, autoimmune diseases, allergic diseases, infectious diseases, degenerative diseases, vascular diseases, nerve/sensory organ diseases, endocrine/metabolic disease, neoplastic diseases, congenital diseases, traumatic diseases, and adverse reactions after organ transplantation.

The invention claimed is:

1. A compound represented by the following formula (1) or a salt thereof:

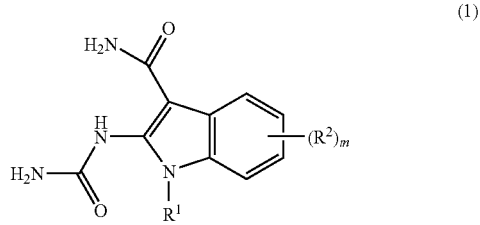

(1)

wherein $R^1$ represents a hydrogen atom, a lower alkyl group which is unsubstituted or substituted by a substituent, an aryl group which is unsubstituted or substituted by a substituent, a hydroxy group, or a lower alkoxy group which is unsubstituted or substituted by a substituent;

$R^2$ represents a halogen atom, a lower alkyl group which is unsubstituted or substituted by a substituent, a lower alkenyl group which is unsubstituted or substituted by a substituent, a lower alkynyl group which is unsubstituted or substituted by a substituent, $—X_1—COR^3$, $—X_1—COOR^3$, $—X_1—CONR^aR^b$, $—X_1—SR^3$, $—X_1—NR^aR^b$, $—X_1—NHCO—R^3$, $—X_1—CN$, $—X_1—N_3$, or a group represented by the following formula (2)

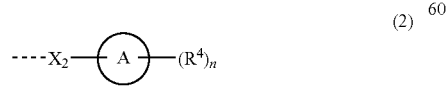

(2)

wherein $X_1$ represents a single bond, a lower alkylene group which is unsubstituted or substituted by a substituent, a lower alkenylene group which is unsubstituted or substituted by a substituent, or a lower alkynylene group which is unsubstituted or substituted by a substituent;

$R^3$ represents a hydrogen atom, a lower alkyl group which is unsubstituted or substituted by a substituent, or a lower alkenyl group which is unsubstituted or substituted by a substituent;

$R^a$ and $R^b$ are the same or different and each represents a hydrogen atom, a lower alkyl group which is unsubstituted or substituted by a substituent, a lower alkenyl group which is unsubstituted or substituted by a substituent, a lower alkoxy group which is unsubstituted or substituted by a substituent, a lower alkylsulfonyl group which is unsubstituted or substituted by a substituent, or an arylsulfonyl group which is unsubstituted or substituted by a substituent;

$X_2$ represents a single bond, a lower alkylene group which is unsubstituted or substituted by a substituent, a lower alkenylene group which is unsubstituted or substituted by a substituent, a lower alkynylene group which is unsubstituted or substituted by a substituent, $—X_3—CO—$, $—X_3—CONH—$, $—X_3—S—$, $—X_3—NH—$, $—X_3—NHCO—$, or $—X_3—NHCONH—$;

$X_3$ represents a single bond, a lower alkylene group which is unsubstituted or substituted by a substituent, a lower alkenylene group which is unsubstituted or substituted by a substituent, or a lower alkynylene group which is unsubstituted or substituted by a substituent, the ring A represents a hydrocarbon ring or a heterocyclic ring;

$R^4$ represents a halogen atom, a lower alkyl group which is unsubstituted or substituted by a substituent, $—X_4—OR^5$, $—X_4—OCOR^5$, $—X_4—COR^5$, $—X_4—COOR^5$, $—X_4—CONR^cR^d$, $—X_4—SR^5$, $—X_4—SOR^5$, $—X_4—SONR^cR^d$, $—X_4—SO_2R^5$, $—X_4—SO_2NR^cR^d$, $—X_4—NR^cR^d$, $—X_4—NHCOR^5$, $—X_4—HCOOR^5$, $—X_4—NHSOR^5$, $—X_4—NHSO_2R^5$, $—X_4—CN$, or $—X_4—NO_2$;

$X_4$ represents a single bond, a lower alkylene group which is unsubstituted or substituted by a substituent, or a lower cycloalkylene group which is unsubstituted or substituted by a substituent;

$R^5$ represents a hydrogen atom, a lower alkyl group which is unsubstituted or substituted by a substituent, a lower cycloalkyl group which is unsubstituted or substituted by a substituent, or an aryl group which is unsubstituted or substituted by a substituent;

$R^c$ and $R^d$ are the same or different and each represents a hydrogen atom, a lower alkyl group which is unsubstituted or substituted by a substituent, a lower cycloalkyl group which is unsubstituted or substituted by a substituent, an aryl group which is unsubstituted or substituted by a substituent, or a heterocyclic group which is unsubstituted or substituted by a substituent; or $R^c$ and $R^d$ are joined to each other to form a monocyclic saturated heterocyclic ring which is unsubstituted or substituted by a substituent;

m represents 0, 1, 2, 3, or 4, provided that $R^2$ is the same or different when m is 2, 3, or 4; and n represents 0, 1, 2, 3, or 4, provided that $R^4$ is the same or different when n is 2, 3, or 4.

2. The compound or a salt thereof according to claim 1, wherein, in the formula (1), $R^1$ represents a hydrogen atom, a lower alkyl group, an aryl-lower alkyl group, an aryl group, a nitroaryl group, a hydroxy group, a lower alkoxy group, or an aryl-lower alkoxy group;

$R^2$ represents a halogen atom, a lower alkyl group, a halogeno-lower alkyl group, a lower alkenyl group, a halogeno-lower alkenyl group, a lower alkynyl group, a halogeno-lower alkynyl group, $-X_1-COR^3$, $-X_1-COOR^3$, $-X_1-CONR^aR^b$, $-X_1-SR^3$, $-X_1-NR^aR^b$, $-X_1-NHCO-R^3$, $-X_1-CN$, $-X_1-N_3$, or a group represented by the following general formula (2):

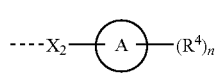

(2)

wherein $X_1$, represents a single bond, a lower alkylene group, a lower alkenylene group, or a lower alkynylene group;

$R^3$ represents a hydrogen atom, a lower alkyl group, a halogeno-lower alkyl group, an aryl-lower alkyl group, a heterocyclic lower alkyl group, a hydroxy lower alkyl group, a lower alkoxy lower alkyl group, a cyano lower alkyl group, a lower alkenyl group, a halogeno-lower alkenyl group, an aryl-lower alkenyl group, a heterocyclic lower alkenyl group, a hydroxy lower alkenyl group, a lower alkoxy lower alkenyl group, or a cyano lower alkenyl group;

$R^a$ and $R^b$ are the same or different and each represents a hydrogen atom, a lower alkyl group, an aryl-lower alkyl group, a heterocyclic lower alkyl group, a hydroxy lower alkyl group, a lower alkoxy lower alkyl group, a cyano lower alkyl group, a lower alkenyl group, an aryl-lower alkenyl group, a heterocyclic lower alkenyl group, a hydroxy lower alkenyl group, a lower alkoxy lower alkenyl group, a cyano lower alkenyl group, a lower alkoxy group, an aryl-lower alkoxy group, a heterocyclic lower alkoxy group, a hydroxy lower alkoxy group, a lower alkoxy lower alkoxy group, a cyano lower alkoxy group, a lower alkylsulfonyl group, or an aryl sulfonyl group;

$X_2$ represents a single bond, a lower alkylene group, a lower alkenylene group, a lower alkynylene group, $-X_3-CO-$, $-X_3-CONH-$, $-X_3-S-$, $-X_3-NH-$, $-X_3-NHCO-$, or $-X_3-NHCONH-$;

$X_3$ represents a single bond, a lower alkylene group, a lower alkenylene group, or a lower alkynylene group;

the ring A represents a hydrocarbon ring or a heterocyclic ring;

$R^4$ represents a halogen atom, a lower alkyl group, a halogeno-lower alkyl group, $-X_4-OR^5$, $-X_4-OCOR^5$, $-X_4-COR^5$, $-X_4-COOR^5$, $-X_4-CONR^cR^d$, $-X_4-SR^5$, $-X_4-SOR^5$, $-X_4-SONR^cR^d$, $-X_4-SO_2R^5$, $-X_4-SO_2NR^cR^d$, $-X_4-NR^cR^d$, $-X_4-NHCOR^5$, $-X_4-NHCOOR^5$, $-X_4-NHSOR^5$, $-X_4-NHSO_2R^5$, $-X_4-CN$, or $-X_4-NO_2$;

$X_4$ represents a single bond, a lower alkylene group, or a lower cycloalkylene group;

$R^5$ represents a hydrogen atom, a lower alkyl group, halogeno-lower alkyl group, a lower cycloalkyl lower alkyl group, an aryl-lower alkyl group, a lower cycloalkyl group, or an aryl group;

$R^c$ and $R^d$ are the same or different and each represents a hydrogen atom, a lower alkyl group, a hydroxy lower alkyl group, a lower alkoxy lower alkyl group, a lower alkyl group having $-NR^eR^f$ as a substituent, a lower cycloalkyl group, a lower alkyl lower cycloalkyl group, an aryl group, a lower alkylaryl group, a heterocyclic group, or a lower alkyl heterocyclic group; or $R^c$ and $R^d$ are joined to each other to form a monocyclic saturated heterocyclic ring;

$R^e$ and $R^f$ are the same or different and each represents a hydrogen atom or a lower alkyl group; or $R^e$ and $R^f$ are joined to each other to form a monocyclic saturated heterocyclic ring;

m represents 0, 1, 2, 3, or 4, provided that $R^2$ is the same or different when m is 2, 3, or 4; and n represents 0, 1, 2, 3, or 4, provided that $R^4$ is the same or different when n is 2, 3, or 4.

3. The compound or a salt thereof according to claim 1, wherein, in the formula (1), $R^1$ represents a hydrogen atom, a lower alkyl group, an aryl-lower alkyl group, a nitroaryl group, or a hydroxy group;

$R^2$ represents a halogen atom, a lower alkyl group, a halogeno-lower alkyl group, a lower alkenyl group, a lower alkynyl group, $-X_1-COR^3$, $-X_1-COOR^3$, $-X_1-CONR^aR^b$, $-X_1-SR^3$, $-X_1-NR^aR^b$, $-X_1-NHCO-R^3$, $-X_1-CN$, $-X_1-N_3$, or a group represented by the following formula (2):

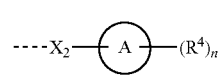

(2)

wherein $X_1$ represents a single bond, a lower alkylene group, a lower alkenylene group, or a lower alkynylene group;

$R^3$ represents a hydrogen atom, a lower alkyl group, a halogeno-lower alkyl group, an aryl-lower alkyl group, a heterocyclic lower alkyl group, a hydroxy lower alkyl group, a cyano lower alkyl group, or a lower alkenyl group;

$R^a$ and $R^b$ are the same or different and each represents a hydrogen atom, a lower alkyl group, an aryl-lower alkyl group, a heterocyclic lower alkyl group, a hydroxy lower alkyl group, a cyano lower alkyl group, a lower alkenyl group, a lower alkoxy group, or an arylsulfonyl group;

$X_2$ represents a single bond, a lower alkylene group, a lower alkenylene group, a lower alkynylene group, $-X_3-CO-$, $-X_3-CONH-$, $-X_3-S-$, $-X_3-NH-$, $-X_3-NHCO-$, or $-X_3-NHCONH-$;

$X_3$ represents a single bond, a lower alkylene group, a lower alkenylene group, or a lower alkynylene group;

the ring A represents a hydrocarbon ring or a heterocyclic ring;

$R^4$ represents a halogen atom, a lower alkyl group, a halogeno-lower alkyl group, , $-X_4-OR^5$, $-X_4-OCOR^5$, $-X_4-COR^5$, $-X_4-COOR^5$, $-X_4-CONR^cR^d$, $-X_4-SO_2R^5$, $-X_4-SO_2NR^cR^d$, $-X_4-NR^cR^d$, $-X_4-NHCOR^5$, $-X_4-NHCOOR^5$, $-X_4-NHSO_2R^5$, $-X_4-CN$, or $-X_4-NO_2$;

$X_4$ represents a single bond, a lower alkylene group, or a lower cycloalkylene group;

$R^5$ represents a hydrogen atom, a lower alkyl group, halogeno-lower alkyl group, an aryl-lower alkyl group, or an aryl group;

$R^c$ and $R^d$ are the same or different and each represents a hydrogen atom, a lower alkyl group, a hydroxy lower alkyl group, a lower alknxy lower alkyl group, a lower alkyl group having $-NR^eR^f$ as a substituent, a lower cycloalkyl group, a heterocyclic group, or a lower alkyl heterocyclic group; or $R^c$ and $R^d$ are joined to each other to form a monocyclic saturated heterocyclic ring;

$R^e$ and $R^f$ are the same or different and each represents a hydrogen atom or a lower alkyl group; or $R^e$ and $R^f$ are joined to each other to form a monocyclic saturated heterocyclic ring;

m represents 0, 1, or 2, provided that $R^2$ is the same or different when m is 2; and n represents 0, 1, 2, 3, or 4, provided that $R^4$ is the same or different when n is 2, 3, or 4.

4. The compound or a salt thereof according to claim 1, wherein, in the formula (1), $R^1$ represents a hydrogen atom, a lower alkyl group, an aryl-lower alkyl group, a nitroaryl group, or a hydroxy group;

$R^2$ represents a halogen atom, a lower alkyl group, a halogeno-lower alkyl group, a lower alkenyl group, a lower alkynyl group, —$X_1$—$COOR^3$, —$X_1$—$SR^3$, —$X_1$—$NR^aR^b$, —$X_1$—NHCO—$R^3$, or a group represented by the following formula (2):

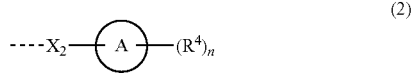

wherein $X_1$ represents a single bond, a lower alkylene group, or a lower alkynylene group;

$R^3$ represents a hydrogen atom, a lower alkyl group, or an aryl-lower alkyl group;

$R^a$ and $R^b$ are the same or different and each represents a hydrogen atom or a lower alkyl group;

$X_2$ represents a single bond, a lower alkylene group, a lower alkynylene group, —$X_3$—NHCO—, or —$X_3$—NHCONH—;

$X_3$ represents a single bond;

the ring A represents a hydrocarbon ring or a heterocyclic ring;

$R^4$ represents a halogen atom, a lower alkyl group, —$X_4$—$OR^5$, —$X_4$—$NR^cR^d$, —$X_4$—$NHSO_2R^5$, —$X_4$—CN, or —$X_4$—$NO_2$;

$X_4$ represents a single bond or a lower alkylene group;

$R^5$ represents a hydrogen atom or a lower alkyl group;

$R^c$ and $R^d$ are the same or different and each represents a hydrogen atom, a lower alkyl group, a lower alkyl group having —$NR^eR^f$ as a substituent, or a lower cycloalkyl group; or $R^c$ and $R^d$ are joined to each other to form a monocyclic saturated heterocyclic ring;

$R^e$ and $R^f$ are the same or different and each represents a hydrogen atom or a lower alkyl group; or $R^e$ and $R^f$ are joined to each other to form a monocyclic saturated heterocyclic ring;

m represents 0, 1, or 2, provided that $R^2$ is the same or different when m is 2; and n represents 0, 1, or 2, provided that $R^4$ is the same or different when n is 2.

5. The compound or a salt thereof according to claim 1, wherein the ring A is a hydrocarbon ring.

6. The compound or a salt thereof according to claim 5, wherein the hydrocarbon ring is selected from the group consisting of cyclopropane, cyclopentane, cyclohexane, cyclohexene, adamantane, benzene, and naphthalene.

7. The compound or a salt thereof according to claim 5, wherein the hydrocarbon ring is selected from the group consisting of cyclohexane and benzene.

8. The compound or a salt thereof according to claim 1, wherein the ring A is a heterocyclic ring.

9. The compound or a salt thereof according to claim 8, wherein the heterocyclic ring is selected from the group consisting of pyrrolidine, pyrrolidone, pyrrole, imidazole, pyrazole, indole, pyridine, pyrimidine, quinoline, furan, benzofuran, thiophene, benzothiophene, isoxazole, thiazole, morpholine, thiomorpholine, dioxaborane, and dithiolane.

10. The compound or a salt thereof according to claim 8, wherein the heterocyclic ring is selected from the group consisting of pyrrolidine, pyrrole, indole, pyridine, quinoline, furan, thiophene, and dithiolane.

11. A compound or a salt thereof selected from the group consisting of

2-Aminocarbonylamino-6-bromo-1-hydroxyindole-3-carboxamide,

2-Aminocarbonylamino-5-methylindole-3-carboxamide,

6-Acetylamino-2-aminocarbonylaminoindole-3-carboxamide,

2-Aminocarbonylamino-6-benzoylaminoindole-3-carboxamide,

2-Aminocarbonylamino-6-(3-phenylureido)indole-3-carboxamide,

2-Aminocarbonylamino-6-dimethylaminoindole-3-carboxamide,

2-Aminocarbonylamino-6-(pyrrolidin-1-yl)indole-3-carboxamide,

2-Aminocarbonylamino-6-(pyrrol-1-yl)indole-3-carboxamide,

2-Aminocarbonylaminoindole-3-carboxamide,

2-Aminocarbonylamino-6-bromo-7-methylindole-3-carboxamide,

2-Aminocarbonylamino-6-trifluoromethylindole-3-carboxamide,

2-Aminocarbonylamino-6-methoxycarbonylindole-3-carboxamide,

2-Aminocarbonylamino-6-bromoindole-3-carboxamide,

2-Aminocarbonylamino-6-(4-fluorophenyl)indole-3-carboxamide,

2-Aminocarbonylamino-6-phenylindole-3-carboxamide,

2-Aminocarbonylamino-6-(3-methoxyphenyl)indole-3-carboxamide,

2-Aminocarbonylamino-6-(thiophen-2-yl)indole-3-carboxamide,

2-Aminocarbonylamino-6-(pyridin-3-yl)indole-3-carboxamide,

2-Aminocarbonylamino-6-(2-fluorophenyl)indole-3-carboxamide,

2-Aminocarbonylamino-6-(3-fluorophenyl)indole-3-carboxamide,

2-Aminocarbonylamino-6-(3-cyanophenyl)indole-3-carboxamide,

2-Aminocarbonylamino-6-(3-nitrophenyl)indole-3-carboxamide,

2-Aminocarbonylamino-6-(3-methylsulfonylaminophenyl)indole-3-carboxamide,

2-Aminocarbonylamino-6-(thiophen-3-yl)indole-3-carboxamide,

2-Aminocarbonylamino-6-(furan-2-yl)indole-3-carboxamide,

2-Aminocarbonylamino-6-(furan-3-yl)indole-3-carboxamide,

2-Aminocarbonylamino-6-(2-chlorothiophen-3-yl)indole-3-carboxamide,

2-Aminocarbonylamino-6-(quinolin-3-yl)indole-3-carboxamide,

2-Aminocarbonylamino-6-vinylindole-3-carboxamide,

2-Aminocarbonylamino-6-[(E)-3-methoxy-1-propenyl]
indole-3-carboxamide,
2-Aminocarbonylamino-6-(indol-5-yl)indole-3-carboxamide,
2-Aminocarbonylamino-6-[(E)-1-pentenyl]indole-3-carboxamide,
2-Aminocarbonylamino-6-(4-dimethylaminophenyl)indole-3-carboxamide,
2-Aminocarbonylamino-6-(furan-3-yl)-7-methylindole-3-carboxamide,
2-Aminocarbonylamino-6-(pyrrol-2-yl)indole-3-carboxamide,
2-Aminocarbonylamino-6-[3-(2-hydroxyethyl)phenyl]indole-3-carboxamide,
2-Aminocarbonylamino-6-(pyridin-4-yl)indole-3-carboxamide,
2-Aminocarbonylamino-6-(4-hydroxymethyl-3-methoxyphenyl)indole 3-carboxamide,
2-Aminocarbonylamino-6-(2-chloropyridin-4-yl)indole-3-carboxamide,
2-Aminocarbonylamino-6-[(1R)-3-(1-hydroxyethyl)phenyl]indole-3-carboxamide,
2-Aminocarbonylamino-6-[(1S)-3-(1-hydroxyethyl)phenyl]indole-3-carboxamide,
2-Aminocarbonylamino-6-(4-aminomethylphenyl)indole-3-carboxamide,
2-Aminocarbonylamino-6-[4-(1-aminoethyl)phenyl]indole-3-carboxamide,
2-Aminocarbonylamino-6-[4-(1-amino-1-methylethyl)phenyl]indole-3-carboxamide,
2-Aminocarbonylamino-6-phenylethynylindole-3-carboxamide,
2-Aminocarbonylamino-6-(3-hydroxy-1-propynyl)indole-3-carboxamide,
2-Aminocarbonylamino-6-(3-dimethylamino-1-propynyl)indole-3-carboxamide,
2-Aminocarbonylamino-6-ethynylindole-3-carboxamide,
2-Aminocarbonylamino-6-ethylindole-3-carboxamide,
2-Aminocarbonylamino-6-(4-hydroxybutyl)indole-3-carboxamide,
2-Aminocarbonylamino-6-(3-dimethylaminopropyl)indole-3-carboxamide,
2-Aminocarbonylamino-6-(3-methoxypropyl)indole-3-carboxamide,
2-Aminocarbonylamino-6-(3-hydroxymethylphenyl)indole-3-carboxamide,
2-Aminocarbonylamino-6-(5-hydroxymethylfuran-2-yl)indole-3-carboxamide,
2-Aminocarbonylamino-6-(3-isopropylaminomethylphenyl)indole-3-carboxamide,
2-Aminocarbonylamino-6-[3-(2-hydroxyethylaminomethyl)phenyl]indole-3-carboxamide,
2-Aminocarbonylamino-6-(5-cyclopropylaminomethylfuran-2-yl)indole-3-carboxamide,
2-Aminocarbonylamino-6-(5-methylaminomethylthiophen-2-yl)indole-3-carboxamide,
2-Aminocarbonylamino-6-hydroxymethylindole-3-carboxamide,
2-Aminocarbonylamino-6-(1,3-dithiolan-2-yl)indole-3-carboxamide,
2-Aminocarbonylamino-6-(pyrrolidin-1-ylcarbonyl)indole-3-carboxamide,
2-Aminocarbonylamino-6-benzylaminocarbonylindole-3-carboxamide,
2-Aminocarbonylamino-6-(pyrrolidin-1-ylmethyl)indole-3-carboxamide, and
2-Aminocarbonylamino-6-ethylthiomethylindole-3-carboxamide.

12. A pharmaceutical composition comprising (i) as an active ingredient the compound or a salt thereof according to claim 1 and (ii) a pharmaceutical carrier.

13. An IKKβ inhibitor comprising as an active ingredient the compound or a salt thereof according to claim 1.

14. The pharmaceutical composition according to claim 12, which is a therapeutic agent for age-related macular degeneration.

15. The pharmaceutical composition according to claim 12, which is a therapeutic agent for diabetic retinopathy or diabetic macular edema.

16. The pharmaceutical composition according to claim 12, which is a therapeutic agent for keratitis, conjunctivitis, or uveitis.

17. The pharmaceutical composition according to claim 12, which is a therapeutic agent for glaucoma.

18. The pharmaceutical composition according to claim 12, which is a therapeutic agent for rheumatoid arthritis.

19. A method for inhibiting IKKβ comprising administering to a patient in need thereof a pharmacologically effective amount of the compound or a salt thereof according to claim 1.

20. A method for treating age-related macular degeneration comprising administering to a patient in need thereof a therapeutically effective amount of the compound or a salt thereof according to claim 1.

21. A method for treating diabetic retinopathy or diabetic macular edema comprising administering to a patient in need thereof a therapeutically effective amount of the compound or a salt thereof according to claim 1.

22. A method for treating keratitis, conjunctivitis, or uveitis comprising administering to a patient in need thereof a therapeutically effective amount of the compound or a salt thereof according to claim 1.

23. A method for treating glaucoma comprising administering to a patient in need thereof a therapeutically effective amount of the compound or a salt thereof according to claim 1.

24. A method for treating rheumatoid arthritis comprising administering to a patient in need thereof a therapeutically effective amount of the compound or a salt thereof according to claim 1.

* * * * *